United States Patent
Ochi et al.

(10) Patent No.: US 9,963,451 B2
(45) Date of Patent: May 8, 2018

(54) FUSED RING PYRIMIDINE COMPOUND AND PEST CONTROL AGENT CONTAINING THE SAME

(71) Applicant: Mitsui Chemicals Agro, Inc., Tokyo (JP)

(72) Inventors: Takahiko Ochi, Omuta (JP); Takeo Wakita, Mobara (JP); Toshiyuki Kono, Chiba (JP); Kazuki Kitajima, Mobara (JP); Shinichi Banba, Chiba (JP); Ayumi Kawase, Yasu (JP); Atsuko Kawahara, Chiba (JP); Kazuyuki Sato, Ratchaburi (TH)

(73) Assignee: Mitsui Chemicals Agro, Inc., Tokyo (JP)

( * ) Notice: Subject to any disclaimer, the term of this patent is extended or adjusted under 35 U.S.C. 154(b) by 89 days.

(21) Appl. No.: 14/763,656

(22) PCT Filed: Jan. 31, 2014

(86) PCT No.: PCT/JP2014/052337
§ 371 (c)(1),
(2) Date: Jul. 27, 2015

(87) PCT Pub. No.: WO2014/119752
PCT Pub. Date: Aug. 7, 2014

(65) Prior Publication Data
US 2015/0368249 A1  Dec. 24, 2015

(30) Foreign Application Priority Data
Jan. 31, 2013 (JP) ................... 2013-017758

(51) Int. Cl.
C07D 487/04 (2006.01)
A01N 43/90 (2006.01)
A01N 47/40 (2006.01)
C07D 495/14 (2006.01)
A01N 47/06 (2006.01)

(52) U.S. Cl.
CPC .......... *C07D 487/04* (2013.01); *A01N 43/90* (2013.01); *A01N 47/06* (2013.01); *A01N 47/40* (2013.01); *C07D 495/14* (2013.01)

(58) Field of Classification Search
None
See application file for complete search history.

(56) References Cited

U.S. PATENT DOCUMENTS 4,950,764 A    8/1990  Nakamura
2015/0105405 A1* 4/2015  Bandur ............... A01N 43/90
                                                        514/256

FOREIGN PATENT DOCUMENTS

| JP | 63270680 | A2 | 11/1988 |
| JP | 7157485 | A2 | 6/1995 |
| JP | 2002056975 | A2 | 2/2002 |
| WO | 2012136751 | A1 | 10/2012 |
| WO | 2012152741 | A1 | 11/2012 |
| WO | 2013144088 | A1 | 10/2013 |
| WO | 2013162061 | | 10/2013 |

OTHER PUBLICATIONS

King, F.D. (Ed.), "Bioisosteres, conformational restriction and pro-drugs—case history: an example of a conformational restriction approach," Medical Chemistry: Principles and Practice, 1994, Chapter 14, 206-209.*
International Search Report dated Apr. 22, 2014 filed in PCT/JP2014/052337.
Gabor Berecz. et al., "On triazoles XLII [1,2]. A new convenient method for the N-alkylation of highly insoluble cyclic amides," Journal of Heterocyclic Chemistry, Vol.38, pp. 237-252, 2001.
G. A. Reynolds. et al., "The Structure of Certain Polyazaindenes. VII. 4-Amino-6-methyl-1,3,3a,7-tetrazaindene and Its Derivatives," Journal of Organic Chemistry, vol. 26, Issue 1, pp. 115-117, 1961.; Cited in International Search Report.

* cited by examiner

*Primary Examiner* — Marcos L Sznaidman
*Assistant Examiner* — Rayna Rodriguez
(74) *Attorney, Agent, or Firm* — Rankin, Hill & Clark LLP

(57) ABSTRACT

Provided is a pest control agent containing a fused ring pyrimidine compound represented by the following formula (I) or a salt thereof as an effective component. In formula (I), A represents a nitrogen atom or C—$R^4$, B represents a nitrogen atom or C—$R^5$, D represents a nitrogen atom or C—$R^6$, X represents an oxygen atom, N—$R^7$ or the like, each of $R^1$, $R^2$, $R^4$ and $R^6$ independently represents a hydrogen atom or the like, each of $R^{3a}$ and $R^{3b}$ independently represents a hydrogen atom or the like, $R^5$ represents an alkylthio group or the like, $R^7$ represents an alkoxy group or the like, and Ht represents a pyridyl group that may be substituted, or the like.

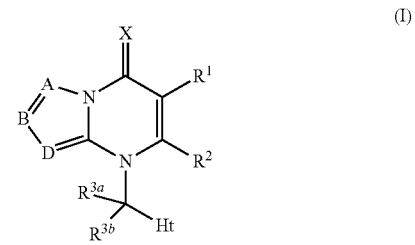

(I)

23 Claims, No Drawings

FUSED RING PYRIMIDINE COMPOUND AND PEST CONTROL AGENT CONTAINING THE SAME

TECHNICAL FIELD

The present invention relates to a fused ring pyrimidine compound and a pest control agent containing the compound.

BACKGROUND ART

Until now, various compounds have been developed as a pest control agent. For example, a fused ring pyrimidine compound with a substituted nitrogen atom is described in literatures of a related art that are described below.

For example, a 1,2,4-triazolo[1,5-a]pyrimidine skeleton is described in Non-Patent Document 1 or Patent Document 1 and a pyrazolo[1,2-a]pyrimidine skeleton is described in Patent Document 1 or the like. Furthermore, as a fused ring compound in which the nitrogen atom has a heteroaryl methyl group like 6-chloropyridin-3-yl methyl group, for example, the structural formula of 4-((6-chloropyridin-3-yl)methyl)-4,5,6,7-tetrahydro-2H-[1,2,4]oxadiazolo[2,3-a]pyrimidin-2-one (Reference Example 1) is described in Patent Document 2, and the structural formula of 4-((6-chloropyridin-3-yl)methyl)oxazolo[4,5-b]pyrimidin-2(4H)-one (Reference Example 2) is described in Patent Document 3.

However, in none of Patent Document 1 and Non-Patent Document 1, a compound in which the substituent group of the nitrogen atom is a substituted benzyl group or the like and has a heteroarylmethyl group is described, and no description is included regarding the use as a pest control agent. In addition, according to Patent Documents 2 and 3, it is essential to have, in a fused ring, a ketone structure or a thioketone structure on a ring which is not bound with a heteroarylmethyl group, and thus it is different from the structure of the invention.

Furthermore, although a fused ring compound which has a 1,2,4-triazolo[1,5-a]pyrimidine skeleton and a heteroarylmethyl group at position 4 is described as a reaction intermediate in Patent Document 4, no description is included regarding the use as a pest control agent.

Still furthermore, although the structural formula of 4-((6-bromopyridin-3-yl)methyl)-2-(methylthio)-[1,2,4]triazolo[1,5-a]pyrimidin-7(4H)-one (Reference Example 3) is described in Patent Document 5, in the examples, it was not exemplified as an exemplary compound which shows an activity of controlling a pest.

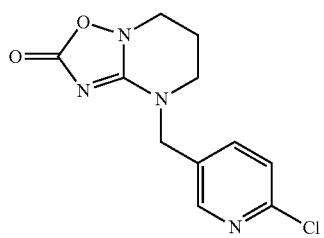

Reference Example 1

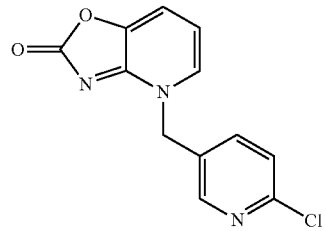

Reference Example 2

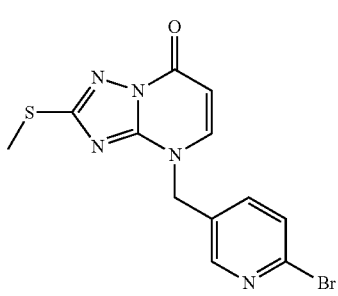

Reference Example 3

CITATION LIST

Patent Documents

[Patent Document 1] Japanese Patent Application Laid-Open (JP-A) No. H07-157485

[Patent Document 2] International Publication No. 2012/136751

[Patent Document 3] International Publication No. 2012/152741

[Patent Document 4] International Publication No. 2013/162061

[Patent Document 5] International Publication No. 2013/144088

Non-Patent Documents

[Non-Patent Document 1] Journal of Heterocyclic Chemistry, 38, 237 (2001)

SUMMARY OF INVENTION

Technical Problem

An object of the invention is to provide a fused ring pyrimidine compound exhibiting an effect of controlling various pests, and a salt thereof.

Solution to Problem

As a result of intensive studies, inventors of the invention found that the fused ring pyrimidine compound represented by formula (I) has an activity of controlling a pest.

Namely, the invention includes the following aspects.

<1> A fused ring pyrimidine compound represented by the following formula (I), or a salt thereof:

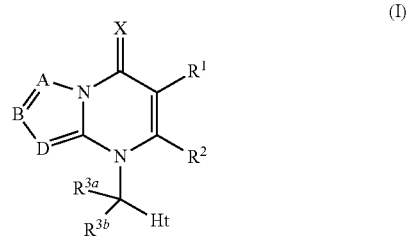

wherein, in formula (I), A represents a nitrogen atom or C—$R^4$;

B represents a nitrogen atom or C—$R^5$;
D represents a nitrogen atom or C—$R^6$;
X represents an oxygen atom, a sulfur atom, or N—$R^7$;
each of $R^1$, $R^2$, $R^4$, and $R^6$ independently represents a hydrogen atom, a halogen atom, a hydroxy group, a nitro group, a cyano group, an amino group, an alkyl group having 1 to 6 carbon atoms, a haloalkyl group having 1 to 6 carbon atoms, an alkenyl group having 2 to 6 carbon atoms, an alkynyl group having 2 to 6 carbon atoms, an alkoxy group having 1 to 6 carbon atoms, a haloalkoxy group having 1 to 6 carbon atoms, an alkoxyalkyl group having 2 to 6 carbon atoms, an alkoxycarbonyl group having 2 to 6 carbon atoms, an aminocarbonyl group having 1 to 6 carbon atoms, an alkylamino group having 1 to 6 carbon atoms, a benzyl group that may be substituted, a heterocyclylmethyl group that may be substituted, a phenyl group that may be substituted, or a heterocyclyl group that may be substituted;

$R^1$ and $R^2$ may bind to each other to form, together with the carbon atom to which each of $R^1$ and $R^2$ is bonded, a saturated or unsaturated ring;

each of $R^{3a}$ and $R^{3b}$ independently represents a hydrogen atom, a halogen atom, a nitro group, a cyano group, an alkyl group having 1 to 6 carbon atoms, a haloalkyl group having 1 to 6 carbon atoms, an alkoxy group having 1 to 6 carbon atoms, an alkylthio group having 1 to 6 carbon atoms, an alkylsulfinyl group having 1 to 6 carbon atoms, or an alkylsulfonyl group having 1 to 6 carbon atoms;

$R^5$ represents a hydrogen atom, a cyano group, a hydroxy group, a thiol group, a halogen atom, an alkyl group having 1 to 6 carbon atoms, a haloalkyl group having 1 to 6 carbon atoms, an alkenyl group with 2 to 6 carbon atoms, an alkynyl group having 2 to 6 carbon atoms, an alkoxyalkyl group having 2 to 6 carbon atoms, a benzyl group that may be substituted, a phenyl group that may be substituted, a heterocyclyl group that may be substituted, an alkoxy group that has 1 to 6 carbon atoms and that may be substituted, an alkenyloxy group having 2 to 6 carbon atoms, an alkynyloxy group having 2 to 6 carbon atoms, a haloalkoxy group having 1 to 6 carbon atoms, an alkoxyalkoxy group having 2 to 6 carbon atoms, an alkylcarbonyloxy group having 2 to 6 carbon atoms, an alkylcarbamate group having 2 to 6 carbon atoms, an alkylcarbonate group having 2 to 6 carbon atoms, a benzyloxy group that may be substituted, a phenoxy group that may be substituted, a heterocyclyloxy group that may be substituted, an alkylthio group having 1 to 6 carbon atoms, a haloalkylthio group having 1 to 6 carbon atoms, an alkylsulfinyl group having 1 to 6 carbon atoms, an alkylsulfonyl group having 1 to 6 carbon atoms, a haloalkylsulfinyl group having 1 to 6 carbon atoms, a haloalkylsulfonyl group with 1 to 6 carbon atoms, an alkylsulfonyloxy group having 1 to 6 carbon atoms, a haloalkylsulfonyloxy group having 1 to 6 carbon atoms, an alkylaminosulfonyloxy group having 1 to 6 carbon atoms, a benzylthio group that may be substituted, a phenylthio group that may be substituted, a phenylsulfinyl group that may be substituted, a phenylsulfonyl group that may be substituted, a phenylsulfonyloxy group that may be substituted, a heterocyclylthio group that may be substituted, a heterocyclylsulfinyl group that may be substituted, a heterocyclylsulfonyl group that may be substituted, a substituted iminosulfinyl group, a substituted iminosulfoxy group, an alkylcarbonyl group having 2 to 6 carbon atoms, an alkoxycarbonyl group having 2 to 6 carbon atoms, an alkylaminocarbonyl group having 2 to 6 carbon atoms, an alkylamino group that has 1 to 6 carbon atoms and that may be substituted, or an alkylcarbonylamino group having 2 to 6 carbon atoms;

when A represents C—$R^4$ and B represents C—$R^5$, $R^4$ and $R^5$ may bind to each other to form, together with the carbon atom to which each of $R^4$ and $R^5$ is bonded, a saturated or unsaturated ring;

when B represents C—$R^5$ and D represents C—$R^6$, $R^5$ and $R^6$ may bind to each other to form, together with the carbon atom to which each of $R^5$ and $R^6$ is bonded, a saturated or unsaturated ring;

$R^7$ represents a hydrogen atom, a cyano group, a hydroxy group, an alkyl group having 1 to 6 carbon atoms, a haloalkyl group having 1 to 6 carbon atoms, a phenyl group that may be substituted, an alkoxy group having 1 to 6 carbon atoms, an alkenyloxy group having 2 to 6 carbon atoms, an alkylcarbonyloxy group having 2 to 6 carbon atoms, a benzyloxy group that may be substituted, a phenoxy group that may be substituted, an alkylsulfonyl group having 1 to 6 carbon atoms, an alkylcarbonyl group having 2 to 6 carbon atoms, a haloalkylcarbonyl group having 2 to 6 carbon atoms, an alkoxycarbonyl group having 2 to 6 carbon atoms, or an amino group that may be substituted; and Ht represents a 5-membered or 6-membered aromatic or non-aromatic heterocycle, wherein, there is no case in which A is N, B is C—$R^5$, D is N, all of $R^1$, $R^2$, $R^{3a}$, and $R^{3b}$ are hydrogen atoms, $R^5$ is a methylthio group, and Ht is a 6-bromo-3-pyridyl group, simultaneously.

<2> The fused ring pyrimidine compound or a salt thereof described in above <1>, in which, in formula (I):

each of $R^1$ and $R^2$ represents a hydrogen atom, a halogen atom, a hydroxy group, a nitro group, an alkyl group having 1 to 6 carbon atoms, a haloalkyl group having 1 to 6 carbon atoms, an alkoxy group having 1 to 6 carbon atoms, an alkoxyalkyl group having 2 to 6 carbon atoms, an alkoxycarbonyl group having 2 to 6 carbon atoms, an aminocarbonyl group having 1 to 6 carbon atoms, a benzyl group that may be substituted, a heterocyclylmethyl group that may be substituted, or a phenyl group that may be substituted;

$R^4$ represents a hydrogen atom, a cyano group, or an alkyl group having 1 to 6 carbon atoms;

$R^5$ represents a hydrogen atom, a cyano group, a hydroxy group, a thiol group, a halogen atom, an alkyl group having 1 to 6 carbon atoms, a haloalkyl group having 1 to 6 carbon atoms, an alkoxyalkyl group having 2 to 6 carbon atoms, a benzyl group that may be substituted, a phenyl group that may be substituted, a heterocyclyl group that may be substituted, an alkoxy group that has 1 to 6 carbon atoms and that may be substituted, an alkenyloxy group having 2 to 6 carbon atoms, an alkynyloxy group having 2 to 6 carbon atoms, a haloalkoxy group having 1 to 6 carbon atoms, an alkoxyalkoxy group having 2 to 6 carbon atoms, an alkylcarbonyloxy group having 2 to 6 carbon atoms, an alkylcarbamate group having 2 to 6 carbon atoms, an alkylcarbonate group having 2 to 6 carbon atoms, a benzyloxy group that may be substituted, a phenoxy group that may be substituted, a heterocyclyloxy group that may be substituted, an alkylthio group having 1 to 6 carbon atoms, a haloalkylthio group having 1 to 6 carbon atoms, an alkylsulfinyl group having 1 to 6 carbon atoms, an alkylsulfonyl group having 1 to 6 carbon atoms, a haloalkylsulfinyl group having 1 to 6 carbon atoms, a haloalkylsulfonyl group having 1 to 6 carbon atoms, an alkylsulfonyloxy group having 1 to 6 carbon atoms, a haloalkylsulfonyloxy group having 1 to 6 carbon atoms, an alkylaminosulfonyloxy group having 1 to 6 carbon atoms, a benzylthio group that may be substituted, a phenylthio group that may be substituted, a phenylsulfinyl group that may be substituted, a phenylsulfonyl group that may be substituted, a phenylsulfonyloxy group that may be substituted, a heterocyclylthio group that may be substituted, a heterocyclylsulfinyl group that may be substituted, a heterocyclylsulfonyl group that may be substituted, a substituted iminosulfinyl group, a substituted iminosulfoxy group, an alkylcarbonyl group having 2 to 6 carbon atoms, an alkyloxycarbonyl group having 2 to 6 carbon atoms, an alkylaminocarbonyl group having 2 to 6 carbon atoms, an alkylamino group that has 1 to 6 carbon atoms and that may be substituted, or an alkylcarbonylamino group having 2 to 6 carbon atoms;

$R^6$ represents a hydrogen atom, a halogen atom, a cyano group, or an alkyl having 1 to 6 carbon atoms; and Ht represents a pyridyl group that may be substituted, a pyrimidyl group that may be substituted, a pyrazyl group that may be substituted, a pyridazyl group that may be substituted, a pyrazolyl group that may be substituted, an imidazolyl group that may be substituted, a triazolyl group that may be substituted, a thiazolyl group that may be substituted, or a tetrahydrofuryl group that may be substituted.

<3> The fused ring pyrimidine compound or a salt thereof described in above <2>, in which, in formula (I):

$R^1$ represents a hydrogen atom, a halogen atom, a nitro group, an alkyl group having 1 to 6 carbon atoms, an aminocarbonyl group having 1 to 6 carbon atoms, a benzyl group that may be substituted, a heterocyclylmethyl group that may be substituted, or a phenyl group that may be substituted;

$R^2$ represents a hydrogen atom, a halogen atom, a hydroxy group, an alkyl group having 1 to 6 carbon atoms, a haloalkyl group having 1 to 6 carbon atoms, an alkoxy group having 1 to 6 carbon atoms, an alkoxyalkyl group having 2 to 6 carbon atoms, or a phenyl group that may be substituted;

each of $R^{3a}$ and $R^{3b}$ independently represents a hydrogen atom, or an alkyl group having 1 to 6 carbon atoms; and $R^5$ represents a hydrogen atom, a cyano group, a hydroxy group, a thiol group, a halogen atom, an alkyl group having 1 to 6 carbon atoms, a haloalkyl group having 1 to 6 carbon atoms, an alkoxyalkyl group having 2 to 6 carbon atoms, a benzyl group that may be substituted, a phenyl group that may be substituted, a heterocyclyl group that may be substituted, an alkoxy group that has 1 to 6 carbon atoms and that may be substituted, an alkenyloxy group having 2 to 6 carbon atoms, an alkynyloxy group having 2 to 6 carbon atoms, a haloalkoxy group having 1 to 6 carbon atoms, an alkoxyalkoxy group having 2 to 6 carbon atoms, an alkylcarbonyloxy group having 2 to 6 carbon atoms, an alkylcarbamate group having 2 to 6 carbon atoms, an alkylcarbonate group having 2 to 6 carbon atoms, a benzyloxy group that may be substituted, a phenoxy group that may be substituted, a heterocyclyloxy group that may be substituted, an alkylthio group having 1 to 6 carbon atoms, a haloalkylthio group having 1 to 6 carbon atoms, an alkylsulfinyl group having 1 to 6 carbon atoms, an alkylsulfonyl group having 1 to 6 carbon atoms, a haloalkylsulfinyl group having 1 to 6 carbon atoms, a haloalkylsulfonyl group having 1 to 6 carbon atoms, an alkylsulfonyloxy group having 1 to 6 carbon atoms, a haloalkylsulfonyloxy group having 1 to 6 carbon atoms, an alkylaminosulfonyloxy group having 1 to 6 carbon atoms, a benzylthio group that may be substituted, a phenylthio group that may be substituted, a phenylsulfonyloxy group that may be substituted, a heterocyclylthio group that may be substituted, a substituted iminosulfinyl group, a substituted iminosulfoxy group, an alkylcarbonyl group having 2 to 6 carbon atoms, an alkyloxycarbonyl group having 2 to 6 carbon atoms, an alkylaminocarbonyl group having 2 to 6 carbon atoms, an alkylamino group that has 1 to 6 carbon atoms and that may be substituted, or an alkylcarbonylamino group having 2 to 6 carbon atoms.

<4> The fused ring pyrimidine compound or a salt thereof described in above <1> to <3>, in which, in formula (I), B is C—$R^5$, and $R^5$ is a hydrogen atom, a halogen atom, an alkyl group having 1 to 3 carbon atoms, a haloalkyl group having 1 to 3 carbon atoms, an alkoxyalkyl group having 2 or 3 carbon atoms, an alkoxy group that has 1 to 3 carbon atoms and that may be substituted, an alkenyloxy group having 2 or 3 carbon atoms, an alkynyloxy group having 2 to 4 carbon atoms, a haloalkoxy group having 1 to 3 carbon atoms, an alkoxyalkoxy group having 2 or 3 carbon atoms, an alkylcarbonyloxy group having 2 or 3 carbon atoms, a phenoxy group that may be substituted, a heterocyclyloxy group that may be substituted, an alkylthio group having 1 to 3 carbon atoms, a haloalkylthio group having 1 to 3 carbon atoms, an alkylsulfinyl group having 1 to 3 carbon atoms, an alkylsulfonyl group having 1 to 3 carbon atoms, a haloalkylsulfinyl group having 1 to 3 carbon atoms, a haloalkylsulfonyl group having 1 to 3 carbon atoms, an alkylsulfonyloxy group having 1 to 3 carbon atoms, a haloalkylsulfonyloxy group having 1 to 3 carbon atoms, a phenylthio group that may be substituted, a phenylsulfonyloxy group that may be substituted, a substituted iminosulfinyl group, a substituted iminosulfoxy group, or an alkylamino group having 1 to 3 carbon atoms.

<5> The fused ring pyrimidine compound or a salt thereof described in above <4>, in which, in formula (I), $R^5$ is a hydrogen atom, a halogen atom, an alkyl group having 1 to 3 carbon atoms, a haloalkyl group having 1 to 3 carbon atoms, an alkoxy group having 1 to 3 carbon atoms, a haloalkoxy group having 1 to 3 carbon atoms, a phenoxy group that may be substituted, an alkylthio group having 1 to 3 carbon atoms, a haloalkylthio group having 1 to 3 carbon atoms, an alkylsulfinyl group having 1 to 3 carbon atoms, an alkylsulfonyl group having 1 to 3 carbon atoms, a haloalkylsulfinyl group having 1 to 3 carbon atoms, a haloalkylsulfonyl group having 1 to 3 carbon atoms, an alkylsulfonyloxy group having 1 to 3 carbon atoms, a substituted iminosulfinyl group, or a substituted iminosulfoxy group.

<6> The fused ring pyrimidine compound or a salt thereof described in above <1> to <3>, in which, in formula (I), B is a nitrogen atom.

<7> The fused ring pyrimidine compound or a salt thereof described in above <1> to <6>, in which, in formula (I), A is a nitrogen atom.

<8> The fused ring pyrimidine compound or a salt thereof described in above <1> to <6>, in which, in formula (I), A is C—$R^4$ and $R^4$ is a hydrogen atom.

<9> The fused ring pyrimidine compound or a salt thereof described in above <1> to <6>, in which, in formula (I), D is a nitrogen atom.

<10> The fused ring pyrimidine compound or a salt thereof described in above <1> to <6>, in which, in formula (I), D is C—$R^6$ and $R^6$ is a hydrogen atom.

<11> The fused ring pyrimidine compound or a salt thereof described in above <1> to <4>, in which, in formula (I), A is a nitrogen atom, B is C—$R^5$, D is C—$R^6$, and $R^6$ is a hydrogen atom.

<12> The fused ring pyrimidine compound or a salt thereof described in above <1> to <4>, in which, in formula (I), A is a nitrogen atom, B is C—$R^5$, and D is a nitrogen atom.

<13> The fused ring pyrimidine compound or a salt thereof described in above <1> to <6>, in which, in formula (I), X is an oxygen atom.

<14> The fused ring pyrimidine compound or a salt thereof described in above <1> to <6>, in which, in formula (I), X is N—$R^7$, and $R^7$ is a hydrogen atom, a cyano group, a hydroxy group, an alkyl group having 1 to 3 carbon atoms, a haloalkyl group having 1 to 3 carbon atoms, a phenyl group that may be substituted, an alkoxy group having 1 to 3 carbon atoms, an alkylcarbonyloxy group having 2 or 3 carbon atoms, an alkylsulfonyl group having 1 to 3 carbon atoms, an alkylcarbonyl group having 2 or 3 carbon atoms, a haloalkylcarbonyl group having 2 or 3 carbon atoms, an alkyloxycarbonyl group having 2 or 3 carbon atoms, or an alkylamino group that has 1 to 3 carbon atoms and that may be substituted.

<15> The fused ring pyrimidine compound or a salt thereof described in above <14>, in which, in formula (I), $R^7$ is a hydroxy group, an alkyl group having 1 to 3 carbon atoms, a haloalkyl group having 1 to 3 carbon atoms, a phenyl group that may be substituted, an alkoxy group having 1 to 3 carbon atoms, an alkylcarbonyloxy group having 2 or 3 carbon atoms, an alkylsulfonyl group having 1 to 3 carbon atoms, an alkylcarbonyl group having 2 or 3 carbon atoms, a haloalkylcarbonyl group having 2 or 3 carbon atoms, an alkyloxycarbonyl group having 2 or 3 carbon atoms, or an alkylamino group that has 1 to 3 carbon atoms and that may be substituted.

<16> The fused ring pyrimidine compound or a salt thereof described in above <1> to <6>, in which, in formula (I), $R^2$ is a hydroxy group, an alkyl group having 1 to 6 carbon atoms, or a haloalkyl group having 1 to 6 carbon atoms.

<17> The fused ring pyrimidine compound or a salt thereof described in above <16>, in which, in formula (I), $R^2$ is a methyl group or an ethyl group.

<18> The fused ring pyrimidine compound or a salt thereof described in above <1> to <6>, in which, in formula (I), $R^1$ is a hydrogen atom, a halogen atom, an alkyl group having 1 to 6 carbon atoms, or a haloalkyl group having 1 to 6 carbon atoms.

<19> The fused ring pyrimidine compound or a salt thereof described in above <18>, in which, in formula (I), $R^1$ is a hydrogen atom, a methyl group, an ethyl group, or a fluorine atom.

<20> The fused ring pyrimidine compound or a salt thereof described in above <1> to <6>, in which, in formula (I), Ht is a pyridyl group that may be substituted, a pyrimidyl group that may be substituted, or a thiazolyl group that may be substituted.

<21> The fused ring pyrimidine compound or a salt thereof described in above <20>, in which, in formula (I), Ht is a 3-pyridyl group that may be substituted or a 3-thiazolyl group that may be substituted.

<22> The fused ring pyrimidine compound or a salt thereof described in above <21>, in which, in formula (I), Ht is a 6-chloro-3-pyridyl group.

<23> The fused ring pyrimidine compound or a salt thereof described in above <1> to <6>, in which, in formula (I), at least one of $R^{3a}$ or $R^{3b}$ is a hydrogen atom.

<24> The fused ring pyrimidine compound or a salt thereof described in above <23>, in which, in formula (I), one of $R^{3a}$ and $R^{3b}$ is a hydrogen atom and the other is a hydrogen atom, a methyl group, or an ethyl group.

<25> A pest control agent comprising, as an effective component, the fused ring pyrimidine compound or a salt thereof described in any one of <1> to <24>.

<26> A method of controlling a pest including treating crops or soil with a medicament that contains an effective amount of the fused ring pyrimidine compound or a salt thereof described in any one of <1> to <24>, or applying the medicament to a subject of control.

Advantageous Effects of Invention

According to the invention, a novel fused ring pyrimidine compound can be provided. In addition, the pest control agent containing the fused ring pyrimidine compound of the invention as an effective component is useful not only as a control agent which exhibits a sufficient control effect against various harmful insects but also as a pest control agent which exhibits the control effect against resistant harmful insects.

DESCRIPTION OF EMBODIMENTS

As described herein, the "fused ring pyrimidine compound represented by the above formula (I) or a salt thereof" can be referred to as a "compound of the invention."

As described herein, the term "step" encompasses not only an independent step but also a case in which the desired purpose of the step is achieved even if it is not clearly distinguished from other step. Furthermore, the numerical range expressed with use of the term "to" indicates a range including the numerical values that are described either before and after "to" as a maximum value and a minimum value, respectively.

Furthermore, each of the terms that are used for the formula of the present specification has the meaning described below.

"n-" means normal, "i-" means iso, "s-" means secondary, and "t-" means tertiary.

The "halogen atom" for the substituent groups $R^1$, $R^2$, $R^{3a}$, $R^{3b}$, $R^4$, $R^5$, and $R^6$ of the invention indicates a fluorine atom, a chlorine atom, a bromine atom, or an iodine atom.

Hereinbelow, each substituent group for the above formula (I) indicating the compounds of the invention is described in detail.

The "alkyl group having 1 to 6 carbon atoms" for the substituent groups $R^1$, $R^2$, $R^4$, and $R^6$ in the above formula (I) indicates a linear, branched, or cyclic alkyl group having 1 to 6 carbon atoms such as methyl, ethyl, n-propyl, i-propyl, n-butyl, s-butyl, t-butyl, n-pentyl, 2-pentyl, neopentyl, 4-methyl-2-pentyl, n-hexyl, 3-methyl-n-pentyl, cyclopropyl, cyclobutyl, cyclopentyl 2-methylcyclopentyl, 3-methylcyclopentyl, and cyclohexyl. It is preferably an alkyl group having 1 to 3 carbon atoms, and more preferably a methyl group or an ethyl group.

Furthermore, when the substituent groups with the same type are different only in terms of the number of constituting carbon atoms, only the specific examples with matching carbon atom number are the corresponding specific examples among the specific examples of the substituent groups that are exemplified below.

The "haloalkyl group having 1 to 6 carbon atoms" for the substituent groups $R^1$, $R^2$, $R^4$, and $R^6$ indicates a linear, branched, or cyclic alkyl group that has 1 to 6 carbon atoms and that is substituted with one or more halogen atoms that may be the same or different from each other, such as trifluoromethyl, pentafluoroethyl, heptafluoro-n-propyl, heptafluoro-i-propyl, 2,2-difluoroethyl, 2,2-dichloroethyl, 2,2,2-trifluoroethyl, 2-fluoroethyl, 2-chloroethyl, 2-bromoethyl, 2-iodoethyl, 2,2,2-trichloroethyl, 2,2,2-tribromoethyl, 1,3-difluoro-2-propyl, 1,3-dichloro-2-propyl, 1-chloro-3-fluoro-2-propyl, 1,1,1-trifluoro-2-propyl, 3,3,3-trifluoro-n-propyl, 4,4,4-trifluoro-n-butyl, 1,1,1,3,3,3-hexafluoro-2-propyl, 1,1,1,3,3,3-hexafluoro-2-chloro-2-propyl, 1,1,1,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3-hexafluoro-1-bromo-2-propyl, 2,2,3,3,3-pentafluoro-n-propyl, 3-fluoro-n-propyl, 3-chloro-n-propyl, 3-bromo-n-propyl, 3,3,4,4,4-pentafluoro-2-butyl, nonafluoro-n-butyl, nonafluoro-2-butyl, 5,5,5-trifluoro-n-pentyl, 4,4,5,5,5-pentafluoro-2-pentyl, 3-chloro-n-pentyl, 4-bromo-2-pentyl, 1-fluorocyclopropyl, and 2,2-difluorocyclobutyl. It is preferably a haloalkyl group having 1 to 3 carbon atoms, and more preferably a trifluoromethyl group.

The "alkenyl group having 2 to 6 carbon atoms" for the substituent groups $R^1$, $R^2$, $R^4$, and $R^6$ indicates a linear, branched, or cyclic alkenyl group having 2 to 6 carbon atoms such as a vinyl group, an allyl group, a 3-butenyl group, a 2-methyl-3-butenyl group, and a 3-cyclohexenyl group. Their hydrogen atom may be substituted with one or more halogen atoms that may be the same or different from each other. It is preferably an allyl group.

The "alkynyl group having 2 to 6 carbon atoms" for the substituent groups $R^1$, $R^2$, $R^4$, and $R^6$ indicates a linear, branched, or cyclic alkynyl group having 2 to 6 carbon atoms such as an ethynyl group, a 2-propynyl group, a 2-butynyl group, a 2-methyl-3-butynyl group, and a 3-cyclohexynyl group. Their hydrogen atom may be substituted with one or more halogen atoms that may be the same or different from each other. It is preferably an ethynyl group.

The "alkoxy group having 1 to 6 carbon atoms" for the substituent groups $R^1$, $R^2$, $R^4$, and R indicates a linear, branched, or cyclic alkoxy group having 1 to 6 carbon atoms such as methoxy, ethoxy, n-propoxy, i-propoxy, n-butoxy, i-butoxy, 2-methyl-butoxy, n-hexyloxy, cyclopropoxy, and cyclobutoxy. It is preferably an alkoxy group having 1 to 3 carbon atoms, and more preferably a methoxy group or an ethoxy group.

The "haloalkoxy group having 1 to 6 carbon atoms" for the substituent groups $R^1$, $R^2$, $R^4$, and $R^6$ indicates a linear, branched, or cyclic alkoxy group that has 1 to 6 carbon atoms and that is substituted with one or more halogen atoms that may be the same or different from each other, such as fluoromethoxy, difluoromethoxy, trifluoromethoxy, bromodifluoromethoxy, pentafluoroethoxy, heptafluoro-n-propoxy, heptafluoro-i-propoxy, 1,1-difluoroethoxy, 2,2-difluoroethoxy, 2,2-dichloroethoxy, 2,2,2-trifluoroethoxy, 2-fluoroethoxy, 2-chloroethoxy, 2-bromoethoxy, 2-iodoethoxy, 2,2,2-trichloroethoxy, 2,2,2-tribromoethoxy, 1,3-difluoro-2-propoxy, 1,1,1-trifluoro-2-propoxy, 3,3,3-trifluoro-n-propoxy, 4,4,4-trifluoro-n-butoxy, 3-fluoro-n-propoxy, 3-chloro-n-propoxy, nonafluoro-n-butoxy, nonafluoro-2-butoxy, 5,5,5-trifluoro-n-pentoxy, 4,4,5,5,5-pentafluoro-2-pentoxy, 1-fluorocyclopropoxy, and 2,2-difluorocyclobutoxy. It is preferably a haloalkoxy group having 1 to 3 carbon atoms, and more preferably a difluoromethoxy group, a trifluoromethoxy group, or a bromodifluoromethoxy group.

The "alkoxyalkyl group having 2 to 6 carbon atoms" for the substituent groups $R^1$, $R^2$, $R^4$, and $R^6$ indicates a linear, branched, or cyclic alkyl group having 2 to 6 carbon atoms such as methoxymethyl, methoxyethyl, methoxy-n-propyl, methoxy-i-propyl, ethoxymethyl, and cyclopropoxymethyl. Their hydrogen atom may be substituted with one or more halogen atoms that may be the same or different from each other. It is preferably an alkoxyalkyl group having 2 or 3 carbon atoms, and more preferably a methoxymethyl group.

The "alkoxycarbonyl group having 2 to 6 carbon atoms" for the substituent groups $R^1$, $R^2$, $R^4$, and $R^6$ indicates a linear, branched, or cyclic alkoxycarbonyl group having 2 to 6 carbon atoms such as methoxycarbonyl, ethoxycarbonyl, isopropoxycarbonyl, cyclopropoxycarbonyl, n-butoxycarbonyl, s-butoxycarbonyl, t-butoxycarbonyl, n-pentyloxycarbonyl, 2-pentyloxycarbonyl, neopentyloxycarbonyl, and cyclopentyloxycarbonyl. Their hydrogen atom may be substituted with one or more halogen atoms that may be the same or different from each other. It is preferably a methoxycarbonyl group.

The "aminocarbonyl group having 1 to 6 carbon atoms" for the substituent groups $R^1$, $R^2$, $R^4$, and $R^6$ indicates a linear, branched, or cyclic aminocarbonyl group having 1 to 6 carbon atoms such as aminocarbonyl, methylaminocarbonyl, dimethylaminocarbonyl, ethylmethylaminocarbonyl, ethylaminocarbonyl, diethylaminocarbonyl, methyl-n-propylaminocarbonyl, i-propylaminocarbonyl, and cyclopropylaminocarbonyl. Their hydrogen atom may be substituted with one or more halogen atoms that may be the same or different from each other. It is preferably an aminocarbonyl group.

The "alkylamino group having 1 to 6 carbon atoms" for the substituent groups $R^1$, $R^2$, $R^4$, and $R^6$ indicates a linear, branched, or cyclic alkylamino group having 1 to 6 carbon atoms such as methylamino, dimethylamino, ethylamino, n-propylamino, i-propylamino, methylethylamino, diethylamino, and cyclopropylamino. Their hydrogen atom may be substituted with one or more halogen atoms that may be the same or different from each other. It is preferably a methylamino group.

The "benzyl group that may be substituted" for the substituent groups $R^1$, $R^2$, $R^4$, and $R^6$ indicates unsubstituted benzyl; or a substituted benzyl group including benzyl in which one hydrogen on the phenyl group is substituted such as 2-fluorobenzyl, 3-fluorobenzyl, 4-fluorobenzyl, 2-methylbenzyl, 3-methylbenzyl, 4-methylbenzyl, 2-methoxybenzyl, 3-methoxybenzyl, and 4-trifluoromethylbenzyl; benzyl in which two hydrogens on the phenyl group are substituted such as 2,3-difluorobenzyl and 2-fluoro-4-methylbenzyl; and benzyl in which three to five hydrogens on the phenyl group are substituted such as 2,3,5-trifluorobenzyl. It is preferably a benzyl group.

The "heterocyclylmethyl group that may be substituted" for the substituent groups $R^1$, $R^2$, $R^4$, and $R^6$ indicates unsubstituted heterocyclyl including pyridylmethyl, pyrimidinylmethyl, and thiazolylmethyl; or a substituted heterocyclylmethyl group including 6-chloro-3-pyridylmethyl. It is preferably a pyridylmethyl group or a 6-chloro-3-pyridylmethyl group.

The "phenyl group that may be substituted" for the substituent groups $R^1$, $R^2$, $R^4$, and $R^6$ indicates unsubstituted phenyl or a substituted phenyl group including monosubstituted phenyl such as 2-fluorophenyl, 3-fluorophenyl, 4-fluorophenyl, 2-methylphenyl, 3-methylphenyl, 4-methylphenyl, 2-methoxyphenyl, 3-methoxyphenyl, and 4-trifluoromethylphenyl; disubstituted phenyl such as 2,3-difluorophenyl and 2-fluoro-4-methylphenyl; and tri- to pentasubstituted phenyl such as 2,3,5-trifluorophenyl. It is preferably a phenyl group.

The "heterocyclyl group that may be substituted" for the substituent groups $R^1$, $R^2$, $R^4$, and $R^6$ indicates unsubstituted heterocyclyl including 2-pyridyl, 3-pyridyl, 2-thiophene, 2-thiazolyl, and 2-tetrahydrofuranyl, or a substituted heterocyclyl group including 6-chloro-3-pyridyl. It is preferably a pyridylmethyl group or a 6-chloro-3-pyridyl group.

The ring for the case that "$R^1$ and $R^2$ bind to each other to form, together with the adjacent carbon atom, a saturated or unsaturated ring" according to the invention means a saturated ring such as cyclopentane or cyclohexane or an unsaturated ring such as benzene. Their hydrogen atom may be substituted with one or more halogen atoms that may be the same or different from each other. It is preferably a cyclohexane ring.

The "alkyl group having 1 to 6 carbon atoms" for the substituent groups $R^{3a}$ and $R^{3b}$ indicates a linear, branched, or cyclic alkyl group having 1 to 6 carbon atoms such as methyl, ethyl, n-propyl, i-propyl, n-butyl, s-butyl, t-butyl, n-pentyl, 2-pentyl, neopentyl, 4-methyl-2-pentyl, n-hexyl, 3-methyl-n-pentyl, cyclopropyl, cyclobutyl, cyclopentyl, 2-methylcyclopropyl, and cyclohexyl. It is preferably an alkyl group having 1 to 3 carbon atoms, and more preferably a methyl group or an ethyl group.

The "haloalkyl group having 1 to 6 carbon atoms" for the substituent groups $R^{3a}$ and $R^{3b}$ indicates a linear, branched, or cyclic alkyl group that has 1 to 6 carbon atoms and that is substituted with one or more halogen atoms that may be the same or different from each other, such as trifluoromethyl, pentafluoroethyl, heptafluoro-n-propyl, heptafluoro-i-propyl, 2,2-difluoroethyl, 2,2-dichloroethyl, 2,2,2-trifluoroethyl, 2-fluoroethyl, 2-chloroethyl, 2-bromoethyl, 2-iodoethyl, 2,2,2-trichloroethyl, 2,2,2-tribromoethyl, 1,3-difluoro-2-propyl, 1,3-dichloro-2-propyl, 1-chloro-3-fluoro-2-propyl, 1,1,1-trifluoro-2-propyl, 3,3,3-trifluoro-n-propyl, 4,4,4-trifluoro-n-butyl, 1,1,1,3,3,3-hexafluoro-2-propyl, 1,1,1,3,3,3-hexafluoro-2-chloro-2-propyl, 1,1,1,3,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3,3-hexafluoro-1-bromo-2-propyl, 2,2,3,3,3-pentafluoro-n-propyl, 3-fluoro-n-propyl, 3-chloro-n-propyl, 3-bromo-n-propyl, 3,3,4,4,4-pentafluoro-2-butyl, nonafluoro-n-butyl, nonafluoro-2-butyl, 5,5,5-trifluoro-n-pentyl, 4,4,5,5,5-pentafluoro-2-pentyl, 3-chloro-n-pentyl, 4-bromo-2-pentyl, 1-fluorocyclopropyl, and 2,2-difluorocyclobutyl. It is preferably a haloalkyl group having 1 to 3 carbon atoms, and more preferably a trifluoromethyl group.

The "alkoxy group having 1 to 6 carbon atoms" for the substituent groups $R^{3a}$ and $R^{3b}$ indicates a linear, branched, or cyclic alkoxy group having 1 to 6 carbon atoms such as methoxy, ethoxy, n-propoxy, i-propoxy, n-butoxy, i-butoxy, 2-methyl-butoxy, n-hexyloxy, cyclopropoxy, and cyclobutoxy. It is preferably an alkoxy group having 1 to 3 carbon atoms, and more preferably a methoxy group or an ethoxy group.

The "alkylthio group having 1 to 6 carbon atoms" for the substituent groups $R^{3a}$ and $R^{3b}$ indicates a linear, branched, or cyclic alkylthio group having 1 to 6 carbon atoms such as methylthio, ethylthio, n-propylthio, i-propylthio, n-butylthio, s-butylthio, t-butylthio, n-pentylthio, 2-pentylthio, neopentylthio, 4-methyl-2-pentylthio, n-hexylthio, 3-methyl-n-pentylthio, cyclopropylthio, cyclobutylthio, cyclopentylthio, 2-methylcyclopentylthio, 3-methylcyclopentylthio, and cyclohexylthio. It is preferably an alkylthio group having 1 to 3 carbon atoms, and more preferably a methylthio group or an ethylthio group.

The "alkylsulfinyl group having 1 to 6 carbon atoms" for the substituent groups $R^{3a}$ and $R^{3b}$ indicates a linear, branched, or cyclic alkylsulfinyl group having 1 to 6 carbon atoms such as methylsulfinyl, ethylsulfinyl, n-propylsulfinyl, i-propylsulfinyl, n-butylsulfinyl, s-butylsulfinyl, t-butylsulfinyl, n-pentylsulfinyl, 2-pentylsulfinyl, neopentylsulfinyl, 4-methyl-2-pentylsulfinyl, n-hexylsulfinyl, 3-methyl-n-pentylsulfinyl, cyclopropylsulfinyl, cyclobutylsulfinyl, cyclopentylsulfinyl, 2-methylcyclopentylsulfinyl, 3-methylcyclopentylsulfinyl, and cyclohexylsulfinyl. It is preferably an alkylsulfinyl group having 1 to 3 carbon atoms, and more preferably a methylsulfinyl group.

The "alkylsulfonyl group having 1 to 6 carbon atoms" for the substituent groups $R^{3a}$ and $R^{3b}$ indicates a linear, branched, or cyclic alkylsulfonyl group having 1 to 6 carbon atoms such as methylsulfonyl, ethylsulfonyl, n-propylsulfonyl, i-propylsulfonyl, n-butylsulfonyl, s-butylsulfonyl, t-butylsulfonyl, n-pentylsulfonyl, 2-pentylsulfonyl, neopentylsulfonyl, 4-methyl-2-pentylsulfonyl, n-hexylsulfonyl, 3-methyl-n-pentylsulfonyl, cyclopropylsulfonyl, cyclobutylsulfonyl, cyclopentylsulfonyl, 2-methylcyclopentylsulfonyl, 3-methylcyclopentylsulfonyl, and cyclohexylsulfonyl. It is preferably an alkylsulfonyl group having 1 to 3 carbon atoms, and more preferably a methylsulfonyl group.

The "alkyl group having 1 to 6 carbon atoms" for the substituent group $R^5$ indicates a linear, branched, or cyclic alkyl group having 1 to 6 carbon atoms such as methyl, ethyl, n-propyl, i-propyl, n-butyl, s-butyl, t-butyl, n-pentyl, 2-pentyl, neopentyl, 4-methyl-2-pentyl, n-hexyl, 3-methyl-n-pentyl, cyclopropyl, cyclobutyl, cyclopentyl, 2-methylcyclopropyl, and cyclohexyl. It is preferably an alkyl group having 1 to 3 carbon atoms, and more preferably a methyl group, an ethyl group, or a cyclopropyl group.

The "haloalkyl group having 1 to 6 carbon atoms" for the substituent group $R^5$ indicates a linear, branched, or cyclic alkyl group that has 1 to 6 carbon atoms and that is substituted with one or more halogen atoms that may be the same or different from each other, such as fluoromethyl, difluoromethyl, trifluoromethyl, pentafluoroethyl, heptafluoro-n-propyl, heptafluoro-i-propyl, 1,1-difluoroethyl, 2,2-difluoroethyl, 2,2-dichloroethyl, 2,2,2-trifluoroethyl, 2-fluoroethyl, 2-chloroethyl, 2-bromoethyl, 2-iodoethyl, 2,2,2-trichloroethyl, 2,2,2-tribromoethyl, 1,3-difluoro-2-propyl, 1,3-dichloro-2-propyl, 1-chloro-3-fluoro-2-propyl, 1,1,1-trifluoro-2-propyl, 3,3,3-trifluoro-n-propyl, 4,4,4-trifluoro-n-butyl, 1,1,1,3,3,3-hexafluoro-2-propyl, 1,1,1,3,3,3-hexafluoro-2-chloro-2-propyl, 1,1,1,3,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3,3-hexafluoro-1-bromo-2-propyl, 2,2,3,3,3-pentafluoro-n-propyl, 3-fluoro-n-propyl, 3-chloro-n-propyl, 3-bromo-n-propyl, 3,3,4,4,4-pentafluoro-2-butyl, nonafluoro-n-butyl, nonafluoro-2-butyl, 5,5,5-trifluoro-n-pentyl, 4,4,5,5,5-pentafluoro-2-pentyl, 3-chloro-n-pentyl, 4-bromo-2-pentyl, 1-fluorocyclopropoxy, and 2,2-difluorocyclobutoxy. It is preferably a haloalkyl group having 1 to 3 carbon atoms, and more preferably a difluoromethyl group, a trifluoromethyl group, or a 1,1-difluoroethyl group.

The "alkenyl group having 2 to 6 carbon atoms" for the substituent group $R^5$ indicates a linear, branched, or cyclic alkenyl group having 2 to 6 carbon atoms such as a vinyl group, an allyl group, a 3-butenyl group, a 2-methyl-3-butenyl group, and a 3-cyclohexenyl group. Their hydrogen atom may be substituted with one or more halogen atoms that may be the same or different from each other. It is preferably an allyl group.

The "alkynyl group having 2 to 6 carbon atoms" for the substituent group $R^5$ indicates a linear, branched, or cyclic alkynyl group having 2 to 6 carbon atoms such as an ethynyl group, a 2-propynyl group, a 2-butynyl group, a 2-methyl-3-butynyl group, and a 3-cyclohexynyl group. Their hydrogen atom may be substituted with one or more halogen atoms that may be the same or different from each other. It is preferably an ethynyl group.

The "alkoxyalkyl group having 2 to 6 carbon atoms" for the substituent group $R^5$ indicates a linear, branched, or cyclic alkyl group having 2 to 6 carbon atoms such as methoxymethyl, methoxyethyl, methoxy-n-propyl, methoxy-i-propyl, ethoxymethyl, and cyclopropoxymethyl. Their hydrogen atom may be substituted with one or more halogen atoms that may be the same or different from each other. It is preferably an alkoxyalkyl group having 2 or 3 carbon atoms, and more preferably a methoxymethyl group.

The "benzyl group that may be substituted" for the substituent group $R^5$ indicates unsubstituted benzyl; or a substituted benzyl group including benzyl in which one hydrogen on the phenyl group is substituted such as 2-fluorobenzyl, 3-fluorobenzyl, 3-fluorobenzyl, 4-fluorobenzyl, 2-methylbenzyl, 3-methylbenzyl, 4-methylbenzyl, 2-methoxybenzyl, 3-methoxybenzyl, and 4-trifluoromethylbenzyl; benzyl in which two hydrogens on the phenyl group are substituted such as 2,3-difluorobenzyl and 2-fluoro-4-methylbenzyl; and benzyl in which three to five hydrogens on the phenyl group are substituted such as 2,3,5-trifluorobenzyl. It is preferably a benzyl group.

The "phenyl group that may be substituted" for the substituent group $R^5$ indicates unsubstituted phenyl or a substituted phenyl group including monosubstituted phenyl such as 2-fluorophenyl, 3-fluorophenyl, 4-fluorophenyl, 2-methylphenyl, 3-methylphenyl, 4-methylphenyl, 2-methoxyphenyl, 3-methoxyphenyl, and 4-trifluoromethylphenyl; disubstituted phenyl such as 2,3-difluorophenyl and 2-fluoro-4-methylphenyl; and tri- to pentasubstituted phenyl such as 2,3,5-trifluorobenzyl. It is preferably a phenyl group.

The "heterocyclyl group that may be substituted" for the substituent group $R^5$ indicates an unsubstituted heterocyclyl group including 2-pyridyl, 3-pyridyl, 4-pyridyl, 2-thiophene, 3-furanyl, morpholyl, and 1-pyrazolyl or a substituted heterocyclyl group such as 6-methyl-3-pyridyl. It is preferably 3-pyridyl.

The "alkoxy group having 1 to 6 carbon atoms that may be substituted" for the substituent group $R^5$ indicates an unsubstituted linear, branched, or cyclic alkoxy group having 1 to 6 carbon atoms such as methoxy, ethoxy, n-propoxy, i-propoxy, n-butoxy, i-butoxy, 2-methyl-butoxy, n-hexyloxy, cyclopropoxy, and cyclobutoxy; or a linear, branched, or cyclic alkoxy group that has 1 to 6 carbon atoms and that is substituted such as a cyanomethoxy group, a methylcarbonylmethoxy group, a dihydrocarbamoylmethoxy group, a methoxycarbonylmethoxy group, a 1-cyanoethoxy group, a 3-cyano-n-propoxy group, a 2-hydroxyethoxy group, and a 2-cyanocyclopropoxy. It is preferably an alkoxy group that has 1 to 3 carbon atoms and that may be substituted, and more preferably a methoxy group or an ethoxy group.

The "alkenyloxy group having 2 to 6 carbon atoms" for the substituent group $R^5$ indicates a linear, branched, or cyclic alkenyloxy group having 2 to 6 carbon atoms such as vinyloxy, allyloxy, 3-butenyloxy, 2-methyl-3-butenyloxy, and 3-cyclohexenyloxy. Their hydrogen atom may be substituted with one or more halogen atoms that may be the same or different from each other. It is preferably an allyloxy group.

The "alkynyloxy group having 2 to 6 carbon atoms" for the substituent group $R^5$ indicates a linear, branched, or cyclic alkynyloxy group having 2 to 6 carbon atoms such as ethynyloxy, 2-propynyloxy, 2-butynyloxy, 2-methyl-3-butynyloxy, and 3-cyclohexynyloxy. Their hydrogen atom may be substituted with one or more halogen atoms that may be the same or different from each other. It is preferably a 2-propynyloxy group or a 2-butynyloxy group.

The "haloalkoxy group having 1 to 6 carbon atoms" for the substituent group $R^5$ indicates a linear, branched, or cyclic alkoxy group that has 1 to 6 carbon atoms and that is substituted with one or more halogen atoms that may be the same or different from each other, such as fluoromethoxy, difluoromethoxy, trifluoromethoxy, bromodifluoromethoxy, pentafluoroethoxy, heptafluoro-n-propoxy, heptafluoro-i-propoxy, 1,1-difluoroethoxy, 2,2-difluoroethoxy, 2,2-dichloroethoxy, 2,2,2-trifluoroethoxy, 2-fluoroethoxy, 2-chloroethoxy, 2-bromoethoxy, 2-iodoethoxy, 2,2,2-trichloroethoxy 2,2,2-tribromoethoxy, 1,3-difluoro-2-propoxy, 1,1,1-trifluoro-2-propoxy, 3,3,3-trifluoro-n-propoxy, 4,4,4-trifluoro-n-butoxy, 3-fluoro-n-propoxy, 3-chloro-n-propoxy, nonafluoro-n-butoxy, nonafluoro-2-butoxy, 5,5,5-trifluoro-n-pentoxy, 4,4,5,5,5-pentafluoro-2-pentoxy, 1-fluorocyclopropoxy, and 2,2-difluorocyclobutoxy. It is preferably a $C_1$ to $C_3$ haloalkoxy group, and more preferably a difluoromethoxy group, a trifluoromethoxy group, or a bromodifluoromethoxy group.

The "alkoxyalkoxy group having 2 to 6 carbon atoms" for the substituent group $R^5$ indicates a linear, branched, or cyclic alkoxyalkoxy group having 2 to 6 carbon atoms such as methoxymethoxy, 2-methoxyethoxy, 3-methoxy-n-propoxy, ethoxymethoxy, and 2-methoxy-n-propoxy. Their hydrogen atom may be substituted with one or more halogen atoms that may be the same or different from each other. It is preferably an alkoxyalkoxy group having 2 or 3 carbon atoms, and more preferably a methoxymethoxy group.

The "alkylcarbonyloxy group having 2 to 6 carbon atoms" for the substituent group $R^5$ indicates a linear, branched, or cyclic alkylcarbonyloxy group having 2 to 6 carbon atoms such as methylcarbonyloxy, ethylcarbonyloxy, and i-propylcarbonyloxy. Their hydrogen atom may be substituted with one or more halogen atoms that may be the same or different from each other. It is preferably a methylcarbonyloxy group.

The "alkylcarbamate group having 2 to 6 carbon atoms" for the substituent group $R^5$ indicates a linear, branched, or cyclic alkylcarbamate group having 2 to 6 carbon atoms such as dimethylcarbamate, methylethylcarbamate, and methyl-i-propylcarbamate. Their hydrogen atom may be substituted with one or more halogen atoms that may be the same or different from each other. It is preferably a dimethylcarbamate group.

The "alkylcarbonate group having 2 to 6 carbon atoms" for the substituent group $R^5$ indicates a linear, branched, or cyclic alkylcarbonate group having 2 to 6 carbon atoms such as methylcarbonate, ethylcarbonate, and i-propylcarbonate. Their hydrogen atom may be substituted with one or more halogen atoms that may be the same or different from each other. It is preferably a methylcarbonate group.

The "benzyloxy group that may be substituted" for the substituent group $R^5$ indicates unsubstituted benzyloxy, or a substituted benzyloxy group including benzyloxy in which one hydrogen on the phenyl group is substituted such as 2-fluorobenzyloxy, 3-fluorobenzyloxy, 4-fluorobenzyloxy, 4-trifluoromethylbenzyloxy, and 2-methylbenzyloxy; benzyloxy in which two hydrogens on the phenyl group are substituted such as 2,3-difluorobenzyloxy and 2-fluoro-4-methylbenzyloxy; and benzyloxy in which three to five hydrogens on the phenyl group are substituted such as 2,3,5-trifluorobenzyloxy. Furthermore, methylene of the benzyl group may be branched. It is a methyl-4-trifluoromethylbenzyloxy group, for example. It is preferably a benzyloxy group.

The "phenoxy group that may be substituted" for the substituent group $R^5$ indicates unsubstituted phenoxy or a substituted phenoxy group including monosubstituted phenoxy such as 2-fluorophenoxy, 3-fluorophenoxy, 4-fluorophenoxy, 2-methylphenoxy, 3-methylphenoxy, 4-methylphenoxy, 4-methoxyphenoxy, 4-cyanophenoxy, 4-trifluoromethoxyphenoxy, 4-trifluoromethylphenoxy, and 4-t-butylphenoxy; disubstituted phenoxy such as 2,3-difluorophenoxy and 2-fluoro-4-methylphenoxy; and tri- to pentasubstituted phenoxy such as 2,3,5-trifluorophenoxy. It is preferably an unsubstituted or monosubstituted phenoxy group, and more preferably a phenoxy group, or a 4-cyanophenoxy group.

The "heterocyclyloxy group that may be substituted" for the substituent group $R^4$ indicates an unsubstituted heterocyclyloxy group such as 2-pyridyloxy, 3-pyridyloxy, 4-pyridyloxy, 2-thipheneoxy, and 3-furanyloxy; or a substituted heterocyclyloxy group such as 6-methyl-3-pyridyloxy. It is preferably 3-pyridyloxy.

The "alkylthio group having 1 to 6 carbon atoms" for the substituent group $R^5$ indicates a linear, branched, or cyclic alkylthio group having 1 to 6 carbon atoms such as methylthio, ethylthio, n-propylthio, i-propylthio, n-butylthio, s-butylthio, t-butylthio, n-pentylthio, 2-pentylthio, neopentylthio, 4-methyl-2-pentylthio, n-hexylthio, 3-methyl-n-pentylthio, cyclopropylthio, cyclobutylthio, cyclopentylthio, 2-methylcyclopentylthio, 3-methylcyclopentylthio, and cyclohexylthio. It is preferably an alkylthio group having 1 to 3 carbon atoms, and more preferably a methylthio group or an ethylthio group.

The "haloalkylthio group having 1 to 6 carbon atoms" for the substituent group $R^5$ indicates a linear, branched, or cyclic alkylthio group that has 1 to 6 carbon atoms and that is substituted with one or more halogen atoms that may be the same or different from each other, such as fluoromethylthio, difluoromethylthio, trifluoromethylthio, pentafluoroethylthio, heptafluoro-n-propylthio, 1,1-difluoroethylthio, 2,2-difluoroethylthio, 2,2-dichloroethylthio, 2,2,2-trifluoroethylthio, 2-fluoroethylthio, 2-chloroethylthio, 2-bromoethylthio, 2-iodoethylthio, 2,2,2-trichloroethylthio, 1,3-difluoro-2-propylthio, 1-chloro-3-fluoro-2-propylthio, 1,1,1-trifluoro-2-propylthio, 3,3,3-trifluoro-n-propylthio, 4,4,4-trifluoro-n-butylthio, 1,1,1,3,3,3-hexafluoro-2-propylthio, 1,1,1,3,3,3-hexafluoro-2-chloro-2-propylthio, 2,2,3,3,3-pentafluoro-n-propylthio, 3-fluoro-n-propylthio, 3-chloro-n-propylthio, 3-bromo-n-propylthio, 3,3,4,4,4-pentafluoro-2-butylthio, nonafluoro-n-butylthio, 5,5,5-trifluoro-n-pentylthio, 4,4,5,5,5-pentafluoro-2-pentylthio, 3-chloro-n-pentylthio, 4-bromo-2-pentylthio, 1-fluorocyclopropylthio, and 2,2-difluorocyclobutylthio. It is preferably a haloalkylthio group having 1 to 3 carbon atoms, and more preferably a trifluoromethylthio group or a 2,2,2-trifluoroethylthio group.

The "alkylsulfinyl group having 1 to 6 carbon atoms" for the substituent group $R^5$ indicates a linear, branched, or cyclic alkylsulfinyl group having 1 to 6 carbon atoms such as methylsulfinyl, ethylsulfinyl, n-propylsulfinyl, i-propylsulfinyl, n-butylsulfinyl, s-butylsulfinyl, t-butylsulfinyl, n-pentylsulfinyl, 2-pentylsulfinyl, neopentylsulfinyl, 4-methyl-2-pentylsulfinyl, n-hexylsulfinyl, 3-methyl-n-pentylsulfinyl, cyclopropylsulfinyl, cyclobutylsulfinyl, cyclopentylsulfinyl, 2-methylcyclopentylsulfinyl, 3-methylcyclopentylsulfinyl, and cyclohexylsulfinyl. It is preferably an alkylsulfinyl group having 1 to 3 carbon atoms, and more preferably a methylsulfinyl group.

The "alkylsulfonyl group having 1 to 6 carbon atoms" for the substituent group $R^5$ indicates a linear, branched, or cyclic alkylsulfonyl group having 1 to 6 carbon atoms such as methylsulfonyl, ethylsulfonyl, n-propylsulfonyl, i-propylsulfonyl, n-butylsulfonyl, s-butylsulfonyl, t-butylsulfonyl, n-pentylsulfonyl, 2-pentylsulfonyl, neopentylsulfonyl, 4-methyl-2-pentylsulfonyl, n-hexylsulfonyl, 3-methyl-n-pentylsulfonyl, cyclopropylsulfonyl, cyclobutylsulfonyl, cyclopentylsulfonyl, 2-methylcyclopentylsulfonyl, 3-methylcyclopentylsulfonyl, and cyclohexylsulfonyl. It is preferably an alkylsulfonyl group having 1 to 3 carbon atoms, and more preferably a methylsulfonyl group.

The "haloalkylsulfinyl group having 1 to 6 carbon atoms" for the substituent group $R^5$ indicates a linear, branched, or cyclic alkylsulfinyl group that has 1 to 6 carbon atoms and that is substituted with one or more halogen atoms that may be the same or different from each other, such as fluoromethylsulfinyl, difluoromethylsulfinyl, trifluoromethylsulfinyl, pentafluoroethylsulfinyl, heptafluoro-n-propylsulfinyl, 1,1-difluoroethylsulfinyl, 2,2-difluoroethylsulfinyl, 2,2-dichloroethylsulfinyl, 2,2,2-trifluoroethylsulfinyl, 2-fluoroethylsulfinyl, 2-chloroethylsulfinyl, 2-bromoethylsulfinyl, 2-iodoethylsulfinyl, 2,2,2-trichloroethylsulfinyl, 1,3-difluoro-2-propylsulfinyl, 1-chloro-3-fluoro-2-propylsulfinyl, 1,1,1-trifluoro-2-propylsulfinyl, 3,3,3-trifluoro-n-propylsulfinyl, 4,4,4-trifluoro-n-butylsulfinyl, 1,1,1,3,3,3-hexafluoro-2-propylsulfinyl, 1,1,1,3,3,3-hexafluoro-2-chloro-2-propylsulfinyl, 2,2,3,3,3-pentafluoro-n-propylsulfinyl, 3-fluoro-n-propylsulfinyl, 3-chloro-n-propylsulfinyl, 3-bromo-n-propylsulfinyl, 3,3,4,4,4-pentafluoro-2-butylsulfinyl, nonafluoro-n-butylsulfinyl, 5,5,5-trifluoro-n-pentylsulfinyl, 4,4,5,5,5-pentafluoro-2-pentylsulfinyl, 3-chloro-n-pentylsulfinyl, 4-bromo-2-pentylsulfinyl, 1-fluorocyclopropylsulfinyl, and 2,2-difluorocyclobutylsulfinyl. It is preferably a haloalkylsulfinyl group having 1 to 3 carbon atoms, and more preferably a 2,2,2-trifluoroethylsulfinyl group.

The "haloalkylsulfonyl group having 1 to 6 carbon atoms" for the substituent group $R^5$ indicates a linear, branched, or cyclic alkylsulfonyl group that has 1 to 6 carbon atoms and that is substituted with one or more halogen atoms that may be the same or different from each other, such as fluoromethylsulfonyl, difluoromethylsulfonyl, trifluoromethylsulfonyl, pentafluoroethylsulfonyl heptafluoro-n-propylsulfonyl, 1,1-difluoroethylsulfonyl, 2,2-difluoroethylsulfonyl, 2,2-dichloroethylsulfonyl, 2,2,2-trifluoroethylsulfonyl, 2-fluoroethylsulfonyl, 2-chloroethylsulfonyl, 2-bromoethylsulfonyl, 2-iodoethylsulfonyl, 2,2,2-trichloroethylsulfonyl, 1,3-difluoro-2-propylsulfonyl, 1-chloro-3-fluoro-2-propylsulfonyl, 1,1,1-trifluoro-2-propylsulfonyl, 3,3,3-trifluoro-n-propylsulfonyl, 4,4,4-trifluoro-n-butylsulfonyl, 1,1,1,3,3,3-hexafluoro-2-propylsulfonyl, 1,1,1,3,3,3-hexafluoro-2- chloro-2-propylsulfonyl, 2,2,3,3,3-pentafluoro-n-propylsulfonyl, 3-fluoro-n-propylsulfonyl, 3-chloro-n-propylsulfonyl, 3-bromo-n-propylsulfonyl, 3,3,4,4,4-pentafluoro-2-butylsulfonyl, nonafluoro-n-butylsulfonyl, 5,5,5-trifluoro-n-pentylsulfonyl, 4,4,5,5,5-pentafluoro-2-pentylsulfonyl, 3-chloro-n-pentylsulfonyl, 4-bromo-2-pentylsulfonyl, 1-fluorocyclopropylsulfonyl, and 2,2-difluorocyclobutylsulfonyl. It is preferably a haloalkylsulfonyl group having 1 to 3 carbon atoms, and more preferably a 2,2,2-trifluoroethylsulfonyl group.

The "alkylsulfonyloxy group having 1 to 6 carbon atoms" for the substituent group $R^5$ indicates a linear, branched, or cyclic alkylsulfonyloxy group having 1 to 6 carbon atoms such as methylsulfonyloxy, ethylsulfonyloxy, n-propylsulfonyloxy, i-propylsulfonyloxy, n-butylsulfonyloxy, s-butylsulfonyloxy, t-butylsufonyloxy, n-pentylsulfonyloxy, 2-pentylsulfonyloxy, neopentylsulfonyloxy, 4-methyl-2-pentylsulfonyloxy, n-hexylsulfonyloxy, 3-methyl-n-pentylsulfonyloxy, cyclopropylsulfonyloxy, cyclobutylsulfonyloxy, cyclopentylsulfonyloxy, 2-methylcyclopentylsulfonyloxy, 3-methylcyclopentylsulfonyloxy, and cyclohexylsulfonyloxy. It is preferably an alkylsulfonyloxy group having 1 to 3 carbon atoms, and more preferably a methylsulfonyloxy group.

The "haloalkylsulfonyloxy group having 1 to 6 carbon atoms" for the substituent group $R^5$ indicates a linear, branched, or cyclic alkylsulfonyloxy group that has 1 to 6 carbon atoms and that is substituted with one or more halogen atoms that may be the same or different from each other, such as fluoromethylsulfonyloxy, difluoromethylsulfonyloxy, trifluoromethylsulfonyloxy, pentafluoroethylsulfonyloxy, heptafluoro-n-propylsulfonyloxy, 1,1-difluoroethylsulfonyloxy, 2,2-difluoroethylsulfonyloxy, 2,2-dichloroethylsulfonyloxy, 2,2,2-trifluoroethylsulfonyloxy, 2-fluoroethylsulfonyloxy, 1,1,1-trifluoro-2-pro-2-propylsulfonyloxy, 3,3,3-trifluoro-n-propylsulfonyloxy, 4,4,4-trifluoro-n-butylsulfonyloxy, 1-fluorocyclopropylsulfonyloxy, and 2,2-difluorocyclobutylsulfonyloxy. It is preferably a haloalkylsulfonyloxy group having 1 to 3 carbon atoms, and more preferably a trifluoromethylsulfonyloxy group.

The "alkylaminosulfonyloxy group having 1 to 6 carbon atoms" for the substituent group $R^5$ indicates a linear, branched, or cyclic alkylaminosulfonyloxy group having 1 to 6 carbon atoms such as methylaminosulfonyloxy, dimethylaminosulfonyloxy, ethylaminosulfonyloxy, n-propylaminosulfonyloxy, i-propylaminosulfonyloxy, methylethylaminosulfonyloxy, diethylaminosulfonyloxy, and cyclopropylaminosulfonyloxy. Their hydrogen atom may be substituted with one or more halogen atoms that may be the same or different from each other. It is preferably an alkylaminosulfonyloxy group having 1 to 3 carbon atoms, and more preferably a dimethylaminosulfonyloxy group.

The "benzylthio group that may be substituted" for the substituent group $R^5$ indicates unsubstituted benzylthio; or a substituted benzylthio group including benzylthio in which one hydrogen on the phenyl group is substituted such as 2-fluorobenzylthio, 3-fluorobenzylthio, 4-fluorobenzylthio, 3-trifluoromethylbenzylthio, and 2-methylbenzylthio; benzylthio in which two hydrogens on the phenyl group are substituted such as 2,3-difluorobenzylthio and 2-fluoro-4-methylbenzylthio; and benzylthio in which three to five hydrogens on the phenyl group are substituted such as 2,3,5-trifluorobenzylthio. It is preferably a benzylthio group.

The "phenylthio group that may be substituted" for the substituent group $R^5$ indicates unsubstituted phenylthio or a substituted phenylthio group including monosubstituted phenylthio such as 2-fluorophenylthio, 3-fluorophenylthio, 4-fluorophenylthio, 2-methylphenylthio, 3-methylphenylthio, 4-methylphenylthio, 4-methoxyphenylthio, 4-cyanophenylthio, 4-trifluoromethoxyphenylthio, 4-trifluoromethylphenylthio, and 4-t-butylphenylthio; disubstituted phenylthio such as 2,3-difluorophenylthio and 2-fluoro-4-methylphenylthio; or tri- to pentasubstituted phenylthio such as 2,3,5-trifluorophenylthio. It is preferably a phenylthio group.

The "phenylsulfinyl group that may be substituted" for the substituent group $R^5$ indicates unsubstituted phenylsulfinyl or a substituted phenylsulfinyl group including monosubstituted phenylsulfinyl such as 4-fluorophenylsulfinyl, 4-chlorophenylsulfinyl, 2-methylphenylsulfinyl, 3-methylphenylsulfinyl, 4-methylphenylsulfinyl, 4-methoxyphenylsulfinyl, 4-trifluoromethylphenylsulfinyl, and 4-t-butylphenylsulfinyl; disubstituted phenylsulfinyl such as 2,3-difluorophenylsulfinyl and 2-fluoro-4-methylsulfinyl; or tri- to pentasubstituted phenylsulfinyl such as 2,3,5-trifluorophenylsulfinyl. It is preferably a 4-methylphenylsulfinyl group.

The "phenylsulfonyl group that may be substituted" for the substituent group $R^5$ indicates unsubstituted phenylsulfonyl or a substituted phenylsulfonyl group including monosubstituted phenylsulfonyl such as 4-fluorophenylsulfonyl, 4-chlorophenylsulfonyl, 2-methylphenylsulfonyl, 3-methylphenylsulfonyl, 4-methylphenylsulfonyl, 4-methoxyphenylsulfonyl, 4-trifluoromethylphenylsulfonyl, and 4-t-butylphenylsulfonyl; disubstituted phenylsulfonyl such as 2,3-difluorophenylsulfonyl and 2-fluoro-4-methylsulfonyl; or tri- to pentasubstituted phenylsulfonyl such as 2,3,5-trifluorophenylsulfonyl. It is preferably a 4-methylphenylsulfonyl group.

The "phenylsulfonyloxy group that may be substituted" for the substituent group $R^5$ indicates unsubstituted phenylsulfonyloxy or a substituted phenylsulfonyloxy group including monosubstituted phenylsulfonyloxy such as 4-fluorophenylsulfonyloxy, 4-chlorophenylsulfonyloxy, 2-methylphenylsulfonyloxy, 3-methylphenylsulfonyloxy, 4-methylphenylsulfonyloxy, 4-methoxyphenylsulfonyloxy, 4-trifluoromethylphenylsulfonyloxy, and 4-t-butylphenylsulfonyloxy; disubstituted phenylsulfonyloxy such as 2,3-difluorophenylsulfonyloxy and 2-fluoro-4-methylsulfonyloxy; or tri- to pentasubstituted phenylsulfonyl such as 2,3,5-trifluorophenylsulfonyloxy. It is preferably a 4-methylphenylsulfonyloxy group.

The "heterocyclylthio group that may be substituted" for the substituent group $R^5$ indicates an unsubstituted heterocyclylthio group such as 2-pyridylthio, 3-pyridylthio, 4-pyridylthio, 2-thiophenethio, and 3-furanylthio; or a substituted heterocyclylthio group such as 3-chloro-5-trifluoromethyl-2-pyridylthio. It is preferably a 3-chloro-5-trifluoromethyl-2-pyridylthio group.

The "heterocyclylsulfinyl group that may be substituted" for the substituent group $R^5$ indicates an unsubstituted heterocyclylsulfinyl group such as 2-pyridylsulfinyl, 3-pyridylsulfinyl, 4-pyridylsulfinyl, 2-thiophenesulfinyl, and 3-furanylsulfinyl; or a substituted heterocyclylsulfinyl group such as 3-chloro-5-trifluoromethyl-2-pyridylsulfinyl. It is preferably a 3-chloro-5-trifluoromethyl-2-pyridylsulfinyl group.

The "heterocyclylsulfonyl group that may be substituted" for the substituent group $R^5$ indicates an unsubstituted heterocyclylsulfonyl group such as 2-pyridylsulfonyl, 3-pyridylsulfonyl, 4-pyridylsulfonyl, 2-thiophenesulfonyl, and 3-furanylsulfonyl; or a substituted heterocyclylsulfonyl group such as 3-chloro-5-trifluoromethyl-2-pyridylsulfonyl. It is preferably a 3-chloro-5-trifluoromethyl-2-pyridylsulfonyl group.

The "substituted iminosulfinyl group" for the substituent group $R^5$ indicates a substituted iminosulfinyl group such as N-cyanoiminomethylsulfinyl, N-cyanoiminoethylsulfinyl, N-cyanoimino-n-propylsulfinyl, and N-cyanoiminobenzylsulfinyl. Their hydrogen atom may be substituted with one or more halogen atoms that may be the same or different from each other. It is preferably an N-cyanoiminomethylsulfinyl group.

The "substituted iminosulfoxy group" for the substituent group $R^5$ indicates a substituted iminosulfoxy group such as N-cyanoiminomethylsulfoxy, N-cyanoiminoethylsulfoxy, N-cyanoimino-n-propylsulfoxy, and N-cyanoiminobenzylsulfoxy. It is preferably an N-cyanoiminomethylsulfoxy group.

The "alkylcarbonyl group having 2 to 6 carbon atoms" for the substituent group $R^5$ indicates a linear, branched, or cyclic alkylcarbonyl group having 2 to 6 carbon atoms such as methylcarbonyl, ethylcarbonyl, n-propylcarbonyl, i-propylcarbonyl, n-butylcarbonyl, s-butylcarbonyl, t-butylcarbonyl, n-pentylcarbonyl, 2-pentylcarbonyl, neopentylcarbonyl, 4-methyl-2-pentylcarbonyl, n-hexylcarbonyl, 3-methyl-n-pentylcarbonyl, and cyclopropylcarbonyl. Their hydrogen atom may be substituted with one or more halogen atoms that may be the same or different from each other. It is preferably a methylcarbonyl group.

The "alkoxycarbonyl group having 2 to 6 carbon atoms" for the substituent group $R^5$ indicates a linear, branched, or cyclic alkyloxycarbonyl group having 2 to 6 carbon atoms such as methoxycarbonyl, ethoxycarbonyl, n-propoxycarbonyl, i-propoxycarbonyl, n-butoxycarbonyl, s-butoxycarbonyl, t-butoxycarbonyl, n-pentyloxycarbonyl, 2-pentyloxycarbonyl, neopentyloxycarbonyl, 4-methyl-2-pentyloxycarbonyl, n-hexyloxycarbonyl, 3-methyl-n-pentyloxycarbonyl, and cyclopropyloxycarbonyl. Their hydrogen atom may be substituted with one or more halogen atoms that may be the same or different from each other. It is preferably a methoxycarbonyl group.

The "alkylaminocarbonyl group having 2 to 6 carbon atoms" for the substituent group $R^5$ indicates a linear, branched, or cyclic alkylaminocarbonyl group having 2 to 6 carbon atoms such as methylaminocarbonyl, dimethylaminocarbonyl, ethylaminocarbonyl, n-propylaminocarbonyl, i-propylaminocarbonyl, methylethylaminocarbonyl, diethylaminocarbonyl, and piperidine-1-carbonyl. It is preferably a piperidine-1-carbonyl group.

The "alkylamino group having 1 to 6 carbon atoms that may be substituted" for the substituent group $R^5$ indicates an unsubstituted linear, branched, or cyclic alkylamino group having 1 to 6 carbon atoms such as methylamino, dimethylamino, ethylamino, n-propylamino, i-propylamino, methylethylamino, diethylamino, and cyclopropylamino; or a linear, branched, or cyclic alkylamino group that has 1 to 6 carbon atoms and that is substituted such as a methoxymethylmethylamino group, a methylthiomethylmethylamino group, and a tetrahydrofuran-3-ylmethylamino group. Their hydrogen atom may be substituted with one or more halogen atoms that may be the same or different from each other. It is preferably a methylamino group.

The "alkylcarbonylamino group having 2 to 6 carbon atoms" for the substituent group $R^5$ indicates a linear, branched, or cyclic alkylcarbonylamino group having 2 to 6 carbon atoms such as methylcarbonylamino, methylcarbonylmethylamino, ethylcarbonylamino, i-propylcarbonylamino, methylcarbonylethylamino, and ethylcarbonylmethylamino. Their hydrogen atom may be substituted with one or more halogen atoms that may be the same or different from each other. It is preferably a methylcarbonylmethylamino group.

The ring for the case that "$R^4$ and $R^5$ bind to each other to form, together with the adjacent carbon atom, a saturated or unsaturated ring" according to the invention means a saturated ring such as cyclopentane or cyclohexane or an unsaturated ring such as benzene. It is preferably a benzene ring.

The ring for the case "$R^5$ and $R^6$ bind to each other to form, together with the adjacent carbon atom, a saturated or unsaturated ring" means a saturated ring such as cyclopentane, cyclohexane, tetrahydrothiophen, tetrahydrothiophene oxide, and tetrahydrothiophene dioxide, or an unsaturated ring such as benzene. Their hydrogen atom may be substituted with one or more halogen atoms that may be the same or different from each other. It is preferably a cyclohexane ring.

The "alkyl group having 1 to 6 carbon atoms" for the substituent group $R^7$ indicates a linear, branched, or cyclic alkyl group having 1 to 6 carbon atoms such as methyl, ethyl, n-propyl, i-propyl, n-butyl, s-butyl, t-butyl, n-pentyl, 2-pentyl, neopentyl, 4-methyl-2-pentyl, n-hexyl, 3-methyl-n-pentyl, cyclopropyl, cyclobutyl, cyclopentyl, 2-methylcyclopentyl, 3-methylcyclopentyl, and cyclohexyl. It is preferably an alkyl group having 1 to 3 carbon atoms, and more preferably a methyl group or an ethyl group.

The "haloalkyl group having 1 to 6 carbon atoms" for the substituent group $R^7$ indicates a linear, branched, or cyclic alkyl group that has 1 to 6 carbon atoms and that is substituted with one or more halogen atoms that may be the same or different from each other, such as fluoromethyl, difluoromethyl, trifluoromethyl, pentafluoroethyl, heptafluoro-n-propyl, heptafluoro-i-propyl, 1,1-difluoroethyl, 2,2-dichloroethyl, 2,2-dichloroethyl, 2,2,2-trifluoroethyl, 2-fluoroethyl, 2-chloroethyl, 2-bromoethyl, 2-iodoethyl, 2,2,2-trichloroethyl, 2,2,2-tribromoethyl, 1,3-difluoro-2-propyl, 1,3-dichloro-2-propyl, 1-chloro-3-fluoro-2-propyl, 1,1,1-trifluoro-2-propyl, 3,3,3-trifluoro-n-propyl, 4,4,4-trifluoro-n-butyl, 1,1,1,3,3,3-hexafluoro-2-propyl, 1,1,1,3,3,3-hexafluoro-2-chloro-2-propyl, 1,1,1,3,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3,3-hexafluoro-1-bromo-2-propyl, 2,2,3,3,3-pentafluoro-n-propyl, 3-fluoro-n-propyl, 3-chloro-n-propyl, 3-bromo-n-propyl, 3,3,4,4,4-pentafluoro-2-butyl, nonafluoro-n-butyl, nonafluoro-2-butyl, 5,5,5-trifluoro-n-pentyl, 4,4,5,5,5-pentafluoro-2-pentyl, 3-chloro-n-pentyl, 4-bromo-2-pentyl1-fluorocyclopropyl, and 2,2-difluorocyclobutyl. It is preferably a haloalkyl group having 1 to 3 carbon atoms, and more preferably a difluoromethyl group, a trifluoromethyl group, or a 2,2,2-trifluoroethyl group.

The "phenyl group that may be substituted" for the substituent group $R^7$ indicates unsubstituted phenyl or a substituted phenyl group including monosubstituted phenyl such as 2-fluorophenyl, 3-fluorophenyl, 4-fluorophenyl, 2-methylphenyl, 3-methylphenyl, 4-methylphenyl, 2-methoxyphenyl, 3-methoxyphenyl, 3-trifluoromethylphenyl, and 4-trifluoromethylphenyl; disubstituted phenyl such as 2,3-difluorophenyl and 2-fluoro-4-methylphenyl; and tri- to pentasubstituted phenyl such as 2,3,5-trifluorobenzyl. It is preferably a phenyl group.

The "alkoxy group having 1 to 6 carbon atoms" for the substituent group $R^7$ indicates a linear, branched, or cyclic alkoxy group having 1 to 6 carbon atoms such as methoxy, ethoxy, n-propoxy, i-propoxy, n-butoxy, i-butoxy, 2-methylbutoxy, n-hexyloxy, cyclopropoxy, and cyclobutoxy. Their hydrogen atom may be substituted with one or more halogen atoms that may be the same or different from each other. It is preferably an alkoxy group having 1 to 3 carbon atoms, and more preferably a methoxy group or an ethoxy group.

The "alkenyloxy group having 2 to 6 carbon atoms" for the substituent group $R^7$ indicates a linear, branched, or cyclic alkenyloxy group having 2 to 6 carbon atoms such as vinyloxy, allyloxy, 3-butenyloxy, 2-methyl-3-butenyloxy, and 3-cyclohexenyloxy. Their hydrogen atom may be substituted with one or more halogen atoms that may be the same or different from each other. It is preferably an allyloxy group.

The "alkylcarbonyloxy group having 2 to 6 carbon atoms" for the substituent group $R^7$ indicates a linear, branched, or cyclic alkylcarbonyloxy group having 2 to 6 carbon atoms such as methylcarbonyloxy, ethylcarbonyloxy, and i-propylcarbonyloxy. Their hydrogen atom may be substituted with one or more halogen atoms that may be the same or different from each other. It is preferably a methylcarbonyloxy group.

The "benzyloxy group that may be substituted" for the substituent group $R^7$ indicates an unsubstituted benzyloxy; or a substituted benzyloxy group including benzyloxy in which one hydrogen on the phenyl group is substituted such as 2-fluorobenzyloxy, 3-fluorobenzyloxy, 4-fluorobenzyloxy, 4-trifluoromethylbenzyloxy, and 2-methylbenzyloxy; benzyloxy in which two hydrogens on the phenyl group are substituted such as 2,3-difluorobenzyloxy and 2-fluoro-4-methylbenzyloxy; and benzyloxy in which three to five hydrogens on the phenyl group are substituted such as 2,3,5-trifluorobenzyloxy. It is preferably a benzyloxy group.

The "phenoxy group that may be substituted" for the substituent group $R^7$ indicates unsubstituted phenoxy or a substituted phenoxy group including monosubstituted phenoxy such as 2-fluorophenoxy, 3-fluorophenoxy, 4-fluorophenoxy, 2-methylphenoxy, 3-methylphenoxy, 4-methylphenoxy, 4-methoxyphenoxy, 4-cyanophenoxy, 4-trifluoromethoxyphenoxy, 4-trifluoromethylphenoxy, and 4-t-butylphenoxy; disubstituted phenoxy such as 2,3-difluorophenoxy and 2-fluoro-4-methylphenoxy; or tri- to pentasubstituted phenoxy such as 2,3,5-trifluorophenoxy. It is preferably a phenoxy group.

The "alkylsulfonyl group having 1 to 6 carbon atoms" for the substituent group $R^7$ indicates a linear, branched, or cyclic alkylsulfonyl group having 1 to 6 carbon atoms such as methylsulfonyl, ethylsulfonyl, n-propylsulfonyl, i-propylsulfonyl, n-butylsulfonyl, s-butylsulfonyl, t-butylsulfonyl, n-pentylsulfonyl, 2-pentylsulfonyl, neopentylsulfonyl, 4-methyl-2-pentylsulfonyl, n-hexylsulfonyl, 3-methyl-n-pentylsulfonyl, and cyclopropylsulfonyl. Their hydrogen atom may be substituted with one or more halogen atoms that may be the same or different from each other. It is preferably a methylsulfonyl group.

The "alkylcarbonyl group having 2 to 6 carbon atoms" for the substituent group $R^7$ indicates a linear, branched, or cyclic alkylcarbonyl group having 2 to 6 carbon atoms such as methylcarbonyl, ethylcarbonyl, n-propylcarbonyl, i-propylcarbonyl, n-butylcarbonyl, s-butylcarbonyl, t-butylcarbonyl, n-pentylcarbonyl, 2-pentylcarbonyl, neopentylcarbonyl, 4-methyl-2-pentylcarbonyl, n-hexylcarbonyl, 3-methyl-n-pentylcarbonyl, and cyclopropylcarbonyl. It is preferably an alkoxycarbonyl group having 2 or 3 carbon atoms, and more preferably a methylcarbonyl group.

The "haloalkylcarbonyl group having 2 to 6 carbon atoms" for the substituent group $R^7$ indicates a linear, branched, or cyclic alkylcarbonyl group that has 2 to 6 carbon atoms and that is substituted with one or more halogen atoms that may be the same or different from each other, such as fluoromethylcarbonyl, difluoromethylcarbonyl, trifluoromethylcarbonyl, pentafluoroethylcarbonyl, heptafluoro-n-propylcarbonyl, 1,1-difluoroethylcarbonyl, 2,2-difluoroethylcarbonyl, 2,2-dichloroethylcarbonyl, 2,2,2-trifluoroethylcarbonyl, 2-fluoroethylcarbonyl, 1,1,1-trifluoro-2-propylcarbonyl, 3,3,3-trifluoro-n-propylcarbonyl, 4,4,4-trifluoro-n-butylcarbonyl, 1-fluorocyclopropylcarbonyl, and 2,2-difluorocyclopropylcarbonyl. It is preferably a haloalkylcarbonyl group having 2 or 3 carbon atoms, and more preferably a trifluoromethylcarbonyl group.

The "alkyloxycarbonyl group having 2 to 6 carbon atoms" for the substituent group $R^7$ indicates a linear, branched, or cyclic alkyloxycarbonyl group having 2 to 6 carbon atoms such as methoxycarbonyl, ethoxycarbonyl, n-propoxycarbonyl, i-propoxycarbonyl, n-butoxycarbonyl, s-butoxycarbonyl, t-butoxycarbonyl, n-pentyloxycarbonyl, 2-pentyloxycarbonyl, neopentyloxycarbonyl, 4-methyl-2-pentyloxycarbonyl, n-hexyloxycarbonyl, 3-methyl-n-pentyloxycarbonyl, and cyclopropyloxycarbonyl. Their hydrogen atom may be substituted with one or more halogen atoms that may be the same or different from each other. It is preferably a methoxycarbonyl group.

The "amino group that may be substituted" for the substituent group $R^7$ indicates an unsubstituted amino group or a substituted amino group including a linear, branched, or cyclic alkylamino group such as methylamino, dimethylamino, ethylamino, n-propylamino, i-propylamino, methylethylamino, diethylamino, and cyclopropylamino; and a substituted amino group such as a methylcarbonylamino group and a methoxycarbonylamino group. Their hydrogen atom may be substituted with one or more halogen atoms that may be the same or different from each other. It is preferably a methylamino group.

The "5-membered or 6-membered aromatic or non-aromatic heterocycle" for the substituent group Ht indicates an aromatic heterocycle such as a pyridyl group that may be substituted, a pyrimidyl group that may be substituted, a pyrazyl group that may be substituted, a pyridazyl group that may be substituted, a pyrazolyl group that may be substituted, an imidazolyl group that may be substituted, a triazolyl group that may be substituted, a thiazolyl group that may be substituted, an oxazolyl group that may be substituted, a thiophenyl group that may be substituted, a furyl group that may be substituted, or a thiadiazolyl group that may be substituted or a non-aromatic heterocycle such as a tetrahydrofuryl group that may be substituted. It is preferably a pyridyl group that may be substituted, a pyrimidyl group that may be substituted, a pyrazyl group that may be substituted, a pyridazyl group that may be substituted, a pyrazolyl group that may be substituted, an imidazolyl group that may be substituted, a triazolyl group that may be substituted, a thiazolyl group that may be substituted, or a tetrahydrofuryl group that may be substituted, and more preferably a pyridyl group that may be substituted, a pyrimidyl group that may be substituted, or a thiazolyl group that may be substituted.

The "pyridyl group that may be substituted" for the substituent group Ht indicates an unsubstituted pyridyl group such as 2-pyridyl, 3-pyridyl, and 4-pyridyl; a monosubstituted pyridyl group such as 6-methyl-3-pyridyl, 5-methyl-3-pyridyl, 6-fluoro-3-pyridyl, 5-fluoro-3-pyridyl, 6-chloro-3-pyridyl, 5-chloro-3-pyridyl, 2-chloro-3-pyridyl, 6-bromo-3-pyridyl, 6-iodo-3-pyridyl, 6-methoxy-3-pyridyl, 6-trifluoromethyl-3-pyridyl, and 6-cyano-3-pyridyl; a disubstituted pyridyl group such as 5,6-dichloro-3-pyridyl, 5,6-difluoro-3-pyridyl, 5,6-dibromo-3-pyridyl, 2,6-dichloro-3-pyridyl, 4,6-dichloro-3-pyridyl, 5-fluoro-6-chloro-3- pyridyl, 5-fluoro-6-bromo-3-pyridyl, 5-methyl-6-chloro-3-pyridyl, 5-methyl-6-fluoro-3-pyridyl, 5-bromo-6-chloro-3-pyridyl, 5-fluoro-6-methyl-3-pyridyl, 5-chloro-6-trifluoromethyl-3-pyridyl, 3-chloro-5-trifluoromethyl-2-pyridyl, and 5,6-dimethyl-3-pyridyl; or a trisubstituted pyridyl group such as 4,5,6-trichloro-3-pyridyl. It is preferably a 3-pyridyl group, a 6-methyl-3-pyridyl group, a 6-fluoro-3-pyridyl group, a 6-chloro-3-pyridyl group, a 6-bromo-3-pyridyl group, a 5-chloro-3-pyridyl group, a 6-methoxy-3-pyridyl group, a 6-trifluoromethyl-3-pyridyl group, a 5,6-dichloro-3-pyridyl group, a 5-fluoro-6-bromo-3-pyridyl group, a 5-methyl-6-chloro-3-pyridyl group, a 5-methyl-6-fluoro-3-pyridyl group, a 5-bromo-6-chloro-3-pyridyl group, or a 5-fluoro-6-methyl-3-pyridyl group, and more preferably a 6-methyl-3-pyridyl group, a 6-fluoro-3-pyridyl group, a 6-chloro-3-pyridyl group, a 6-bromo-3-pyridyl group, a 5,6-dichloro-3-pyridyl group, or a 5-fluoro-6-chloro-3-pyridyl group.

The "pyrimidyl group that may be substituted" for the substituent group Ht indicates an unsubstituted pyrimidyl group such as 2-pyrimidyl and 5-pyrimidyl; a monosubstituted pyrimidyl group such as 2-methyl-5-pyrimidyl, 2-fluoro-5-pyrimidyl, 2-chloro-5-pyrimidyl, 2-bromo-5-pyrimidyl, 4-chloro-5-pyrimidyl, and 5-chloro-2-pyrimidyl; or a disubstituted pyrimidyl group such as 2,4-dichloro-5-pyrimidyl and 2,4-dimethyl-5-pyrimidyl. It is preferably a 2-pyrimidyl group, a 5-pyrimidyl group, or a 2-chloro-5-pyrimidyl group.

The "pyrazyl group that may be substituted" for the substituent group Ht indicates an unsubstituted pyrazyl group such as 2-pyrazyl; a monosubstituted pyrazyl group such as 5-methyl-2-pyrazyl, 5-fluoro-2-pyrazyl, 5-chloro-2-pyrazyl, and 5-trifluoromethyl-2-pyrazyl; or a disubstituted pyrazyl group such as 3,5-dichloro-2-pyrazyl and 5,6-dichloro-2-pyrazyl. It is preferably a 2-pyrazyl group or a 5-chloro-2-pyrazyl group.

The "pyridazyl group that may be substituted" for the substituent group Ht indicates an unsubstituted pyridazyl group such as 3-pyridazyl and 4-pyridazyl; a monosubstituted pyridazyl group such as 6-chloro-3-pyridazyl, 6-methyl-3-pyridazyl, 5-chloro-3-pyridazyl, and 6-chloro-4-pyridazyl; or a disubstituted pyridazyl group such as 5,6-dichloro-3-pyridazyl. It is preferably a 4-pyridazyl group or a 6-chloro-3-pyridazyl group.

The "pyrazolyl group that may be substituted" for the substituent group Ht indicates an unsubstituted pyrazolyl group such as 1-pyrazolyl; or a substituted pyrazolyl group such as 3-chloro-1-pyrazolyl and 3-trifluoromethyl-1-pyrazolyl. It is preferably a 1-pyrazolyl group or a 3-trifluoromethyl-1-pyrazolyl group.

The "imidazolyl group that may be substituted" for the substituent group Ht indicates an unsubstituted imidazolyl group such as 1-imidazolyl; or a substituted imidazolyl group such as 4-chloro-1-imidazolyl and 4-trifluoromethyl-1-imidazolyl. It is preferably a 1-imidazolyl group or a 3-trifluoromethyl-1-imidazolyl group.

The "triazolyl group that may be substituted" for the substituent group Ht indicates an unsubstituted triazolyl group such as 1-triazolyl; or a substituted triazolyl group such as 3-chloro-1-triazolyl, 3-trifluoromethyl-1-triazolyl, and 3,5-dichloro-1-triazolyl. It is preferably a 1-triazolyl group or a 3-trifluoromethyl-1-triazolyl group.

The "thiazolyl group that may be substituted" for the substituent group Ht indicates an unsubstituted thiazolyl group such as 5-thiazolyl; a monosubstituted thiazolyl group such 2-methyl-5-thiazolyl, 2-fluoro-5-thiazolyl, 2-chloro-5-thiazolyl, and 2-trifluoromethyl-5-thiazolyl; or a disubstituted thiazolyl group such as 2,4-dichloro-5-thiazolyl. It is preferably a 2-methyl-5-thiazolyl group, a 2-fluoro-5-thiazolyl group, or a 2-chloro-5-thiazolyl group, and more preferably a 2-chloro-5-thiazolyl group.

The "oxazolyl group that may be substituted" for the substituent group Ht indicates an unsubstituted oxazolyl group such as 5-oxazolyl; or a substituted oxazolyl group such as 2-methyl-5-oxazolyl, 2-chloro-5-oxazolyl, 2-trifluoromethyl-5-oxazolyl, and 2,4-dichloro-5-oxazolyl. It is preferably a 2-methyl-5-oxazolyl group or a 2-chloro-5-oxazolyl group.

The "thiophenyl group that may be substituted" for the substituent group Ht indicates an unsubstituted thiophenyl group such as 2-thiophenyl and 3-thiophenyl; or a substituted thiophenyl group such as 3-methyl-2-thiophenyl, 3-chloro-2-thiophenyl, and 2-chloro-3-thiophenyl. It is preferably a 3-chloro-2-thiophenyl group.

The "furyl group that may be substituted" for the substituent group Ht indicates an unsubstituted furyl group such as 2-furyl and 3-furyl; or a substituted furyl group such as 3-methyl-2-furyl, 3-chloro-2-furyl, and 2-chloro-3-furyl. It is preferably a 3-chloro-2-furyl group.

The "thiadiazolyl group that may be substituted" for the substituent group Ht indicates an unsubstituted thiadiazolyl group such as 1,3,4-thiadiazol-2-yl, 1,2,4-thiadiazol-5-yl, and 1,2,4-thiadiazol-3-yl; or a substituted thiadiazolyl group such as 5-chloro-1,3,4-thiadiazol-2-yl, 3-chloro-1,2,4-thiadiazol-5-yl, and 5-chloro-1,2,4-thiadiazol-3-yl. It is preferably a 1,3,4-thiadiazol-2-yl group.

The "tetrahydrofuryl group that may be substituted" for the substituent group Ht indicates an unsubstituted tetrahydrofuryl group such as a 2-tetrahydrofuryl group and a 3-tetrahydrofuryl group; or a substituted tetrahydrofuryl group such as a 5-methyl-3-tetrahydrofuryl group. It is preferably a 3-tetrahydrofuryl group.

Hereinbelow, the preferred modes of the formula (I) of the invention are described.

A preferably represents a nitrogen atom or C—$R^4$ in which $R^4$ is a hydrogen atom. More preferably, A is a nitrogen atom.

B preferably represents a nitrogen atom or C—$R^5$ in which $R^5$ is a hydrogen atom, a halogen atom, an alkyl group having 1 to 3 carbon atoms, a haloalkyl group having 1 to 3 carbon atoms, an alkoxyalkyl group having 1 to 3 carbon atoms, an alkoxy group that has 1 to 3 carbon atoms and that may be substituted, an alkenyloxy group having 2 or 3 carbon atoms, an alkynyloxy group having 2 to 4 carbon atoms, a haloalkoxy group having 1 to 3 carbon atoms, an alkoxyalkoxy group having 1 to 3 carbon atoms, an alkylcarbonyloxy group having 1 to 3 carbon atoms, a phenoxy group that may be substituted, a heterocyclyloxy group that may be substituted, an alkylthio group having 1 to 3 carbon atoms, a haloalkylthio group having 1 to 3 carbon atoms, an alkylsulfinyl group having 1 to 3 carbon atoms, an alkylsulfonyl group having 1 to 3 carbon atoms, a haloalkylsulfinyl group having 1 to 3 carbon atoms, a haloalkylsulfonyl group having 1 to 3 carbon atoms, an alkylsulfonyloxy group having 1 to 3 carbon atoms, a haloalkylsulfonyloxy group having 1 to 3 carbon atoms, a phenylthio group that may be substituted, a phenylsulfonyloxy group that may be substituted, a substituted iminosulfyl group, a substituted iminosulfoxy group, or an alkylamino group having 1 to 3 carbon atoms. More preferably, B is C—$R^5$ in which $R^5$ is a hydrogen atom, an alkyl group having 1 to 3 carbon atoms, a haloalkyl group having 1 to 3 carbon atoms, an alkoxy group having 1 to 3 carbon atoms, a haloalkoxy group having 1 to 3 carbon atoms, a phenoxy group that may be substituted, an alkylthio group having 1 to 3 carbon atoms, a haloalkylthio group having 1 to 3 carbon atoms, an alkylsulfinyl group having 1 to 3 carbon atoms, an alkylsulfonyl group having 1 to 3 carbon atoms, a haloalkylsulfinyl group having 1 to 3 carbon atoms, a haloalkylsulfonyl group having 1 to 3 carbon atoms, an alkylsulfonyloxy group having 1 to 3 carbon atoms, a substituted iminosulfinyl group, or a substituted iminosulfoxy group. Even more preferably, B is C—$R^5$ in which $R^5$ is a methyl group, an ethyl group, a difluoromethyl group, a trifluoromethyl group, a 1,1-difluoroethyl group, a pentafluoroethyl group, a methoxy group, an ethoxy group, a difluoromethoxy group, a trifluoromethoxy group, a methylthio group, an ethylthio group, a trifluoromethylthio group, a 2,2,2-trifluoroethylthio group, a methylsulfinyl group, an ethylsulfinyl group, a methylsulfonyl group, an ethylsulfonyl group, a trifluoromethylsulfinyl group, a trifluoromethylsulfonyl group, a N-cyanoiminomethylsulfinyl group, or a N-cyanoiminomethylsulfoxy group.

D preferably represents a nitrogen atom or C—$R^6$ in which $R^6$ is a hydrogen atom.

X preferably represents an oxygen atom, a sulfur atom, or N—$R^7$ in which $R^7$ is a hydrogen atom, a cyano group, a hydroxy group, an alkyl group having 1 to 3 carbon atoms, a haloalkyl group having 1 to 3 carbon atoms, a phenyl group that may be substituted, an alkoxy group having 1 to 3 carbon atoms, an alkylcarbonyloxy group having 1 to 3 carbon atoms, an alkylsulfonyl group having 1 to 3 carbon atoms, an alkylcarbonyl group having 1 to 3 carbon atoms, a haloalkylcarbonyl group having 1 to 3 carbon atoms, an alkyloxycarbonyl group having 1 to 3 carbon atoms, or an amino group that has 1 to 3 carbon atoms and that may be substituted. More preferably, X is an oxygen atom, a sulfur atom, or N—$R^7$ in which $R^7$ is a hydroxy group, an alkyl group having 1 to 3 carbon atoms, a haloalkyl group having 1 to 3 carbon atoms, a phenyl group that may be substituted, an alkoxy group having 1 to 3 carbon atoms, an alkylcarbonyloxy group having 2 or 3 carbon atoms, an alkylsulfonyl group having 1 to 3 carbon atoms, an alkoxycarbonyl group having 2 or 3 carbon atoms, a haloalkylcarbonyl group having 2 or 3 carbon atoms, an alkyloxycarbonyl group having 2 or 3 carbon atoms, or an amino group that has 1 to 3 carbon atoms and that may be substituted. Even more preferably, X is an oxygen atom, a sulfur atom, or N—$R^7$ in which $R^7$ is a hydroxy group, a methyl group, a methoxy group, or a methylamino group. Most preferably, X is an oxygen atom.

$R^1$ is preferably a hydrogen atom, a halogen atom, an alkyl group having 1 to 6 carbon atoms, or a haloalkyl group having 1 to 6 carbon atoms. More preferably, $R^1$ is a hydrogen atom, a methyl group, an ethyl group, or a fluorine atom. Even more preferably, $R^1$ is a hydrogen atom or a methyl group. Most preferably, $R^1$ is a hydrogen atom.

$R^2$ is preferably a hydrogen atom, a hydroxy group, an alkyl group having 1 to 6 carbon atoms, or a haloalkyl group having 1 to 6 carbon atoms. More preferably, $R^2$ is a methyl group or an ethyl group.

At least one of $R^{3a}$ or $R^{3b}$ is preferably a hydrogen atom, a methyl group, or an ethyl group. More preferably, one of $R^{3a}$ or $R^{3b}$ is a hydrogen atom and the other is a hydrogen atom, a methyl group, or an ethyl group. Even more preferably, $R^{3a}$ and $R^{3b}$ are hydrogen atoms.

Ht is preferably a pyridyl group that may be substituted, a pyrimidyl group that may be substituted, or a thiazolyl group that may be substituted. More preferably, Ht is a 3-pyridyl group that may be substituted or a 3-thiazolyl group that may be substituted, and even more preferably Ht is a 6-chloro-3-pyridyl group.

The fused ring pyrimidine compound represented by the formula (I) of the invention can be a salt such as sulfuric acid salt, hydrochloric acid salt, nitric acid salt, and a phosphoric acid salt. As long as those salts can be used as a pest control agent, they are included in the invention.

The fused ring pyrimidine compound represented by the formula (I) of the invention and a salt thereof can be a solvate, and a solvate thereof is also included in the invention. The solvate is preferably a hydrate.

The fused ring pyrimidine compound represented by the formula (I) of the invention includes a compound having an asymmetric center. One optically active type and a mixture of two optically active types at any ratio are also included in the invention.

The representative compounds of the fused ring pyrimidine compound of the invention are illustrated hereinbelow [Compound No. 1 to Compound No. 367]. However, it is evident that the invention is not limited to the group of those compounds.

| Compound No. | Structure |
|---|---|
| 1 | 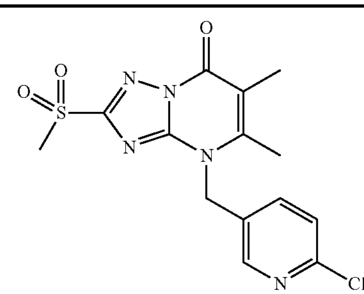 |
| 2 | 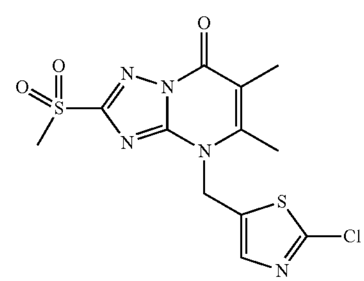 [SMILES: Cc1c(C)n(Cc2cnc(Cl)s2)c2nc(S(C)(=O)=O)nn2c1=O] |
| 3 | 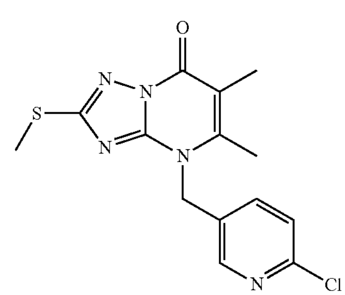 |

-continued

| Compound No. | Structure |
|---|---|
| 4 | [triazolopyrimidinone with 6-methyl, N-CH2-(6-chloropyridin-3-yl)] |
| 5 | [2-methylthio-triazolopyrimidinone, 6-methyl, N-CH2-(6-chloropyridin-3-yl)] |
| 6 | [2-methylthio-triazolopyrimidinone, 7-F, 6-methyl, N-CH2-(6-chloropyridin-3-yl)] |
| 7 | [2-methylthio-triazolopyrimidinone, 7-Cl, 6-methyl, N-CH2-(6-chloropyridin-3-yl)] |
| 8 | [2-methylthio-triazolopyrimidinone, 7-benzyl, 6-methyl, N-CH2-(6-chloropyridin-3-yl)] |

-continued

| Compound No. | Structure |
|---|---|
| 9 | [triazolopyrimidinone with 7-methyl, 6-methyl, N-CH2-(6-chloropyridin-3-yl)] |
| 10 | [2-methylsulfonyl-triazolopyrimidinone, 6-methyl, N-CH2-(6-chloropyridin-3-yl)] |
| 11 | [2-methylsulfonyl-triazolopyrimidinone, 7-benzyl, 6-methyl, N-CH2-(6-chloropyridin-3-yl)] |
| 12 | [2-methylthio-triazolopyrimidinone, 6-ethyl, N-CH2-(6-chloropyridin-3-yl)] |
| 13 | [2-methylthio-triazolopyrimidinone, 6-propyl, N-CH2-(6-chloropyridin-3-yl)] |

| Compound No. | Structure |
|---|---|
| 14 | 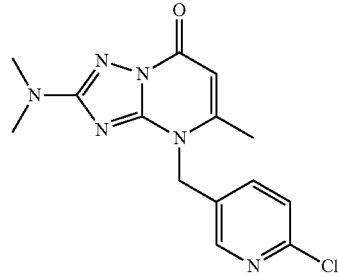 [SMILES: Cc1cc(=O)n2nc(N(C)C)nc2n1Cc1ccc(Cl)nc1] |
| 15 | 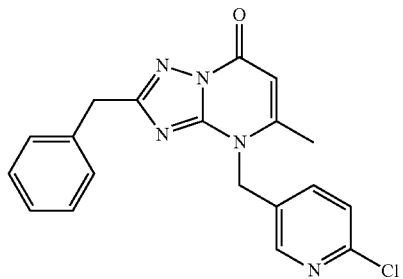 [SMILES: Cc1cc(=O)n2nc(Cc3ccccc3)nc2n1Cc1ccc(Cl)nc1] |
| 16 | 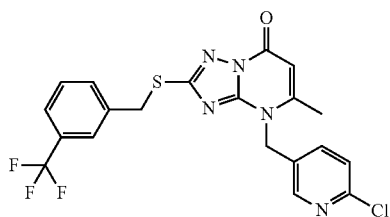 [SMILES: Cc1cc(=O)n2nc(SCc3cccc(C(F)(F)F)c3)nc2n1Cc1ccc(Cl)nc1] |
| 17 | 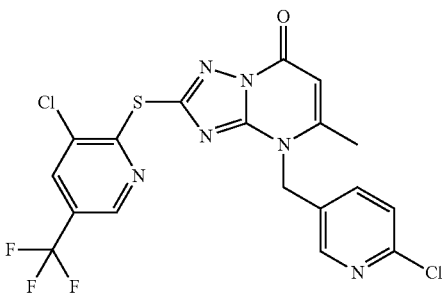 [SMILES: Cc1cc(=O)n2nc(Sc3ncc(C(F)(F)F)cc3Cl)nc2n1Cc1ccc(Cl)nc1] |
| 18 | 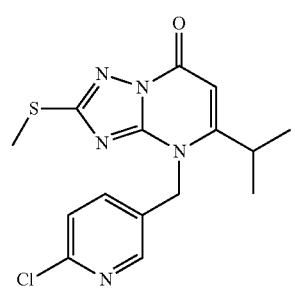 [SMILES: CSc1nc2n(Cc3ccc(Cl)nc3)c(C(C)C)cc(=O)n2n1] |
| Compound No. | Structure |
|---|---|
| 19 | 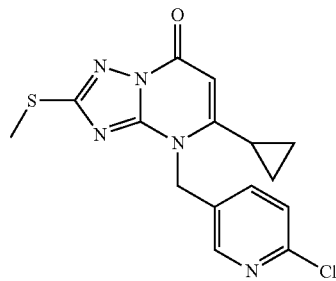 [SMILES: CSc1nc2n(Cc3ccc(Cl)nc3)c(C3CC3)cc(=O)n2n1] |
| 20 | 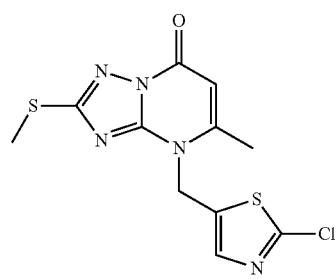 |
| 21 | 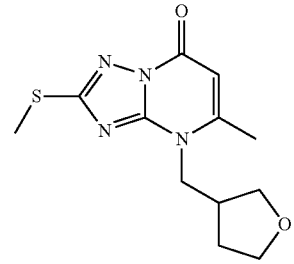 [SMILES: CSc1nc2n(CC3CCOC3)c(C)cc(=O)n2n1] |
| 22 | 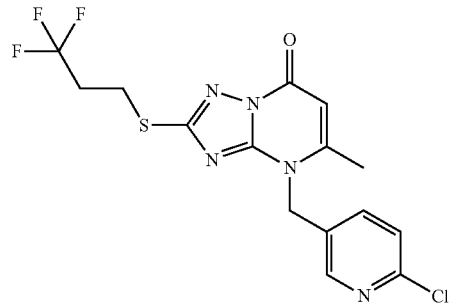 [SMILES: Cc1cc(=O)n2nc(SCCC(F)(F)F)nc2n1Cc1ccc(Cl)nc1] |
| 23 | 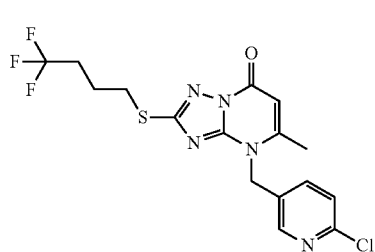 [SMILES: Cc1cc(=O)n2nc(SCCCC(F)(F)F)nc2n1Cc1ccc(Cl)nc1] |

US 9,963,451 B2
| Compound No. | Structure | | Compound No. | Structure |
|---|---|---|---|---|
| 24 | 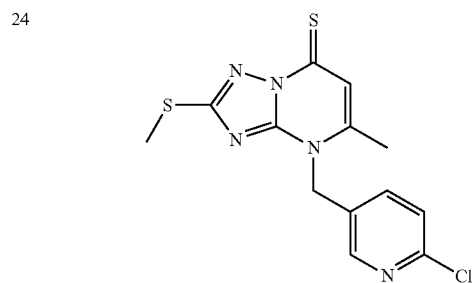 | | 29 | 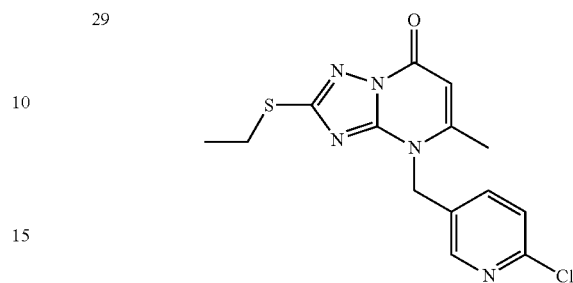 |
| 25 | 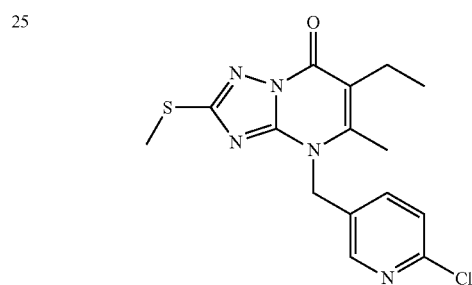 | | 30 | 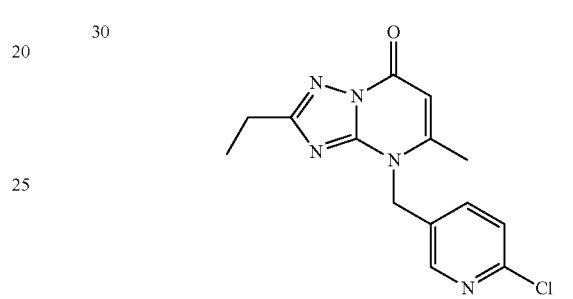 |
| 26 | 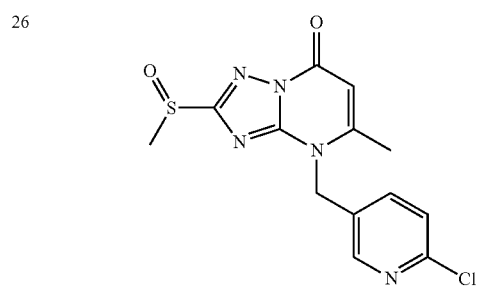 | | 31 | 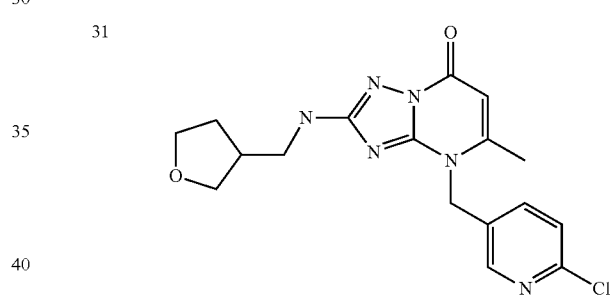 |
| 27 | 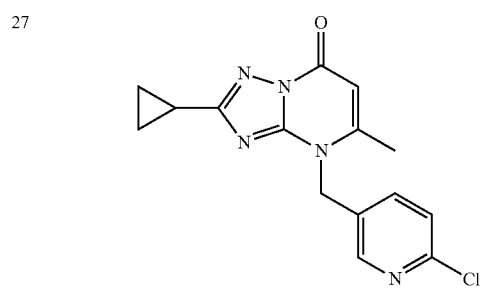 | | 32 | 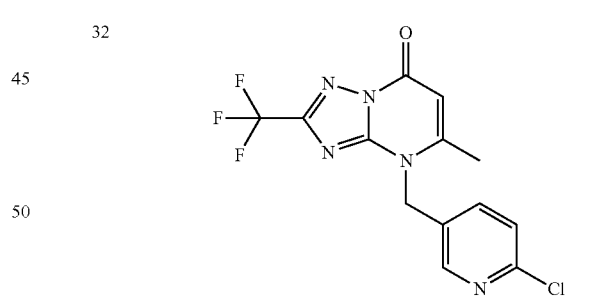 |
| 28 | 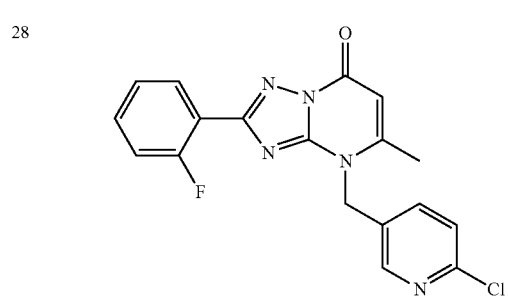 | | 33 | 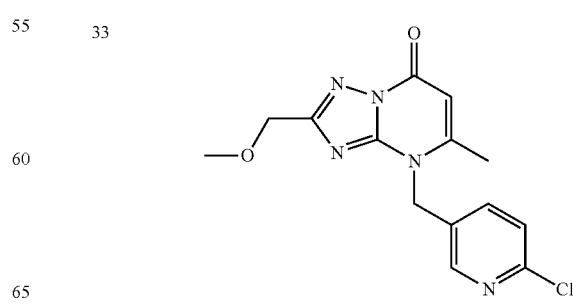 |

-continued
| Compound No. | Structure |
|---|---|
| 34 | 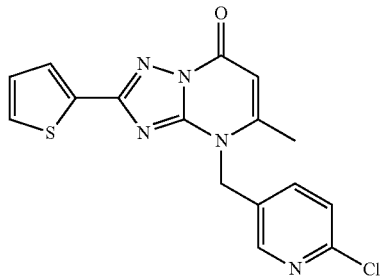 [SMILES: Cc1cc(=O)n2nc(-c3cccs3)nc2n1Cc1ccc(Cl)nc1] |
| 35 | 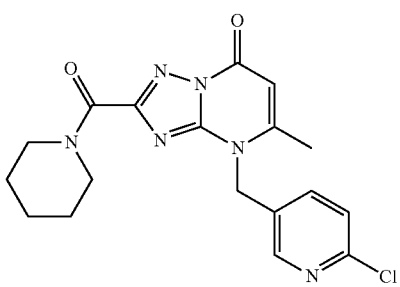 [SMILES: Cc1cc(=O)n2nc(C(=O)N3CCCCC3)nc2n1Cc1ccc(Cl)nc1] |
| 36 | 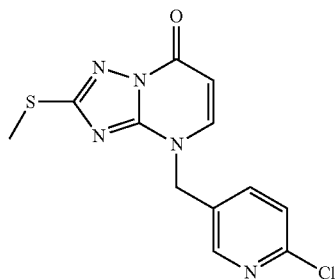 [SMILES: CSc1nc2n(Cc3ccc(Cl)nc3)ccc(=O)n2n1] |
| 37 | 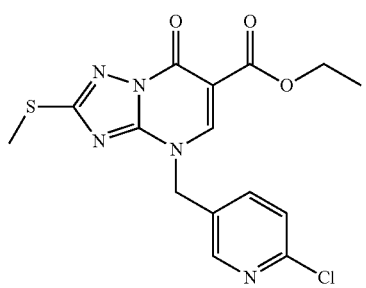 [SMILES: CCOC(=O)c1cn(Cc2ccc(Cl)nc2)c2nc(SC)nn2c1=O] |
| 38 | 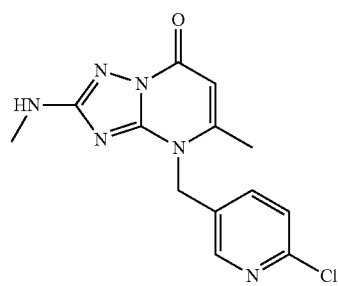 [SMILES: CNc1nc2n(Cc3ccc(Cl)nc3)c(C)cc(=O)n2n1] |
-continued
| Compound No. | Structure |
|---|---|
| 39 | 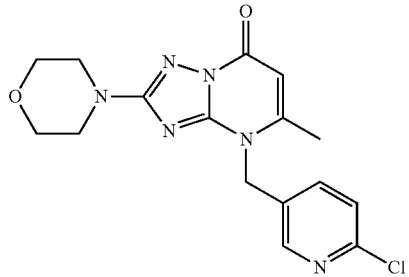 [SMILES: Cc1cc(=O)n2nc(N3CCOCC3)nc2n1Cc1ccc(Cl)nc1] |
| 40 | 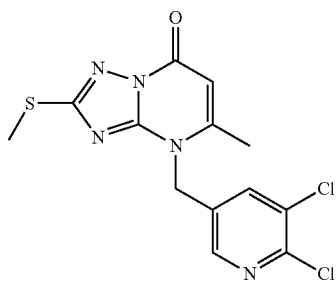 [SMILES: CSc1nc2n(Cc3cnc(Cl)c(Cl)c3)c(C)cc(=O)n2n1] |
| 41 | 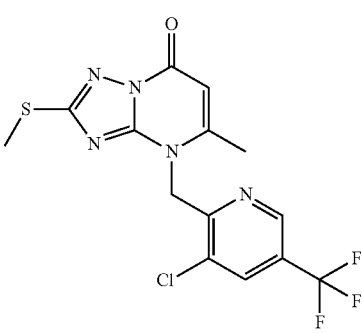 [SMILES: CSc1nc2n(Cc3ncc(C(F)(F)F)cc3Cl)c(C)cc(=O)n2n1] |
| 42 | 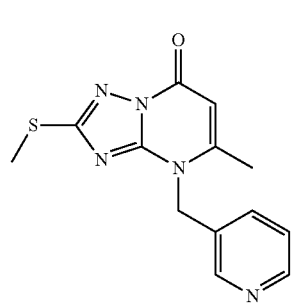 [SMILES: CSc1nc2n(Cc3cccnc3)c(C)cc(=O)n2n1] |
| 43 | 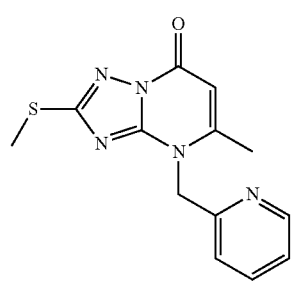 [SMILES: CSc1nc2n(Cc3ccccn3)c(C)cc(=O)n2n1] |

| Compound No. | Structure |
|---|---|
| 44 | 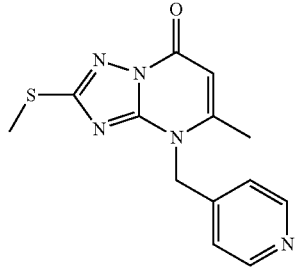 [SMILES: CSc1nc2n(Cc3ccncc3)c(C)cc(=O)n2n1] |
| 45 | 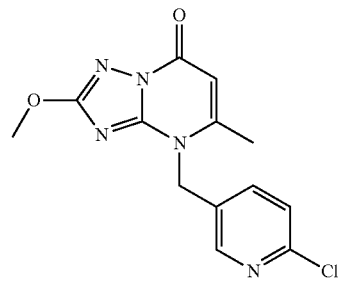 [SMILES: COc1nc2n(Cc3ccc(Cl)nc3)c(C)cc(=O)n2n1] |
| 46 | 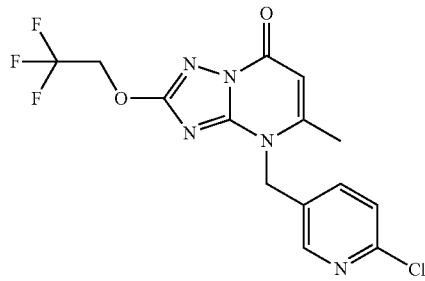 [SMILES: Cc1cc(=O)n2nc(OCC(F)(F)F)nc2n1Cc1ccc(Cl)nc1] |
| 47 | 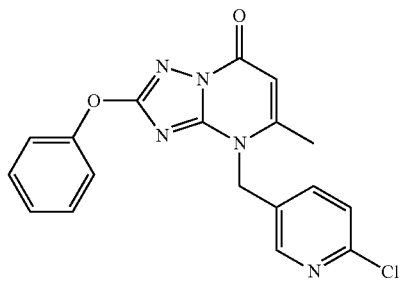 |
| 48 | 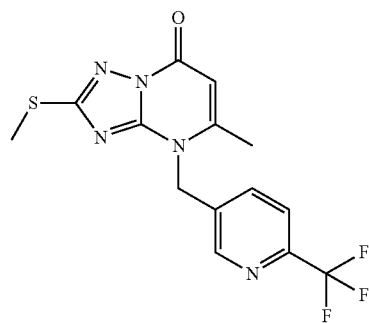 [SMILES: CSc1nc2n(Cc3ccc(C(F)(F)F)nc3)c(C)cc(=O)n2n1] |
| Compound No. | Structure |
|---|---|
| 49 | 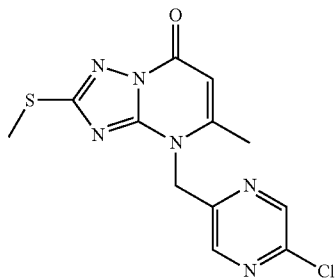 [SMILES: CSc1nc2n(Cc3cnc(Cl)cn3)c(C)cc(=O)n2n1] |
| 50 | 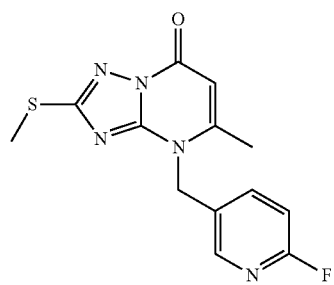 [SMILES: CSc1nc2n(Cc3ccc(F)nc3)c(C)cc(=O)n2n1] |
| 51 | 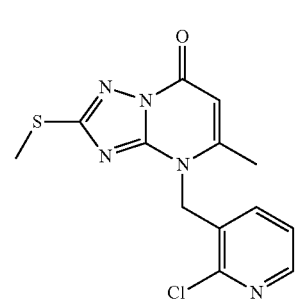 [SMILES: CSc1nc2n(Cc3cccnc3Cl)c(C)cc(=O)n2n1] |
| 52 | 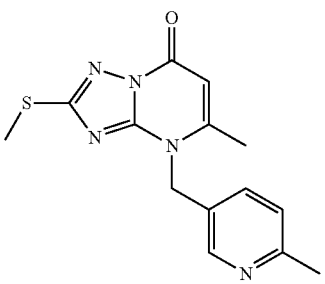 |
| 53 | 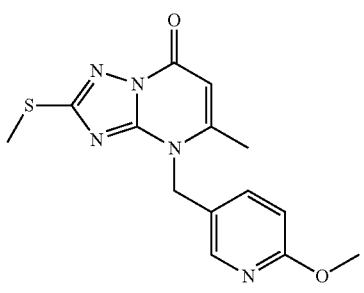 |

| Compound No. | Structure |
|---|---|
| 54 | 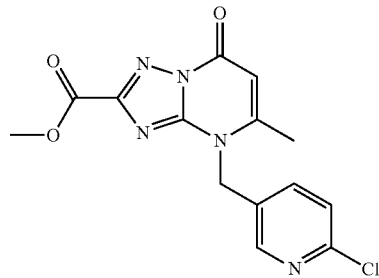 [SMILES: COC(=O)c1nc2n(Cc3ccc(Cl)nc3)c(C)cc(=O)n2n1] |
| 55 | 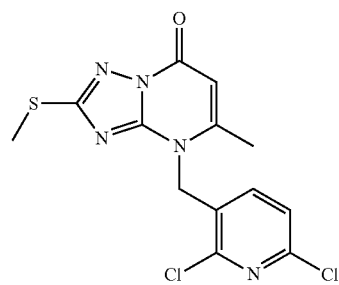 [SMILES: CSc1nc2n(Cc3ccc(Cl)nc3Cl)c(C)cc(=O)n2n1] |
| 56 | 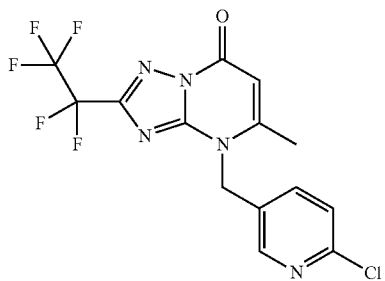 [SMILES: Cc1cc(=O)n2nc(C(F)(F)C(F)(F)F)nc2n1Cc1ccc(Cl)nc1] |
| 57 | 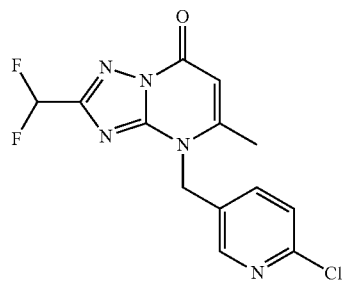 [SMILES: Cc1cc(=O)n2nc(C(F)F)nc2n1Cc1ccc(Cl)nc1] |
| 58 | 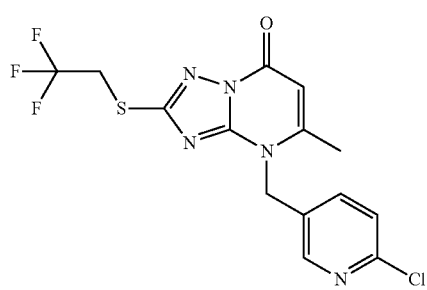 |
| Compound No. | Structure |
|---|---|
| 59 | 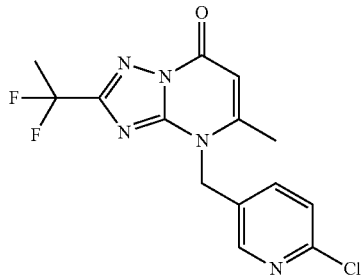 |
| 60 | 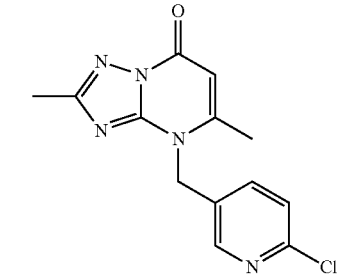 |
| 61 | 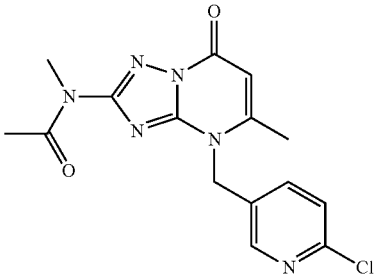 [SMILES: CC(=O)N(C)c1nc2n(Cc3ccc(Cl)nc3)c(C)cc(=O)n2n1] |
| 62 | 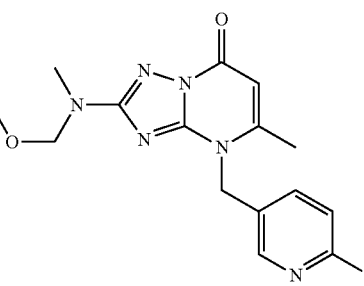 |
| 63 | 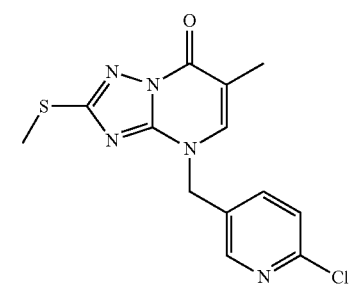 [SMILES: CSc1nc2n(Cc3ccc(Cl)nc3)cc(C)c(=O)n2n1] |

TABLE-continued
| Compound No. | Structure |
|---|---|
| 64 | 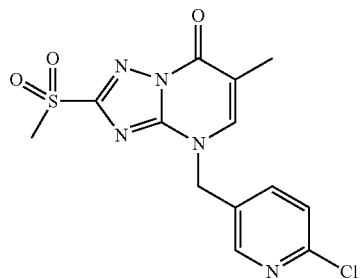 [SMILES: Cc1cn(Cc2ccc(Cl)nc2)c2nc(S(C)(=O)=O)nn2c1=O] |
| 65 | 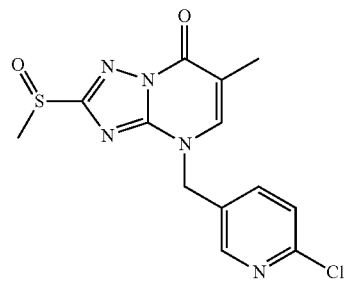 [SMILES: Cc1cn(Cc2ccc(Cl)nc2)c2nc(S(C)=O)nn2c1=O] |
| 66 | 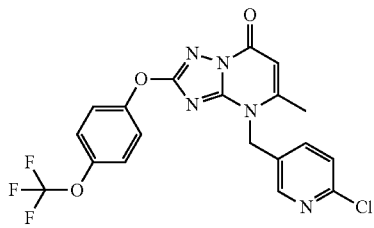 [SMILES: Cc1cc(=O)n2nc(Oc3ccc(OC(F)(F)F)cc3)nc2n1Cc1ccc(Cl)nc1] |
| 67 | 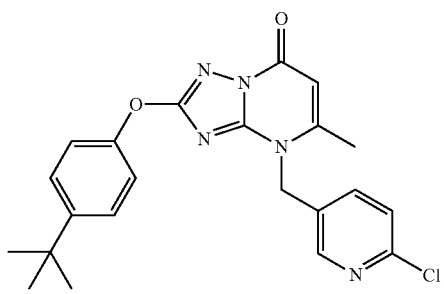 [SMILES: Cc1cc(=O)n2nc(Oc3ccc(C(C)(C)C)cc3)nc2n1Cc1ccc(Cl)nc1] |
| 68 | 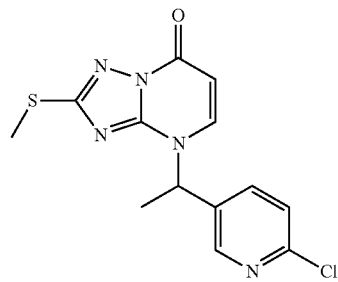 [SMILES: CSc1nc2n(C(C)c3ccc(Cl)nc3)ccc(=O)n2n1] |
| 69 | 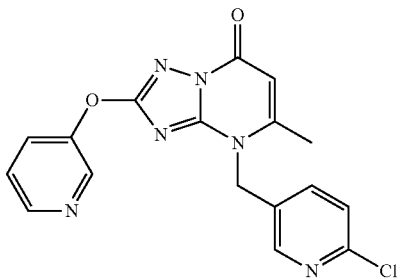 |
| 70 | 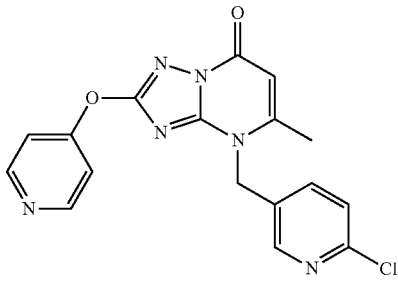 |
| 71 | 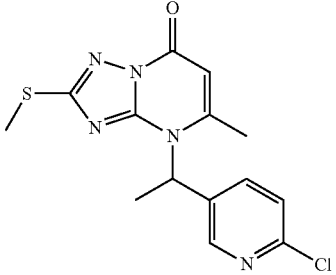 [SMILES: CSc1nc2n(C(C)c3ccc(Cl)nc3)c(C)cc(=O)n2n1] |
| 72 | 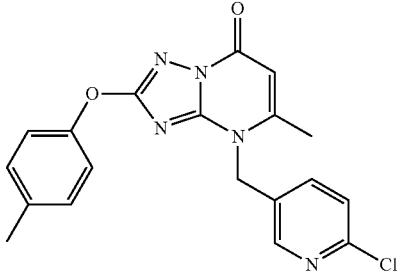 [SMILES: Cc1ccc(Oc2nc3n(Cc4ccc(Cl)nc4)c(C)cc(=O)n3n2)cc1] |
| 73 | 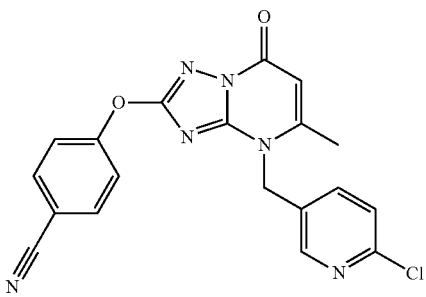 [SMILES: Cc1cc(=O)n2nc(Oc3ccc(C#N)cc3)nc2n1Cc1ccc(Cl)nc1] |

-continued
| Compound No. | Structure |
|---|---|
| 74 | 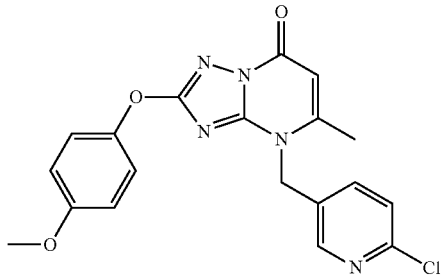 [SMILES: COc1ccc(Oc2nc3n(Cc4ccc(Cl)nc4)c(C)cc(=O)n3n2)cc1] |
| 75 | 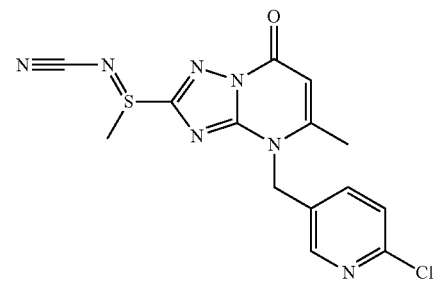 [SMILES: Cc1cc(=O)n2nc(/S(C)=N/C#N)nc2n1Cc1ccc(Cl)nc1] |
| 76 | 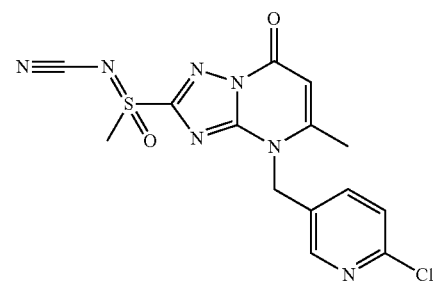 [SMILES: Cc1cc(=O)n2nc(S(C)(=O)=NC#N)nc2n1Cc1ccc(Cl)nc1] |
| 77 | 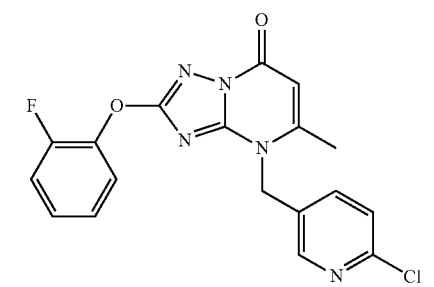 [SMILES: Cc1cc(=O)n2nc(Oc3ccccc3F)nc2n1Cc1ccc(Cl)nc1] |
| 78 | 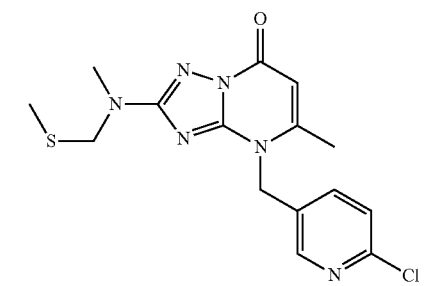 [SMILES: CSCN(C)c1nc2n(Cc3ccc(Cl)nc3)c(C)cc(=O)n2n1] |
-continued
| Compound No. | Structure |
|---|---|
| 79 | 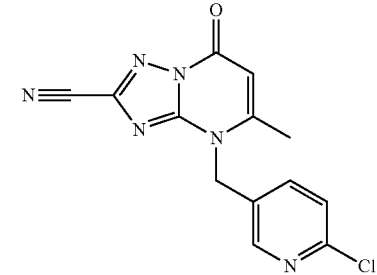 [SMILES: Cc1cc(=O)n2nc(C#N)nc2n1Cc1ccc(Cl)nc1] |
| 80 | 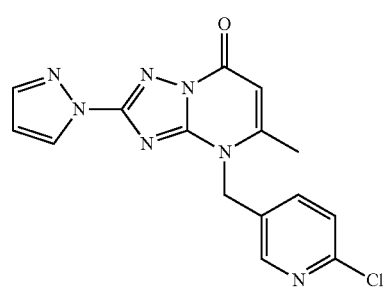 [SMILES: Cc1cc(=O)n2nc(-n3cccn3)nc2n1Cc1ccc(Cl)nc1] |
| 81 | 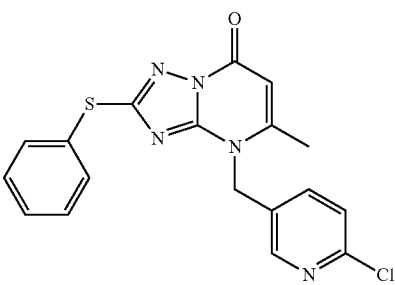 |
| 82 | 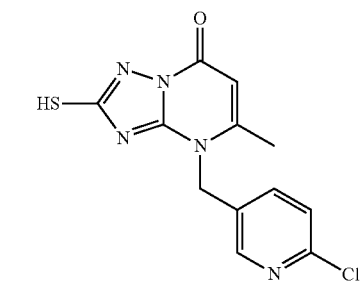 |
| 83 | 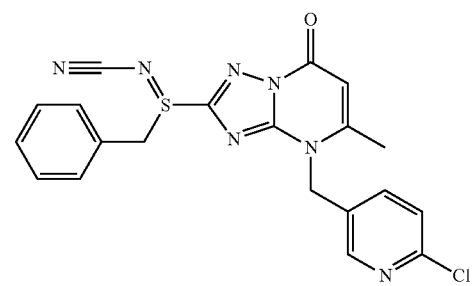 [SMILES: Cc1cc(=O)n2nc(/S(Cc3ccccc3)=N/C#N)nc2n1Cc1ccc(Cl)nc1] |

| Compound No. | Structure |
|---|---|
| 84 | 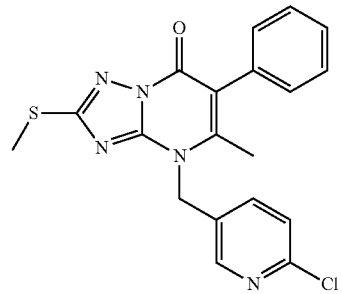 [SMILES: CSc1nc2n(Cc3ccc(Cl)nc3)c(C)c(-c3ccccc3)c(=O)n2n1] |
| 85 | 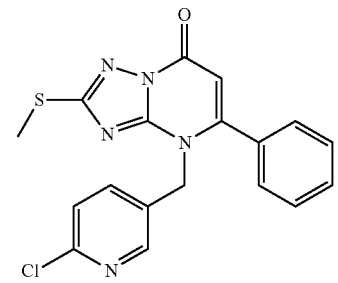 [SMILES: CSc1nc2n(Cc3ccc(Cl)nc3)c(-c3ccccc3)cc(=O)n2n1] |
| 86 | 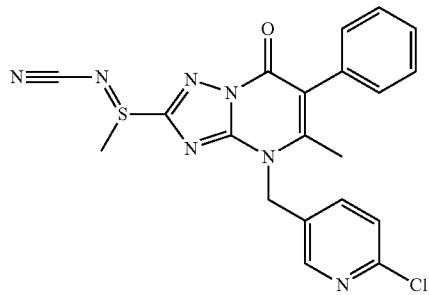 [SMILES: Cc1c(-c2ccccc2)c(=O)n2nc(/S(C)=N/C#N)nc2n1Cc1ccc(Cl)nc1] |
| 87 | 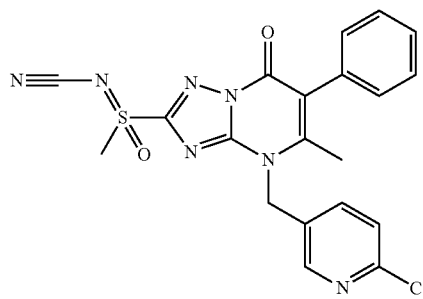 |
| 88 | 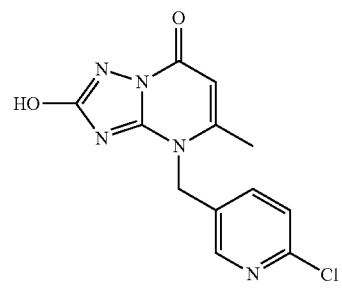 |
| Compound No. | Structure |
|---|---|
| 89 | 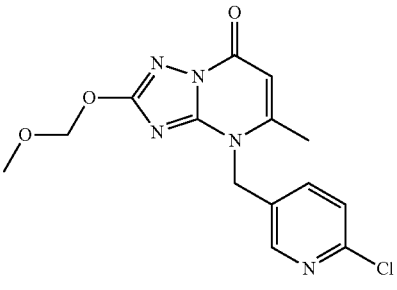 [SMILES: COCOc1nc2n(Cc3ccc(Cl)nc3)c(C)cc(=O)n2n1] |
| 90 | 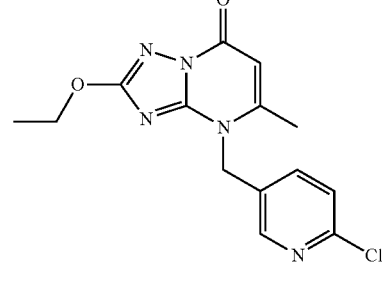 |
| 91 | 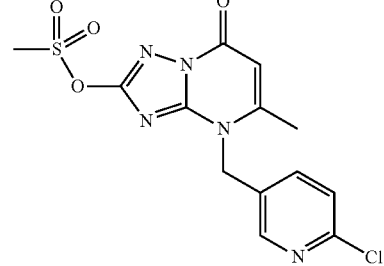 |
| 92 | 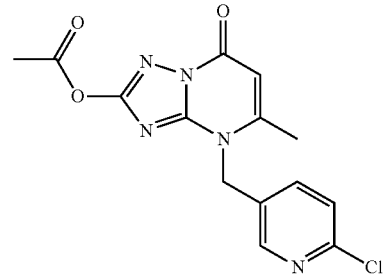 [SMILES: CC(=O)Oc1nc2n(Cc3ccc(Cl)nc3)c(C)cc(=O)n2n1] |
| 93 | 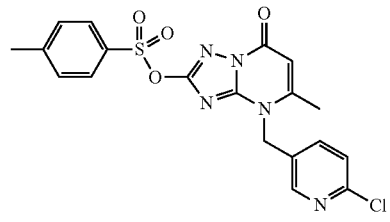 [SMILES: Cc1ccc(S(=O)(=O)Oc2nc3n(Cc4ccc(Cl)nc4)c(C)cc(=O)n3n2)cc1] |

-continued
| Compound No. | Structure |
|---|---|
| 94 | 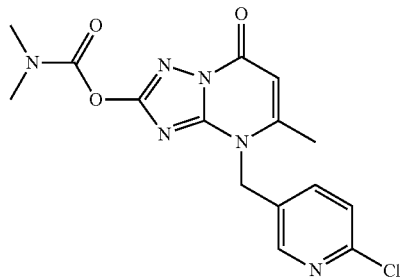 [SMILES: Cc1cc(=O)n2nc(OC(=O)N(C)C)nc2n1Cc1ccc(Cl)nc1] |
| 95 | 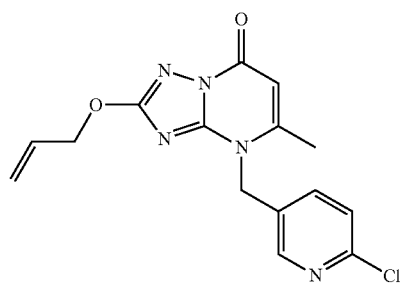 [SMILES: C=CCOc1nc2n(Cc3ccc(Cl)nc3)c(C)cc(=O)n2n1] |
| 96 | 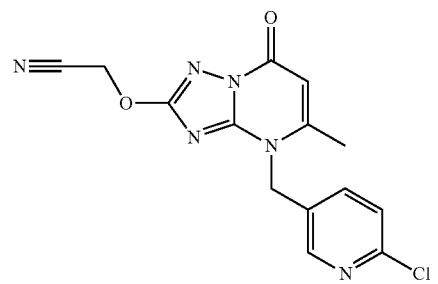 [SMILES: Cc1cc(=O)n2nc(OCC#N)nc2n1Cc1ccc(Cl)nc1] |
| 97 | 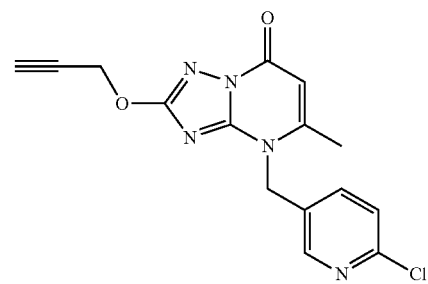 [SMILES: C#CCOc1nc2n(Cc3ccc(Cl)nc3)c(C)cc(=O)n2n1] |
| 98 | 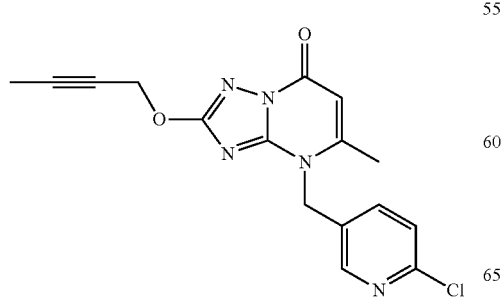 |
-continued
| Compound No. | Structure |
|---|---|
| 99 | 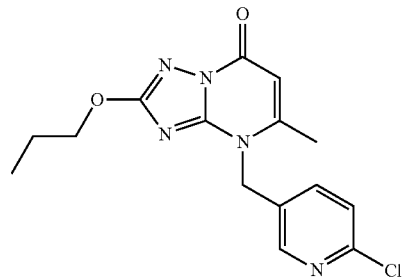 |
| 100 | 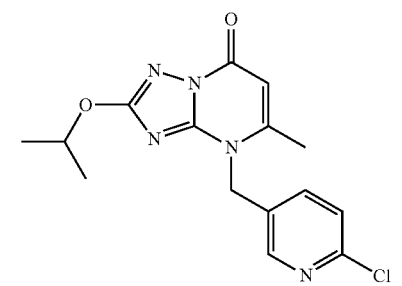 [SMILES: Cc1cc(=O)n2nc(OC(C)C)nc2n1Cc1ccc(Cl)nc1] |
| 101 | 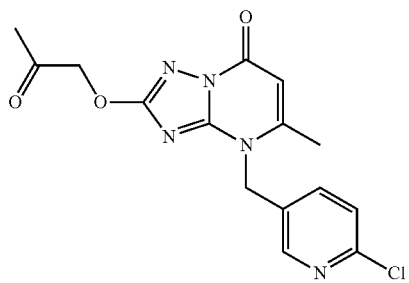 [SMILES: CC(=O)COc1nc2n(Cc3ccc(Cl)nc3)c(C)cc(=O)n2n1] |
| 102 | 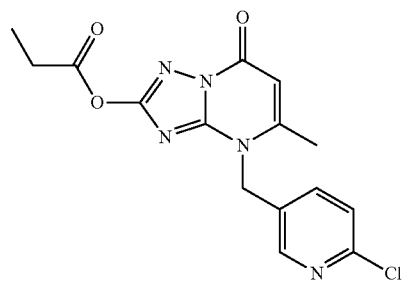 [SMILES: CCC(=O)Oc1nc2n(Cc3ccc(Cl)nc3)c(C)cc(=O)n2n1] |
| 103 | 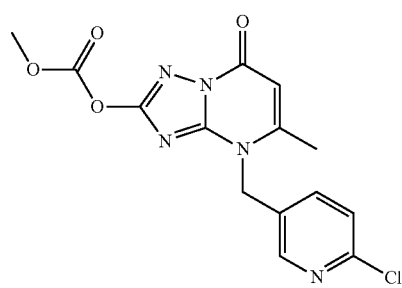 [SMILES: COC(=O)Oc1nc2n(Cc3ccc(Cl)nc3)c(C)cc(=O)n2n1] |

| Compound No. | Structure |
|---|---|
| 104 | 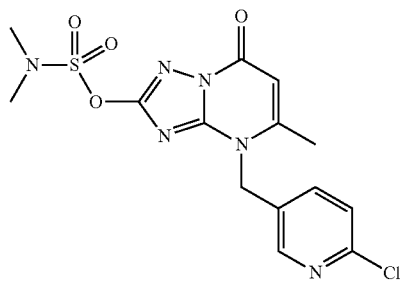 [SMILES: Cc1cc(=O)n2nc(OS(=O)(=O)N(C)C)nc2n1Cc1ccc(Cl)nc1] |
| 105 | 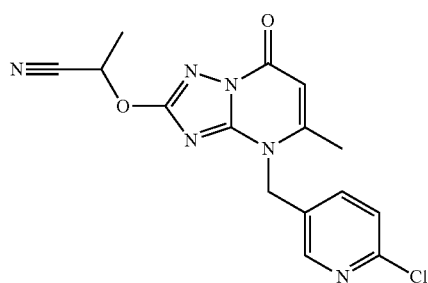 [SMILES: Cc1cc(=O)n2nc(OC(C)C#N)nc2n1Cc1ccc(Cl)nc1] |
| 106 | 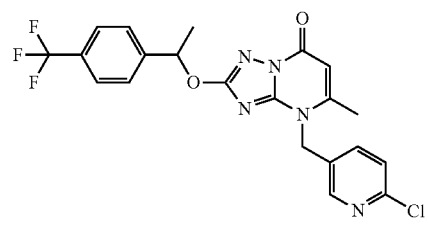 [SMILES: Cc1cc(=O)n2nc(OC(C)c3ccc(C(F)(F)F)cc3)nc2n1Cc1ccc(Cl)nc1] |
| 107 | 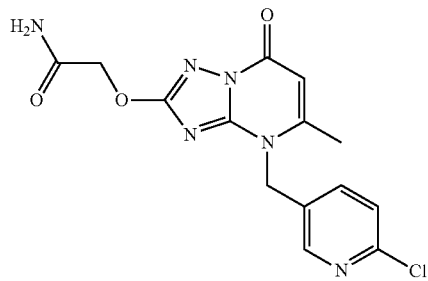 [SMILES: Cc1cc(=O)n2nc(OCC(N)=O)nc2n1Cc1ccc(Cl)nc1] |
| 108 | 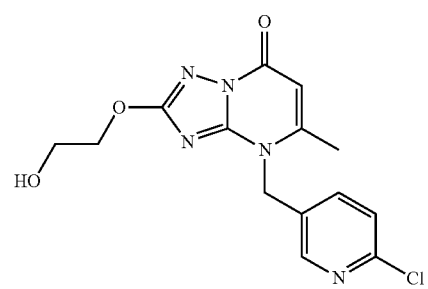 [SMILES: Cc1cc(=O)n2nc(OCCO)nc2n1Cc1ccc(Cl)nc1] |
| Compound No. | Structure |
|---|---|
| 109 | 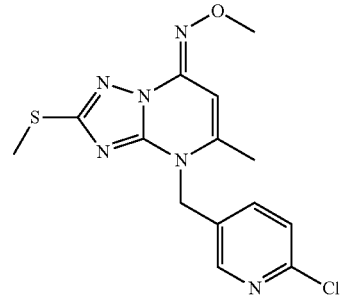 [SMILES: CO/N=c1\cc(C)n(Cc2ccc(Cl)nc2)c2nc(SC)nn12] |
| 110 | 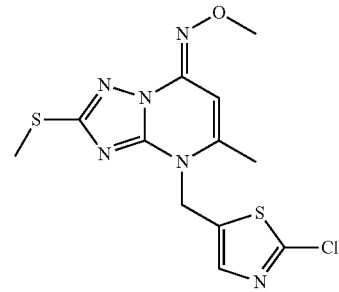 [SMILES: CO/N=c1\cc(C)n(Cc2cnc(Cl)s2)c2nc(SC)nn12] |
| 111 | 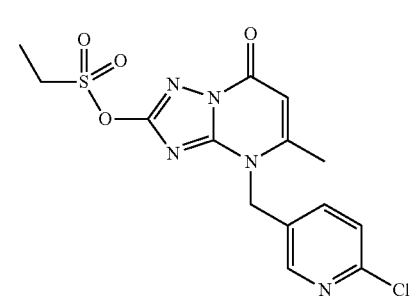 [SMILES: CCS(=O)(=O)Oc1nc2n(Cc3ccc(Cl)nc3)c(C)cc(=O)n2n1] |
| 112 | 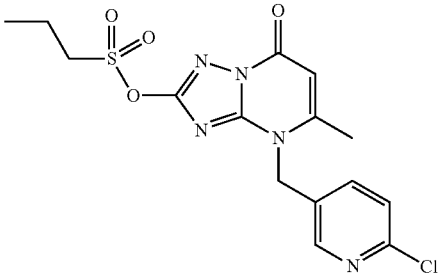 [SMILES: CCCS(=O)(=O)Oc1nc2n(Cc3ccc(Cl)nc3)c(C)cc(=O)n2n1] |
| 113 | 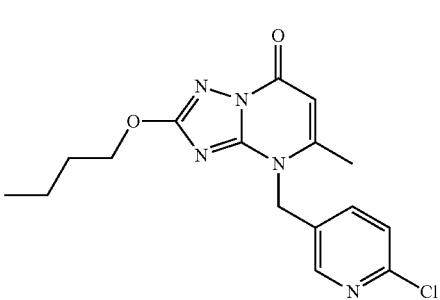 [SMILES: CCCCOc1nc2n(Cc3ccc(Cl)nc3)c(C)cc(=O)n2n1] |

| Compound No. | Structure |
|---|---|
| 114 | 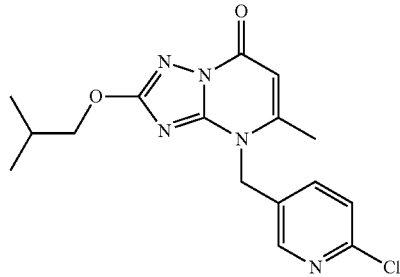 [SMILES: Cc1cc(=O)n2nc(OCC(C)C)nc2n1Cc1ccc(Cl)nc1] |
| 115 | 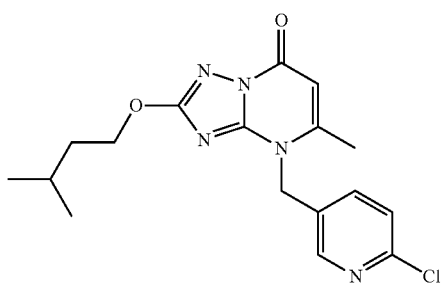 [SMILES: Cc1cc(=O)n2nc(OCCC(C)C)nc2n1Cc1ccc(Cl)nc1] |
| 116 | 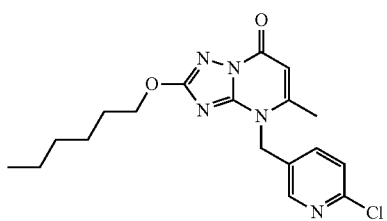 [SMILES: CCCCCCOc1nc2n(Cc3ccc(Cl)nc3)c(C)cc(=O)n2n1] |
| 117 | 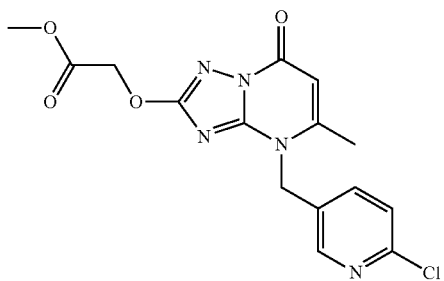 [SMILES: COC(=O)COc1nc2n(Cc3ccc(Cl)nc3)c(C)cc(=O)n2n1] |
| 118 | 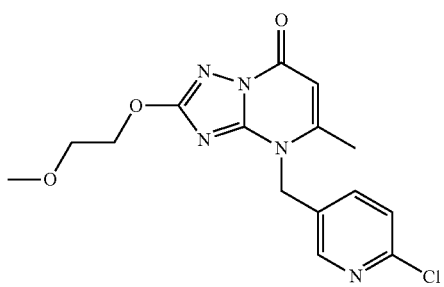 |
| Compound No. | Structure |
|---|---|
| 119 | 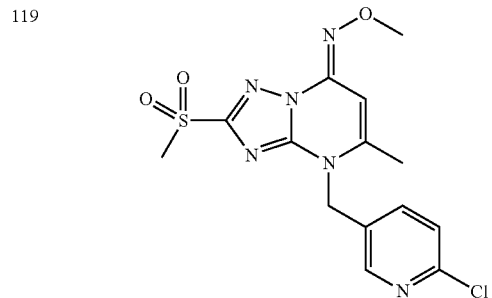 |
| 120 | 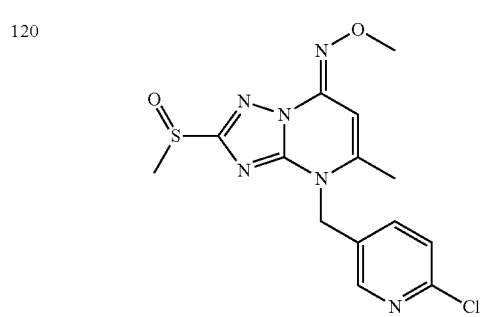 |
| 121 | 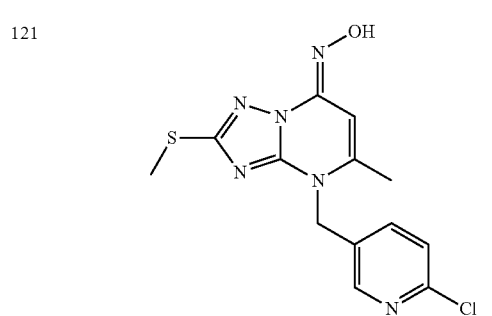 |
| 122 | 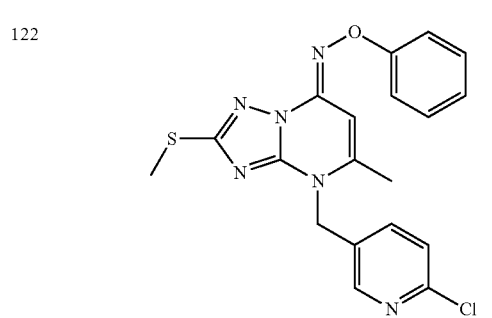 |
| 123 | 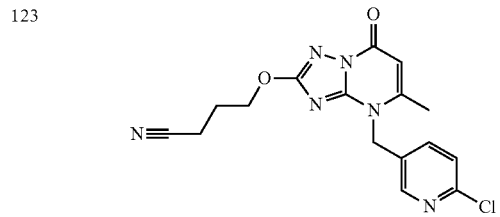 |

-continued

| Compound No. | Structure |
|---|---|
| 124 | *(structure)* |
| 125 | *(structure)* |
| 126 | *(structure)* |
| 127 | *(structure)* |

-continued

| Compound No. | Structure |
|---|---|
| 128 | *(structure)* |
| 129 | *(structure)* |
| 130 | *(structure)* |
| 131 | *(structure)* |
| 132 | *(structure)* |

-continued
| Compound No. | Structure |
|---|---|
| 133 | 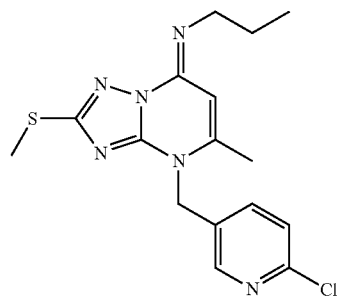 [SMILES: CCC/N=c1\cc(C)n(Cc2ccc(Cl)nc2)c2nc(SC)nn12] |
| 134 | 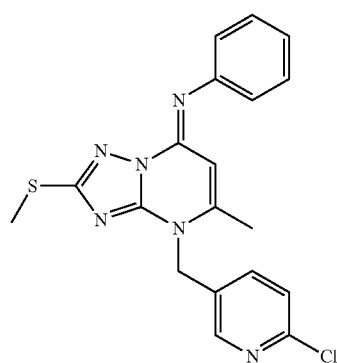 [SMILES: CSc1nc2n(Cc3ccc(Cl)nc3)c(C)c/c(=N\c3ccccc3)n2n1] |
| 135 | 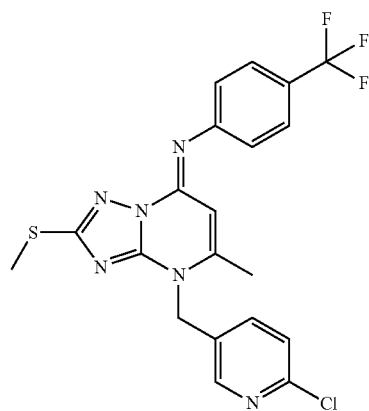 [SMILES: CSc1nc2n(Cc3ccc(Cl)nc3)c(C)c/c(=N\c3ccc(C(F)(F)F)cc3)n2n1] |
| 136 | 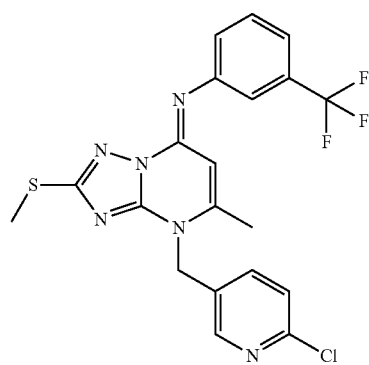 [SMILES: CSc1nc2n(Cc3ccc(Cl)nc3)c(C)c/c(=N\c3cccc(C(F)(F)F)c3)n2n1] |
-continued
| Compound No. | Structure |
|---|---|
| 137 | 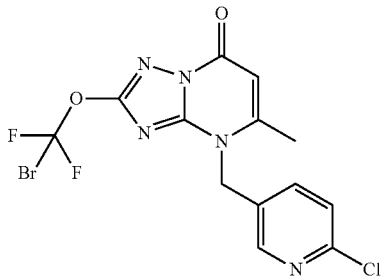 [SMILES: Cc1cc(=O)n2nc(OC(F)(F)Br)nc2n1Cc1ccc(Cl)nc1] |
| 138 | 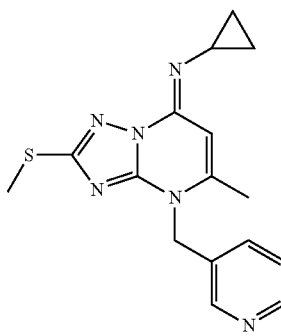 |
| 139 | 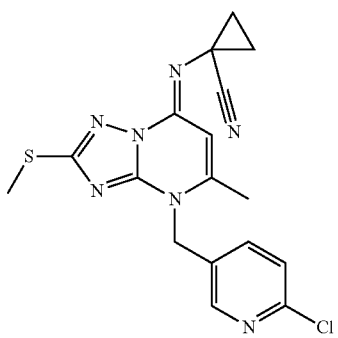 [SMILES: CSc1nc2n(Cc3ccc(Cl)nc3)c(C)c/c(=N\C3(C#N)CC3)n2n1] |
| 140 | 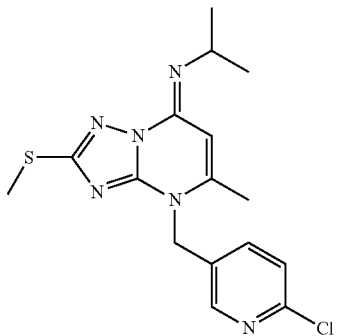 [SMILES: CSc1nc2n(Cc3ccc(Cl)nc3)c(C)c/c(=N\C(C)C)n2n1] |

-continued
| Compound No. | Structure |
|---|---|
| 141 | 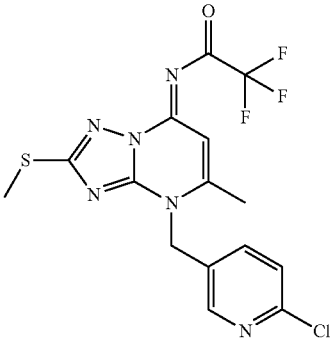 [SMILES: CSc1nc2n(Cc3ccc(Cl)nc3)c(C)c/c(=N\C(=O)C(F)(F)F)n2n1] |
| 142 | 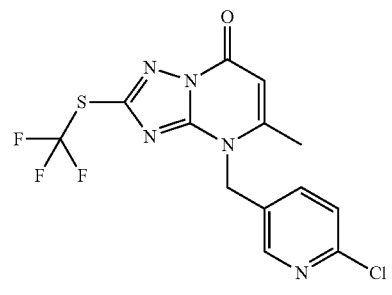 [SMILES: Cc1cc(=O)n2nc(SC(F)(F)F)nc2n1Cc1ccc(Cl)nc1] |
| 143 | 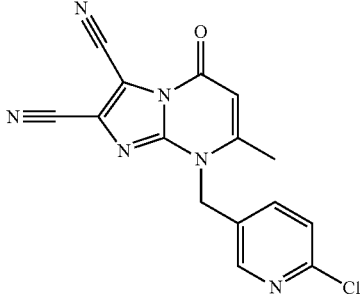 [SMILES: Cc1cc(=O)n2c(C#N)c(C#N)nc2n1Cc1ccc(Cl)nc1] |
| 144 | 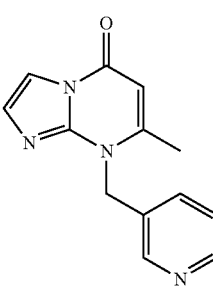 |
| 145 | 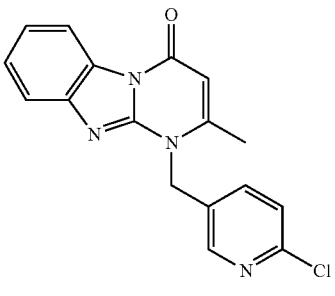 [SMILES: Cc1cc(=O)n2c3ccccc3nc2n1Cc1ccc(Cl)nc1] |
-continued
| Compound No. | Structure |
|---|---|
| 146 | 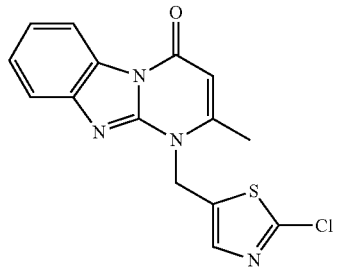 [SMILES: Cc1cc(=O)n2c3ccccc3nc2n1Cc1cnc(Cl)s1] |
| 147 | 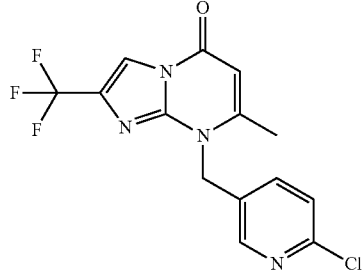 [SMILES: Cc1cc(=O)n2cc(C(F)(F)F)nc2n1Cc1ccc(Cl)nc1] |
| 148 | 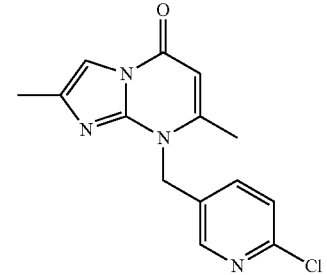 [SMILES: Cc1cn2c(=O)cc(C)n(Cc3ccc(Cl)nc3)c2n1] |
| 149 | 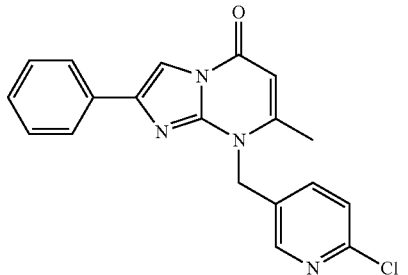 [SMILES: Cc1cc(=O)n2cc(-c3ccccc3)nc2n1Cc1ccc(Cl)nc1] |
| 150 | 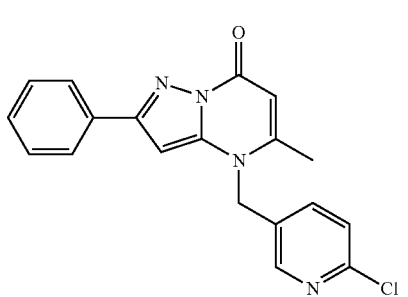 [SMILES: Cc1cc(=O)n2nc(-c3ccccc3)cc2n1Cc1ccc(Cl)nc1] |

-continued
| Compound No. | Structure |
|---|---|
| 151 | 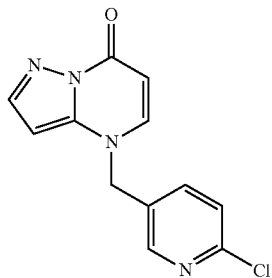 [SMILES: O=c1ccn(Cc2ccc(Cl)nc2)c2ccnn12] |
| 152 | 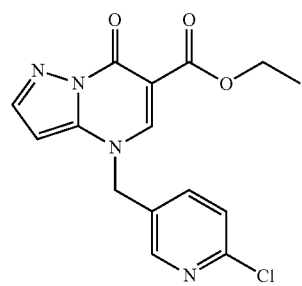 [SMILES: CCOC(=O)c1cn(Cc2ccc(Cl)nc2)c2ccnn2c1=O] |
| 153 | 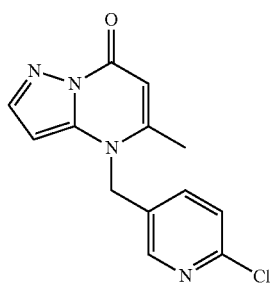 [SMILES: Cc1cc(=O)n2nccc2n1Cc1ccc(Cl)nc1] |
| 154 | 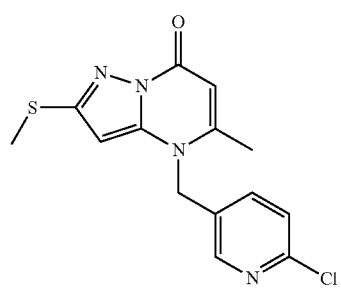 |
| 155 | 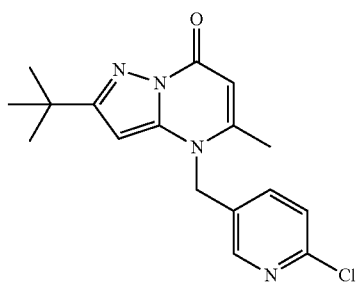 [SMILES: Cc1cc(=O)n2nc(C(C)(C)C)cc2n1Cc1ccc(Cl)nc1] |
-continued
| Compound No. | Structure |
|---|---|
| 156 | 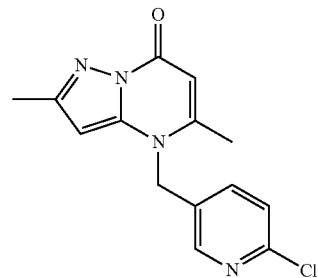 [SMILES: Cc1cc2n(Cc3ccc(Cl)nc3)c(C)cc(=O)n2n1] |
| 157 | 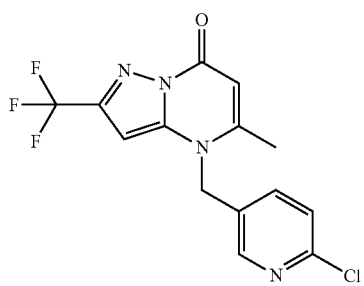 [SMILES: Cc1cc(=O)n2nc(C(F)(F)F)cc2n1Cc1ccc(Cl)nc1] |
| 158 | 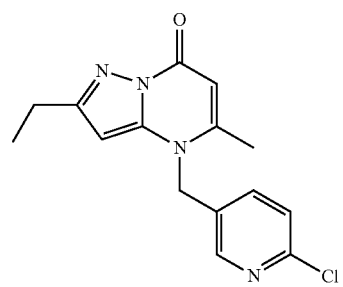 [SMILES: CCc1cc2n(Cc3ccc(Cl)nc3)c(C)cc(=O)n2n1] |
| 159 | 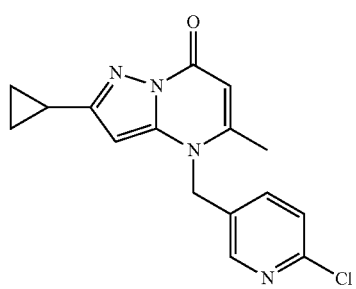 |
| 160 | 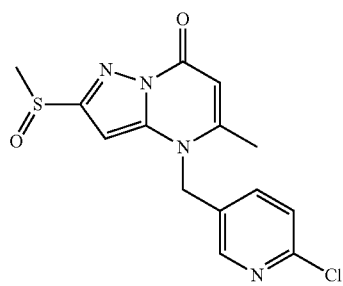 [SMILES: Cc1cc(=O)n2nc(S(C)=O)cc2n1Cc1ccc(Cl)nc1] |

-continued
| Compound No. | Structure |
|---|---|
| 161 | 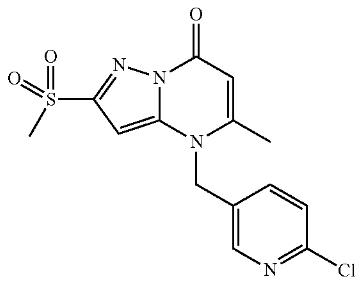 [SMILES: Cc1cc(=O)n2nc(S(C)(=O)=O)cc2n1Cc1ccc(Cl)nc1] |
| 162 | 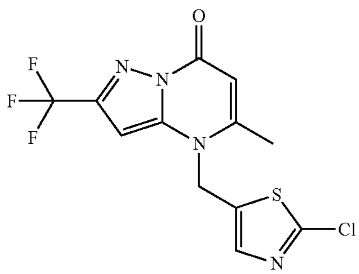 [SMILES: Cc1cc(=O)n2nc(C(F)(F)F)cc2n1Cc1cnc(Cl)s1] |
| 163 | 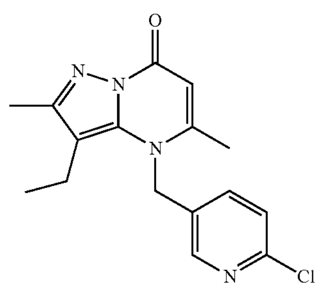 [SMILES: CCc1c(C)nn2c(=O)cc(C)n(Cc3ccc(Cl)nc3)c12] |
| 164 | 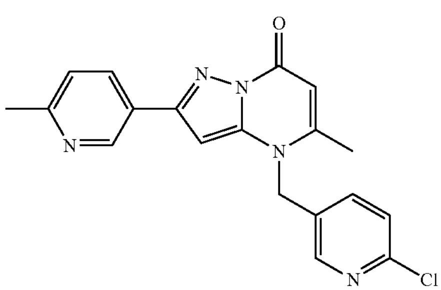 [SMILES: Cc1ccc(-c2cc3n(Cc4ccc(Cl)nc4)c(C)cc(=O)n3n2)cn1] |
| 165 | 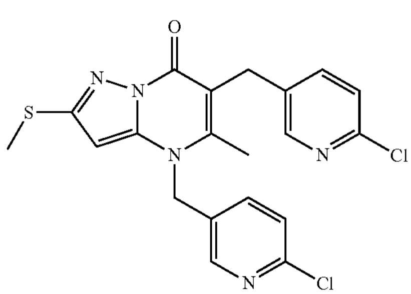 [SMILES: CSc1cc2n(Cc3ccc(Cl)nc3)c(C)c(Cc3ccc(Cl)nc3)c(=O)n2n1] |
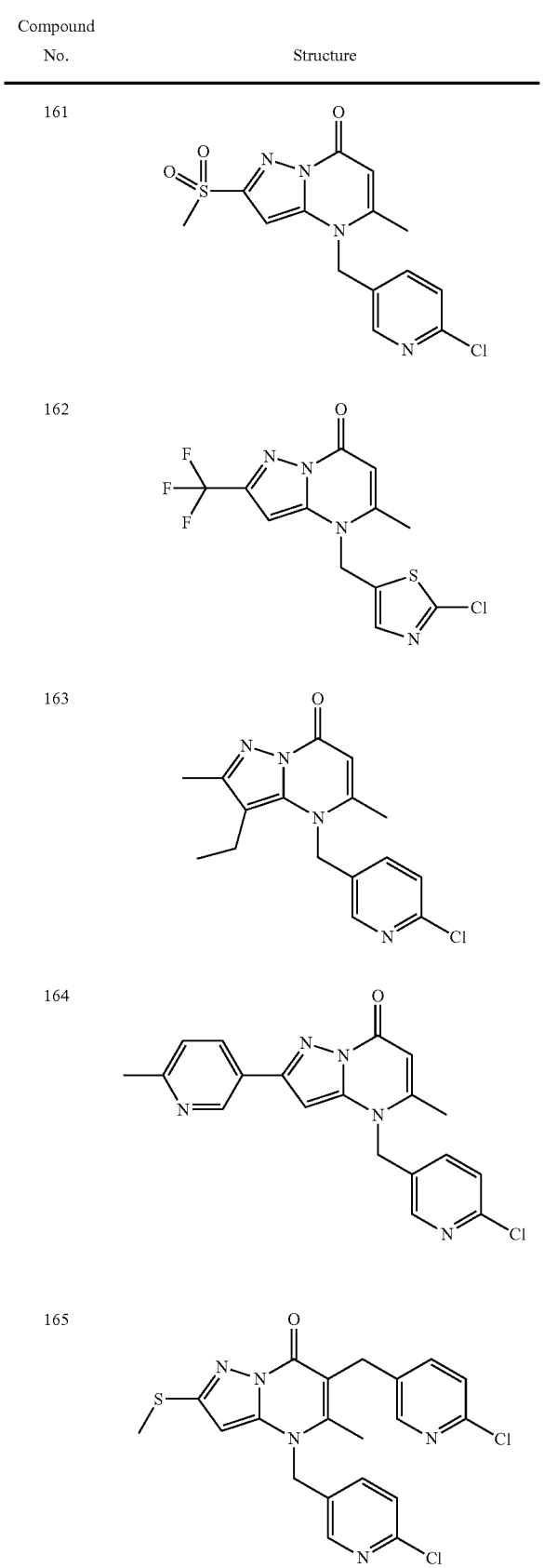
-continued
| Compound No. | Structure |
|---|---|
| 166 | 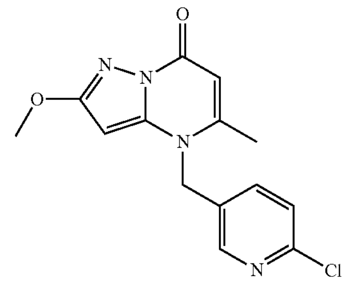 [SMILES: COc1cc2n(Cc3ccc(Cl)nc3)c(C)cc(=O)n2n1] |
| 167 | 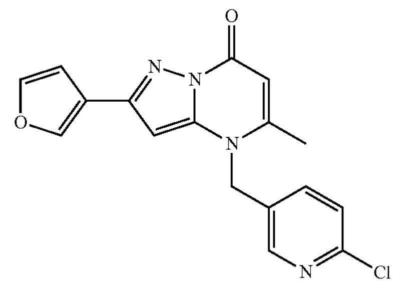 [SMILES: Cc1cc(=O)n2nc(-c3ccoc3)cc2n1Cc1ccc(Cl)nc1] |
| 168 | 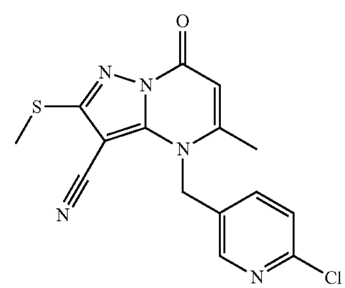 [SMILES: CSc1nn2c(=O)cc(C)n(Cc3ccc(Cl)nc3)c2c1C#N] |
| 169 | 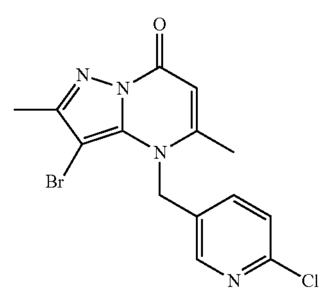 [SMILES: Cc1nn2c(=O)cc(C)n(Cc3ccc(Cl)nc3)c2c1Br] |
| 170 | 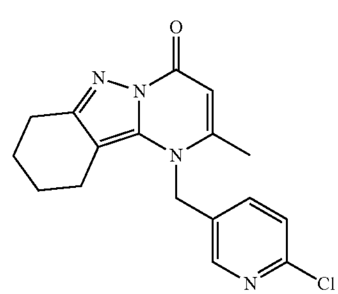 [SMILES: Cc1cc(=O)n2nc3c(c2n1Cc1ccc(Cl)nc1)CCCC3] |
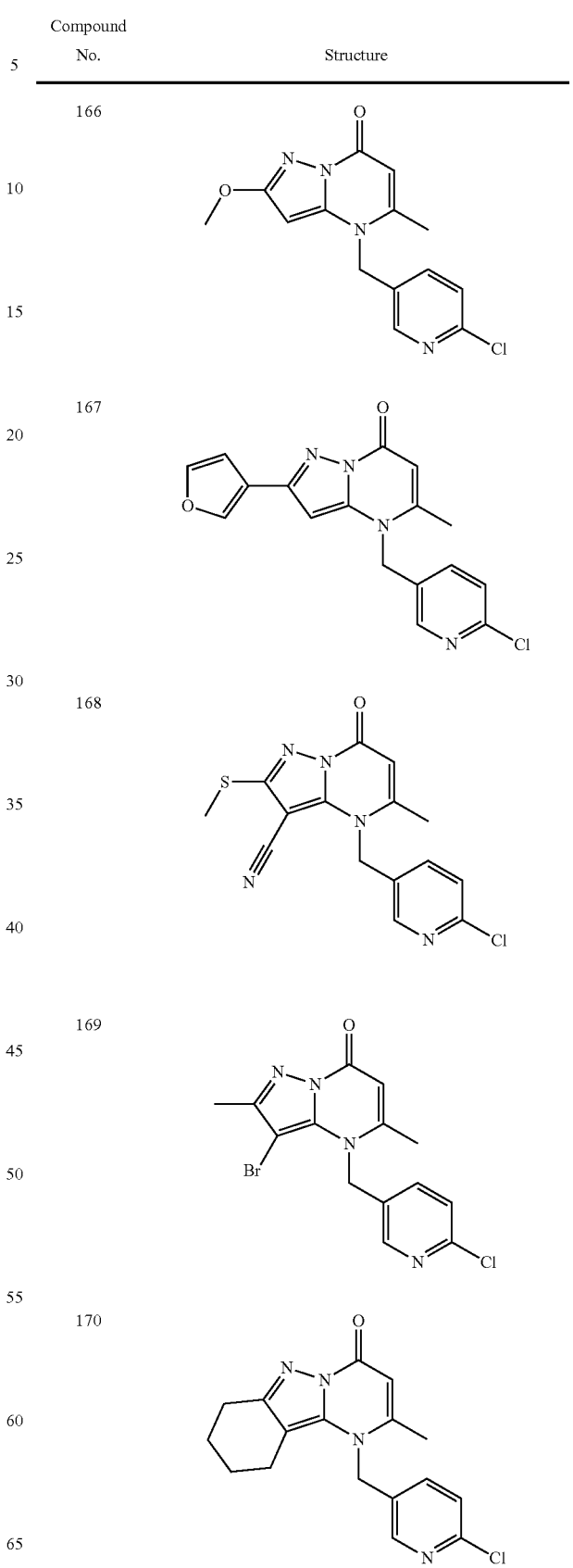

US 9,963,451 B2
| Compound No. | Structure |
|---|---|
| 171 | 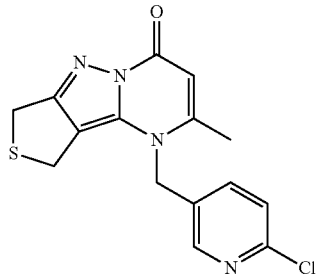 [SMILES: Cc1cc(=O)n2nc3c(c2n1Cc1ccc(Cl)nc1)CSC3] |
| 172 | 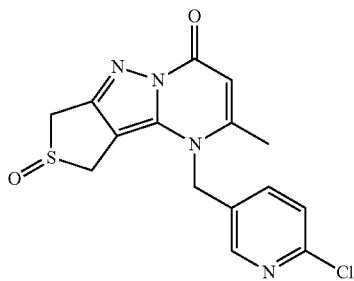 [SMILES: Cc1cc(=O)n2nc3c(c2n1Cc1ccc(Cl)nc1)CS(=O)C3] |
| 173 | 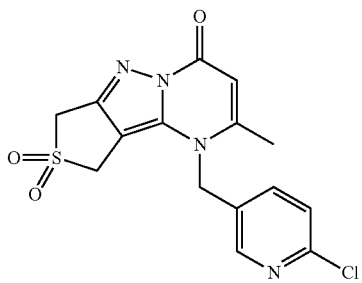 [SMILES: Cc1cc(=O)n2nc3c(c2n1Cc1ccc(Cl)nc1)CS(=O)(=O)C3] |
| 174 | 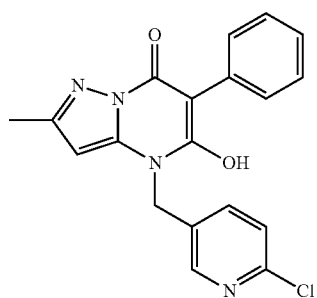 [SMILES: Cc1cc2n(Cc3ccc(Cl)nc3)c(O)c(-c3ccccc3)c(=O)n2n1] |
| 175 | 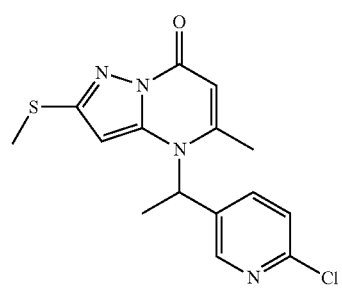 [SMILES: CSc1cc2n(C(C)c3ccc(Cl)nc3)c(C)cc(=O)n2n1] |
| Compound No. | Structure |
|---|---|
| 176 | 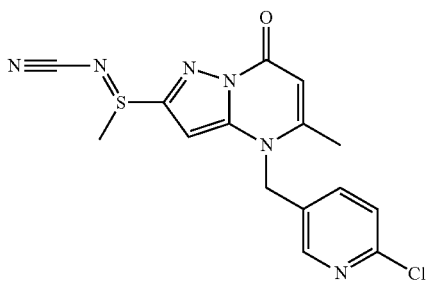 [SMILES: Cc1cc(=O)n2nc(/S(C)=N/C#N)cc2n1Cc1ccc(Cl)nc1] |
| 177 | 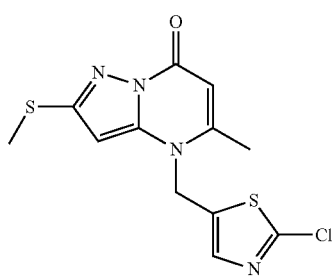 [SMILES: CSc1cc2n(Cc3cnc(Cl)s3)c(C)cc(=O)n2n1] |
| 178 | 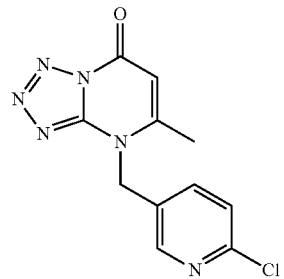 [SMILES: Cc1cc(=O)n2nnnc2n1Cc1ccc(Cl)nc1] |
| 179 | 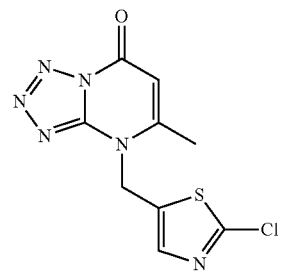 [SMILES: Cc1cc(=O)n2nnnc2n1Cc1cnc(Cl)s1] |
| 180 | 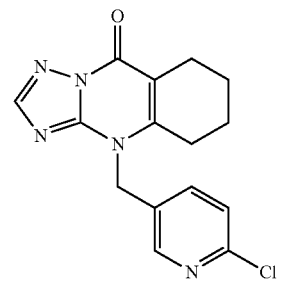 [SMILES: O=c1c2c(n(Cc3ccc(Cl)nc3)c3ncnn13)CCCC2] |

-continued

| Compound No. | Structure |
|---|---|
| 181 | (structure) |
| 182 | (structure) |
| 183 | (structure) |
| 184 | (structure) |

-continued

| Compound No. | Structure |
|---|---|
| 185 | (structure) |
| 186 | (structure) |
| 187 | (structure) |
| 188 | (structure) |
| 189 | (structure) |

| Compound No. | Structure |
|---|---|
| 190 | 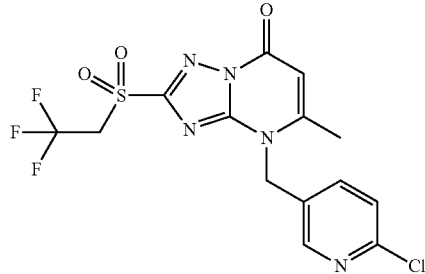 [SMILES: Cc1cc(=O)n2nc(S(=O)(=O)CC(F)(F)F)nc2n1Cc1ccc(Cl)nc1] |
| 191 | 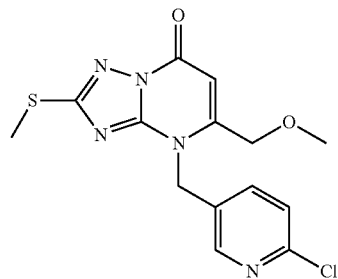 |
| 192 | 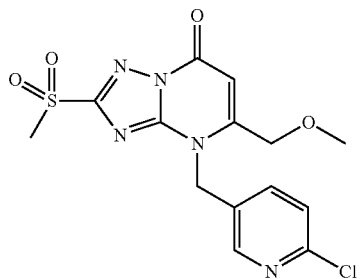 [SMILES: COCc1cc(=O)n2nc(S(C)(=O)=O)nc2n1Cc1ccc(Cl)nc1] |
| 193 | 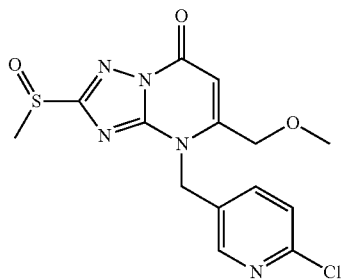 |
| 194 | 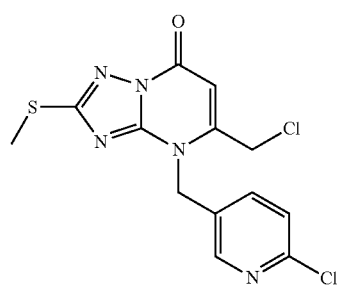 |
| Compound No. | Structure |
|---|---|
| 195 | 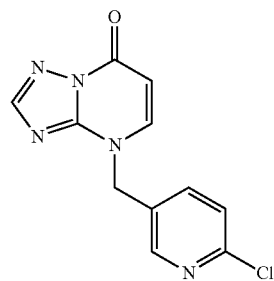 |
| 196 | 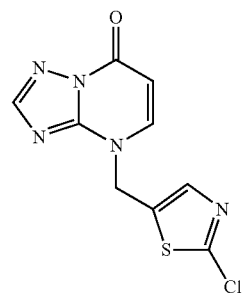 [SMILES: O=c1ccn(Cc2cnc(Cl)s2)c2ncnn12] |
| 197 | 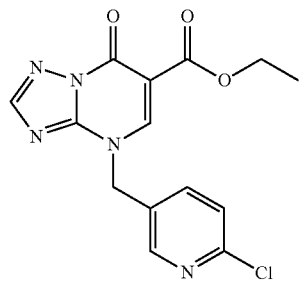 [SMILES: CCOC(=O)c1cn(Cc2ccc(Cl)nc2)c2ncnn2c1=O] |
| 198 | 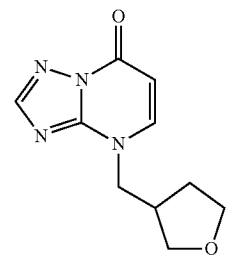 [SMILES: O=c1ccn(CC2CCOC2)c2ncnn12] |
| 199 | 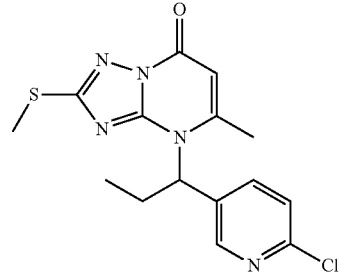 [SMILES: CCC(c1ccc(Cl)nc1)n1c(C)cc(=O)n2nc(SC)nc12] |

-continued
| Compound No. | Structure |
|---|---|
| 200 | 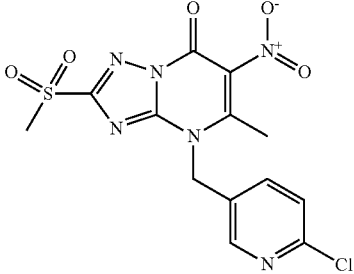 [SMILES: Cc1c([N+](=O)[O-])c(=O)n2nc(S(C)(=O)=O)nc2n1Cc1ccc(Cl)nc1] |
| 201 | 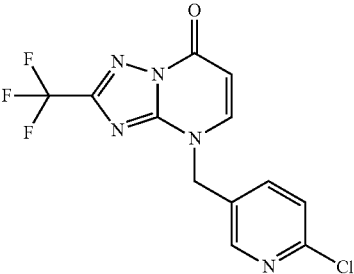 [SMILES: O=c1ccn(Cc2ccc(Cl)nc2)c2nc(C(F)(F)F)nn12] |
| 202 | 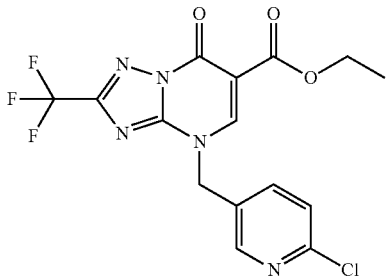 |
| 203 | 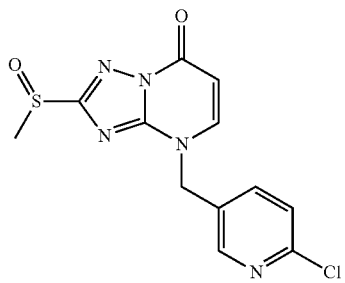 [SMILES: CS(=O)c1nc2n(Cc3ccc(Cl)nc3)ccc(=O)n2n1] |
| 204 | 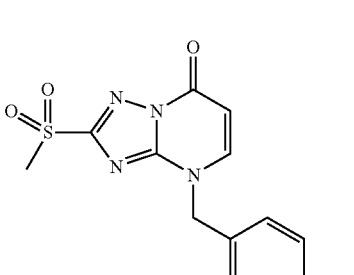 |
-continued
| Compound No. | Structure |
|---|---|
| 205 | 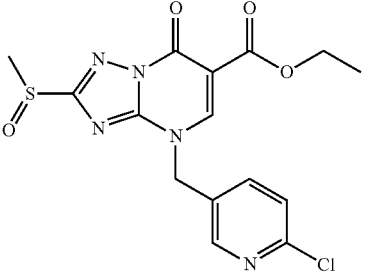 [SMILES: CCOC(=O)c1cn(Cc2ccc(Cl)nc2)c2nc(S(C)=O)nn2c1=O] |
| 206 | 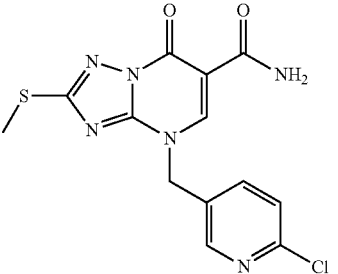 [SMILES: CSc1nc2n(Cc3ccc(Cl)nc3)cc(C(N)=O)c(=O)n2n1] |
| 207 | 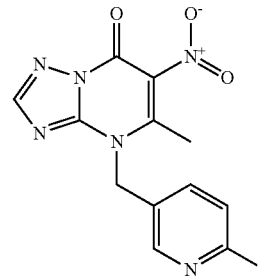 |
| 208 | 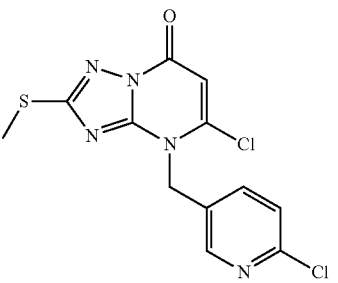 [SMILES: CSc1nc2n(Cc3ccc(Cl)nc3)c(Cl)cc(=O)n2n1] |
| 209 | 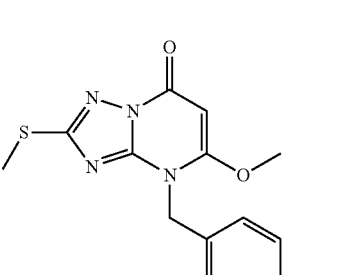 |

| Compound No. | Structure |
|---|---|
| 210 | 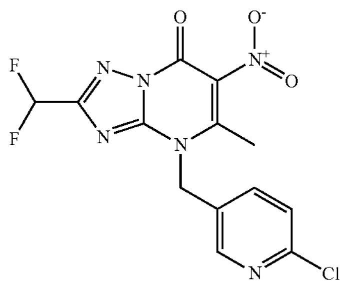 [SMILES: Cc1c([N+](=O)[O-])c(=O)n2nc(C(F)F)nc2n1Cc1ccc(Cl)nc1] |
| 211 | 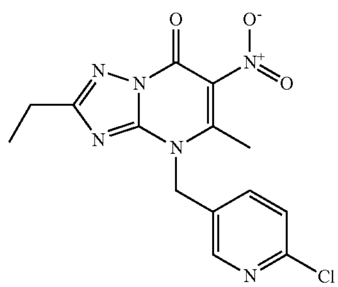 [SMILES: CCc1nc2n(Cc3ccc(Cl)nc3)c(C)c([N+](=O)[O-])c(=O)n2n1] |
| 212 | 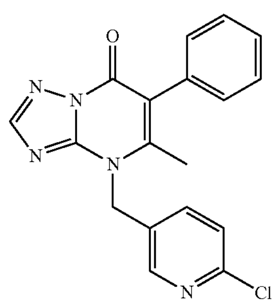 [SMILES: Cc1c(-c2ccccc2)c(=O)n2ncnc2n1Cc1ccc(Cl)nc1] |
| 213 | 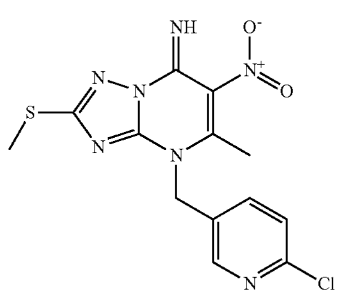 [SMILES: CSc1nc2n(Cc3ccc(Cl)nc3)c(C)c([N+](=O)[O-])c(=N)n2n1] |
| 214 | 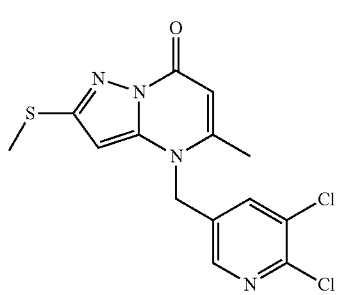 [SMILES: CSc1cc2n(Cc3cnc(Cl)c(Cl)c3)c(C)cc(=O)n2n1] |

| Compound No. | Structure |
|---|---|
| 215 | 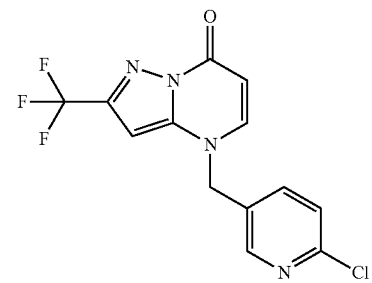 |
| 216 | 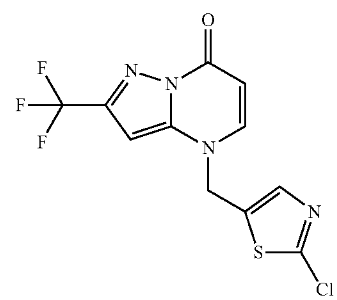 [SMILES: O=c1ccn(Cc2cnc(Cl)s2)c2cc(C(F)(F)F)nn12] |
| 217 | 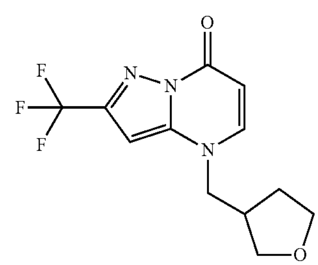 [SMILES: O=c1ccn(CC2CCOC2)c2cc(C(F)(F)F)nn12] |
| 218 | 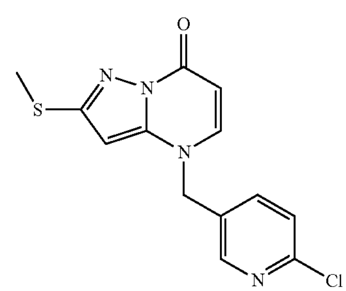 [SMILES: CSc1cc2n(Cc3ccc(Cl)nc3)ccc(=O)n2n1] |
| 219 | 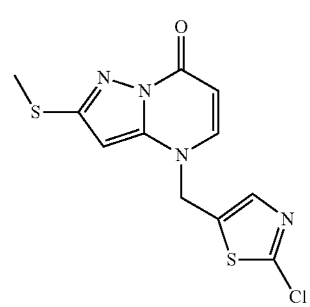 [SMILES: CSc1cc2n(Cc3cnc(Cl)s3)ccc(=O)n2n1] |

| Compound No. | Structure |
|---|---|
| 220 | ethyl 2-(methylthio)-7-oxo-4-((6-chloropyridin-3-yl)methyl)-4,7-dihydropyrazolo[1,5-a]pyrimidine-6-carboxylate |
| 221 | ethyl 2-(methylthio)-7-oxo-4-((2-chlorothiazol-5-yl)methyl)-4,7-dihydropyrazolo[1,5-a]pyrimidine-6-carboxylate |
| 222 | ethyl 2-(trifluoromethyl)-7-oxo-4-((6-chloropyridin-3-yl)methyl)-4,7-dihydropyrazolo[1,5-a]pyrimidine-6-carboxylate |
| 223 | 2-(methylthio)-5-methyl-4-((6-methylpyridin-3-yl)methyl)-4H-pyrazolo[1,5-a]pyrimidin-7-one |
| 224 | 2-(methylthio)-5-methyl-4-((6-(trifluoromethyl)pyridin-3-yl)methyl)-4H-pyrazolo[1,5-a]pyrimidin-7-one |
| 225 | 2-ethyl-4-((6-chloropyridin-3-yl)methyl)-4H-pyrazolo[1,5-a]pyrimidin-7-one |
| 226 | 2-ethyl-4-((2-chlorothiazol-5-yl)methyl)-4H-pyrazolo[1,5-a]pyrimidin-7-one |
| 227 | ethyl 2-ethyl-7-oxo-4-((6-chloropyridin-3-yl)methyl)-4,7-dihydropyrazolo[1,5-a]pyrimidine-6-carboxylate |
| 228 | 2-(methylthio)-5-ethyl-4-((6-chloropyridin-3-yl)methyl)-4H-pyrazolo[1,5-a]pyrimidin-7-one |
| 229 | 2-(methylthio)-5-ethyl-4-((2-chlorothiazol-5-yl)methyl)-4H-pyrazolo[1,5-a]pyrimidin-7-one |

-continued
| Compound No. | Structure |
|---|---|
| 230 | 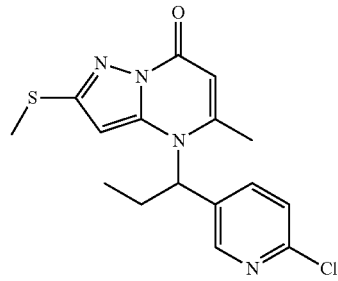 [SMILES: CCC(c1ccc(Cl)nc1)n1c(C)cc(=O)n2nc(SC)cc12] |
| 231 | 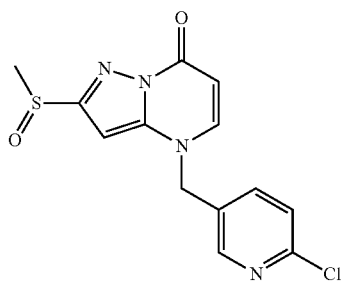 [SMILES: CS(=O)c1cc2n(Cc3ccc(Cl)nc3)ccc(=O)n2n1] |
| 232 | 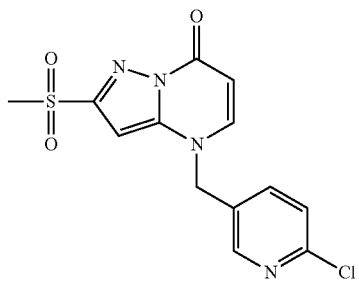 [SMILES: CS(=O)(=O)c1cc2n(Cc3ccc(Cl)nc3)ccc(=O)n2n1] |
| 233 | 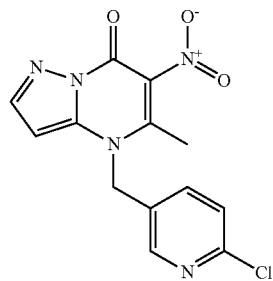 [SMILES: Cc1c([N+](=O)[O-])c(=O)n2nccc2n1Cc1ccc(Cl)nc1] |
| 234 | 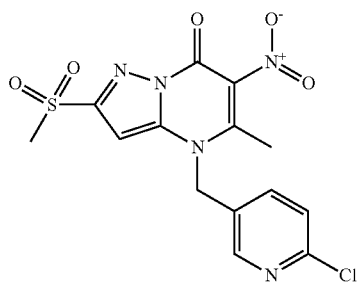 [SMILES: Cc1c([N+](=O)[O-])c(=O)n2nc(S(C)(=O)=O)cc2n1Cc1ccc(Cl)nc1] |
-continued
| Compound No. | Structure |
|---|---|
| 235 | 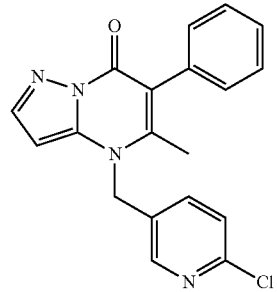 |
| 236 | 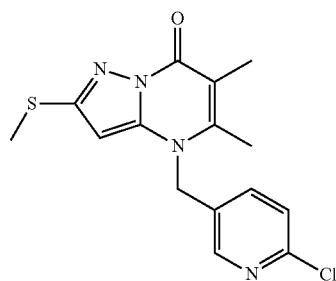 [SMILES: CSc1cc2n(Cc3ccc(Cl)nc3)c(C)c(C)c(=O)n2n1] |
| 237 | 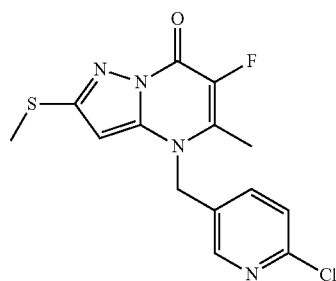 [SMILES: CSc1cc2n(Cc3ccc(Cl)nc3)c(C)c(F)c(=O)n2n1] |
| 238 | 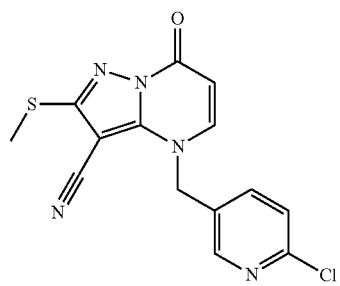 [SMILES: CSc1nn2c(=O)ccn(Cc3ccc(Cl)nc3)c2c1C#N] |
| 239 | 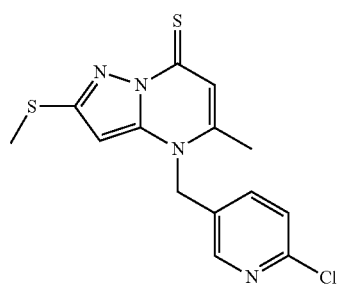 [SMILES: CSc1cc2n(Cc3ccc(Cl)nc3)c(C)cc(=S)n2n1] |

| Compound No. | Structure |
|---|---|
| 240 | (pyrazolo[1,5-a]pyrimidine with =N-OMe, 2-SMe, N-CH2-(6-chloropyridin-3-yl), 5-methyl) |
| 241 | (7-oxo-pyrazolo[1,5-a]pyrimidine, 2-CHF2, 5-methyl, N-CH2-(6-chloropyridin-3-yl)) |
| 242 | (7-oxo-pyrazolo[1,5-a]pyrimidine, 2-CF2CH3, 5-methyl, N-CH2-(6-chloropyridin-3-yl)) |
| 243 | (7-oxo-pyrazolo[1,5-a]pyrimidine, 2-SEt, 5-methyl, N-CH2-(6-chloropyridin-3-yl)) |
| 244 | (7-oxo-pyrazolo[1,5-a]pyrimidine, 2-S(O)Et, 5-methyl, N-CH2-(6-chloropyridin-3-yl)) |

| Compound No. | Structure |
|---|---|
| 245 | (7-oxo-pyrazolo[1,5-a]pyrimidine, 2-SO2Et, 5-methyl, N-CH2-(6-chloropyridin-3-yl)) |
| 246 | (7-oxo-pyrazolo[1,5-a]pyrimidine, 2-CF3, 5-methyl, N-CH2-(6-bromopyridin-3-yl)) |
| 247 | (7-oxo-pyrazolo[1,5-a]pyrimidine, 2-SEt, 5-methyl, N-CH2-(6-bromopyridin-3-yl)) |
| 248 | (7-oxo-pyrazolo[1,5-a]pyrimidine, 2-CF3, 5-methyl, N-CH2-(4,6-dichloropyridin-3-yl)) |
| 249 | (7-oxo-pyrazolo[1,5-a]pyrimidine, 2-SEt, 5-methyl, N-CH2-(4,6-dichloropyridin-3-yl)) |

| Compound No. | Structure |
|---|---|
| 250 | 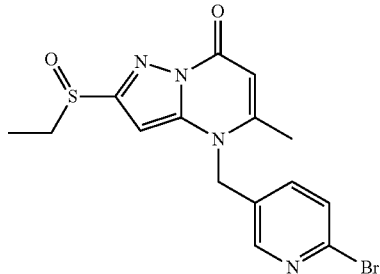 [SMILES: CCS(=O)c1cc2n(Cc3ccc(Br)nc3)c(C)cc(=O)n2n1] |
| 251 | 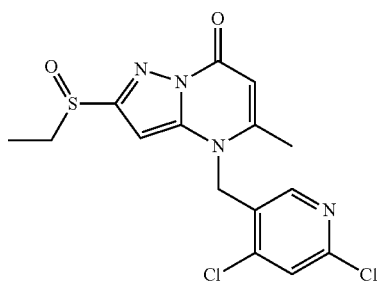 [SMILES: CCS(=O)c1cc2n(Cc3cnc(Cl)cc3Cl)c(C)cc(=O)n2n1] |
| 252 | 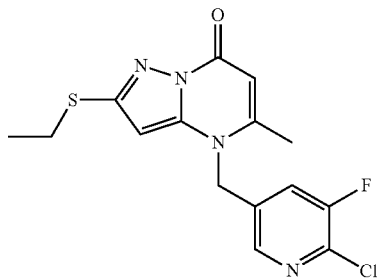 |
| 253 | 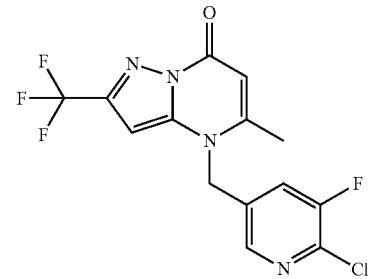 [SMILES: Cc1cc(=O)n2nc(C(F)(F)F)cc2n1Cc1cnc(Cl)c(F)c1] |
| 254 | 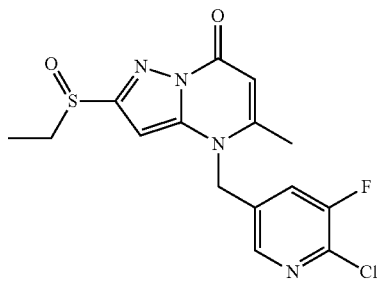 [SMILES: CCS(=O)c1cc2n(Cc3cnc(Cl)c(F)c3)c(C)cc(=O)n2n1] |
| Compound No. | Structure |
|---|---|
| 255 | 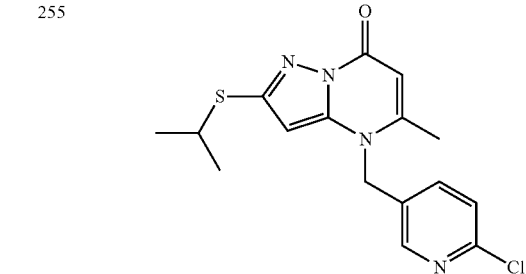 |
| 256 | 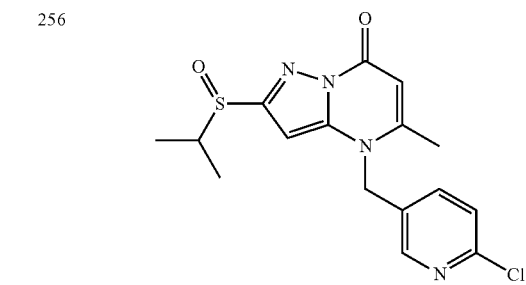 |
| 257 | 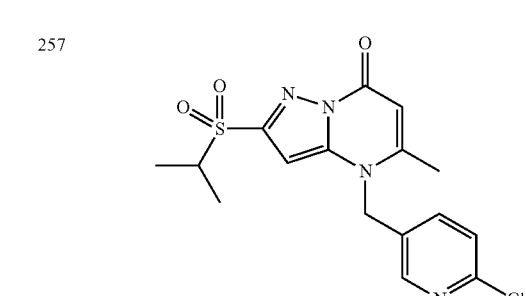 |
| 258 | 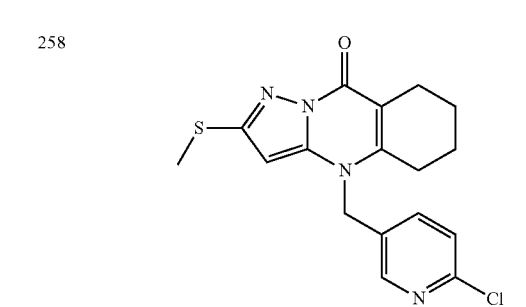 |
| 259 | 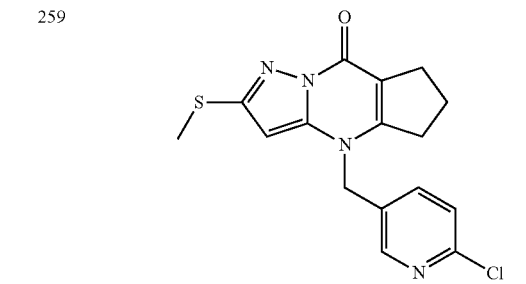 |

| Compound No. | Structure |
|---|---|
| 260 | (ethylsulfonyl-pyrazolopyrimidinone, N-CH2-6-bromopyridin-3-yl, 5-methyl) |
| 261 | (ethylsulfonyl-pyrazolopyrimidinone, N-CH2-5-fluoro-6-chloropyridin-3-yl, 5-methyl) |
| 262 | (ethylsulfonyl-pyrazolopyrimidinone, N-CH2-4,6-dichloropyridin-3-yl, 5-methyl) |
| 263 | (propylthio-pyrazolopyrimidinone, N-CH2-6-chloropyridin-3-yl, 5-methyl) |
| 264 | (methylsulfinyl-cyclopenta-fused pyrazolopyrimidinone, N-CH2-6-chloropyridin-3-yl) |

| Compound No. | Structure |
|---|---|
| 265 | (methylsulfonyl-cyclopenta-fused pyrazolopyrimidinone, N-CH2-6-chloropyridin-3-yl) |
| 266 | (propylsulfinyl-pyrazolopyrimidinone, N-CH2-6-chloropyridin-3-yl, 5-methyl) |
| 267 | (propylsulfonyl-pyrazolopyrimidinone, N-CH2-6-chloropyridin-3-yl, 5-methyl) |
| 268 | (nitro-tetrazolopyrimidinone, N-CH2-6-chloropyridin-3-yl, 5-methyl) |
| 269 | (difluoromethoxy-triazolopyrimidinone, N-CH2-6-chloropyridin-3-yl, 5-methyl) |

| Compound No. | Structure |
|---|---|
| 270 | 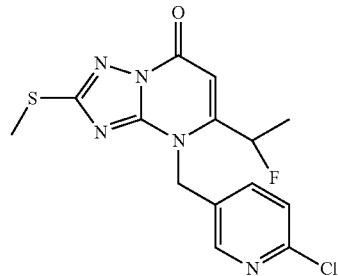 [SMILES: CSc1nc2n(Cc3ccc(Cl)nc3)c(C(C)F)cc(=O)n2n1] |
| 271 | 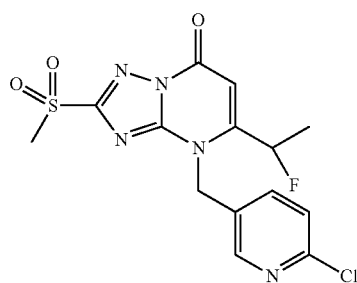 [SMILES: CC(F)c1cc(=O)n2nc(S(C)(=O)=O)nc2n1Cc1ccc(Cl)nc1] |
| 272 | 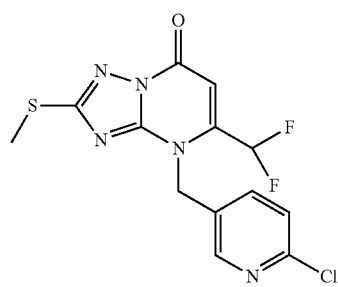 |
| 273 | 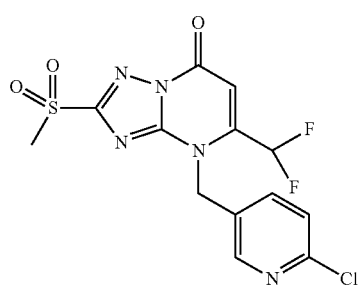 [SMILES: CS(=O)(=O)c1nc2n(Cc3ccc(Cl)nc3)c(C(F)F)cc(=O)n2n1] |
| 274 | 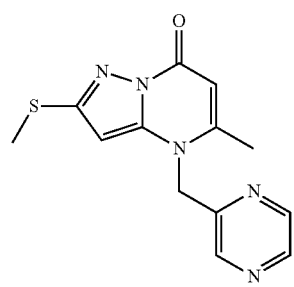 [SMILES: CSc1cc2n(Cc3cnccn3)c(C)cc(=O)n2n1] |
| Compound No. | Structure |
|---|---|
| 275 | 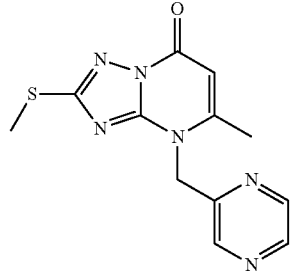 |
| 276 | 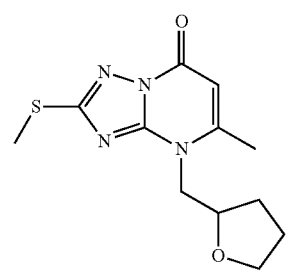 [SMILES: CSc1nc2n(CC3CCCO3)c(C)cc(=O)n2n1] |
| 277 | 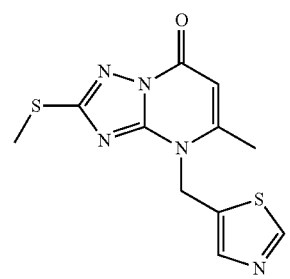 [SMILES: CSc1nc2n(Cc3cncs3)c(C)cc(=O)n2n1] |
| 278 | 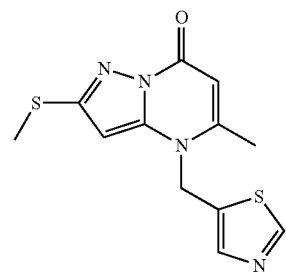 [SMILES: CSc1cc2n(Cc3cncs3)c(C)cc(=O)n2n1] |
| 279 | 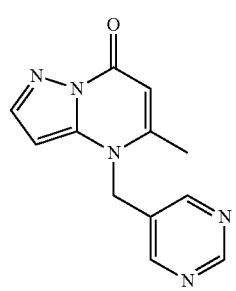 [SMILES: Cc1cc(=O)n2nccc2n1Cc1cncnc1] |

| Compound No. | Structure |
|---|---|
| 280 | 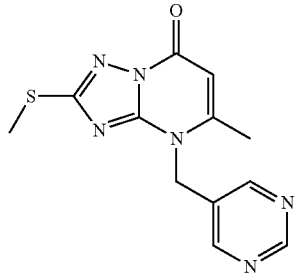 [SMILES: CSc1nc2n(Cc3cncnc3)c(C)cc(=O)n2n1] |
| 281 | 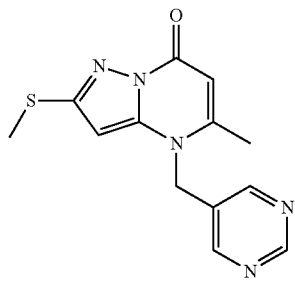 [SMILES: CSc1cc2n(Cc3cncnc3)c(C)cc(=O)n2n1] |
| 282 | 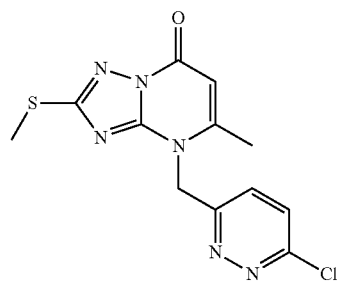 [SMILES: CSc1nc2n(Cc3ccc(Cl)nn3)c(C)cc(=O)n2n1] |
| 283 | 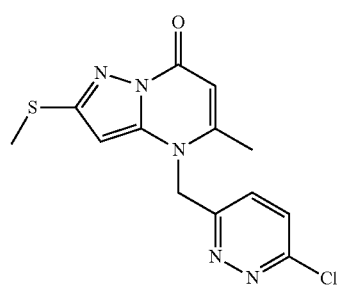 |
| 284 | 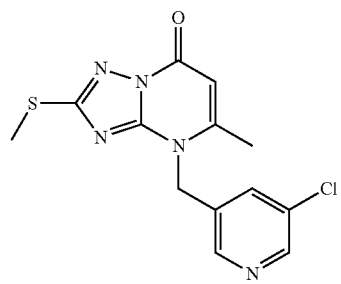 [SMILES: CSc1nc2n(Cc3cncc(Cl)c3)c(C)cc(=O)n2n1] |
| Compound No. | Structure |
|---|---|
| 285 | 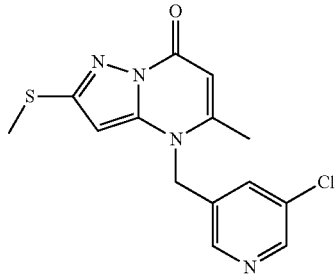 [SMILES: CSc1cc2n(Cc3cncc(Cl)c3)c(C)cc(=O)n2n1] |
| 286 | 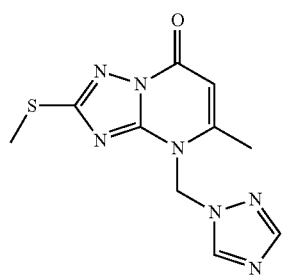 [SMILES: CSc1nc2n(Cn3cncn3)c(C)cc(=O)n2n1] |
| 287 | 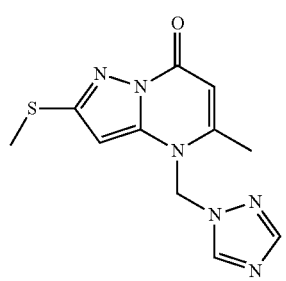 [SMILES: CSc1cc2n(Cn3cncn3)c(C)cc(=O)n2n1] |
| 288 | 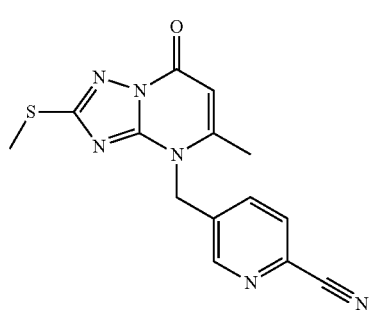 [SMILES: CSc1nc2n(Cc3ccc(C#N)nc3)c(C)cc(=O)n2n1] |
| 289 | 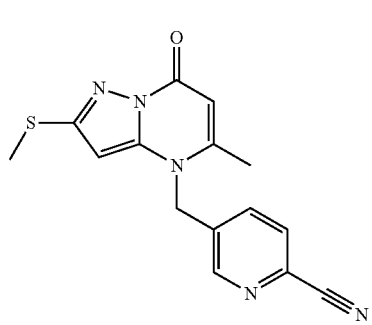 [SMILES: CSc1cc2n(Cc3ccc(C#N)nc3)c(C)cc(=O)n2n1] |

| Compound No. | Structure |
|---|---|
| 290 | 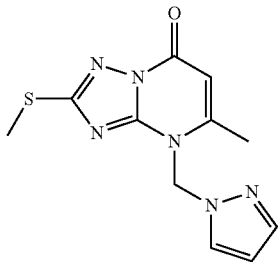 [SMILES: CSc1nc2n(Cn3cccn3)c(C)cc(=O)n2n1] |
| 291 | 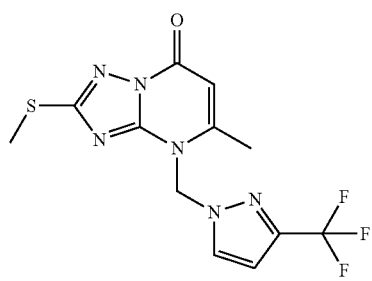 [SMILES: CSc1nc2n(Cn3ccc(C(F)(F)F)n3)c(C)cc(=O)n2n1] |
| 292 | 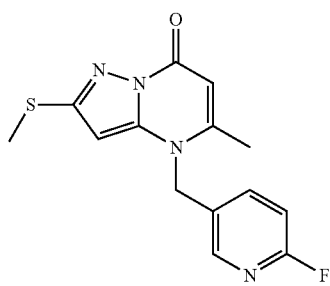 [SMILES: CSc1cc2n(Cc3ccc(F)nc3)c(C)cc(=O)n2n1] |
| 293 | 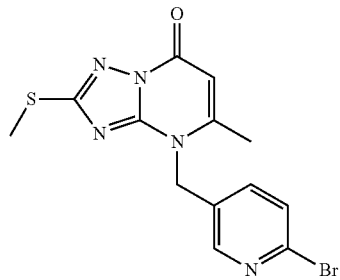 [SMILES: CSc1nc2n(Cc3ccc(Br)nc3)c(C)cc(=O)n2n1] |
| 294 | 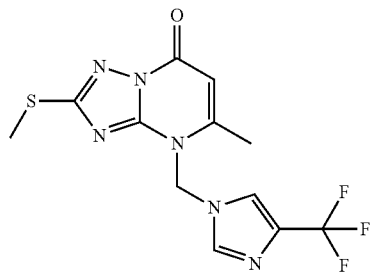 [SMILES: CSc1nc2n(Cn3cnc(C(F)(F)F)c3)c(C)cc(=O)n2n1] |
| Compound No. | Structure |
|---|---|
| 295 | 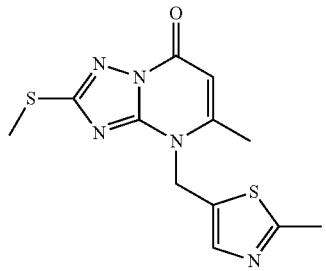 |
| 296 | 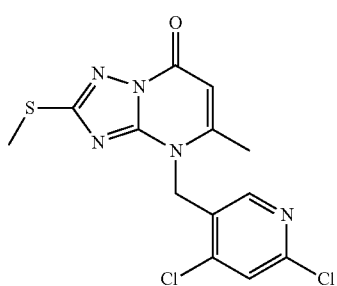 [SMILES: CSc1nc2n(Cc3cnc(Cl)cc3Cl)c(C)cc(=O)n2n1] |
| 297 | 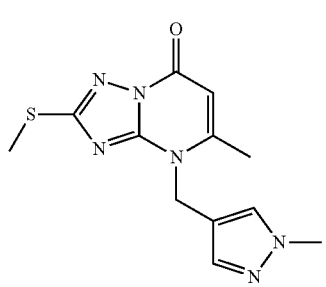 |
| 298 | 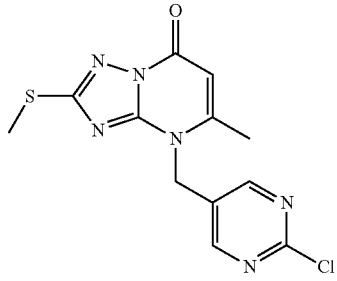 [SMILES: CSc1nc2n(Cc3cnc(Cl)nc3)c(C)cc(=O)n2n1] |
| 299 | 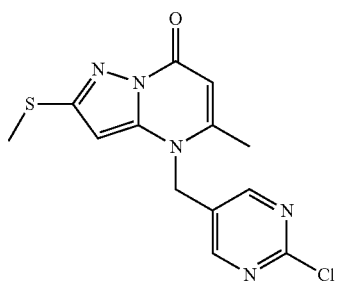 [SMILES: CSc1cc2n(Cc3cnc(Cl)nc3)c(C)cc(=O)n2n1] |

| Compound No. | Structure |
|---|---|
| 300 | 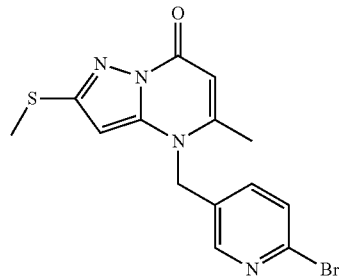 [SMILES: CSc1cc2n(Cc3ccc(Br)nc3)c(C)cc(=O)n2n1] |
| 301 | 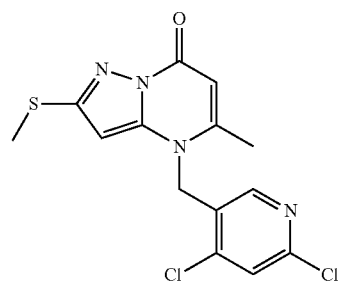 [SMILES: CSc1cc2n(Cc3cnc(Cl)cc3Cl)c(C)cc(=O)n2n1] |
| 302 | 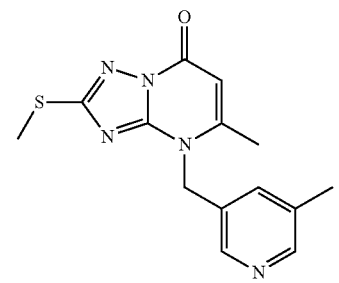 |
| 303 | 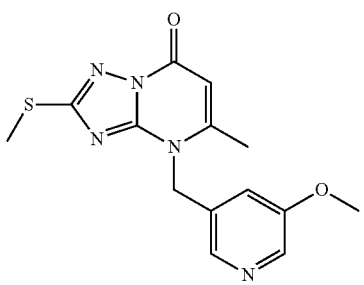 |
| 304 | 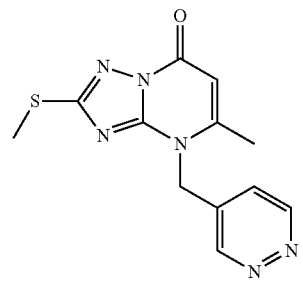 [SMILES: CSc1nc2n(Cc3ccnnc3)c(C)cc(=O)n2n1] |
| Compound No. | Structure |
|---|---|
| 305 | 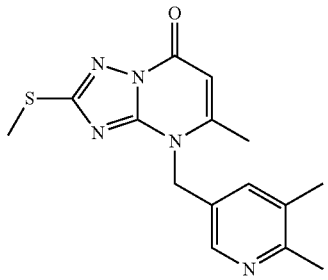 |
| 306 | 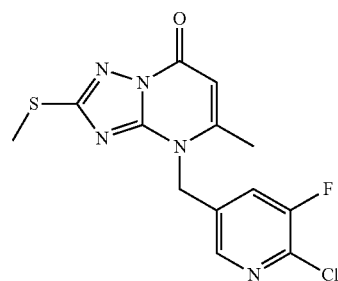 |
| 307 | 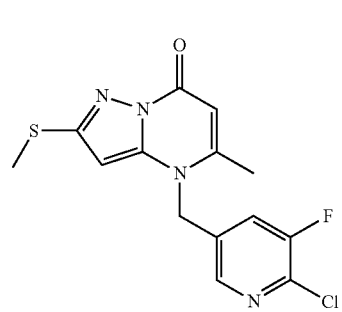 [SMILES: CSc1cc2n(Cc3cnc(Cl)c(F)c3)c(C)cc(=O)n2n1] |
| 308 | 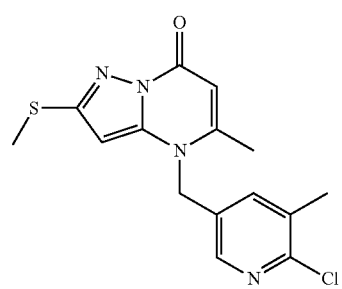 [SMILES: CSc1cc2n(Cc3cnc(Cl)c(C)c3)c(C)cc(=O)n2n1] |
| 309 | 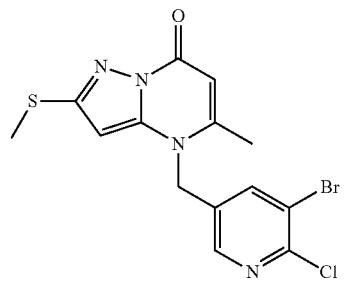 [SMILES: CSc1cc2n(Cc3cnc(Cl)c(Br)c3)c(C)cc(=O)n2n1] |

| Compound No. | Structure |
|---|---|
| 310 | 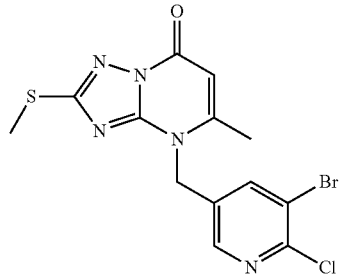 [SMILES: CSc1nc2n(Cc3cnc(Cl)c(Br)c3)c(C)cc(=O)n2n1] |
| 311 | 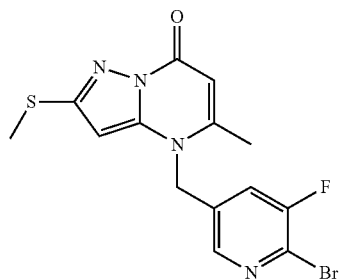 [SMILES: CSc1cc2n(Cc3cnc(Br)c(F)c3)c(C)cc(=O)n2n1] |
| 312 | 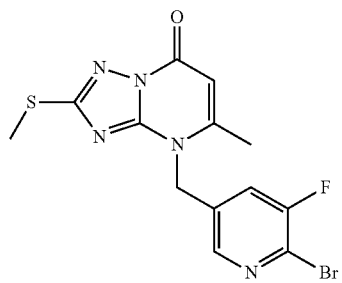 [SMILES: CSc1nc2n(Cc3cnc(Br)c(F)c3)c(C)cc(=O)n2n1] |
| 313 | 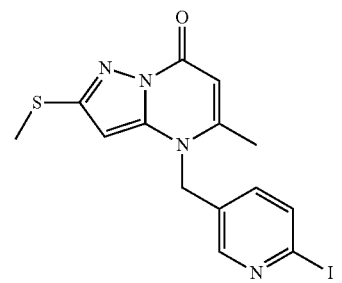 [SMILES: CSc1cc2n(Cc3ccc(I)nc3)c(C)cc(=O)n2n1] |
| 314 | 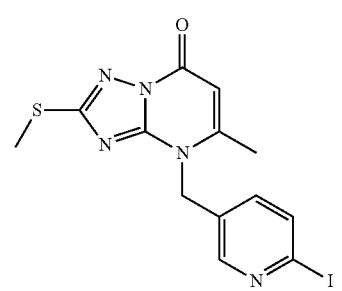 [SMILES: CSc1nc2n(Cc3ccc(I)nc3)c(C)cc(=O)n2n1] |
| Compound No. | Structure |
|---|---|
| 315 | 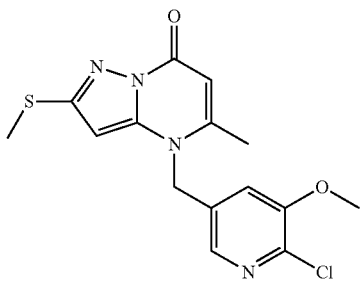 |
| 316 | 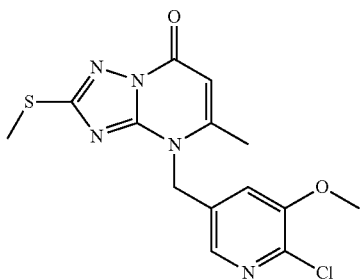 |
| 317 | 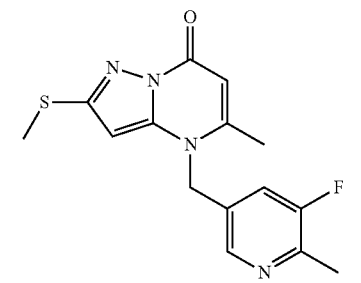 [SMILES: CSc1cc2n(Cc3cnc(C)c(F)c3)c(C)cc(=O)n2n1] |
| 318 | 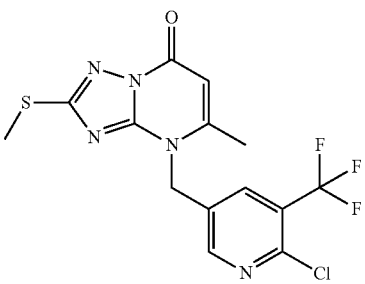 [SMILES: CSc1nc2n(Cc3cnc(Cl)c(C(F)(F)F)c3)c(C)cc(=O)n2n1] |
| 319 | 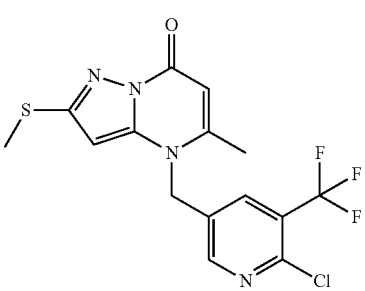 [SMILES: CSc1cc2n(Cc3cnc(Cl)c(C(F)(F)F)c3)c(C)cc(=O)n2n1] |

| Compound No. | Structure |
|---|---|
| 320 | 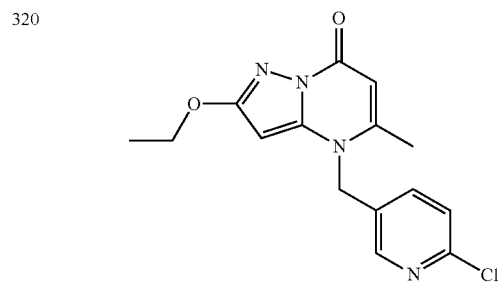 |
| 321 | 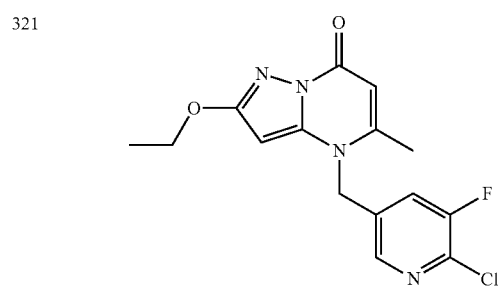 |
| 322 | 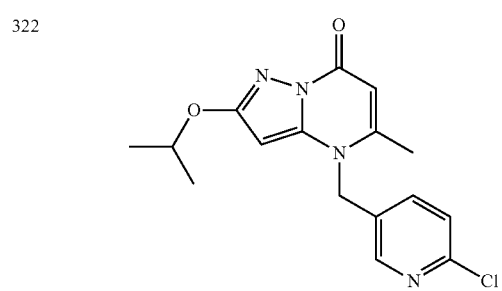 |
| 323 | 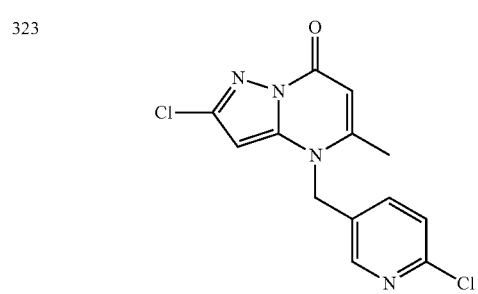 |
| 324 | 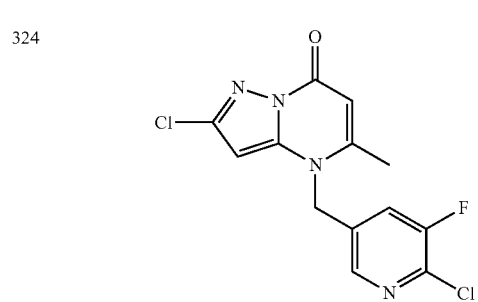 |
| Compound No. | Structure |
|---|---|
| 325 | 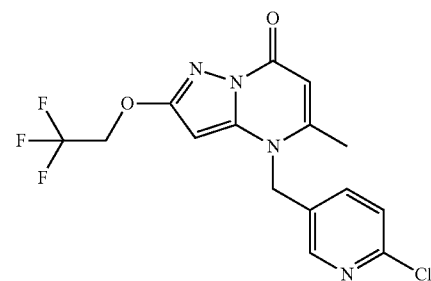 [SMILES: Cc1cc(=O)n2nc(OCC(F)(F)F)cc2n1Cc1ccc(Cl)nc1] |
| 326 | 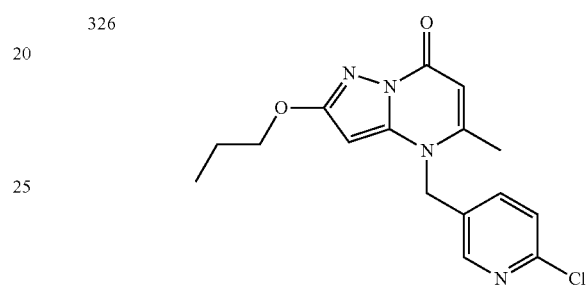 |
| 327 | 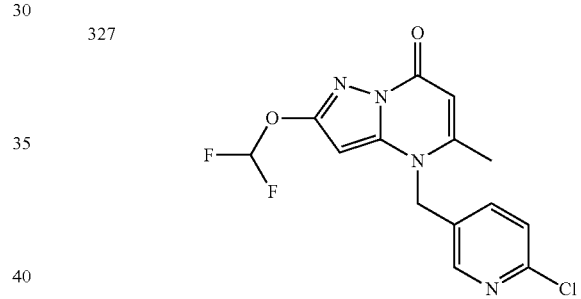 |
| 328 | 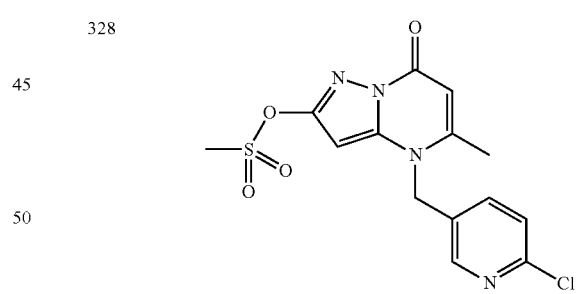 |
| 329 | 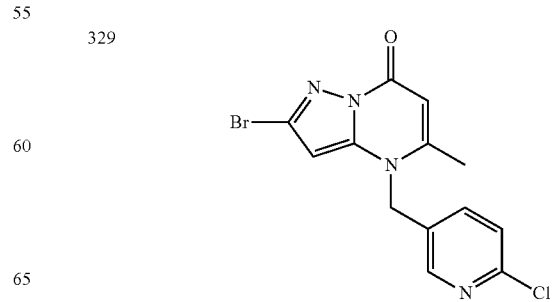 |

| Compound No. | Structure |
|---|---|
| 330 | 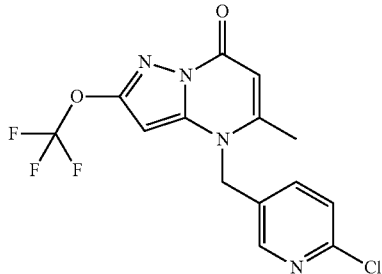 [SMILES: Cc1cc(=O)n2nc(OC(F)(F)F)cc2n1Cc1ccc(Cl)nc1] |
| 331 | 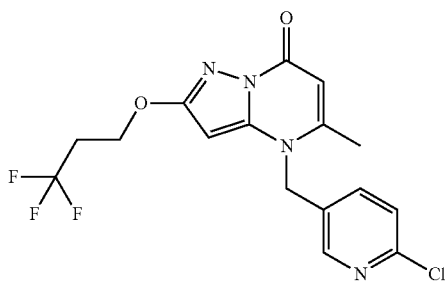 [SMILES: Cc1cc(=O)n2nc(OCCC(F)(F)F)cc2n1Cc1ccc(Cl)nc1] |
| 332 | 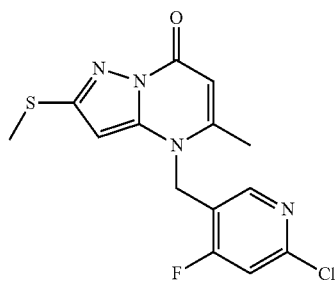 [SMILES: CSc1cc2n(Cc3cnc(Cl)cc3F)c(C)cc(=O)n2n1] |
| 333 | 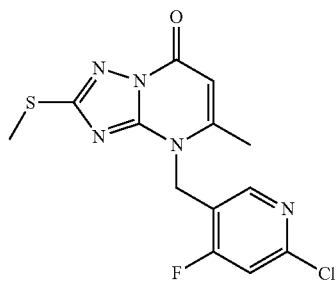 [SMILES: CSc1nc2n(Cc3cnc(Cl)cc3F)c(C)cc(=O)n2n1] |
| 334 | 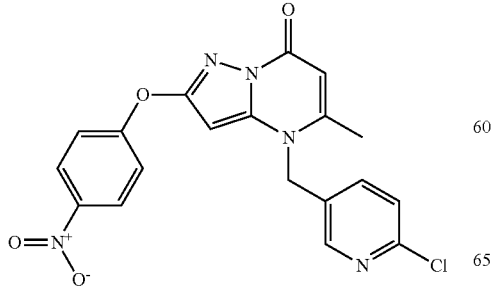 |
| Compound No. | Structure |
|---|---|
| 335 | 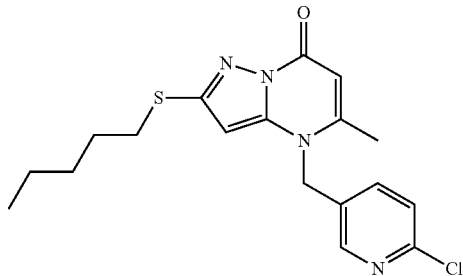 [SMILES: CCCCCSc1cc2n(Cc3ccc(Cl)nc3)c(C)cc(=O)n2n1] |
| 336 | 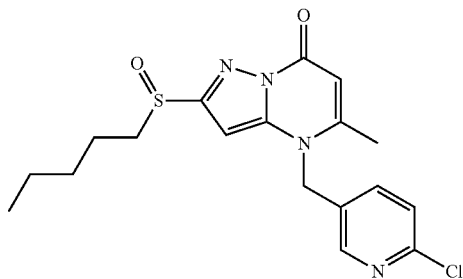 [SMILES: CCCCCS(=O)c1cc2n(Cc3ccc(Cl)nc3)c(C)cc(=O)n2n1] |
| 337 | 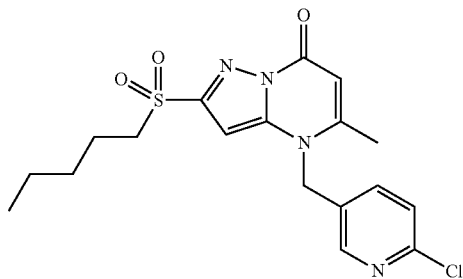 [SMILES: CCCCCS(=O)(=O)c1cc2n(Cc3ccc(Cl)nc3)c(C)cc(=O)n2n1] |
| 338 | 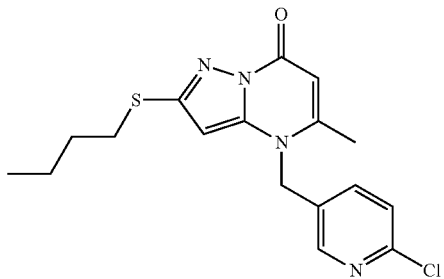 [SMILES: CCCCSc1cc2n(Cc3ccc(Cl)nc3)c(C)cc(=O)n2n1] |
| 339 | 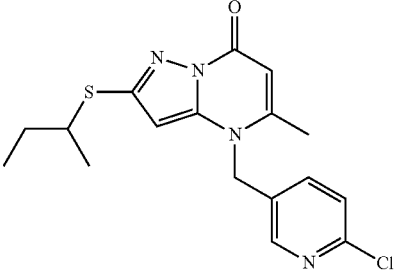 [SMILES: CCC(C)Sc1cc2n(Cc3ccc(Cl)nc3)c(C)cc(=O)n2n1] |

| Compound No. | Structure |
|---|---|
| 340 | 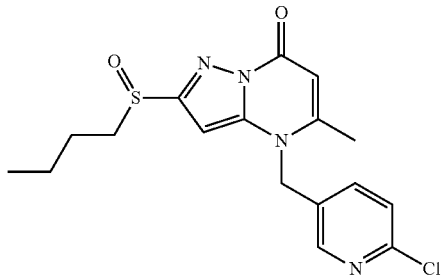 [SMILES: CCCCS(=O)c1cc2n(Cc3ccc(Cl)nc3)c(C)cc(=O)n2n1] |
| 341 | 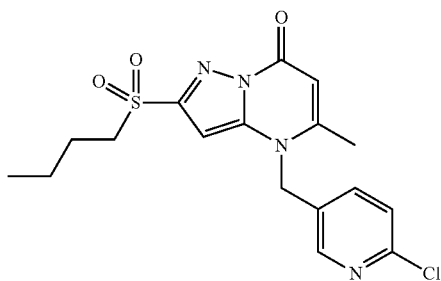 [SMILES: CCCCS(=O)(=O)c1cc2n(Cc3ccc(Cl)nc3)c(C)cc(=O)n2n1] |
| 342 | 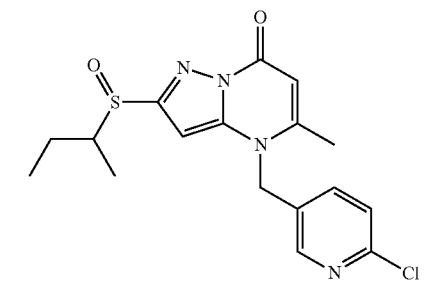 [SMILES: CCC(C)S(=O)c1cc2n(Cc3ccc(Cl)nc3)c(C)cc(=O)n2n1] |
| 343 | 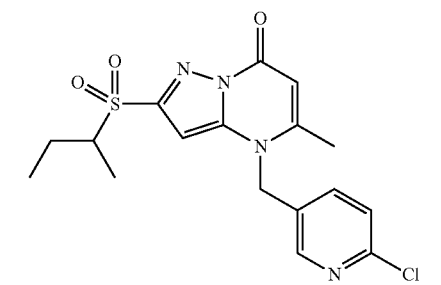 [SMILES: CCC(C)S(=O)(=O)c1cc2n(Cc3ccc(Cl)nc3)c(C)cc(=O)n2n1] |
| 344 | 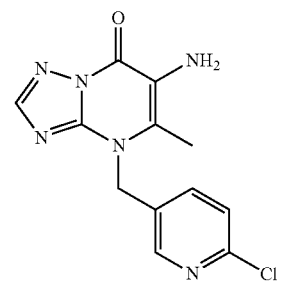 [SMILES: Cc1c(N)c(=O)n2ncnc2n1Cc1ccc(Cl)nc1] |
| Compound No. | Structure |
|---|---|
| 345 | 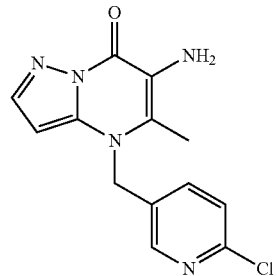 [SMILES: Cc1c(N)c(=O)n2nccc2n1Cc1ccc(Cl)nc1] |
| 346 | 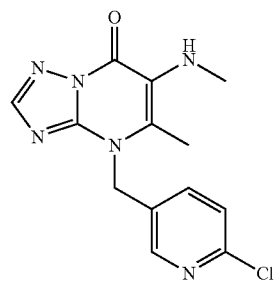 [SMILES: CNc1c(C)n(Cc2ccc(Cl)nc2)c2ncnn2c1=O] |
| 347 | 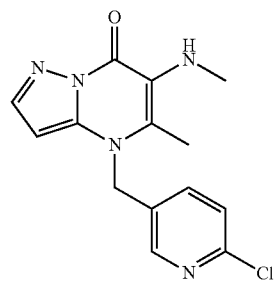 [SMILES: CNc1c(C)n(Cc2ccc(Cl)nc2)c2ccnn2c1=O] |
| 348 | 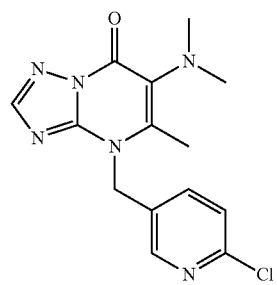 |
| 349 | 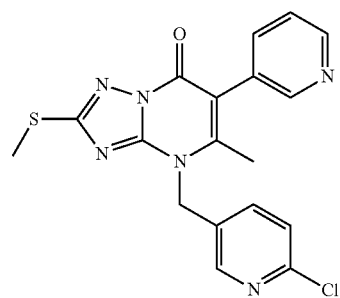 [SMILES: CSc1nc2n(Cc3ccc(Cl)nc3)c(C)c(-c3cccnc3)c(=O)n2n1] |

| Compound No. | Structure |
|---|---|
| 350 | 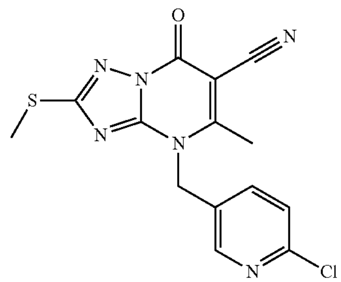 [SMILES: CSc1nc2n(Cc3ccc(Cl)nc3)c(C)c(C#N)c(=O)n2n1] |
| 351 | 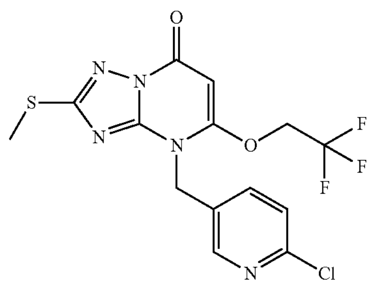 [SMILES: CSc1nc2n(Cc3ccc(Cl)nc3)c(OCC(F)(F)F)cc(=O)n2n1] |
| 352 | 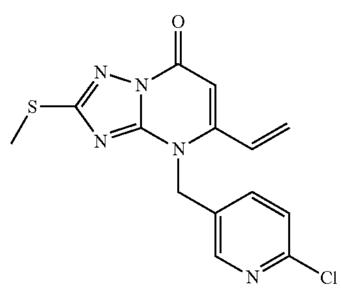 [SMILES: C=Cc1cc(=O)n2nc(SC)nc2n1Cc1ccc(Cl)nc1] |
| 353 | 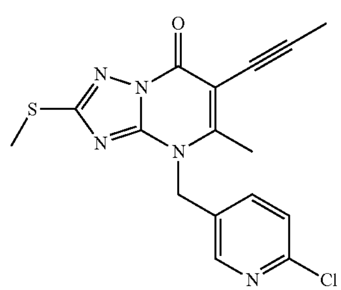 [SMILES: CC#Cc1c(C)n(Cc2ccc(Cl)nc2)c2nc(SC)nn2c1=O] |
| 354 | 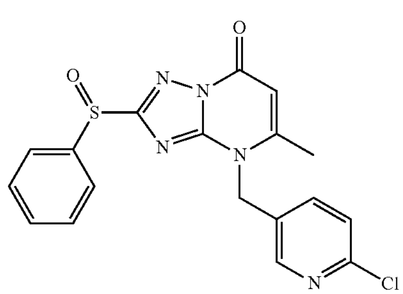 [SMILES: Cc1cc(=O)n2nc(S(=O)c3ccccc3)nc2n1Cc1ccc(Cl)nc1] |
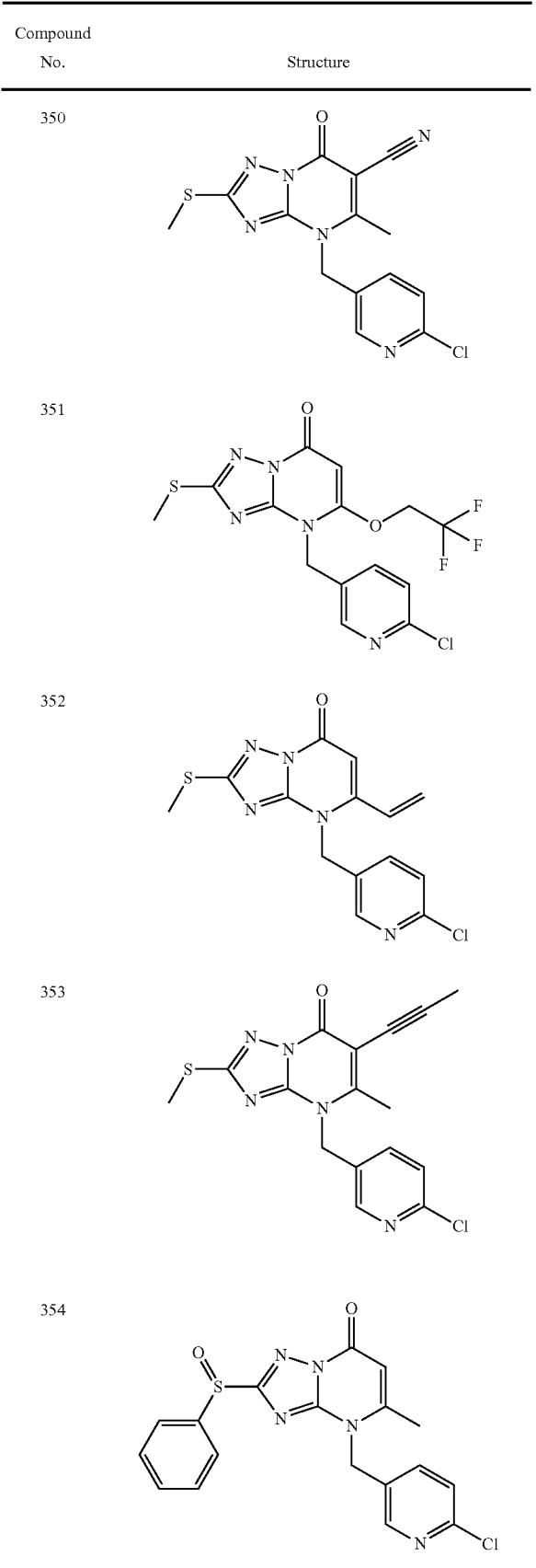
| Compound No. | Structure |
|---|---|
| 355 | |
| 356 | |
| 357 | |
| 358 | |
| 359 | |
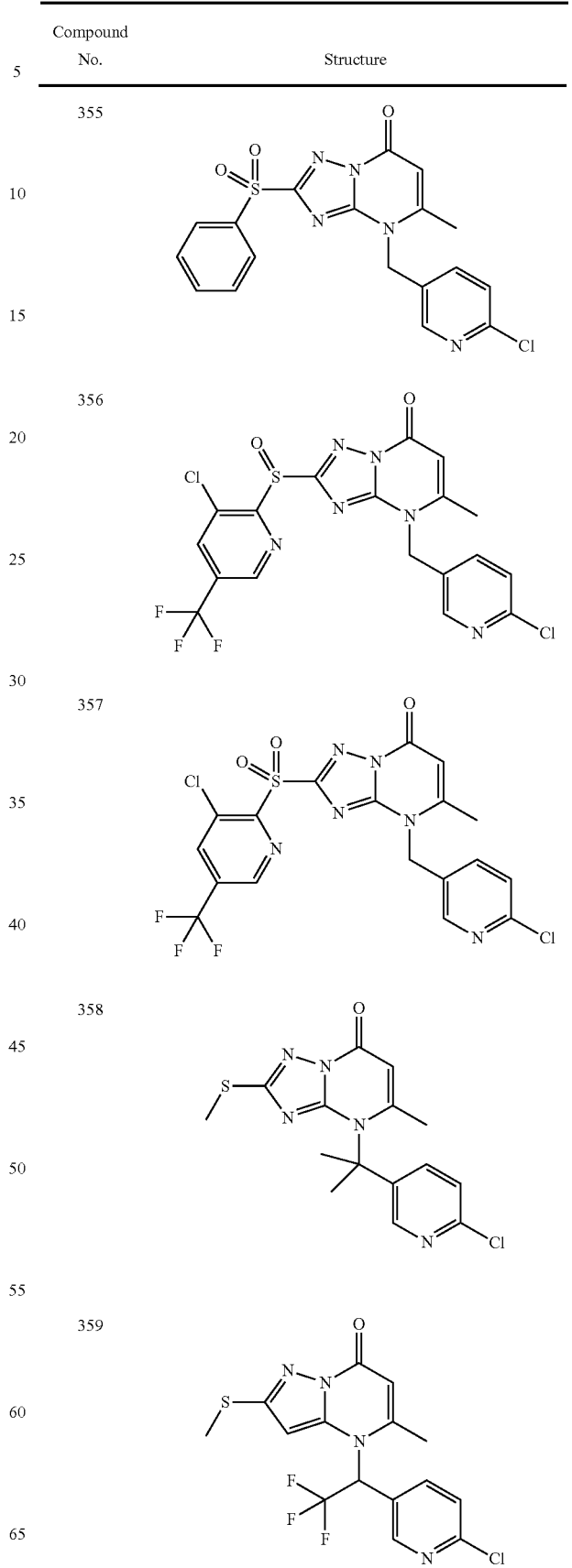

| Compound No. | Structure |
|---|---|
| 360 | (2-methylthio-pyrazolo[1,5-a]pyrimidin-7(4H)-one with N-substituent: CH(cyclopropyl)(6-chloropyridin-3-yl), 5-methyl) |
| 361 | (2-methylthio-[1,2,4]triazolo[1,5-a]pyrimidin-7(4H)-one with N-substituent: CH(CN)(6-chloropyridin-3-yl), 5-methyl) |
| 362 | (2-methylthio-[1,2,4]triazolo[1,5-a]pyrimidin-7(4H)-one with N-substituent: CH(NO₂)(6-chloropyridin-3-yl), 5-methyl) |
| 363 | (2-methylthio-[1,2,4]triazolo[1,5-a]pyrimidin-7(4H)-one with N-substituent: CH(F)(6-chloropyridin-3-yl), 5-methyl) |
| 364 | (2-methylthio-pyrazolo[1,5-a]pyrimidin-7(4H)-one with N-substituent: CH(OMe)(6-chloropyridin-3-yl), 5-methyl) |

| Compound No. | Structure |
|---|---|
| 365 | (2-methylthio-pyrazolo[1,5-a]pyrimidin-7(4H)-one with N-substituent: CH(SMe)(6-chloropyridin-3-yl), 5-methyl) |
| 366 | (2-methylsulfinyl-pyrazolo[1,5-a]pyrimidin-7(4H)-one with N-substituent: CH(S(O)Me)(6-chloropyridin-3-yl), 5-methyl) |
| 367 | (2-methylsulfonyl-pyrazolo[1,5-a]pyrimidin-7(4H)-one with N-substituent: CH(SO₂Me)(6-chloropyridin-3-yl), 5-methyl) |

Among the fused ring pyrimidine compounds represented by the above formula (I) of the invention, the compound in which X in the formula (I) is an oxygen atom (i.e., compound represented by formula (I-1) or formula (I-2)) can be produced by Method A, Method B, or Method C that are described below.

<Method A>

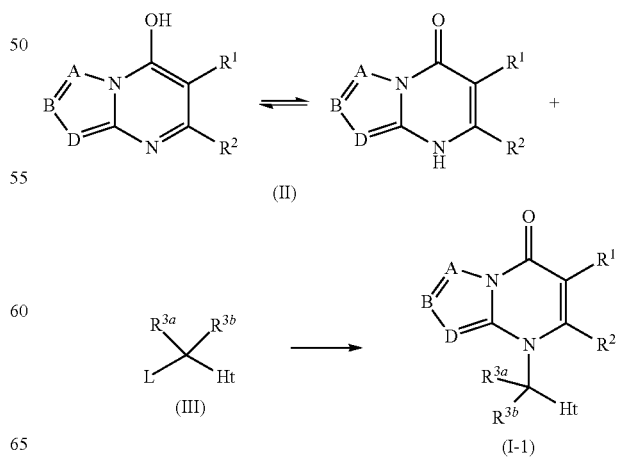

In formula (II), formula (III), and formula (I-1), A, B, D, $R^1$, $R^2$, $R^{3a}$, $R^{3b}$ and Ht have the same meanings as A, B, D, $R^1$, $R^2$, $R^{3a}$, $R^{3b}$ and Ht, respectively, of the above formula (I). L represents a leaving group.

In Method A of this embodiment, the "leaving group" represents any one of a halogen atom and an ester-based leaving group such as sulfonic acid ester, carbonic acid ester, phosphorus acid ester, or imide acid ester.

Method A is a method in which a structural isomer (II) of a hydroxy fused ring pyrimidine compound or a fused ring pyrimidin-7-one compound and the compound (III) having the leaving group L are reacted in the presence of a base to produce the fused ring pyrimidine compound (I-1) of the invention.

The use amount of the compound (III) is, relative to 1 mol of the compound (II), generally 1 mol to 10 mol and preferably 1 mol to 2 mol.

The base used for Method A is not particularly limited if it is a base generally used for a common reaction. Examples thereof include alkali metal carbonate such as sodium carbonate, potassium carbonate, or cesium carbonate; alkali metal hydrogen carbonate such as sodium hydrogen carbonate or potassium hydrogen carbonate; alkali metal hydride such as sodium hydride, lithium hydride, or potassium hydride; alkali metal hydroxide and alkali earth metal hydroxide such as sodium hydroxide, potassium hydroxide, or barium hydroxide; alkali metal alkoxide such as sodium methoxide, sodium ethoxide, or potassium t-butoxide; an organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO), or 1,8-diazabicyclo[5.4.0]-7-undecene (DBU); and organometals such as butyl lithium or lithium diisopropylamide. It is preferably alkali metal carbonate, and more preferably potassium carbonate or cesium carbonate.

The use amount of the base is, relative to 1 mol of the compound (II), generally 0.5 mol to 10 mol and preferably 0.5 mol to 5 mol.

The solvent used for Method A is not particularly limited if it does not inhibit the reaction. Examples thereof include a hydrocarbon solvent such as hexane, cyclohexane, benzene, or toluene; a halogenated hydrocarbon solvent such as dichloromethane, dichloroethane, chloroform, or tetrachloroethane; an ether solvent such as dioxane, diethyl ether, tetrahydrofuran (THF), or ethylene glycol dimethyl ether; an amide solvent such as N,N-dimethyl formamide (DMF), N,N-dimethylacetamide, or hexamethyl phosphoric acid triamide; a ketone solvent such as acetone, methyl ethyl ketone, methyl isobutyl ketone, or cyclohexanone; a nitrile solvent such as acetonitrile or isobutyronitrile; an ester solvent such as methyl acetate, ethyl acetate, or propyl acetate; and dimethyl sulfoxide (DMSO). Preferably, it is an amide solvent, and more preferably DMF.

The reaction temperature varies depending on a raw material compound, a reaction reagent, a solvent, or the like. However, it is generally −20° C. to 150° C. and preferably 0° C. to 100° C.

The reaction time varies depending on a raw material compound, a reaction reagent, a solvent, reaction temperature, or the like. However, it is generally 10 minutes to 120 hours and preferably 30 minutes to 24 hours.

The compound (II) as a starting material used for Method A is either a known compound or a compound which can be prepared according to a known method (for example, the method described in Journal of Medicinal Chemistry, Vol. 51, page 3649 (2008), International Publication No. 2011/041304 pamphlet, or Journal of Heterocyclic Chemistry, Vol. 37, page 1265 (2000)).

As for the compound (III) having the leaving group L, which is used for Method A, when the leaving group L is a halogen atom, a known compound can be used or it can be prepared by halogenation of the hydroxy group by a known method. When the leaving group L is an ester-based leaving group such as sulfonic acid ester, carbonic acid ester, phosphorus acid ester, or imide acid ester, it can be prepared by esterification of the hydroxy group by a known method.

<Method B>

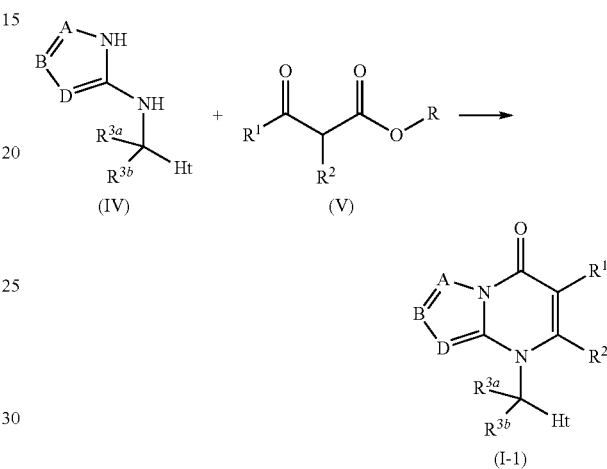

In formula (IV), formula (V), and formula (I-1), A, B, D, $R^1$, $R^2$, $R^{3a}$, $R^{3b}$ and Ht have the same meanings as A, B, D, $R^1$, $R^2$, $R^{3a}$, $R^{3b}$ and Ht, respectively, of the above formula (I). R represents an alkyl group having 1 to 6 carbon atoms.

Method B is a method in which the amine compound (IV) and the β-ketoester compound (V) are condensed by cyclization to produce the fused ring pyrimidine compound (I-1) of the invention. As for the condensation by cyclization, a method of condensation by cyclization according to heating in the presence of an acid can be mentioned.

The use amount of the compound (V) is, relative to 1 mol of the compound (IV), generally 1 mol to 10 mol and preferably 1 mol to 5 mol.

The acid used for this method is not particularly limited, if it is an acid generally used for a common reaction. Examples thereof include inorganic acid including hydrogen halide acid such as hydrogen fluoride acid, hydrogen chloride acid, hydrogen bromide acid, or hydrogen iodide acid, nitric acid, perchloric acid, sulfuric acid, or phosphoric acid; lower alkylsulfonic acid such as methane sulfonic acid, trifluoromethane sulfonic acid, and ethane sulfonic acid, arylsulfonic acid such as benzene sulfonic acid, or p-toluene sulfonic acid, and a salt of an organic acid such as formic acid, acetic acid, or oxalic acid. It is preferably hydrogen chloride acid, sulfuric acid, p-toluene sulfonic acid, or acetic acid, and more preferably p-toluene sulfonic acid or acetic acid.

The use amount of the acid is, relative to 1 mol of the compound (IV), generally 1 mol to 200 mol and preferably 1 mol to 50 mol.

The solvent used for this method is not particularly limited if it does not inhibit the reaction. Examples thereof include a hydrocarbon solvent such as hexane, cyclohexane, benzene, toluene, xylene, or mesitylene; a halogenated hydrocarbon solvent such as dichloromethane, chloroform, or carbon tetrachloride; an ether solvent such as dioxane, diethyl ether, tetrahydrofuran (THF), or dibutyl ether; and a nitrile solvent such as acetonitrile or propionitrile. When the acid is liquid, it is acceptable not to have any solvent. It is preferably toluene, xylene, or no solvent.

The reaction temperature varies depending on a raw material compound, a reaction reagent, a solvent, or the like, but it is generally 20° C. to 200° C. and preferably 50° C. to 150° C.

The reaction time varies depending on a raw material compound, a reaction reagent, a solvent, reaction temperature, or the like, but it is generally 1 hour to 120 hours and preferably 3 hours to 72 hours.

The amine compound (IV) as a starting material of Method B may be a known compound or for example, the amine compound (IV-1) produced by the following Method B-1 can be used.
(Method B-1)

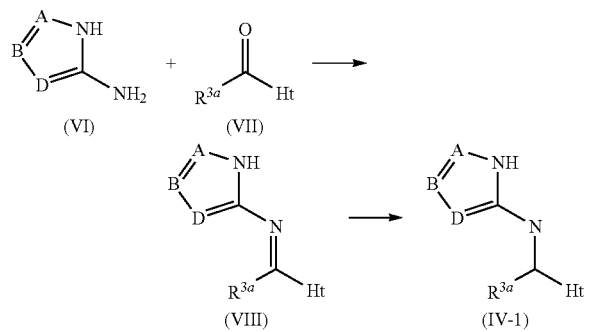

In formula (VI), formula (VII), formula (VIII), and formula (IV-1), A, B, D, $R^{3a}$ and Ht have the same meanings as A, B, D, $R^{3a}$ and Ht, respectively, of the above formula (I).

The imine compound (VIII) can be produced by reacting a known amine compound (VI) and a known heterocyclic carbonyl compound (VII). For example, a method of synthesizing an imine compound (VIII) by heating in a suitable solvent can be mentioned.

The solvent used for synthesizing the imine compound (VIII) is not particularly limited if it does not inhibit the reaction. Examples thereof include a hydrocarbon solvent such as hexane, cyclohexane, benzene, toluene, xylene, or mesitylene; a halogenated hydrocarbon solvent such as dichloromethane, chloroform, or carbon tetrachloride; an ether solvent such as dioxane, diethyl ether, tetrahydrofuran (THF), or dibutyl ether; and an alcohol solvent such as methanol or ethanol. It is also acceptable not to have any solvent. It is preferably methanol or ethanol.

The reaction temperature varies depending on a raw material compound, a reaction reagent, a solvent, or the like, but it is generally 0° C. to 150° C. and preferably 20° C. to 100° C.

The reaction time varies depending on a raw material compound, a reaction reagent, a solvent, reaction temperature, or the like, but it is generally 10 minutes to 60 hours and preferably 1 hour to 24 hours.

By reducing the imine compound (VIII), the amine compound (IV-1) can be synthesized.

As for the reducing agent, it is not particularly limited if it is used for a common reducing reaction. Examples thereof include borohydrides such as sodium borohydride, sodium cyanoborohydride, or sodium triacetate borohydride.

The use amount of the reducing agent is, relative to 1 mol of the imine compound (VIII), generally 0.5 mol to 5 mol and preferably 0.5 mol to 2 mol.

The solvent for the reducing reaction is not particularly limited if it does not inhibit the reducing reaction. Examples thereof include an alcohol solvent such as methanol or ethanol. It is preferably ethanol.

The reaction temperature varies depending on a raw material compound, a reaction reagent, a solvent, or the like, but it is generally −78° C. to 100° C. and preferably −50° C. to 50° C.

The reaction time varies depending on a raw material compound, a reaction reagent, a solvent, reaction temperature, or the like, but it is generally 10 minutes to 24 hours and preferably 30 minutes to 10 hours.

The β-ketoester compound (V) as a starting material of Method B may be either a known compound or can be prepared according to a known method.
<Method C>

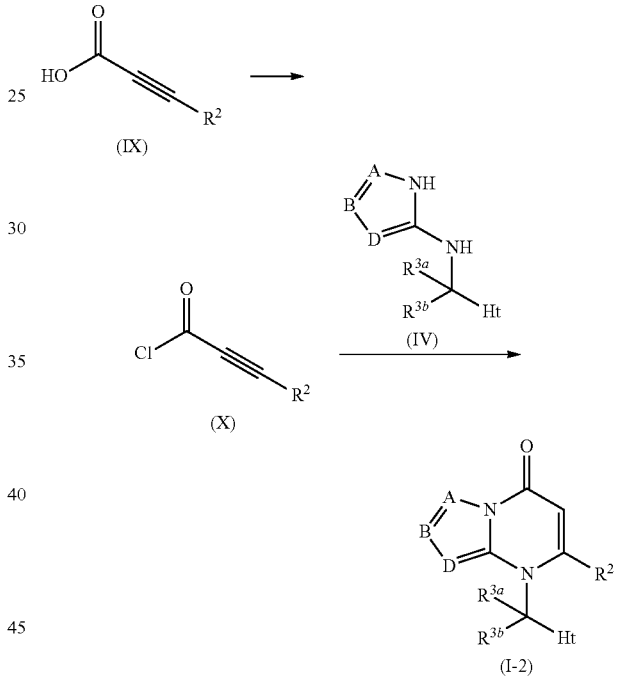

In formula (IX), formula (X), formula (IV) and formula (I-2), A, B, D, $R^2$, $R^{3a}$, $R^{3b}$ and Ht have the same meanings as A, B, $R^1$, $R^2$, $R^{3a}$, $R^{3b}$ and Ht, respectively, of the above formula (I).

Method C is a method of producing the fused ring pyrimidine compound (I-2) of the invention by reacting the acid chloride compound (X), which is prepared from the known carboxylic acid compound (IX) containing a triple bond by a known method (for example, the method described in Journal of Organic Chemistry, Vol. 46, page 2273 (1981)), and the amine compound (IV) as a starting material of Method B in the presence of a base.

The use amount of the compound (IX) is, relative to 1 mol of the imine compound (IV), generally 1 mol to 5 mol and preferably 1 mol to 2 mol.

The base used for this method is not particularly limited if it is a base generally used for a common reaction. Examples thereof include alkali metal carbonate such as sodium carbonate, potassium carbonate, or cesium carbonate; alkali metal hydrogen carbonate such as sodium hydrogen carbonate or potassium hydrogen carbonate; alkali metal hydride such as sodium hydride, lithium hydride, or potassium hydride; alkali metal hydroxide and alkali earth metal hydroxide such as sodium hydroxide, potassium hydroxide, or barium hydroxide; alkali metal alkoxide such as sodium methoxide, sodium ethoxide, or potassium t-butoxide; an organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO), or 1,8-diazabicyclo[5.4.0]-7-undecene (DBU); and organometals such as butyl lithium or lithium diisopropylamide. It is preferably alkali metal hydride, and more preferably sodium hydride.

The use amount of the base is, relative to 1 mol of the compound (IV), generally 1 mol to 10 mol and preferably 1 mol to 5 mol.

The solvent used for this method is not particularly limited if it does not inhibit the reaction. Examples thereof include a halogenated hydrocarbon solvent such as dichloromethane, dichloroethane, chloroform, or tetrachloroethane; an ether solvent such as dioxane, diethyl ether, tetrahydrofuran (THF), or ethylene glycol dimethyl ether; an amide solvent such as N,N-dimethyl formamide (DMF), N,N-dimethylacetamide, or hexamethyl phosphoric acid triamide; a ketone solvent such as acetone, methyl ethyl ketone, methyl isobutyl ketone, or cyclohexanone; a nitrile solvent such as acetonitrile or isobutyronitrile; an ester solvent such as methyl acetate, ethyl acetate, or propyl acetate; and dimethyl sulfoxide (DMSO). Preferably, it is DMF.

The reaction temperature varies depending on a raw material compound, a reaction reagent, a solvent, or the like, but it is generally 0° C. to 150° C. and preferably 0° C. to 50° C.

The reaction time varies depending on a raw material compound, a reaction reagent, a solvent, reaction temperature, or the like, but it is generally 15 minutes to 24 hours and preferably 1 hour to 8 hours.

The fused ring pyrimidine compound of the formula (I) in which X in formula (I) of the invention is a sulfur atom (i.e., compound represented by formula (I-3)) can be produced by Method D described below, for example.

<Method D>

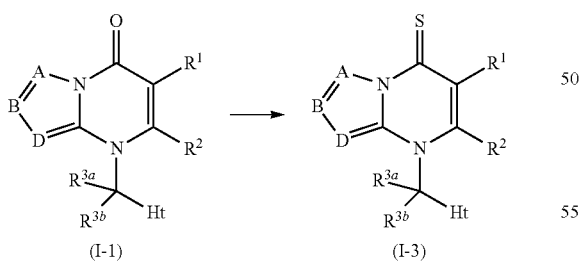

(I-1)    (I-3)

In formula (I-1) and formula (I-3), A, B, D, $R^1$, $R^2$, $R^{3a}$, $R^{3b}$ and Ht have the same meanings as A, B, D, $R^1$, $R^2$, $R^{3a}$, $R^{3b}$ and Ht, respectively, of the above formula (I).

Method D is a method of producing the fused ring pyrimidine compound (I-3) of the invention by reacting the fused ring pyrimidine compound (I-1) of the invention in the presence of a sulfurization agent.

The sulfurization agent used for this method is not particularly limited if it is commonly used as a sulfurization agent for converting an oxygen atom to a sulfur atom, and examples thereof include a Lawesson's Reagent. The use amount of the sulfurization agent is, relative to the compound (I-1), generally 0.5 mol to 5 mol and preferably 0.5 mol to 1 mol.

The solvent used for this method is not particularly limited if it does not inhibit the reaction. Examples thereof include a hydrocarbon solvent such as hexane, cyclohexane, benzene, toluene, xylene, or mesitylene; and an ether solvent such as dioxane, diethyl ether, tetrahydrofuran (THF), or dibutyl ether. It is preferably toluene or THF.

The reaction temperature varies depending on a raw material compound, a reaction reagent, a solvent, or the like, but it is generally 20° C. to 150° C. and preferably 50° C. to 120° C.

The reaction time varies depending on a raw material compound, a reaction reagent, a solvent, reaction temperature, or the like, but it is generally 10 minutes to 24 hours and preferably 10 minutes to 8 hours.

The fused ring pyrimidine compound of formula (I) in which X in the formula (I) of the invention is N—$R^7$ (i.e., compound represented by formula (I-4)) can be produced by Method E described below, for example.

<Method E>

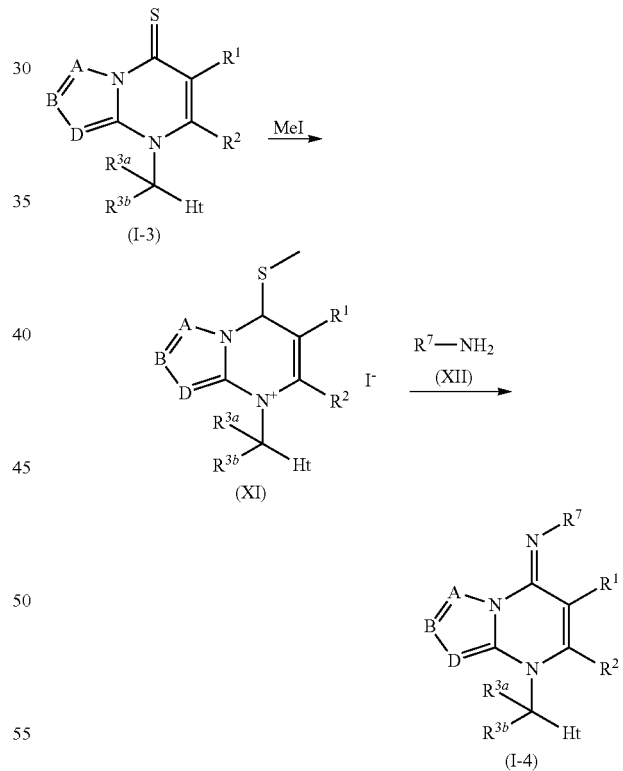

(I-3)

(XI)

(I-4)

In the above formula, A, B, D, $R^1$, $R^2$, $R^{3a}$, $R^{3b}$, $R^7$ and Ht have the same meanings as A, B, D, $R^1$, $R^2$, $R^{3a}$, $R^{3b}$, $R^7$ and Ht, respectively, of the above formula (I).

Method E is a method in which the compound (XI) is synthesized by reacting the fused ring pyrimidine compound (I-3) of the invention with methyl iodide (the first step) and subsequently the compound (XI) is reacted with the amine compound (XII) (the second step) to prepare the fused ring pyrimidine compound (I-4) of the invention.

According to the first step of this method, the compound (XI) can be prepared by reacting the fused ring pyrimidine compound (I-3) of the invention in the presence of a methylation agent.

The methylation agent used for the first step is not particularly limited it if is commonly used as a methylation agent. Examples thereof include methyl iodide, dimethyl sulfuric acid, and methyl trifluoromethane sulfonic acid. Use amount of the methylation agent is, relative to the compound (I-3), generally 0.5 mol to 5 mol and preferably 0.5 mol to 2 mol.

The solvent used for the first step is not particularly limited if it does not inhibit the reaction. Examples thereof include an ether solvent such as dioxane, diethyl ether, tetrahydrofuran (THF), or ethylene glycol dimethyl ether. It is preferably THF.

The reaction temperature varies depending on a raw material compound, a reaction reagent, a solvent, or the like, but it is generally 20° C. to 100° C. and preferably 20° C. to 80° C.

The reaction time varies depending on a raw material compound, a reaction reagent, a solvent, reaction temperature, or the like, but it is generally 1 hour to 72 hours and preferably 1 hour to 24 hours.

According to the second step of this method, the fused ring pyrimidine compound (I-4) of the invention can be prepared by reacting the compound (XI) and the amine compound (XII) in the presence of a base.

The base used for the second step is not particularly limited if it is a base generally used for a common reaction. Examples thereof include alkali metal carbonate such as sodium carbonate, potassium carbonate, or cesium carbonate; alkali metal acetate such as sodium acetate, potassium acetate, or cesium acetate; alkali metal hydride such as sodium hydride, lithium hydride, or potassium hydride; alkali metal hydroxide and alkali earth metal hydroxide such as sodium hydroxide, potassium hydroxide, or barium hydroxide; and an organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO), or 1,8-diazabicyclo[5.4.0]-7-undecene (DBU). Furthermore, the amine compound (XII) as a reaction reagent can be also used as a base. It is preferably alkali metal acetic acid salt and the amine compound (XII), and more preferably sodium acetate.

The solvent used for the second step is not particularly limited if it does not inhibit the reaction. Examples thereof include an alcohol solvent such as methanol or ethanol. It is preferably ethanol.

The reaction temperature varies depending on a raw material compound, a reaction reagent, a solvent, or the like, but it is generally 20° C. to 100° C. and preferably 20° C. to 80° C.

The reaction time varies depending on a raw material compound, a reaction reagent, a solvent, reaction temperature, or the like, but it is generally 10 minutes to 8 hours and preferably 10 minutes to 4 hours.

By using a known method, it is also possible to produce other fused ring pyrimidine compound represented by formula (I) from the fused ring pyrimidine represented by formula (I), which has been produced by the above Method A to Method E.

In the above Method A to Method E, the target compound of each reaction can be collected according to a general method from a reaction mixture upon the completion of the reaction. For example, the reaction mixture is neutralized if appropriate, and also insolubles are removed by filtration if there are any, an organic solvent not miscible like water and ethyl acetate is added followed by washing with water, an organic layer containing the target compound is separated, drying is performed by using anhydrous magnesium sulfate, and the solvent is distilled off.

If necessary, the obtained target compound can be further purified by a common method like recrystallization, reprecipitation, fractional crystallization, and chromatography.

The step for producing a salt of the fused ring pyrimidine compound which is represented by formula (I) of the invention is performed by adding acid to an extraction concentrate of a reaction mixture containing the fused ring pyrimidine compound represented by formula (I), which has been produced by each method, or to a liquid in which the fused ring pyrimidine compound represented by formula (I) is dissolved in a suitable solvent.

The acid used for producing a salt include inorganic acid including hydrogen halide acid such as hydrogen fluoride acid, hydrogen chloride acid, hydrogen bromide acid, or hydrogen iodide acid, nitric acid, perchloric acid, sulfuric acid, or phosphoric acid; lower alkylsulfonic acid such as methane sulfonic acid, trifluoromethane sulfonic acid, or ethane sulfonic acid, arylsulfonic acid such as benzene sulfonic acid or p-toluene sulfonic acid, salt of an organic acid such as succinic acid or oxalic acid; and an organic acid amide compound such as saccharine.

The acid is generally used in an amount of 1 eqv. to 10 eqv. Preferably, it is 1 eqv. to 5 eqv.

The solvent used for the reaction is not particularly limited if it does not inhibit the reaction. Preferred examples thereof include ethers such as ether, diisopropyl ether, tetrahydrofuran (THF), or dioxane and alcohols such as methanol or ethanol.

The reaction temperature is −20° C. to 50° C. and preferably −10° C. to 30° C.

The reaction time varies depending on the type of the solvent which is used and the temperature or the like. It is generally 10 minutes to 1 hour.

The produced salt is isolated by a common method. Namely, when it is precipitated as a crystal, it is isolated by filtration collection, and when it is water soluble, it is isolated as an aqueous solution by liquid separation between an organic solvent and water.

The fused ring pyrimidine compound of the invention or a salt thereof has an excellent effect as an effective component of a pest control agent. Hereinbelow, the main use for which the fused ring pyrimidine compound of the invention shows an activity and the effect are described below.

a control effect is exhibited against a pest as a control subject in various agricultural fields in which agricultural/horticultural crops and woods are damaged.

according to application to plant seeds, damages caused by a pest like agricultural insets which thrive on a plant after seeding can be prevented.

a control effect is exhibited against stored grain insects which damage grain and the like stored in a warehouse.

a control effect is exhibited against insects like wood-eating insects which damage wood such as buildings, furniture, stored woods, or the like.

a control effect is exhibited against hygiene insects adversely affecting the living environment of humans such as houses, or the like.

a control effect is exhibited against external or internal parasites of birds or mammals.

Meanwhile, the fused ring pyrimidine of the invention can control, at low concentration, any pest like mites, crustaceans, mollusks, and nematodes which are propagated and cause damage in the same manner as above.

Specific examples of the insects, the mites, the crustaceans, the mollusks and the nematodes which can be controlled using the compound according to the invention include Lepidopteran insects such as *Adoxophyes honmai, Adoxophyes orana faciata, Archips breviplicanus, Grapholita inopinata, Archips fuscocupreanus, Grapholita molesta, Choristoneura magnanima, Leguminivora glycinivorella, Olethreutes mori, Caloptilia zachrysa, Argyresthia conjugella, Spulerrina astaurota, Matsumuraeses phaseoli, Pandemis heparana, Bucculatrix pyrivorella, Lyonetia clerkella, Carposina niponensis, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Chilo suppressalis, Cnaphalocrocis medinalis, Ephestia clutella, Conogethes punctiferalis, Diaphania indica, Etiella zinckenella, Glyphodes pyloalis, Scirpophaga incertulas, Hellula undalis, Ostrinia furnacalis, Ostrinia scapulalis, Parapediasia teterrella, Parnara guttata, Pieris brassicae, Pieris rapae crucivora, Papilio xuthus, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Cydla pomonella, Helicoverpa armigera, Helicoverpa assulta, Helicoverpa zea, Heliothis virescens, Ostrinia nubilalis, Mamestra brassicae, Mythimna separata, Sesamia inferens, Naranga aenescens, Spodoptera eridania, Spodoptera exigua, Spodoptera frugiperda, Spodoptera littoralis, Spodoptera litura, Spodoptera depravata, Trichoplusia ni, Endopiza viteana, Manduca quinquemaculata,* and *Manduca sexta,*

Hemipteran insects such as *Arboridia apicalis, Balclutha saltuella, Epiacanthus stramineus, Empoasca fabae, Empoasca nipponica, Empoasca onukii, Empoasca sakaii, Macrosteles striifrons, Nephotettix cinetinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bemisia tabaci, Dialeurodes citri, Trialeurodes vaporariorum, Aleurolobus taonabae, Viteus vitifolii, Lipaphis erysimi, Aphis gossypii, Aphis spiraecola, Myzus persicae, Toxoptera aurantii, Drosicha corpulenta, Icerya purchasi, Phenacoccus solani, Pulvinaria aurantii, Planococcus citri, Pseudaonidia duplex, Planococcus kuraunhiae, Pseudococcus comstocki, Comstockaspis perniciosa, Ceroplastes ceriferus, Ceroplastes rubens, Aonidiella aurantii, Fiorinia theae, Pseudaonidia paeoniae, Pseudaulacaspis pentagona, Pseudaulacaspis prunicola, Unaspis euonymi, Unaspis yanonensis, Cimex lectularius, Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipterus, Dysdercus cingulatus, Stephanitis pyrioides, Halticus insularis, Lygus lineolaris, Stenodema sibiricum, Stenotus rubrovittatus,* and *Trigonotylus caelestialium,*

Coleopteran insects such as *Anomala cuprea, Anomala rufocuprea, Gametis jucunda, Heptophylla picea, Popillia japonica, Lepinotarsa decemlineata, Epilachna varivestis, Melanotus fortnumi, Melanotus tamsuyensis, Lasioderma serricorne, Lyctusbrunneus, Tomicus piniperda, Rhizopertha dominica, Epuraea domina, Epilachna varivestis, Epilachna vigintioctopunctata, Tenebrio molitor, Tribolium castaneum, Anoplophora malasiaca, Monochamus ahernatus, Psacothea hilaris, Xylotrechus pyrrhoderus, Callosobruchus chinensis, Aulacophora femoralis, Oulema oryzae, Chaetocnema concinna, Diabrotica undecimpunctata, Diabrotica virgifera, Diabrotica barberi, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sulcatus, Sitophilus granarius, Sitophilus zeamais, Sphenophorus venatus vestitus,* and *Paederus fuscipes,*

Thysanopteran insects such as *Frankliniella intonsa, Thrips flavus, Frankliniella occidentalis, Heliothrips haemorrhoidalis, Scirtothrips dorsalis, Thrips palmi, Thrips tabaci,* and *Ponticulothrips diospyrosi,*

Diptera insects such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Delia antique, Pegomya cunicularia, Rhagoletis pomonella, Mayetiola destructor, Musca domestica, Stomoxys calcitrans, Melophagus ovinus, Hypoderma bovis, Hypoderma lineatum, Oestrus ovis, Glossina palpalis (Glossina morsitans), Prosimulium yezoensis, Tabanus trigonus, Telmatoscopus albipunctatus, Leptoconops nipponensis, Culex pipiens pallens, Aedes aegypti, Aedes albopicutus,* and *Anopheles hyracanus sinesis,*

Hymenopteran insects such as *Apethymus kuri, Athalia rosae, Arge pagana, Neodiprion sertifer, Dryocosmus kuriphilus, Eciton burchelli (Eciton schmitti), Camponotus japonicus, Vespa mandarina, Myrmecia* spp., *Solenopsis* spp., and *Monomorium pharaonis,*

Orthopteran insects such as *Teleogryllus emma, Gryllotalpa orientalis, Locusta migratoria, Oxya yezoensis,* and *Schistocerca gregaria,*

Collembolan insects such as *Onychiurus folsomi, Onychiurus sibiricus,* and Bourletiella hortensis, Dictyopteran insects such as *Periplaneta fuliginosa, Periplaneta japonica, Blattella germanica,* and *Periplaneta Americana,*

Isopterous insects such as *Coptotermes formosanus, Reticulitermes speratus,* and *Odontotermes formosanus,*

Isopterous insects such as *Ctenocephalidae felis, Ctenocephalides canis, Echidnophaga gallinacea, Pulex irritans,* and *Xenopsylla cheopis,*

Mallophaga insects such as *Menacanthus stramincus* and *Bovicola bovis,*

Anoplura insects such as *Haematopinus eurysternus, Haematopinus suis, Linognathus vituli,* and *Solenopotes capillatus,*

Tarsonemidae such as *Phytonemus pallidus, Polyphagotarsonemus latus,* and *Tarsonemus bilobatus,*

Penthaleidae such as *Penthaleus crythrocephalus* and *Penthaleus major,*

Tetranychidae such as *Oligonychus shinkajii, Panonychus citri, Panonychus mori, Panonychus ulmi, Tetranychus kanzawai,* and *Tetranychus urticae,*

Eriophyidae such as *Acaphylla theavagrans, Aceria tulipae, Aculops lycopersici, Aculops pelekassi, Aculus schlechtendali, Eriophyes chibaensis,* and *Phyllocoptruta oleivora,*

Acaridae such as *Rhizoglyphus robini, Tyrophagus putrescentiae,* and *Tyrophagus similis,*

Varroidae such as *Varroa jacobsoni,*

Ixodidae such as *Boophilus microplus, Rhipicephalus sanguineus, Haemaphysalis longicornis, Haemophysalis flava, Haemophysalis campanulata, Haemaphysalis japonica, Haemaphysalis megaspinosa, Ixodes ovatus, Ixodes persulcatus, Ixodes nipponensis, Ixodes pacifcus, Ixodes ricinus, Ixodes scapularis, Amblyomma americanum, Amblyomma maculatum, Amblyomma* spp., *Dermacentor recticulatus, Dermacentor taiwanensis, Dermacentor andersoni, Dermacentor occidentalis, Dermacentor variabilis*, and *Dermacentor* spp., Cheyletidae such as *Cheyletiella yasguri* and *Cheyletiella blakei*, Demodicidae such as *Demodex canis* and *Demodex cati*, Psoroptidae such as *Psoroptes ovis*

Sarcoptidae such as *Sarcoptes scabiei, Notoedres cati*, and *Knemidocoptes* spp., Crustacea such as *Armadillidium vulgare*, Gastropoda such as *Pomacea canaliculata, Achatina fulica, Meghimatium bilineatum, Limax Valentiana, Acusta despecta sieboldiana*, and *Euhadra peliomphala*, and Nematoda such as *Prathylenchus coffeae, Prathylenchus penetrans, Prathylenchus vulnus, Globodera rostochiensis, Heterodera glycines, Meloidogyne hapla, Meloidogyne incognita, Aphelenchoides besseyi*, and *Bursaphelenchus xylophilus*.

However, the invention is not limited to them.

The compound of the invention has a significant control effect against the aforementioned pests which damage paddy field crops, field crops, fruit trees, vegetables, other crops, flowers, horticultural plants, and the like. Therefore, the effect as a pest control agent of the invention can be obtained by treating paddy field water for paddy field, field, fruit tree, vegetable, another crop, flower, horticultural plant, or the like, or stems, leaves, or soil in accordance with the period when the occurrence of a pest is expected, before the occurrence of a pest is observed, or at a time point when the occurrence of a pest is observed.

The compound of the invention has a significant control effect against stored-grain insects and the like that occur during storage of harvest. Specifically, the pest control agent containing, as an effective component, the compound of the invention can be used for post-harvest treatment on the harvest or a storage place for the harvest, such as spraying, smearing, coating, dipping, dressing, fumigation/smoking, or pressure-injection.

A damage caused by a pest like agricultural pests occurring on a plant after seeding can be prevented by applying, to a plant seed, the compound of the invention. Specifically, the pest control agent containing, as an effective component, the compound of the invention can be, in an effective amount for pest control, for treatment on a plant seed by spraying, smearing, dipping, or dressing, thereby contacting the compound of the invention with the plant seed, in which the pest control agent may be used for the treatment as it is, or after diluted with water or the like if approve, or in the form of a suspension.

In such case, the plant seed indicates an entity that stores nutrients for germination of a young plant and that is used for breeding in agriculture. Examples thereof include: seeds such as of corn, soybeans, red beans, cotton, rice, sugar beet, wheat, barley, sunflower, tomato, cucumber, eggplant, spinach, podded pea, squash, sugarcane, tobacco, green pepper, and canola; seed tubers such as taro, potato, sugar cane, and konjac; bulbs such as of edible lily, and tulips; and seed bulbs such as shallot.

The compound of the invention has a significant effect in terms of controlling wood-eating insects such as termites, *Lyctusbrunneus, Rhizopertha dominica*, Anobiidae, and Cerambycidae. Therefore, the wood-eating insects can be controlled by treating soil or wood of buildings or the like with the compound of the invention.

The compound of the invention exhibits a control effect against various pests and also exhibits an excellent control effect as an insecticide or a miticide at low chemical amount so that it has an effect of significantly contributing to reduction of environmental loads. In addition, the compound of the invention exhibits an excellent control effect even when used in mixture with another agro-horticultural insecticide, a miticide, a nematicide, a germicide, a herbicide, a plant growth regulating agent, a biological agrochemical, or the like.

(Preparation of Formulation of Compound of Invention)

When the compound of the invention is used, it is usually mixed with an appropriate solid carrier or liquid carrier, and a surface active agent, a penetrating agent, a spreading agent, a thickening agent, an anti-freeze agent, a binding agent, a solidification preventing agent, a disintegrant, a defoaming agent, a preservative, a degradation preventing agent, and the like are optionally added thereto; the resultant may be used in practical applications as a formulation of an arbitrary formulation form such as soluble concentrate, emulsifiable concentrate, wettable powder, water soluble powder, water dispersible granule, water soluble granule, suspension concentrate, concentrated emulsion, suspoemulsion, microemulsion, dustable powder, granule, tablet, or emulsifiable gel. Further, the formulation of an arbitrary formulation form may be encapsulated in a water-soluble package such as a water-soluble capsule or a water-soluble film bag, from the viewpoints of labor saving and safety improvement.

An inert carrier that can be used in the invention may be in a solid form or a liquid form, and examples of the material that can serve as a solid inert carrier include a soybean powder, a cereal powder, a wood powder, a bark powder, a saw powder, a tobacco stalk powder, a walnut shell powder, bran, a cellulose powder, a residue obtained as a result of extraction of a plant extract, a synthetic polymer such as a pulverized synthetic resin, a clay (for example, kaolin, bentonite, or acidic white clay), a talc (for example, talc or pyrofilide), a silica (for example, diatomaceous earth, silica sand, mica, or white carbon (synthetic, highly-dispersed silicic acid, which is also referred to as water-containing micro-silica or water-containing silicic acid, and of which some products contain calcium silicate as a main component)), activated carbon, sulfur powder, pumice, calcined diatomaceous earth, ground brick, fly ash, sand, inorganic mineral powder such as of calcium carbonate or calcium phosphate, chemical fertilizers such as ammonium sulfate, ammonium phosphate, ammonium nitrate, urea, or ammonium chloride, and compost. These are used singly, or in mixture of two or more thereof.

The material that can be used as a liquid inert carrier is selected from materials that intrinsically have solvent power, and materials which do not have solvent power and in which the effective component compound can be dispersed when assisted by an auxiliary agent. Representative examples of the carrier, which may be used singly or in mixture of two or more thereof, include the following: water, alcohols (for example, methanol, ethanol, isopropanol, butanol, and ethylene glycol), ketones (for example, acetone, methyl ethyl ketone, methyl isobutyl ketone, diisobutyl ketone, and cyclohexanone), ethers (for example, diethyl ether, dioxane, cellosolve, diisopropyl ether, and tetrahydrofuran), aliphatic hydrocarbons (for example, kerosine and mineral oil), aromatic hydrocarbons (for example, benzene, toluene, xylene, solvent naphtha, and alkylnaphthalene), halogenated hydrocarbons (for example, dichloromethane, chloroform, carbon tetrachloride, and chlorobenzene), esters (for example, ethyl acetate, butyl acetate, ethyl propionate, diisobutyl phthalate, dibutyl phthalate, and dioctyl phthalate), amides (for example, dimethylformamide, diethylformamide, and dimethylacetamide), and nitriles (for example, acetonitrile).

These solid and liquid carriers may be used singly, or in combination of two or more thereof.

Examples of the surface active agent include: nonionic surface active agents such as polyoxyethylene alkyl ether, polyoxyethylene alkyl (mono- or di-)phenyl ether, polyoxyethylene (mono-, di-, or tri-)styryl phenyl ether, polyoxyethylene polyoxypropylene block copolymer, polyoxyethylene fatty acid (mono- or di-) ester, sorbitan fatty acid ester, polyoxyethylene sorbitan fatty acid ester, castor oil ethylene oxide adduct, acetylene glycol, acetylene alcohol, ethylene oxide adduct of acetylene glycol, ethylene oxide adduct of acetylene alcohol, and alkyl glycosides; anionic surface active agents such as alkyl sulfate salts, alkyl benzenesulfonates, lignin sulfonates, alkyl sulfosuccinates, naphthalenesulfonates, alkyl naphthalenesulfonates, salts of formalin condensates of naphthalene sulfonic acid, salts of formalin condensates of alkyl naphthalene sulfonic acid, polyoxyethylene alkyl ether sulfuric ester salts or phosphoric ester salts, polyoxyethylene (mono- or di-)alkyl phenyl ether sulfuric ester salts or phosphoric ester salts, polyoxyethylene (mono-, di- or tri-)styryl phenyl ether sulfuric ester salts or phosphoric ester salts, polycarbonates (for example, polyacrylates, polymaleates, and copolymers of maleic acid and olefins), and polystyrenesulfonates; cationic surface active agents such as alkylamine salts and alkyl quaternary ammonium salts; amphoteric surface active agents such as of amino acid type or betaine type; silicon-based surface active agents; and fluorine-based surface active agents.

There are no particular limitations on the content of surface active agents, such as those described above. The content of surface active agents is usually preferably in the range of from 0.05 parts by weight to 20 parts by weight with respect to 100 parts by weight of the formulation of the invention. Further, the surface active agent may be used singly, or in combination of two or more thereof.

In order to control various pests, it may be applied, in an amount effective for disease control, to crops in which occurrence of a pest is expected, or to a place at which occurrence of a pest is undesired, wherein it may be applied as it is, or after diluted with water or the like if appropriate, or in a suspended form. The use amount may vary with various factors such as the purpose, subject pest, the growth conditions of the crop, the tendency of occurrence of insects, climate, environmental conditions, formulation form, method of application, place of application, and the timing of application. It may be used at an effective component concentration of preferably 0.0001 ppm to 5000 ppm, and more preferably 0.01 ppm to 1000 ppm. Further, the amount of the effective component to be applied per 10 acres is generally 1 g to 300 g.

The amount of the effective component of the compound of the invention which is represented by the formula (I) is 0.1% by weight to 90% by weight, preferably 1% by weight to 90% by weight, more preferably 1% by weight to 50% by weight, even more preferably 3% by weight to 50% by weight, and most preferably 3% by weight to 20% by weight.

The amount of the effective component of the compound of the invention which is represented by the formula (I) is usually from 0.1% by weight to 20% by weight in a dustable powder, from 5% by weight to 50% by weight in an emulsion formulation, from 3% by weight to 90% by weight in a wettable powder, from 0.1% by weight to 20% by weight in a granule, from 5% by weight to 90% by weight in a flowable formulation, and from 3% by weight to 90% by weight in a water dispersible granule. In regard to the amount of carrier in each formulation form, the amount of carrier is usually from 60% by weight to 99.9% by weight in a dustable powder, from 40% by weight to 95% by weight in an emulsion formulation, from 10% by weight to 90% by weight in a wettable powder, from 80% by weight to 99.9% by weight in a granule, from 10% by weight to 95% by weight in a flowable formulation, and from 10% by weight to 90% by weight in a water dispersible granule. Further, the amount of the auxiliary agent is usually from 0.1% by weight to 20% by weight in a dustable powder, from 1% by weight to 20% by weight in an emulsion formulation, from 0.1% by weight to 20% by weight in a wettable powder, from 0.1% by weight to 20% by weight in a granule, from 0.1% by weight to 20% by weight in a flowable formulation, and from 0.1% by weight to 20% by weight in a water dispersible granule.

Further, in a case in which the compound according to the invention is used as an agrochemical agent, it may be used, if necessary, as a mixture with other herbicides, various insecticides, miticides, nematocides, germicides, plant growth regulating agents, synergists, fertilizers, soil improving agents, and the like during the production of the formulation or at the time of spreading.

With regard to the mixed formulation of the invention for controlling a pest, examples of an insecticide, a miticide, a nematicide as a compound which can be combined with the fused ring pyrimidine compound of the invention include a compound which is selected from a pyrethroid-based compound, an organo phosphorus-based compound, an oxime-carbamate-based compound, a carbamate-based compound, a neonicotinoid-based compound, a diacylhydrazine-based compound, a benzoyl urea-based compound, a juvenile hormone-based compound, a cyclodiene organic chlorine-based compound, a 2-dimethylaminopropane-1,3-dithiol-based compound, an amidine-based compound, a phenylpyrazole-based compound, an organo tin-based compound, a METI-based compound, a benzylate-based compound, an allylpyrrol-based compound, a dinitrophenol-based compound, an anthranyl-diamide-based compound, an oxadiazine-based compound, a semicarbazone-based compound, a tetronic acid-based compound, a carbamoyl-triazole-based compound, and a tetrazine-based compound. Examples of the germicide include a compound selected from a strovilurin-based compound, an anilinopyrimidine-based compound, an azole-based compound, an azole-based compound, a dithiocarbamate-based compound, a phenylcarbamate-based compound, an organic chlorine-based compound, a benzimidazole-based compound, a phenylamide-based compound, a sulfenic acid-based compound, a copper-based compound, an isoxazole-based compound, an organo phosphorus-based compound, a N-halogenothio-alkyl-based compound, a carboxyanilide-based compound, a morpholine-based compound, an organo tin-based compound, and a cyanopyrrol-based compound. A fumigating agent such as chloropicrin and a natural product compound like nicotine can be also mentioned. Furthermore, a compound other than the above group can be also mentioned.

Specific examples include the following compounds.

Pyrethroid-based compound and various isomers thereof such as acrinathrin, allethrin [(1R)-isomer], bifenthrin, bioallethrin, bioallethrin S-cyclopentenyl isomer, bioresmethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, methothrin, metofluthrin, permethrin, phenothrin [(1R)-trans-isomer], prallethrin, resmethrin, RU15525 (kadethrin), silafluofen, tefluthrin, tetramethrin, tetramethrin [(1R)-isomer], tralomethrin, transfluthrin, ZXI8901, biopermethrin, furamethrin, profluthrin, flubrocythrinate, or dimefluthrin, Organo phosphorus-based compound such as acephate, azamethiphos, azinphos-methyl, azinphos-ethyl, cadusafos, chlorethoxyfos, chlorfenvinphos, chlormephos, chlorpyrifos, chlorpyrifos-methyl, coumaphos, CYAP (cyanophos), demeton-S-methyl, diazinon, ECP (dichlofenthion), DDVP (dichlorvos), dicrotophos, dimethoate, dimethylvinphos, disulfoton (ethylthiometon), EPN (O-ethyl O-4-nitrophenyl phenylphosphonothioate), ethion, ethoprophos, Famphur, fenamiphos, MEP (fenitrothion), MPP (fenthion), fosthiazate, heptenophos, isofenphos-methyl, Isocarbophos (isopropyl O-(methoxyaminothio=phosphosphoryl) salicylate), isoxathion, malathion, mecarbam, methamidophos, DMTP (methidathion), mevinphos, monocrotophos, BRP (naled), onmethoate, oxydemeton-methyl, parathions, parathion-methyl, PAP (phenthoate), phorate, phosalone, phosmet, phosphamidon, phoxim, pirimiphos-methyl, profenofos, propetamphos, prothiofos, pyraclofos, pyridaphenthion, quinalphos, Sulfotep, tebupirimfos, temephos, terbufos, thiometon, triazophos, DEP (trichlorfon), vamidothion, Bayer 22/190 (chlorothion), bromfenvinfos, bromophos, bromophos-ethyl butathiofos, carbophenothion. Chlorphoxim, sulprofos, diamidafos, CVMP (tetrachlorvinphos), propaphos, mesulfenfos, dioxabenzofos (salithion), etrimfos, oxydeprofos, formothion, fensulfothion, isazofos, imicyafos (AKD3088), isamidofos, thionazin, or fosthietan, Oxime-carbamate-based compound such as phosphocarb, alanycarb, butocarboxim, butoxycarboxim, thiodicarb, or Thiofanox.

Carbamate-based compound such as aldicarb, bendiocarb, benfuracarb, NAC (carbaryl), carbofuran, carbosulfan, ethiofencarb, BPMC (fenobucarb), Formetanate, furathiocarb, MIPC (isoprocarb), methiocarb, methomyl, oxamyl, pirimicarb, PHC (propoxur) trimethacarb, XMC (3,5-xylyl methylcarbamate), allyxycarb, aldoxycarb, bufencarb, butacarb, carbanolate, MTMC (metoloarb), MPMC (xylylcarb), fenothiocarb, xylylcarb, or bendiocarb, Neonicotinoid-based compound such as acetamiprid, clothianidin, dinotefuran, imidacloprid, nitenpyram, thiaclo-prid, or thiamethoxam, Diacylhydrazine-based compound such as chromafenozide, halofenozide, methoxyfenozide, or tebufenozide, Benzoyl urea-based compound such as bistrifluron, chlortluazuron, ditlubenzuron, flucycloxuron, flufenoxuron, hexaflumuron, lufenuron, novaluron, noviflumuron, teflubenzuron, or triflumuron, Juvenile hormone-based compound such as fenoxycarb, hydroprene, kinoprene, methoprene, pyriproxyfen, methoprene, or hydroprene, Cyclodiene organic chlorine-based compound such as chlordane, endosulfan, lindane (gamma-HCH), or dienochlor, 2-Dimethylaminopropane-1,3-dithiol-based compound such as Cartap hydrochloride or thiocyclam, Amidine-based compound such as amitraz, Phenylpyrazole-based compound such as ethiprole, fipronil, or acetoprole, Organo tin-based compound such as azocyclotin, cyhexatin, or fenbutatin oxide, METI-based compound such as fenazaquin, fenpyroximate, pyridaben, pylimidifen, tebufenpyrad, or tolfenpyrad, Benzylate-based compound such as bromopropylate, Allylpyrrol-based compound such as chlorfenapyl, Dinitrophenol-based compound such as DNOC or binapacryl, Anthranyl-diamide-based compound such as chlorantraniliprole or cyantraniliprole;

Oxadiazine-based compound such as indoxacarb,

Semicarbazone-based compound such as metaflumizone,

Tetronic acid-based compound such as spirodiclofen, spiromesifen, or spirotetramat, Carbamoyltriazole-based compound such as triazamate, Tetrazine-based compound such as diflovidazin, abamectin, emamectin benzoate, milbemectin, lepimectin, acequinocyl, azadirachtin, bensultap, Benzoximate, bifenazate, buprofezin, CCA-50439, chinomethionat, clofentezine, cryolite, cyromazine, dazomet, DCIP, DDT, diafenthiuron, D-D (1,3-Dichloropropene), dicofol, dicyclanil, dinobuton, dinocap, ENT 8184, etoxazole, flonicamid, fluacrypyrim, flubendiamide, GY-81 (peroxocarbonate), hexythiazox, hydramethylnon, Hydrogen cyanide, methyl iodide, karanjin, MB-599 (verbutin), mercury chloride, Insecticide, a miticide, a nematicide such as metam, methoxychlor, methyl isothiocyanate, pentachlorophenol, phosphine, piperonyl butoxide, polynactins, BPPS (propargite), pymetrozine, pyrethrins, pyridalyl, rotenone, S421 (bis (2,3,3,3-tetrachloropropyl)ether), sabadilla, spinosad, spinetoram, sulcofuron-sodium, sulfluramid, tetradifon, thiosultap, Tribufos, aldrin, amidithion, amidothioate, aminocarb, amiton, aramite, athidathion, azothoate, barium polysulphide, Bayer 22408, Bayer 32394, benclothiaz, 5-(1,3-benzodioxole-5-yl)-3-hexylcyclohexa-2-enone, 1,1-bis(4-chlorophenyl)-2-ethoxyethanol, butonate, butopyronoxyl, 2-(2-butoxyethoxy)ethyle thiocyanate, camphechlor, chlorbenside, chlordecone, chlordimeform, chlorfenethol, chlorfenson, isoprothiolane, fluazuron, metaldehyde, phenisobromolate, fluazinam, bialaphos, benomyl, levamisol, pyrifluquinazon, cyflumetofen, amidoflumet, IKA-2005, cyenopyrafen (NC512), sulfoxaflor, pyrafluprole (V3039), pyriprole (V3086), tralopyril, flupyrazofos, diofenolan, chlorobenzilate, flufenzine, benzomate, flufenerim, Tripropyl isocyanurate (TPIC), albendazole, oxibendazole, fenbendazole, metam-sodium, 1,3-dichloropropene, flupyradifurone, afidopyropen, flometoquin, pyflubumide, fluensulfone), or IKI-3106.

Strovilurin-based compound such as azoxystrobin, kresoxym-methyl, trifloxystrobin, metominostrobin, or orysastrobin, Anilinopyrimidine-based compound such as mepanipyrim, pyrimethanil, or cyprodinil, Azole-based compound such as triadimefon, bitertanol, triflumizole, metoconazole, propiconazole, penconazole, flusilazole, myclobutanil, cyproconazole, tebuconazole, hexaconazole, prochloraz, or simeconazole, Quinoxaline-based compound such as quinomethionate, Dithiocarbamate-based compound such as maneb, zineb, mancozeb, polycarbamate, or propineb, Phenylcarbamate-based compound such as diethofencarb, Organic chlorine-based compound such as chlorothalonil or quintozene, Benzimidazole-based compound such as benomyl, thiophanate-methyl, or carbendazole, Phenylamide-based compound such as metalaxyl, oxadixyl, ofurase, benalaxyl, furalaxyl, or cyprofuram, Sulfenic acid-based compound such as dichlofluanid, Copper-based compound such as copper hydroxide or oxine-copper, Isoxazole-based compound such as hydroxyisoxazole, Organo phosphorus-based compound such as fosetyl-aluminium or tolclofos-methyl, N-Halogenothioalkyl-based compound such as captan, captafol, or folpet, Dicarboxyimide-based compound such as procymidone, iprodione, or vinchlozolin, Carboxyanilide-based compound such as flutolanil, meproniL furamepyr, thifluzamide, boscalid, or penthiopyrad, Morpholine-based compound such as fenpropimorph or dimethomorph, Organo tin-based compound such as fenthin hydroxide or fenthin acetate, Cyanopyrrol-based compound such as fludioxonil or fenpiclonil, in addition, Germicide such as tricyclazole, pyroquilon, carpropamid, diclocymet, fenoxanil, fthalide, fluazinam, cymoxanil, triforine, pyrifenox, fenarimol, fenpropidin, pencycuron, ferimzone, cyazofamid, iprovalicarb, benthiavalicarb-isopropyl, iminoctadin-albesilate, cyflufenamid, kasugamycin, validamycin, streptomycin, oxolinic-acid, tebufloquin, probenazole, tiadinil, isotianil, tolprocarb, or isofetamid, Fumigating agent such as chloropicrin, ethylene dibromide (EDB), sulfuryl fluoride, acrylonitrile, bis(2-chloroethyl) ether, 1-bromo-2-chloroethane, 3-bromo-1-chloroprop-1-ene, bromocyclen, carbon disulfide, tetrachloromethane, metham sodium, nemadectin, or aluminum phosphide.

Natural compound such as *Bacillus thuringiensis* delta-endotoxin, borax, calcium polysulfide, cryolite, cytokinin, nicotine, 2-(octylthio)ethanol, potassium oleate, sodium oleate, machine oil, sulfur, tar oil, anabasine, morantel tartrate, pyrethrum, nicotine sulfate, rape seed oil, soybean lecithin, starch, hydroxypropylstarch, decanoyloctanoylglycerol, propylene glycol fatty acid ester, diatomite, or *Bacillus thuringiensis*.

Furthermore, the compound represented by the following formula (AA) and a salt thereof, the compound represented by the following formula (BB), the compound represented by the following formula (CC), the compound represented by the following formula (DD)), the compound represented by the following formula (EE), and the like can be mentioned. Details of the substituent group in the following formula (AA) to the formula (EE), for example, "alkyl group having 1 to 6 carbon atoms" or "a halogen atom", are the same as the details of each substituent group which has been described for the substituent groups $R^1$, $R^2$, $R^4$, $R^6$, $R^5$, and Ht of the above formula (I) of the invention.

The compound represented by the formula (AA) is as described below.

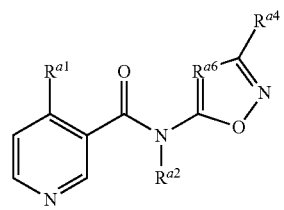

In formula (AA), $R^{a1}$ represents an alkyl group having 1 to 6 carbon atoms or a haloalkyl group having 1 to 6 carbon atoms, $R^{a2}$ represents a hydrogen atom, an alkyl group having 1 to 6 carbon atoms, a haloalkyl group having 1 to 6 carbon atoms, or an alkenyl group having 2 to 6 carbon atoms, and $R^{a6}$ represents a group represented by formula C—$R^{a3}$ or a nitrogen atom.

Each of $R^{a3}$ and $R^{a4}$ independently represents a hydrogen atom, a halogen atom, an alkyl group having 1 to 6 carbon atoms, a haloalkyl group having 1 to 6 carbon atoms, a cyano group, a phenyl group that may be substituted, a heterocyclyl group that may be substituted, or a phenoxy group that may be substituted.

The compound represented by (BB) is as described below.

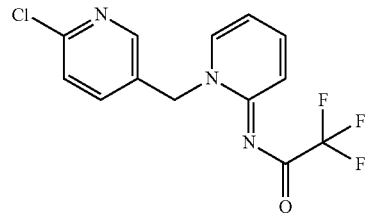

The compound represented by the formula (CC) is as described below.

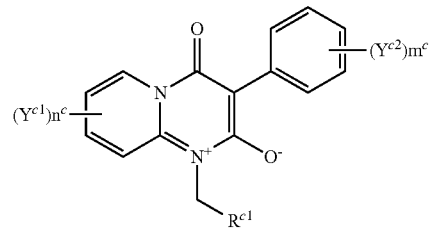

In formula (CC), $R^{c1}$ represents a pyridyl group that may be substituted, a thiazolyl group that may be substituted, or a pyrimidyl group that may be substituted, $Y^{c1}$ represents a halogen atom, an alkyl group having 1 to 6 carbon atoms, or an alkoxy group having 1 to 6 carbon atoms, $Y^{c2}$ represents a halogen atom, a cyano group, an alkyl group having 1 to 6 carbon atoms, an alkoxy group having 1 to 6 carbon atoms, or a phenyl group that may be substituted, n represents an integer of from 0 to 4, and $m^e$ represents an integer of from 0 to 5. When n is 2 to 4, each $Y^{c1}$ may be the same or different from each other, and when m is 2 to 5, each $Y^{c2}$ may be the same or different from each other.

The compound represented by the formula (DD) is as described below.

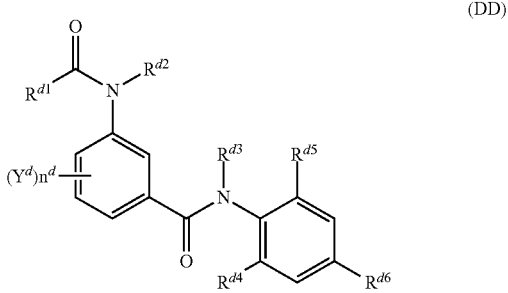

In formula (DD), $R^{d1}$ represents a phenyl group that may be substituted or a heterocyclyl group that may be substituted, each of $R^{d2}$ and $R^{d3}$ independently represents a hydrogen atom or an alkyl group having 1 to 6 carbon atoms, each of $R^{d4}$ and $R^{d5}$ independently represents a halogen atom, an alkyl group having 1 to 6 carbon atoms, or a haloalkyl group having 1 to 6 carbon atoms, $R^{d6}$ represents a haloalkyl group having 1 to 6 carbon atoms, $Y^d$ represents a halogen atom or a cyano group, and $n^d$ represents an integer of from 1 to 4. When $n^d$ is 2 to 4, each $Y^d$ may be the same or different from each other.

The compound represented by the formula (EE) is as described below.

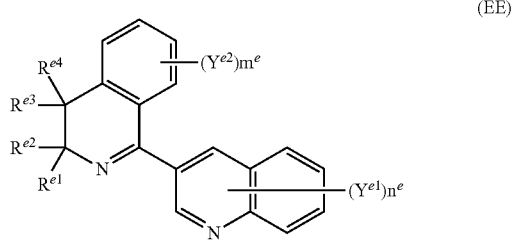

In formula (EE), each of $R^{e1}$, $R^{e2}$, $R^{e3}$ and $R^{e4}$ independently represents a hydrogen atom, a halogen atom, an alkyl group having 1 to 6 carbon atoms, a haloalkyl group having 1 to 6 carbon atoms, or a phenyl group that may be substituted, each of $Y^{e1}$ and $Y^{e2}$ independently represents a halogen atom, an alkyl group having 1 to 6 carbon atoms, or an alkoxy group having 1 to 6 carbon atoms, $n^e$ represents an integer of from 0 to 5, and $m^e$ represents an integer of from 0 to 4. When $n^e$ is 2 to 5, each $Y^{e1}$ may be the same or different from each other, and when $m^e$ is 2 to 4, each $Y^{e2}$ may be the same or different from each other.

Among the compounds described above, there is a compound which can have a stereoisomer, and the invention includes those isomers.

With regard to a mixture of the compound of the invention and other insecticide or germicide, the mixing ratio between the compound of the invention and other insecticide or germicide is, although not particularly limited, 0.01:100 to 100:0.01, or 0.1:100 to 100:0.1, or 1:100 to 100:1, or 1:10 to 10:1, or 1:1 (all in terms of weight) when expressed as the compound of the invention:other insecticide or germicide. In addition, any combination range of the upper limit and the lower limit of them is also included in the mixing ratio. Meanwhile, when there are two or more other insecticides or germicides, the aforementioned mixing ratio indicates the ratio of the total of other insecticides or germicides relative to the compound of the invention.

The compound of the invention has a significant control effect against hygiene pests such as Dipterous pests (*Culex pipiens, Culex plumosus, Chironomidae, Musca domestica, Psychodidae, Tabanus trigonus*, and the like), Dictyoptera pests (*Blattella germanica, Periplaneta fuliginosa, Periplaneta americana*, and the like), or the like.

Furthermore, the compound of the invention can be used, as an agent for controlling arthropods which directly present serious harm or arthropods which mediate a disease for an environment in which such harmful organisms may be present, by a means spraying-injection-irrigation-coating of an oil formulation, an emulsion, or a wettable powder, spraying of a powder formulation, treatment with a fumigating agent, an insect coil self-combustion type fumigating agent, a heating and fogging agent like chemical reaction type fogging agent, a fumigating agent like fogging, a ULV formulation, installation of tablets and poison baits, or dropwise addition of floating powder or granules to a water path, a well, a reservoir, a water tank and other running water or still water. Furthermore, poison moths as an agricultural and forest pest, the control can be achieved by the means as described above. Furthermore, for flies, it is also effective to incorporate it to feeds for livestock so that it can be mixed in feces and also to vaporize it in air using electric mosquito coil to control mosquitoes or the like.

Meanwhile, the formulation in such application type can be also present as a mixed preparation with other active compound such as an insecticide, a miticide, a nematocide, a germicide, a repellent, or a synergistic agent. Those formulations suitably contain the compound of the invention at 0.0001% by weight to 95% by weight in terms of the total amount.

The compound of the invention can be used for control of external or internal parasites of mammals other than human and birds including livestock and pet animals, for example, *Ctenocephalides felis, Ctenocephalides canis, Haemaphyxalis longicornis, Filariidae nematodes*, or the like.

Control of external or internal parasites can be achieved by oral administration, parenteral administration, or intradermal administration.

As for the oral administration, a small amount of the compound of the invention may be added to foods or feeds, or it is also possible that an oral administration agent such as suitable combined pharmaceutical composition which can be orally taken, for example, a tablet, a pill (a round drug), a capsule, a sustained release macro-granule pill, a paste, a gel, a drinkable pharmaceutical, a pharmaceutical feed, a pharmaceutical drink, an animal feed, a pharmaceutical bait, and other device for sustained release in a gastrointestinal tract is prepared and administered orally to livestock or pet animals.

When it is orally administered as a pharmaceutical drink, the pharmaceutical drink can be usually prepared as a suspension or a dispersion by dissolving in a suitable no-toxic solvent or water together with a suspending agent like bentonite, a wetting agent, or other vehicles. Furthermore, a common pharmaceutical drink also contains an anti-foaming agent. In the pharmaceutical drink, the compound of the invention can be contained generally at 0.01% by weight to 1.0% by weight, and preferably 0.01% by weight to 0.1% by weight.

When oral administration in the form of unit dose of a dried matter is preferred, a capsule, a pill, or a tablet containing a pre-determined amount of an effective compound is generally used. Such application form can be prepared by homogeneously mixing the active component with a dilution agent, a filler, a disintegrating agent and/or a binder which has been suitably micro-pulverized, for example, starch, lactose, talc, magnesium stearate, plant rubber, or the like. This unit dose formulation of dried solid can be widely modified, in terms of the mass and content of the control agent, depending on type of a host animal for treatment, severeness of the infection, type of the parasites, and weight of the host.

When administration is made by a means of animal feed, it can be used in the form of homogeneous dispersion in feeds, top dressing, or pellets. In general, to achieve a preferred anti-parasitic effect, the compound of the invention can be contained at 0.0001% by weight to 0.05% by weight, and preferably 0.0005% by weight to 0.01% by weight in the final animal feeds.

As for the intradermal administration, intradermal administration or topical administration can be made by a means of an intradermal administration agent such as spray, powder, grease, crème, ointment, emulsion, lotion, spot-on, pour-on, shampoo or the like.

As a method of intradermal administration or topical administration, a device to be attached on an animal can be used (for example, a necklace, a medallion, or an ear tag) to control locally or systemically arthropods.

In order to achieve the effect of the intradermal administration or topical administration, it is sufficient that the compound of the invention is administered in an amount of 0.0001% by weight to 0.1% by weight and preferably 0.001% by weight to 0.01% by weight. Meanwhile, those obtained by dissolving or dispersing in a liquid carrier vehicle can be administered parenterally to an animal via intra-anterior stomach, intra-muscular, intra-organ, or subcutaneous injection. For having the parenteral administration, the active compound is preferably admixed with suitable plant oil such as peanut oil or cotton seed oil. Such formulation can contain the compound of the invention generally in an amount of 0.05% by weight to 50% by weight and preferably 0.1% by weight to 5.0% by weight.

Furthermore, by admixing with a suitable carrier such as dimethyl sulfoxide or a hydrocarbon solvent, it may be topically administered. This formulation is directly applied on an outer surface of an animal by spraying or direct injection addition.

EXAMPLES

Hereinbelow, the invention is specifically described by way of Examples, but the invention is not limited to them. Chemical shift value of $^1$H-NMR indicates, unless specifically described otherwise, a value which is obtained by using tetramethylsilane as an internal standard material. The value within parentheses in $^1$H-NMR indicates the NMR solvent. CDCl$_3$ indicates heavy chloroform and DMSO-D6 indicates heavy dimethyl sulfoxide. Furthermore, unless specifically described otherwise, "%" is based on mass.

Example 1

Compound of the Invention Obtained by Method A

Synthesis of 4-((6-chloropyridin-3-yl)methyl)-5-methyl-2-(methylthio)-[1,2,4]triazolo[1,5-a]pyrimidin-7(4H)-one (Compound No. 5)

To a suspension of 5-methyl-2-(methylthio)-[1,2,4]triazolo[1,5-a]pyrimidin-7-ol (0.20 g, 1.0 mmol) in N,N-dimethyl formamide (DMF, 2 mL) contained in a 100 mL branched flask, potassium carbonate (0.15 g, 1.1 mmol) and 2-chloro-5-(chloromethyl)pyridine (0.17 g, 1.1 mmol) were added, heated to 80° C. and stirred for 2 hours. After cooling to room temperature, water (30 ml) was added and it was extracted with ethyl acetate (30 ml). After washing twice with water, it was dried over anhydrous magnesium sulfate and the solvent was distilled off under reduced pressure. To the obtained residues, 10 ml of ethyl acetate was added. By collecting the obtained solid by filtration, the target product (0.15 g) was obtained as a white solid with yield of 44%.

$^1$H-NMR(CDCl$_3$)δ ppm: 8.37(1H,d,J=2.6 Hz), 7.59(1H, dd,J=8.3, 2.6 Hz), 7.35(1H,d,J=0.3 Hz), 5.91(1H,s), 5.43 (2H,s), 2.69(3H,s), 2.40(3H,s).

Substitution position of a 6-chloro-3-pyridylmethyl group was determined and confirmed based on correlations by 2-D NMR (HMBC method).

Example 2

Compound of the Invention Obtained by Method B

Synthesis of 4-((6-chloropyridin-3-yl)methyl)-5-methyl-2-(methylthio)-[1,2,4]triazolo[1,5-a]pyrimidin-7(4H)-one (Compound No. 5)

(1) 3-Amino-5-methyl-1,2,4-triazole (1.85 g, 14.2 mmol), 6-chloronicotine aldehyde (2.00 g, 14.1 mmol), and ethanol (15 ml) were refluxed for 4 hours in a 100 mL branched flask. After cooling to room temperature, precipitated solid was collected by filtration to obtain N-((6-chloropyridin-3-yl)methylene)-5-methylthio-1,2,4-triazole-3-imine (2.60 g) as a yellow solid with yield of 73%.

$^1$H-NMR(CDCl$_3$)δ ppm: 9.28(1H,s), 8.88(1H,d,J42.5 Hz), 8.31(1H, broad d, J=8.0 Hz), 7.47(1H,d,J=8.0 Hz), 2.68(3H,s).

(2) To a suspension of N-((6-chloropyridin-3-yl)methylene)-5-methylthio-1,2,4-triazole-3-imine (2.60 g, 10.3 mmol) in ethanol (20 ml) contained in a 100 mL branched flask, sodium borohydride (0.40 g, 10.6 mmol) was added at room temperature and stirred at the same temperature for 30 minutes. The solvent was distilled off under reduced pressure and the obtained residues were added with water (50 ml) and extracted with ethyl acetate (100 ml). After drying over anhydrous magnesium sulfate, the solvent was distilled off under reduced pressure to obtain N-((6-chloropyridin-3-yl)methyl)-5-methylthio-1,2,4-triazole-3-amine (2.21 g) as a white solid with yield of 84%.

$^1$H-NMR(CDCl$_3$)δ ppm: 9.28(1H,s), 8.40(1H,d,J=2.5 Hz), 7.69(1H,dd,J=8.0, 2.5 Hz), 7.29 (1H,d,J=8.0 Hz), 4.48 (2H, s), 2.59 (3H,s).

(3) To a suspension of N-((6-chloropyridin-3-yl)methyl)-5-methylthio-1,2,4-triazole-3-amine (0.20 g, 0.78 mmol) in acetic acid (5 ml) contained in a 50 mL branched flask, ethyl acetoacetate (0.15 g, 12.2 mmol) was added and refluxed for 3 hours. After cooling to room temperature, 20 ml of a mixture of hexane and ethyl acetate (4:1) was added, and the obtained solid was collected by filtration to obtain the target compound (0.09 g) as a white solid with yield of 36%.

$^1$H-NMR(CDCl$_3$)δ ppm: 8.37(1H,d,J=2.6 Hz), 7.59(1H, dd, J=8.3, 2.6 Hz), 7.35 (1H,d,J=8.3 Hz), 5.91 (1H,s), 5.43 (2H,s), 2.69 (3H,s), 2.40 (3H,s).

Example 3

Compound of the Invention Obtained by Method C

Synthesis of 4-((6-chloropyridin-3-yl)methyl)-5-methyl-2-(methylthio)-[1,2,4]triazolo[1,5-a]pyrimidin-7(4H)-one (Compound No. 5)

To a suspension of tetrolic acid (0.16 g, 1.9 mmol) and oxalyl chloride (0.40 g, 3.2 mmol) in benzene (3 ml)

contained in a 50 mL branched flask, one drop of N,N-dimethyl formamide (DMF) was added at room temperature, heated to 45° C. and stirred for 1 hour. The solvent was distilled off under reduced pressure to obtain tetrolic acid chloride (0.20 g). The obtained acid chloride was used for the next step without further purification.

To a suspension of 60% sodium hydride (0.05 g, 1.3 mmol) in DMF (3 ml) contained in a 50 mL branched flask, N-((6-chloropyridin-3-yl)methyl)-5-methylthio-1,2,4-triazole-3-amine (0.25 g, 0.98 mmol) was added under nitrogen stream at room temperature, and stirred at the same temperature for 30 minutes. Subsequently, tetrolic acid chloride (0.20 g) was added thereto at room temperature and stirred at the same temperature for 2 hours. After adding water (30 ml), it was extracted with ethyl acetate (500 ml) and dried over anhydrous magnesium sulfate. The solvent was distilled off under reduced pressure. The obtained residues were purified by silica gel column chromatography to obtain the target product (0.08 g) as a white solid with yield of 25%.

$^1$H-NMR(CDCl$_3$)δ ppm: 8.37(1H,d,J=2.6 Hz), 7.59(1H, dd,J=0.8.3, 2.6 Hz), 7.35(1H,d,J=8.3 Hz), 5.91(1H,s), 5.43 (2H,s), 2.69(3H,s), 2.40 (3H,s).

Example 4

Synthesis of 4-((6-chloropyridin-3-yl)methyl)-5-methyl-2-(methylsulfonyl)-[1,2,4]triazolo[1,5-a]pyrimidin-7(4H)-one (Compound No. 10)

To a suspension of 5-methyl-2-(methylsulfone)-[1,2,4]triazolo[1,5-a]pyrimidin-7-ol (0.20 g, 0.9 mmol) in N,N-dimethyl formamide (DMF, 2 ml) contained in a 100 mL branched flask, potassium carbonate (0.12 g, 0.9 mmol) and 2-chloro-5-(chloromethyl)pyridine (0.15 g, 0.9 mmol) were added, heated to 80° C., and stirred for 6.5 hours. After cooling to room temperature, water (30 ml) was added and it was extracted with ethyl acetate (30 ml). After washing once with water and drying over anhydrous magnesium sulfate, the solvent was distilled off under reduced pressure. The obtained residues were purified by silica gel column chromatography to obtain the target product (0.05 g) as a pale brown solid with yield of 16%.

$^1$H-NMR(CDCl$_3$)δ ppm: 8.37(1H,d,J=2.4 Hz), 7.64(1H, dd,J=8.3, 2.4 Hz), 7.36(1H,d,J=8.3 Hz), 6.06(1H,s), 5.55 (2H,s), 3.42(3H,s), 2.49 (3H,s).

Substitution position of a 6-chloro-3-pyridylmethyl group was determined and confirmed based on correlations by 2-D NMR (HMBC method).

Example 5

Synthesis of 4-((6-chloropyridin-3-yl)methyl)-2-methoxy-5-methyl-[1,2,4]triazolo[1,5-a]pyrimidin-7(4H)-one (Compound No. 45)

To a suspension of 4-((6-chloropyridin-3-yl)methyl)-5-methyl-2-(methylsulfonyl)-[1,2,4]triazolo[1,5-a]pyrimidin-7(4H)-one (0.25 g, 0.7 mmol) in methanol (2.5 mL) contained in a 100 mL branched flask, 28% sodium methoxide/methanol solution (0.22 g, 1.1 mmol) was added, heated to 60° C. and stirred for 1.5 hours. The solvent was concentrated under reduced pressure and water (20 ml) and ethyl acetate (20 ml) were added thereto. By collecting the precipitated solid by filtration, the target product (0.07 g) was obtained as a white solid with yield of 31%.

$^1$H-NMR(CDCl$_3$)δ ppm: 8.36(1H,d,J=2.4 Hz), 7.61(1H, dd,J=8.3, 2.4 Hz), 7.34(1H,d,J=8.3 Hz), 5.93(1H,d,J=0.6 Hz), 5.40(2H,s), 4.13(3H,s), 2.39(3H,d,J=0.6 Hz).

Example 6

Synthesis of 4-((6-chloropyridin-3-yl)methyl)-2-hydroxy-5-methyl-[1,2,4]triazolo[1,5-a]pyrimidin-7(4H)-one (Compound No. 88)

In a 100 mL branched flask, 4-((6-chloropyridin-3-yl)methyl)-2-methoxy-5-methyl-[1,2,4]triazolo[1,5-a]pyrimidin-7(4H)-one (1.70 g, 5.6 mmol) was dissolved in 20 mL of 47 to 49% hydrogen bromide acid, heated to 60° C. and stirred for 9 hours. It was concentrated under reduced pressure, and the obtained residues were added with water. It was concentrated again under reduced pressure. This operation was repeatedly performed. Water was added to the residues, and by collecting the precipitated solid, the target product (1.33 g) was obtained as a white solid with yield of 82%.

$^1$H-NMR(DMSO-D6)δ ppm: 12.10(1H,broad s), 8.43 (1H,d,J=2.4 Hz), 7.78(1H,dd,J=8.3, 2.4 Hz), 7.50(1H,d, J=8.3 Hz), 5.96(1H,s), 5.42(2H,s), 2.32(3H,s).

Example 7

Synthesis of 4-((6-chloropyridin-3-yl)methyl)-2-(methoxymethoxy)-5-methyl-[1,2,4]triazolo[1,5-a]pyrimidin-7(4H)-one (Compound No. 89)

To a suspension of 4-((6-chloropyridin-3-yl)methyl)-2-hydroxy-5-methyl-[1,2,4]triazolo[1,5-a]pyrimidin-7(4H)-one (0.30 g, 1.0 mmol) in N,N-dimethyl formamide (DMF, 10 mL) contained in a 100 mL branched flask, 60% sodium hydride (0.05 g, 1.3 mmol, in oil) was added and stirred for 10 minutes. The mixture was cooled to ice-cold temperature, added with chloromethyl methyl ether (0.13 g, 1.61 mmol) and stirred for 10 minutes. Thereafter, the temperature was raised to room temperature followed by stirring for 3 hours. After that, water (30 ml) was added and it was extracted with ethyl acetate (30 ml). The organic layer was washed with saturated aqueous solution of sodium hydrogen carbonate and saturated aqueous solution of sodium chloride, dried over anhydrous sodium sulfate, and the solvent was distilled off under reduced pressure. The obtained residues were purified by silica gel column chromatography to obtain the target product (0.10 g) as a white solid with yield of 29%.

$^1$H-NMR(CDCl$_3$)δ ppm: 8.37(1H,d,J=2.4 Hz), 7.61(1H, dd,J=8.4, 2.4 Hz), 7.35(1H,d,J=8.4 Hz), 5.93(1H,d,J=0.6 Hz), 5.54(2H,s), 5.42(2H,s), 3.59(3H,s), 2.40 (3H,d,J=0.6 Hz).

Example 8

Compound of the Invention Obtained by Method D

Synthesis of 4-((6-chloropyridin-3-yl)methyl)-5-methyl-2-(methylthio)-[1,2,4]triazolo[1,5-a]pyrimidin-7(4H)-thione (Compound No. 24)

To a suspension of 4-((6-chloropyridin-3-yl)methyl)-5-methyl-2-(methylthio)-[1,2,4]triazolo[1,5-a]pyrimidin-7(4H)-one (1.00 g, 3.1 mmol) in toluene (10 mL) contained in a 100 mL branched flask, Lawesson's Reagent (0.63 g, 1.6 mmol) was added and refluxed for 1 hour. After cooling to room temperature, the solvent was distilled off under reduced pressure. The obtained residues were purified by silica gel column chromatography to obtain the target product (0.31 g) as a yellow solid with yield of 30%.

$^1$H-NMR(DMSO-D6)δ ppm: 8.48(1H,d,J=2.5 Hz), 7.83 (1H,dd,J=8.5, 2.5 Hz), 7.49(1H,d,J=8.5 Hz), 6.95(1H,s), 5.54(2H,s), 2.62(3H,s), 2.36(3H,s).

Example 9

Compound of the Invention Obtained by Method E

Synthesis of 4-((6-chloropyridin-3-yl)methyl)-5-methyl-2-(methylthio)-[1,2,4]triazolo[1,5-a]pyrimidin-7(4H)-oneoxime (Compound No. 121)

(1) To a suspension of 4-((6-chloropyridin-3-yl)methyl)-5-methyl-2-(methylthio)-[1,2,4]triazolo[1,5-a]pyrimidin-7(4H)-thione (0.30 g, 0.9 mmol) in tetrahydrofuran (THF, 10 mL) contained in a 100 mL branched flask, methyl iodide (0.60 g, 4.2 mmol) was added and stirred at room temperature for 30 hours. As a result of collecting by filtration the precipitated solid from the reaction solution, 4-((6-chloropyridin-3-yl)methyl)-5-methyl-2,7-bis(methylthio)-[1,2,4]triazolo[1,5-a]pyrimidin-4-ium iodide (0.38 g) was obtained as an orange solid with yield of 90%.

$^1$H-NMR(DMSO-D6)δ ppm: 8.53(1H,d,J=2.4 Hz), 7.93 (1H,dd,J=8.3, 2.4 Hz), 7.77(1H,s), 7.58(1H,d,J=8.3 Hz), 5.94(2H,s), 2.94(3H,s), 2.84(3H,s), 2.72(3H,s).

(2) To a suspension of 4-((6-chloropyridin-3-yl)methyl)-5-methyl-2,7-bis(methylthio)-[1,2,4]triazolo[1,5-a]pyrimidin-4-ium iodide (0.20 g, 0.4 mmol) in ethanol (4 mL) contained in a 100 mL branched flask, sodium acetate (0.20 g, 2.4 mmol) and hydroxyamine hydrogen chloride acid salt (0.09 g, 1.3 mmol) were added and refluxed for 30 minutes. After cooling to room temperature, water (10 ml) was added and the precipitated solid was collected by filtration. The obtained residues were purified by silica gel column chromatography to obtain the target product (0.05 g) as a pale brown solid with yield of 35%.

$^1$H-NMR(CDCl$_3$)δ ppm: 8.33(1H,d,J=2.4 Hz), 7.56(1H, dd,J=8.3.2.4 Hz), 7.32(1H,d,J=8.3 Hz), 6.75 (1H,s), 6.26 (1H,s), 5.26(2H,s), 2.65(3H,s), 2.26(3H,s).

Example 10

Compound of the Invention Obtained by Method E

Synthesis of 4-((6-chloropyridin-3-yl)methyl)-5-methyl-2-(methylthio)-[1,2,4]triazolo[1,5-a]pyrimidin-7(4H)-imine (Compound No. 131)

To a suspension of 4-((6-chloropyridin-3-yl)methyl)-5-methyl-2,7-bis(methylthio)-[1,2,4]triazolo[1,5-a]pyrimidin-4-ium iodide (1.01 g, 2.1 mmol) in ethanol (10 mL) contained in a 100 mL branched flask, 2 mol/L ammonia/ethanol solution (3.2 ml, 6.4 mmol) was added and refluxed for 30 minutes. After cooling to room temperature, water (30 ml) was injected and it was extracted with ethyl acetate (30 ml). After washing twice with water, it was dried over anhydrous magnesium sulfate and the solvent was distilled off under reduced pressure. The obtained residues were purified by silica gel column chromatography to obtain the target product (0.24 g) as an orange solid with yield of 36%.

$^1$H-NMR(DMSO-D6)δ ppm: 10.01(1H,s), 8.47(1H,d, J=2.4 Hz), 7.87(1H,dd,J=8.3, 2.4 Hz), 7.55(1H,d,J=8.3 Hz), 6.52(1H,s), 5.67(2H,s), 2.70(3H,s), 2.55(3H,s).

Example 11

Synthesis of N-(4-((6-chloropyridin-3-yl)methyl)-5-methyl-2-(methylthio)-[1,2,4]triazolo[1,5-a]pyrimidin-7(4H)-ylidene)-2,2,2-trifluoroacetamide (Compound No. 141)

To a suspension of 4-((6-chloropyridin-3-yl)methyl)-5-methyl-2-(methylthio)-[1,2,4]triazolo[1,5-a]pyrimidin-7 (4H)-imine (0.10 g, 0.3 mmol) in dichloromethane (2 mL) contained in a 100 mL branched flask, triethylamine (0.04 g, 0.4 mmol) was added. After cooling to ice cold temperature, trifluoroacetic anhydride (0.15 g, 0.7 mmol) was added and stirred at the same temperature for 15 minutes. After injecting water (30 ml) at the same temperature, it was extracted with ethyl acetate (30 ml). The temperature was raised to room temperature and it was washed twice with water. After drying over anhydrous magnesium sulfate, the solvent was distilled off under reduced pressure. The obtained residues were purified by silica gel column chromatography to obtain the target product (0.09 g) as a brownish yellow solid with yield of 70%.

$^1$H-NMR(DMSO-D6)δ ppm: 8.41(1H,d,J=2.6 Hz), 7.59 (1H,d,J=-8.3, 2.6 Hz), 7.37(1H,d,J=8.3 Hz), 7.32(1H,s), 5.56(2H,s), 2.70(3H,s), 2.56(3H,s).

Example 12

Compound of the Invention Obtained by Method A

Synthesis of 4-((6-chloropyridin-3-yl)methyl)-5-methyl-2-(methylthio)-pyrazolo[1,5-a]pyrimidin-7 (4H)-one (Compound No. 154)

To a suspension of 5-methyl-2-(methylthio)-pyrazolo[1, 5-a]pyrimidin-7-ol (0.20 g, 1.0 mmol) in N,N-dimethyl formamide (DMF, 2 mL) contained in a 100 mL branched flask, potassium carbonate (0.17 g, 1.2 mmol) and 2-chloro-5-(chloromethyl)pyridine (0.20 g, 1.2 mmol) were added, heated to 80° C., and stirred for 1.5 hours. After cooling to room temperature, water (30 ml) was added and it was extracted with ethyl acetate (30 ml). After washing twice with water, it was dried over anhydrous magnesium sulfate, and the solvent was distilled off under reduced pressure. The obtained residues were with ethyl acetate (10 ml) and the obtained solid was collected by filtration to obtain the target product (0.06 g) as a white solid with yield of 20%.

$^1$H-NMR(CDCl$_3$)δ ppm: 8.29(1H,s), 7.35(1H,s), 7.34 (1H,s), 5.81(1H,s), 5.79(1H,s), 5.12(2H,s), 2.65(3H,s), 2.34 (3H,s).

Substitution position of a 6-chloro-3-pyridylmethyl group was determined and confirmed based on correlations by 2-D NMR (HMBC method).

Example 13

Compound of the Invention Obtained by Method B

Synthesis of 4-((6-chloropyridin-3-yl)methyl)-5-methylpyrazolo[1,5-a]pyrimidin-7(4H)-one (Compound No. 153)

(1) 3-Aminopyrazole (0.30 g, 3.5 mmol), 6-chloropyridin-3-carboxyaldehyde (0.50 g, 3.5 mmol) and ethanol (7 ml) were refluxed in a 100 mL branched flask for 1 hour. After cooling to room temperature, precipitated solid was collected by filtration to obtain N-((6-chloropyridin-3-yl)methylene)pyrazole-3-imine (0.72 g) as a white solid with yield of 100%.

$^1$H-NMR(CDCl$_3$)δ ppm: 8.83(1H,s), 8.78(1H,d,J=2.5 Hz), 8.33(1H,dd,J=2.5 Hz,J=8.5 Hz), 7.59(1H,d,J=2.5 Hz), 7.45(1H,d,J=8.5 Hz), 6.43(1H,d,J=2.5 Hz).

(2) To a suspension of N-((6-chloropyridin-3-yl)methylene)pyrazole-3-imine (0.45 g, 2.2 mmol) in ethanol (10 ml) contained in a 100 mL branched flask, sodium borohydride (0.09 g, 2.4 mmol) was added at room temperature and stirred at the same temperature for 4 hours. The solvent was concentrated under reduced pressure and the obtained residues were added with water (20 ml) and extracted with ethyl acetate (100 ml). After drying over anhydrous magnesium sulfate, the solvent was distilled off under reduced pressure to obtain N-((6-chloropyridin-3-yl)methyl)pyrazole-3-amine (0.33 g) as a white solid with yield of 72%.

$^1$H-NMR(CDCl$_3$)δ ppm: 8.40(1H,d,J=8.5 Hz), 7.71(1H, dd,J=2.5 Hz,J=8.5 Hz), 7.35(1H,d,J=2.5 Hz), 7.28(1H,d, J=8.5 Hz), 5.63(1H,d,J=2.5 Hz), 4.39(2H,s), 4.11(1H, brs).

(3) To a suspension of N-((6-chloropyridin-3-yl)methyl)pyrazole-3-amine (0.33 g, 1.6 mmol) in acetic acid (5 ml) contained in a 100 mL branched flask, ethyl acetoacetate (0.24 g, 1.8 mmol) was added and refluxed for 3 hours. After cooling to room temperature, 20 ml of a mixture of hexane and ethyl acetate (4:1) was added, and the obtained solid was collected by filtration to obtain the target compound (0.12 g) as a white solid with yield of 27%.

$^1$H-NMR(CDCl$_3$)δ ppm: 8.29(1H,d,J=2.0 Hz), 7.83(1H, d,J=2.0 Hz), 7.32-7.36(2H,m), 5.93(1H, 2.0 Hz), 5.81 (1H, J=2.0 Hz), 5.21 (2H,s), 2.37 (3H,s).

Example 14

Synthesis of 4-((6-chloropyridin-3-yl)methyl)-2-(2,2,2-trifluoroethoxy)-5-methylpyrazolo[1,5-a]pyrimidin-7(4H)-one (Compound No. 325)

(1) To a solution of 2-(3-hydroxy-1H-pyrazol-5-yl)isoindoline-1,3-dione (5.85 g, 25.5 mmol) in N,N-dimethyl formamide (DMF, 55 mL) contained in a 200 mL branched flask, 60% sodium hydride (1.2 g, 30.6 mmol) was added under ice cooling and stirred for 30 minutes. Then, 1,1,1-trifluoro-2-iodoethane (8.0 g, 38.3 mmol) was added to the mixture, which was then stirred for 2 hours at 110° C. After cooling to room temperature, water (50 mL) and sodium hydrogen carbonate solution (100 mL) were added. After extraction with ethyl acetate (200 mL), it was washed twice with saturated brine (50 mL). The organic layer was dried over anhydrous magnesium sulfate, and the solvent was distilled off under reduced pressure to obtain 2-(3-(2,2,2-trifluoroethoxy)-1H-pyrazol-5-yl)isoindoline-1,3-dione (542 mg) as a yellow solid with yield of 7%.

$^1$H-NMR(CDCl$_3$)δ: 7.96(2H,dd,J=5.4, 2.9 Hz), 7.84(2H, dd,J=5.4, 2.9 Hz), 6.40(1H,s), 4.63(2H,q,J=17.0 Hz).

(2) To a solution of 2-(3-(2,2,2-trifluoroethoxy)-1H-pyrazol-5-yl)isoindoline-1,3-dione (876 mg, 2.82 mmol) in ethanol (15 mL) contained in a 50 mL branched flask, hydrazine monohydrate (340 mg, 8.46 mmol) was added and stirred at room temperature for 1.5 hours. The solvent was distilled off under reduced pressure. The precipitated solid was filtered, water (30 mL) was added to the filtrate, and it was extracted three times with ethyl acetate (30 mL). The organic layer was dried over anhydrous magnesium sulfate, and the solvent was distilled off under reduced pressure to obtain 3-(2,2,2-trifluoroethoxy)-1H-pyrazole-5-amine.

To a solution of 3-(2,2,2-trifluoroethoxy)-1H-pyrazole-5-amine in acetic acid (5 mL) contained in a 30 mL branched flask, ethyl acetoacetate (440 mg, 3.38 mmol) was added and refluxed for 2 hours. After cooling to room temperature, the solvent was distilled off under reduced pressure. The precipitated solid was washed with ethyl acetate (5 mL) to obtain 2-(2,2,2-trifluoroethoxy)-5-methylpyrazolo[1,5-a]pyrimidin-7-ol (51.2 mg) as a white solid with yield of 7%.

$^1$H-NMR(DMSO-D6)δ: 12.20(1H,s), 5.71(1H,s), 5.54 (1H,s), 4.93(2H,q,J=9.0 Hz), 2.23(3H,s).

(3) To a suspension of 2-(2,2,2-trifluoroethoxy)-5-methylpyrazolo[1,5-a]pyrimidin-7-ol (51.2 mg, 0.21 mmol) in N,N-dimethyl formamide (DMF, 5 mL) contained in a 30 mL branched flask, potassium carbonate (44 mg, 0.32 mmol) and 2-chloro-5-(chloromethyl)pyridine (72 mg, 0.32 mmol) were added and stirred at 80° C. for 3 hours. After cooling to room temperature, water (30 mL) was added, extracted with ethyl acetate (30 mL) and washed twice with saturated brine (30 mL). The organic layer was dried over anhydrous magnesium sulfate, and the solvent was distilled off under reduced pressure. The obtained residues were purified by silica gel column chromatography using NH silica to obtain 4-((6-chloropyridin-3-yl)methyl)-2-(2,2,2-trifluoroethoxy)-5-methylpyrazolo[1,5-a]pyrimidin-7(4H)-one (17.5 mg) as a white solid with yield of 22%.

$^1$H-NMR(CDCl$_3$)δ: 8.30-8.27(1H,m), 7.37-7.36(2H,m), 5.85(1H,s), 5.49(1H,s), 5.11 (2H s), 4.79(2H,q,J=8.5 Hz), 2.35(3H,s).

Example 15

Synthesis of 4-((6-chloropyridin-3-yl)methyl)-2-difluoromethoxy-5-methylpyrazolo[1,5-a]pyrimidin-7(4H)-one (Compound No. 327)

(1) To a solution of 2-(3-hydroxy-1H-pyrazol-5-yl)isoindoline-1,3-dione (5.0 g, 21.8 mmol) in N,N-dimethyl formamide (DMF, 150 mL) contained in a 300 mL branched flask, water (22 mL), difluorochloro sodium acetate (8.3 g, 54.5 mmol), and cesium carbonate (15.4 g, 43.6 mmol) were added and stirred at 110° C. for 19 hours. After cooling to room temperature, water (200 mL) and sodium hydrogen carbonate solution (200 mL) were added. After extraction with ethyl acetate (200 mL), it was washed twice with saturated brine (200 mL). The organic layer was dried over anhydrous magnesium sulfate, and the solvent was distilled off under reduced pressure to obtain 2-(3-difluoromethoxy-1H-pyrazol-5-yl)isoindoline-1,3-dione.

To a solution of 2-(3-difluoromethoxy-1-pyrazol-5-yl)isoindoline-1,3-dione in ethanol (10 mL) contained in a 30 mL branched flask, hydrazine monohydrate (423 mg, 10.4 mmol) was added and stirred at room temperature for 1.5 hours. To the mixture solution, water (30 mL) was added, and it was extracted three times with ethyl acetate (30 mL). The organic layer was dried over anhydrous magnesium sulfate, and the solvent was distilled off under reduced pressure to obtain 3-difluoromethoxy-1H-pyrazole-5-amine.

To a solution of 3-difluoromethoxy-1H-pyrazole-5-amine in acetic acid (5 mL) contained in a 30 mL branched flask, ethyl acetoacetate (540 mg, 4.15 mmol) was added and refluxed for 3 hours. After cooling to room temperature, the solvent was distilled off under reduced pressure. The precipitated solid was washed with ethyl acetate (5 mL) to obtain 2-difluoromethoxy-5-methylpyrazolo[1,5-a]pyrimidin-7-ol (470 mg) as a white solid with yield of 10%.

$^1$H-NMR(DMSO-D6)δ: 12.41(1H,s), 7.50(1H,t,J=72.8 Hz), 5.84(1H,s), 5.61(1H,s), 2.26(3H,s).

(2) To a suspension of 2-difluoromethoxy-5-methylpyrazolo[1,5-a]pyrimidin-7-ol (150 mg, 0.70 mmol) in N,N-dimethyl formamide (DMF, 5 mL) contained in a 30 mL branched flask, potassium carbonate (145 mg, 1.05 mmol) and 2-chloro-5-(chloromethyl)pyridine (236 mg, 1.05 mmol) were added and stirred at 80° C. for 3 hours. After cooling to room temperature, water (30 mL) was added, extracted with ethyl acetate (30 mL) and washed twice with saturated brine (30 mL). The organic layer was dried over anhydrous magnesium sulfate, and the solvent was distilled off under reduced pressure. The obtained residues were washed with ethyl acetate (5 mL) to obtain 4-((6-chloropyridin-3-yl)methyl)-2-difluoromethoxy-5-methylpyrazolo[1,5-a]pyrimidin-7(4H)-one (68.8 mg) as a white solid with yield of 29%.

$^1$H-NMR(CDCl$_3$)δ: 8.29(1H,br s), 7.37(1H,br s), 7.36(1H,br s), 7.31(1H,t,J=72.5 Hz), 5.88(1H,s), 5.57(1H,s), 5.13(2H,s), 2.37(3H,s).

Example 16

Synthesis of 4-((6-chloropyridin-3-yl)methyl)-2-trifluoromethoxy-5-methylpyrazolo[1,5-a]pyrimidin-7(4H)-one (Compound No. 330)

(1) To a solution of 2-(3-hydroxy-1H-pyrazol-5-yl)isoindoline-1,3-dione (1.16 g, 5.05 mmol) in N,N-dimethyl formamide (DMF, 10 mL) contained in a 100 mL branched flask, 1-trifluoromethyl-3,3-dimethyl-1,2-beniodoxol (2.0 g, 6.06 mmol) was added and stirred at 60° C. for 6 hours. After cooling to room temperature, water (50 mL) and sodium hydrogen carbonate solution (50 mL) were added. After extraction with ethyl acetate (50 mL), it was washed twice with saturated brine (50 mL). The organic layer was dried over anhydrous magnesium sulfate, and the solvent was distilled off under reduced pressure to obtain 2-(3-trifluoromethoxy-1H-pyrazol-5-yl)isoindoline-1,3-dione.

To a solution of 2-(3-trifluoromethoxy-1H-pyrazol-5-yl)isoindoline-1,3-dione in ethanol (20 mL) contained in a 100 mL branched flask, hydrazine monohydrate (203 mg, 5.0 mmol) was added and stirred at room temperature for 1.5 hours. To the mixture solution, water (30 mL) was added, and it was extracted three times with ethyl acetate (30 mL). The organic layer was dried over anhydrous magnesium sulfate, and the solvent was distilled off under reduced pressure to obtain 3-trifluoromethoxy-1H-pyrazole-5-amine.

To a solution of 3-trifluoromethoxy-1H-pyrazole-5-amine in acetic acid (5 mL) contained in a 30 mL branched flask, ethyl acetoacetate (400 mg, 5.0 mmol) was added and refluxed for 5 hours. After cooling to room temperature, the solvent was distilled off under reduced pressure. The precipitated solid was washed with ethyl acetate (5 mL). Furthermore, the washed solution was distilled under reduced pressure to remove the solvent and purified by silica gel column chromatography, and according to combination with the above, 2-trifluoromethoxy-5-methylpyrazolo[1,5-a]pyrimidin-7-ol (89.1 mg) was obtained as a white solid with yield of 8%.

$^1$H-NMR(DMSO-D6)δ: 12.55(1H,s), 6.01(1H,s), 5.6(1H,s), 2.28(3H,s).

(2) To a suspension of 2-trifluoromethoxy-5-methylpyrazolo[1,5-a]pyrimidin-7-ol (89 mg, 0.38 mmol) in N,N-dimethyl formamide (DMF, 5 mL) contained in a 30 mL branched flask, potassium carbonate 79 mg, 0.57 mmol) and 2-chloro-5-(chloromethyl)pyridine (128 mg, 0.57 mmol) were added and stirred at 80° C. for 3 hours. After cooling to room temperature, water (30 mL) was added, extracted with ethyl acetate (30 mL) and washed twice with saturated brine (30 mL). The organic layer was dried over anhydrous magnesium sulfate, and the solvent was distilled off under reduced pressure. The obtained residues were purified by silica gel column chromatography using NH silica to obtain 4-((6-chloropyridin-3-yl)methyl)-2-trifluoromethoxy-5-methylpyrazolo[1,5-a]pyrimidin-7(4H)-one (17.5 mg) as a white solid with yield of 32%.

$^1$H-NMR(CDCl$_3$)δ: 8.30(1H,dd,J=2.4, 0.7 Hz), 7.38(1H,dd,J=8.4, 0.7 Hz), 7.35(1H,dd,J=8.6, 2.4 Hz), 5.91(1H,s), 5.73(1H,s), 5.16(2H,s), 2.37(3Hs).

Example 17

Synthesis of 4-((6-chloropyridin-3-yl)methyl)-2-chloro-5-methylpyrazolo[1,5-a]pyrimidin-7(4H)-one (Compound No. 323)

(1) To a solution of ethyl 5-amino-1H-pyrazole-4-carboxylate (5.0 g, 32.2 mmol) in N,N-dimethyl formamide (DMF, 150 mL) contained in a 300 mL branched flask, N-chlorosuccinimide (5.15 g, 38.6 mmol) was added and stirred at room temperature for 2 hours. To the reaction solution, water (200 mL) and saturated brine (200 mL) were added. After extraction twice with ethyl acetate (200 mL), it was washed twice with saturated brine (200mL). The organic layer was dried over anhydrous magnesium sulfate, and the solvent was distilled off under reduced pressure. The residues were purified by silica gel column chromatography to obtain ethyl 5-amino-3-chloro-1H-pyrazole-4-carboxylate (1.04 g) as a yellow solid with yield of 17%.

$^1$H-NMR(CDCl$_3$)δ: 11.63(1H,s), 5.40(2H,s), 4.33(2H,q, J=7.2 Hz), 1.38(3H,t,J=7.2 Hz).

(2) To a solution of 5-amino-3-chloro-1H-pyrazole-4-carboxylate (1.2 g, 6.33 mmol) in acetic acid (10 mL) contained in a 100 mL branched flask, ethyl acetoacetate (990 mg, 7.60 mmol) was added and refluxed for 6 hours. After cooling to room temperature, the solvent was distilled off under reduced pressure. The precipitated solid was washed with ethyl acetate (15 mL) to obtain ethyl-2-chloro-7-hydroxy-5-methylpyrazolo[1,5-a]pyrimidin-3-carboxylate (903 mg) as a brown solid at yield of 56%.

$^1$H-NMR(DMSO-D6)δ: 11.81(1H,s), 5.90(1H,s), 4.34(2H,q,J=7.0 Hz), 2.39(3H,s), 1.33(3H,t,J=7.0 Hz).

(3) Ethyl-2-chloro-7-hydroxy-5-methylpyrazolo[1,5-a]pyrimidin-3-carboxylate (903 mg, 3.53 mmol) was dissolved in 47 to 49% hydrogen bromide acid (5 mL) in a 50 mL branched flask followed by stirring at 120° C. for 4.5 hours. After cooling to room temperature, it was concentrated under reduced pressure, and the obtained residues were added with water, and concentrated again under reduced pressure. The residues were added with water, and the precipitated solid was collected to obtain 2-chloro-5-methylpyrazolo[1,5-a]pyrimidin-7-ol (1.33 g) as a pale brown solid with yield of 61%.

$^1$H-NMR(DMSO-D6)δ: 12.48(1H,s), 6.22(1H,s), 5.64(1H,s), 2.28(3H,s).

(4) To a suspension of 2-chloro-5-methylpyrazolo[1,5-a]pyrimidin-7-ol (200 mg, 1.09 mmol) in N,N-dimethyl formamide (DMF, 5 mL) contained in a 30 mL branched flask, potassium carbonate (227 mg, 1.64 mmol) and 2-chloro-5-(chloromethyl)pyridine (266 mg, 1.64 mmol) were added and stirred at 80° C. for 3 hours. After cooling to room temperature, water (30 mL) was added. After extraction with ethyl acetate (30 mL), it was washed twice with saturated brine (30 mL). The organic layer was dried over anhydrous magnesium sulfate, and the solvent was distilled off under reduced pressure. The obtained solid was washed with ethyl acetate (10 mL) to obtain 4-((6-chloropyridin-3-yl)methyl)-2-chloro-5-methylpyrazolo[1,5-a]pyrimidin-7(4H)-one (68.8 mg) as a white solid with yield of 26%.

$^1$H-NMR(CDCl$_3$)δ: 8.30(1H,dd,J=2.4, 0.9 Hz), 7.37(1H, dd,J=8.4, 0.9 Hz), 7.35(1H,dd,J=8.4, 2.4 Hz), 5.90(1H,s), 5.86(1H,s), 5.14(2H,s), 2.38(3H,s).

The compounds of the invention shown below were produced in the same manner as Examples 1 to 17. The Compound No. in the tables corresponds to the structure of the compound exemplified above. In the Table, the state of each obtained compound, and chemical shift value of $^1$H-NMR (TMS standard), which has been measured according to the method described above, are described.

The compounds of the invention shown in the following Table 1 to Table 27 were produced by using any one of Method A to Method E, or from the fused ring pyrimidine compound of the invention, which has been produced by using any one of Method A to Method E, using a known method.

TABLE 1

| Compound No. | State | 1H-NMR Value δ (ppm) |
|---|---|---|
| 1 | Solid | $^1$H-NMR (CDCl$_3$) δ: 8.34 (1H, d, J = 2.6 Hz), 7.60 (1H, dd, J = 8.4, 2.6 Hz), 7.34 (1H, d, J = 8.4 Hz), 5.62 (2H, s), 3.40 (3H, s), 2.45 (3H, s), 2.19 (3H, s). |
| 2 | Solid | $^1$H-NMR (CDCl$_3$) δ: 7.63 (1H, s), 5.65 (2H, s), 3.45 (3H, s), 2.58 (3H, s), 2.22 (3H, s). |
| 3 | Solid | $^1$H-NMR (CDCl$_3$) δ: 8.35 (1H, d, J = 2.6 Hz), 7.54 (1H, dd, J = 8.4, 2.6 Hz), 7.33 (1H, d, J = 8.4 Hz), 5.49 (2H, s), 2.69 (3H, s), 2.37 (3H, s), 2.15 (3H, s). |
| 4 | Solid | $^1$H-NMR (CDCl$_3$) δ: 8.56 (1H, d, J = 2.4 Hz), 8.31 (1H, s), 7.77 (1H, dd, J = 8.3, 2.4 Hz), 7.38 (1H, d, J = 8.3 Hz), 6.12 (1H, s), 5.30 (2H, s), 2.39 (3H, s). |
| 5 | Solid | $^1$H-NMR (CDCl$_3$) δ: 8.37 (1H, d, J = 2.6 Hz), 7.59 (1H, dd, J = 8.3, 2.6 Hz), 7.35 (1H, d, J = 8.3 Hz), 5.91 (1H, s), 5.43 (2H, s), 2.69 (3H, s), 2.40 (3H, s). |
| 6 | Solid | $^1$H-NMR (CDCl$_3$) δ: 8.39 (1H, d, J = 2.4 Hz), 7.61 (1H, dd, J = 8.3, 2.4 Hz), 7.36 (1H, d, J = 8.3 Hz), 5.46 (2H, s), 2.68 (3H, s), 2.46 (3H, d, J = 3.7 Hz). |
| 7 | Solid | $^1$H-NMR (CDCl$_3$) δ: 8.39 (1H, d, J = 2.4 Hz), 7.59 (1H, dd, J = 8.3, 2.4 Hz), 7.36 (1H, d, J = 8.3 Hz), 5.54 (2H, s), 2.69 (3H, s), 2.60 (3H, s). |
| 8 | Solid | $^1$H-NMR (CDCl$_3$) δ: 8.30 (1H, d, J = 2.1 Hz), 7.55 (1H, dd, J = 8.3, 2.1 Hz), 7.29 (1H, d, J = 8.3 Hz), 7.22-7.16 (5H, m), 5.47 (2H, s), 3.96 (2H, s), 2.65 (3H, s), 2.35 (3H, s). |
| 9 | Solid | $^1$H-NMR (CDCl$_3$) δ: 8.36 (1H, d, J = 2.4 Hz), 8.04 (1H, s), 7.54 (1H, dd, J = 8.3, 2.4 Hz), 7.33 (1H, d, J = 8.3 Hz), 5.55 (2H, s), 2.41 (3H, s), 2.19 (3H, s). |
| 10 | Solid | $^1$H-NMR (CDCl$_3$) δ: 8.37 (1H, d, J = 2.4 Hz), 7.64 (1H, dd, J = 8.3, 2.4 Hz), 7.38 (1H, d, J = 8.3 Hz), 6.06 (1H, s), 5.55 (2H, s), 3.42 (3H, s), 2.49 (3H, s). |
| 11 | Solid | $^1$H-NMR (CDCl$_3$) δ: 8.32 (1H, d, J = 2.1 Hz), 7.59 (1H, dd, J = 6.3, 2.1 Hz), 7.35 (1H, d, J = 8.3 Hz), 7.29-7.25 (2H, m), 7.22-7.20 (3H, m), 5.57 (2H, s), 4.05 (2H, s), 3.44 (3H, s), 2.43 (3H, s). |
| 12 | Solid | $^1$H-NMR (CDCl$_3$) δ: 8.35 (1H, d, J = 2.4 Hz), 7.55 (1H, dd, J = 8.3, 2.4 Hz), 7.34 (1H, d, J = 8.3 Hz), 5.84 (1H, s), 5.46 (2H, s), 2.68 (3H, s), 2.66 (2H, q, J = 7.3 Hz), 1.30 (3H, t, J = 7.3 Hz). |
| 13 | Solid | $^1$H-NMR (CDCl$_3$) δ: 8.34 (1H, d, J = 2.4 Hz), 7.55 (1H, dd, J = 8.3, 2.4 Hz), 7.34 (1H, d, J = 8.3 Hz), 5.91 (1H, s), 5.45 (2H, s), 2.68 (3H, s), 2.58 (2H, t, J = 7.3 Hz), 1.70-1.67 (2H, m), 1.04 (3H, t, J = 7.3 Hz). |
| 14 | Solid | $^1$H-NMR (DMSO-D6) δ: 8.45 (1H, d, J = 2.5 Hz), 7.78 (1H, dd, J = 8.5, 2.5 Hz), 7.50 (1H, d, J = 8.5 Hz), 5.88 (1H, d, J = 1.0 Hz), 5.43 (2H, s), 2.96 (6H, s), 2.32 (3H, s). |
| 15 | Solid | $^1$H-NMR (DMSO-D6) δ: 8.41 (1H, d, J = 2.5 Hz), 7.76 (1H, dd, J = 8.5, 2.5 Hz), 7.20-7.47 (7H, m), 6.00 (1H, d, J = 0.5 Hz), 5.48 (2H, s), 4.06 (2H, s), 2.35 (3H, s). |
| 16 | Solid | $^1$H-NMR (DMSO-D6) δ: 8.43 (1H, d, J = 2.5 Hz), 7.82 (1H, brs), 7.76 (1H, dd, J = 8.5, 2.5 Hz), 7.70 (1H, d, J = 8.5 Hz), 7.45-7.60 (3H, m), 6.03 (1H, s), 5.49 (2H, s), 4.51 (2H, s), 2.34 (3H, s). |
| 17 | Solid | $^1$H-NMR (DMSO-D6) δ: 8.70 (1H, d, J = 0.5 Hz), 8.54 (1H, d, J = 0.5 Hz), 8.43 (1H, d, J = 2.5 Hz), 7.77 (1H, dd, J = 8.5, 2.5 Hz), 7.50 (1H, dd, J = 8.0, 0.5 Hz), 6.14 (1H, s), 5.51 (2H, s), 2.42 (3H, s). |

TABLE 2

| Compound No. | State | $^1$H-NMR Value δ (ppm) |
|---|---|---|
| 18 | Amorphous | $^1$H-NMR (CDCl$_3$) δ: 8.32 (1H, d, J = 2.4 Hz), 7.50 (1H, dd, J = 8.3, 2.4 Hz), 7.34 (1H, d, J = 8.3 Hz), 6.01 (1H, s), 5.50 (2H, s), 2.96-2.91 (1H, m), 2.69 (3H, s), 1.27 (6H, d, J = 6.9 Hz). |
| 19 | Solid | $^1$H-NMR (CDCl$_3$) δ: 8.23 (1H, d, J = 2.6 Hz), 7.61 (1H, dd, J = 8.3, 2.6 Hz), 7.23 (1H, d, J = 8.3 Hz), 5.80 (1H, s), 5.63 (2H, s), 2.69 (3H, s), 1.73-1.71 (1H, m), 1.17-1.12 (2H, m), 0.88-0.87 (2H, m). |
| 20 | Solid | $^1$H-NMR (CDCl$_3$) δ: 7.60 (1H, s), 5.89 (1H, d, J = 0.9 Hz), 5.46 (2H, s), 2.71 (3H, s), 2.51 (3H, d, J = 0.9 Hz). |
| 21 | Solid | $^1$H-NMR (CDCl$_3$) δ: 5.89 (1H, d, J = 0.9 Hz), 4.22-4.21 (1H, m), 4.09-3.99 (2H, m), 3.81-3.79 (1H, m), 3.68-3.66 (1H, m), 3.61-3.59 (1H, m), 3.03-2.98 (1H, m), 2.69 (3H, s), 2.45 (3H, d, J = 0.9 Hz), 2.12-2.05 (1H, m), 1.75-1.69 (1H, m). |

TABLE 2-continued

| Compound No. | State | ¹H-NMR Value δ (ppm) |
|---|---|---|
| 22 | Solid | ¹H-NMR (CDCl₃) δ: 8.36 (1H, d, J = 2.4 Hz), 7.58 (1H, dd, J = 8.3, 2.4 Hz), 7.35 (1H, d, J = 8.3 Hz), 5.94 (1H, s), 5.43 (2H, s), 3.40-3.38 (2H, m), 2.74-2.61 (2H, m), 2.42 (3H, s). |
| 23 | Solid | ¹H-NMR (CDCl₃) δ: 8.37 (1H, d, J = 2.4 Hz), 7.57 (1H, dd, J = 8.3, 2.4 Hz), 7.35 (1H, d, J = 8.3 Hz), 5.93 (1H, d, J = 0.9 Hz), 5.42 (2H, s), 3.32 (2H, t, J = 7.0 Hz), 2.41 (3H, d, J = 0.9 Hz), 2.30-2.26 (2H, m), 2.09-2.07 (2H, m). |
| 24 | Solid | ¹H-NMR (DMSO-D6) δ: 8.48 (1H, d, J = 2.5 Hz), 7.83 (1H, dd, J = 8.5, 2.5 Hz), 7.49 (1H, d, J = 8.5 Hz), 6.95 (1H, s), 5.54 (2H, s), 2.62 (3H, s), 2.36 (3H, s). |
| 25 | Solid | ¹H-NMR (CDCl₃) δ: 8.34 (1H, d, J = 2.4 Hz), 7.54 (1H, dd, J = 8.3, 2.4 Hz), 7.34 (1H, d, J = 8.3 Hz), 5.48 (2H, s), 2.69 (3H, s), 2.65 (2H, q, J = 7.4 Hz), 2.38 (3H, s), 1.11 (3H, t, J = 7.4 Hz). |
| 26 | Solid | ¹H-NMR (CDCl₃) δ: 8.37 (1H, d, J = 2.4 Hz), 7.63 (1H, dd, J = 8.3, 2.4 Hz), 7.36 (1H, d, J = 8.3 Hz), 6.04 (1H, d, J = 0.6 Hz), 5.59 (1H, d, J = 16.2 Hz), 5.53 (1H, d, J = 16.2 Hz), 3.13 (3H, s), 2.48 (3H, d, J = 0.6 Hz). |
| 27 | Solid | ¹H-NMR (CDCl₃) δ: 8.38 (1H, d, J = 2.4 Hz), 7.56 (1H, dd, J = 8.3, 2.4 Hz), 7.34 (1H, d, J = 8.3 Hz), 5.87 (1H, s), 5.42 (2H, s), 2.38 (3H, s), 2.16-2.11 (1H, m), 1.11-1.03 (4H, m). |
| 28 | Solid | ¹H-NMR (CDCl₃) δ: 8.47 (1H, d, J = 2.6 Hz), 8.18-8.15 (1H, m), 7.73 (1H, dd, J = 8.4, 2.6 Hz), 7.48-7.44 (1H, m), 7.35 (1H, d, J = 8.4 Hz), 7.23-7.20 (2H, m), 5.96 (1H, d, J = 0.9 Hz), 5.54 (2H, s), 2.47 (3H, d, J = 0.9 Hz). |
| 29 | Solid | ¹H-NMR (CDCl₃) δ: 8.37 (1H, d, J = 2.4 Hz), 7.59 (1H, dd, J = 8.3, 2.4 Hz), 7.35 (1H, d, J = 8.3 Hz), 5.91 (1H, d, J = 0.9 Hz), 5.43 (2H, s), 3.28 (2H, q, J = 7.3 Hz), 2.40 (3H, d, J = 0.9 Hz), 1.45 (3H, t, J = 7.3 Hz). |
| 30 | Solid | ¹H-NMR (CDCl₃) δ: 8.39 (1H, d, J = 2.4 Hz), 7.58 (1H, dd, J = 8.3, 2.4 Hz), 7.35 (2H, d, J = 8.3 Hz), 5.91 (1H, s), 5.46 (2H, s), 2.77 (2H, q, J = 7.4 Hz), 2.40 (3H, s), 1.43 (3H, t, J = 7.4 Hz). |
| 31 | Solid | ¹H-NMR (CDCl₃) δ: 8.37 (1H, d, J = 2.5 Hz), 7.56 (1H, dd, J = 8.5, 2.5 Hz), 7.34 (1H, d, J = 8.5 Hz), 5.86 (1H, d, J = 1.0 Hz), 5.35 (2H, s), 3.39-3.72 (7H, m), 2.61-2.66 (1H, m), 2.34 (3H, d, J = 1.0 Hz), 2.04-2.11 (1H, m), 1.62-1.70 (1H, m). |
| 32 | Solid | ¹H-NMR (CDCl₃) δ: 8.40 (1H, d, J = 2.4 Hz), 7.62 (1H, dd, J = 8.3, 2.4 Hz), 7.38 (1H, d, J = 8.3 Hz), 6.04 (1H, d, J = 0.6 Hz), 5.51 (2H, s), 2.49 (3H, d, J = 0.6 Hz). |

TABLE 3

| Compound No. | State | ¹H-NMR Value δ (ppm) |
|---|---|---|
| 33 | Solid | ¹H-NMR (CDCl₃) δ: 8.37 (1H, d, J = 2.4 Hz), 7.58 (1H, dd, J = 8.3, 2.4 Hz), 7.34 (1H, d, J = 8.3 Hz), 5.95 (1H, d, J = 0.9 Hz), 5.52 (2H, s), 4.63 (2H, s), 3.48 (3H, s), 2.42 (3H, d, J = 0.9 Hz). |
| 34 | Solid | ¹H-NMR (CDCl₃) δ: 8.44 (1H, d, J = 2.4 Hz), 7.90 (1H, d, J = 3.9 Hz), 7.66 (1H, dd, J = 8.3, 2.4 Hz), 7.46 (1H, d, J = 4.9 Hz), 7.35 (1H, d, J = 8.3 Hz), 7.14 (1H, dd, J = 4.9, 3.9 Hz), 5.94 (1H, s), 5.51 (2H, s), 2.43 (3H, s). |
| 35 | Solid | ¹H-NMR (CDCl₃) δ: 8.37 (1H, d, J = 2.4 Hz), 7.65 (1H, dd, J = 8.3, 2.4 Hz), 7.34 (1H, d, J = 8.3 Hz), 5.99 (1H, s), 5.52 (2H, s), 3.75 (2H, t, J = 5.4 Hz), 3.65 (2H, t, J = 5.4 Hz), 2.45 (3H, s), 1.70-1.69 (4H, m), 1.64-1.63 (2H, m). |
| 36 | Solid | ¹H-NMR (CDCl₃) δ: 8.48 (1H, d, J = 2.4 Hz), 7.74 (1H, dd, J = 8.3, 2.4 Hz), 7.41 (1H, d, J = 8.0 Hz), 7.38 (1H, d, J = 8.3 Hz), 6.06 (1H, d, J = 8.0 Hz), 5.29 (2H, s), 2.70 (3H, s). |
| 37 | Solid | ¹H-NMR (CDCl₃) δ: 8.55 (1H, d, J = 2.4 Hz), 8.41 (1H, s), 7.78 (1H, dd, J = 8.3, 2.4 Hz), 7.39 (1H, d, J = 8.3 Hz), 5.34 (2H, s), 4.39 (2H, q, J = 7.1 Hz), 2.69 (3H, s), 1.38 (3H, t, J = 7.1 Hz). |
| 38 | Solid | ¹H-NMR (CDCl₃) δ: 8.37 (1H, d, J = 2.5 Hz), 7.56 (1H, dd, J = 8.5, 2.5 Hz), 7.33 (1H, d, J = 8.5 Hz), 5.85 (1H, d, J = 1.0 Hz), 5.35 (2H, s), 3.03 (3H, d, J = 5.5 Hz), 2.34 (3H, d, J = 1.0 Hz). |
| 39 | Solid | ¹H-NMR (CDCl₃) δ: 8.44 (1H, d, J = 2.5 Hz), 7.55 (1H, dd, J = 8.5, 2.5 Hz), 7.34 (1H, d, J = 8.5 Hz), 5.87 (1H, d, J = 1.0 Hz), 5.37 (2H, s), 3.78 (4H, t, J = 4.5 Hz), 3.58 (4H, t, J = 4.5 Hz), 2.36 (3H, s). |
| 40 | Solid | ¹H-NMR (CDCl₃) δ: 8.27 (1H, d, J = 2.1 Hz), 7.70 (1H, d, J = 2.1 Hz), 5.94 (1H, d, J = 0.9 Hz), 5.42 (2H, s), 2.70 (3H, s), 2.41 (3H, d, J = 0.9 Hz). |
| 41 | Solid | ¹H-NMR (CDCl₃) δ: 8.59 (1H, d, J = 1.5 Hz), 7.99 (1H, d, J = 1.5 Hz), 5.97 (1H, d, J = 0.6 Hz), 5.66 (2H, s), 2.66 (3H, s), 2.29 (3H, d, J = 0.6 Hz). |
| 42 | Solid | ¹H-NMR (CDCl₃) δ: 8.61 (1H, dd, J = 4.9, 2.4 Hz), 8.58 (1H, d, J = 2.4 Hz), 7.58 (1H, dd, J = 8.0, 2.4 Hz), 7.32 (1H, dd, J = 8.0, 4.9 Hz), 5.92 (1H, s), 5.47 (2H, s), 2.70 (3H, s), 2.39 (3H, s). |
| 43 | Solid | ¹H-NMR (CDCl₃) δ: 8.52 (1H, dd, J = 4.9, 1.8 Hz), 7.70 (1H, td, J = 7.7, 1.8 Hz), 7.33 (1H, d, J = 7.7 Hz), 7.25-7.24 (1H, m), 5.92 (1H, d, J = 0.9 Hz), 5.50 (2H, s), 2.68 (3H, s), 2.49 (3H, d, J = 0.9 Hz). |
| 44 | Solid | ¹H-NMR (CDCl₃) δ: 8.65-8.62 (2H, m), 7.07-7.06 (2H, m), 5.96 (1H, s), 5.46 (2H, s), 2.69 (3H, s), 2.32 (3H, s). |

TABLE 3-continued

| Compound No. | State | $^1$H-NMR Value δ (ppm) |
|---|---|---|
| 45 | solid | $^1$H-NMR (CDCl$_3$) δ: 8.36 (1H, d, J = 2.4 Hz), 7.61 (1H, dd, J = 8.3, 2.4 Hz), 7.34 (1H, d, J = 8.3 Hz), 5.93 (1H, d, J = 0.6 Hz), 5.40 (2H, s), 4.13 (3H, s), 2.39 (3H, d, J = 0.6 Hz). |
| 46 | Solid | $^1$H-NMR (CDCl$_3$) δ: 8.37 (1H, s), 7.63 (1H, d, J = 8.3 Hz), 7.36 (1H, d, J = 8.3 Hz), 5.96 (1H, s), 5.42 (2H, s), 4.82 (2H, q, J = 8.0 Hz), 2.43 (3H, s). |
| 47 | Solid | $^1$H-NMR (CDCl$_3$) δ: 8.36 (1H, d, J = 2.4 Hz), 7.62 (1H, dd, J = 8.4, 2.4 Hz), 7.41-7.32 (5H, m), 7.22-7.19 (1H, m), 5.51 (1H, s), 5.40 (2H, s), 2.40 (3H, s). |
| 48 | Solid | $^1$H-NMR (CDCl$_3$) δ: 8.71 (1H, d, J = 1.5 Hz), 7.78 (1H, dd, J = 8.0, 1.5 Hz), 7.71 (1H, d, J = 8.0 Hz), 5.92 (1H, s), 5.55 (2H, s), 2.68 (3H, s), 2.41 (3H, s). |
| 49 | Solid | $^1$H-NMR (CDCl$_3$) δ: 8.62 (1H, d, J = 1.2 Hz), 8.51 (1H, d, J = 1.2 Hz), 5.93 (1H, d, J = 0.6 Hz) 5.47 (2H, s), 2.66 (3H, s), 2.57 (3H, d, J = 0.6 Hz). |

TABLE 4

| Compound No. | State | $^1$H-NMR Value δ (ppm) |
|---|---|---|
| 50 | Solid | $^1$H-NMR (CDCl$_3$) δ: 8.21 (1H, d, J = 2.4 Hz), 7.77 (1H, td, J = 8.3, 2.4 Hz), 6.97 (1H, dd, J = 8.3, 3.1 Hz), 5.92 (1H, s), 5.44 (2H, s), 2.70 (3H, s), 2.41 (3H, s). |
| 51 | Solid | $^1$H-NMR (CDCl$_3$) δ: 8.40 (1H, dd, J = 4.9, 1.8 Hz), 7.24 (1H, dd, J = 7.8, 4.9 Hz), 7.15 (1H, dd, J = 7.8, 1.8 Hz), 5.98 (1H, d, J = 0.9 Hz), 5.53 (2H, s), 2.68 (3H, s), 2.31 (3H, d, J = 0.9 Hz). |
| 52 | Solid | $^1$H-NMR (CDCl$_3$) δ: 8.46 (1H, d, J = 2.4 Hz), 7.46 (1H, dd, J = 8.3, 2.4 Hz), 7.15 (1H, d, J = 8.3 Hz), 5.90 (1H, d, J = 0.9 Hz), 5.42 (2H, s), 2.70 (3H, s), 2.56 (3H, s), 2.39 (3H, d, J = 0.9 Hz). |
| 53 | Solid | $^1$H-NMR (CDCl$_3$) δ: 8.12 (1H, d, J = 2.4 Hz), 7.54 (1H, dd, J = 8.6, 2.4 Hz), 6.74 (1H, d, J = 8.6 Hz), 5.88 (1H, d, J = 0.9 Hz), 5.37 (2H, s), 3.92 (3H, s), 2.70 (3H, s), 2.42 (3H, d, J = 0.9 Hz). |
| 54 | Solid | $^1$H-NMR (CDCl$_3$) δ: 8.36 (1H, d, J = 2.5 Hz), 7.59 (1H, dd, J = 8.5, 2.5 Hz), 7.36 (1H, d, J = 8.5 Hz), 6.02 (1H, d, J = 1.0 Hz), 5.56 (2H, s), 4.04 (3H, s), 2.45 (3H, d, J = 1.0 Hz). |
| 55 | Solid | $^1$H-NMR (CDCl$_3$) δ: 7.27 (1H, d, J = 8.3 Hz), 7.17 (1H, d, J = 8.3 Hz), 5.97 (1H, d, J = 0.6 Hz), 5.49 (2H, s), 2.68 (3H, s), 2.32 (3H, d, J = 0.6 Hz). |
| 56 | Amorphous | $^1$H-NMR (CDCl$_3$) δ: 8.41 (1H, d, J = 2.4 Hz), 7.65 (1H, dd, J = 8.3, 2.4 Hz), 7.38 (1H, d, J = 8.3 Hz), 6.04 (1H, d, J = 0.9 Hz), 5.52 (2H, s), 2.50 (3H, d, J = 0.9 Hz). |
| 57 | Solid | $^1$H-NMR (CDCl$_3$) δ: 8.39 (1H, d, J = 2.8 Hz), 7.63 (1H, dd, J = 8.3, 2.8 Hz), 7.37 (1H, d, J = 8.3 Hz), 6.78 (1H, t, J = 53.0 Hz), 6.01 (1H, d, J = 0.9 Hz), 5.53 (2H, s), 2.48 (3H, d, J = 0.9 Hz). |
| 58 | Solid | $^1$H-NMR (CDCl$_3$) δ: 8.38 (1H, d, J = 2.4 Hz), 7.59 (1H, dd, J = 8.3, 2.4 Hz), 7.36 (1H, d, J = 8.3 Hz), 5.95 (1H, s), 5.43 (2H, s), 3.96 (2H, q, J = 9.6 Hz), 2.42 (3H, s). |
| 59 | Solid | $^1$H-NMR (CDCl$_3$) δ: 8.39 (1H, d, J = 2.4 Hz), 7.63 (1H, dd, J = 8.3, 2.4 Hz), 7.36 (1H, d, J = 8.3 Hz), 6.01 (1H, s), 5.53 (2H, s), 2.46 (3H, s), 2.16 (3H, t, J = 18.8 Hz). |
| 60 | Solid | $^1$H-NMR (CDCl$_3$) δ: 8.37 (1H, d, J = 2.4 Hz), 7.56 (1H, dd, J = 8.3, 2.4 Hz), 7.35 (2H, d, J = 8.3 Hz), 5.91 (1H, s), 5.45 (2H, s), 2.51 (3H, s), 2.40 (3H, s). |
| 61 | Solid | $^1$H-NMR (CDCl$_3$) δ: 8.39 (1H, d, J = 2.5 Hz), 7.58 (1H, dd, J = 8.5, 2.5 Hz), 7.37 (1H, d, J = 8.5 Hz), 5.98 (1H, d, J = 1.0 Hz), 5.44 (2H, s), 3.47 (3H, s), 2.49 (3H, s), 2.45 (3H, s). |
| 62 | Solid | $^1$H-NMR (CDCl$_3$) δ: 8.40 (1H, d, J = 2.5 Hz), 7.59 (1H, d, J = 8.5. 2.5 Hz), 7.34 (1H, d, J = 8.5 Hz), 5.86 (1H, d, J = 1.0 Hz), 5.39 (2H, s), 4.94 (2H, s), 3.29 (3H, s), 3.18 (3H, s), 2.37 (3H, d, J = 1.0 Hz). |
| 63 | Solid | $^1$H-NMR (CDCl$_3$) δ: 8.47 (1H, d, J = 2.4 Hz), 7.73 (1H, dd, J = 8.3, 2.4 Hz), 7.37 (1H, d, J = 8.3 Hz), 7.27 (2H, d, J = 0.9 Hz), 5.25 (2H, s), 2.70 (3H, s), 2.13 (3H, d, J = 0.9 Hz). |
| 64 | Solid | $^1$H-NMR (CDCl$_3$) δ: 8.48 (1H, d, J = 2.6 Hz), 7.79 (1H, dd, J = 8.3, 2.6 Hz), 7.47 (1H, d, J = 0.9 Hz), 7.39 (1H, d, J = 8.3 Hz), 5.38 (2H, s), 3.44 (3H, s), 2.18 (3H, d, J = 0.9 Hz). |

TABLE 5

| Compound No. | State | $^1$H-NMR Value δ (ppm) |
|---|---|---|
| 65 | Solid | $^1$H-NMR (CDCl$_3$) δ: 8.49 (1H, d, J = 2.8 Hz), 7.78 (1H, dd, J = 8.3, 2.8 Hz), 7.43 (1H, d, J = 0.9 Hz), 7.39 (1H, d, J = 8.3 Hz), 5.41 (1H, d, J = 15.0 Hz), 5.37 (1H, d, J = 15.0 Hz), 3.13 (3H, s), 2.18 (3H, d, J = 0.9 Hz). |
| 66 | Solid | $^1$H-NMR (CDCl$_3$) δ: 8.38 (1H, d, J = 2.4 Hz), 7.62 (1H, dd, J = 8.3, 2.4 Hz), 7.40-7.38 (2H, m), 7.36 (1H, d, J = 8.3 Hz), 7.25 (2H, d, J = 8.6 Hz), 5.96 (1H, s), 5.42 (2H, s), 2.42 (3H, s). |

TABLE 5-continued

| Compound No. | State | $^1$H-NMR Value δ (ppm) |
|---|---|---|
| 67 | Solid | $^1$H-NMR (CDCl$_3$) δ: 8.38 (1H, d, J = 2.4 Hz), 7.63 (1H, dd, J = 8.3, 2.4 Hz), 7.40-7.39 (2H, m), 7.36 (1H, d, J = 8.3 Hz), 7.27-7.26 (2H, m), 5.94 (1H, s), 5.42 (2H, s), 2.41 (3H, s), 1.33 (9H, s). |
| 68 | Oily phase | $^1$H-NMR (CDCl$_3$) δ: 8.48 (1H, d, J = 2.4 Hz), 7.68 (1H, dd, J = 8.3, 2.4 Hz), 7.39-7.37 (2H, m), 6.10 (1H, q, J = 7.2 Hz), 6.05 (1H, d, J = 7.8 Hz), 2.70 (3H, s), 1.95 (3H, d, J = 7.2 Hz). |
| 69 | Solid | $^1$H-NMR (CDCl$_3$) δ: 8.67 (1H, d, J = 2.8 Hz), 8.50 (1H, dd, J = 4.9, 1,4 Hz), 8.38 (1H, d, J = 2.4 Hz), 7.81 (1H, ddd, J = 8.4, 2.8, 1.4 Hz), 7.62 (1H, dd, J = 8.4, 2.4 Hz), 7.38-7.37 (2H, m), 5.98 (1H, d, J = 0.6 Hz), 5.42 (2H, s), 2.43 (3H, d, J = 0.6 Hz). |
| 70 | Solid | $^1$H-NMR (CDCl$_3$) δ: 8.43-8.40 (3H, m), 7.57 (1H, dd, J = 8.3, 2.6 Hz), 7.39 (1H, d, J = 8.3 Hz), 6.47-6.45 (2H, m), 6.07 (1H, s), 5.49 (2H, s), 2.48 (3H, s). |
| 71 | Amorphous | $^1$H-NMR (CDCl$_3$) δ: 8.39 (1H, d, J = 2.4 Hz), 7.67 (1H, brs), 7.35 (1H, d, J = 8.3 Hz), 6.00 (1H, brs), 5.90 (1H, s), 2.63 (3H, s), 2.42 (3H, brs), 2.10 (3H, d, J = 7.3 Hz). |
| 72 | Solid | $^1$H-NMR (CDCl$_3$) δ: 8.37 (1H, d, J = 2.4 Hz), 7.62 (1H, dd, J = 8.3, 2.4 Hz), 7.36 (1H, d, J = 8.3 Hz), 7.24-7.21 (2H, m), 7.18 (2H, d, J = 8.9 Hz), 5.94 (1H, d, J = 0.6 Hz), 5.41 (2H, s), 2.40 (3H, d, J = 0.6 Hz), 2.35 (3H, s). |
| 73 | Solid | $^1$H-NMR (CDCl$_3$) δ: 8.38 (1H, d, J = 2.4 Hz), 7.71 (2H, d, J = 8.8 Hz), 7.61 (1H, dd, d = 8.3, 2.4 Hz), 7.52 (2H, d, J = 8.8 Hz), 7.37 (1H, d, J = 8.3 Hz), 5.99 (1H, s), 5.43 (2H, s), 2.44 (3H, s). |
| 74 | Solid | $^1$H-NMR (CDCl$_3$) δ: 8.37 (1H, d, J = 2.4 Hz), 7.62 (1H, dd, J = 8.3, 2.4 Hz), 7.36 (1H, d, J = 8.3 Hz), 7.29-7.27 (2H, m), 6.91-6.89 (2H, m), 5.93 (1H, s), 5.41 (2H, s), 3.81 (3H, s), 2.40 (3H, s). |
| 75 | Solid (4:1 diastereo mixtures) | major: $^1$H-NMR (CDCl$_3$) δ: 8.40 (1H, d, J = 2.5 Hz), 7.88 (1H, dd, J = 8.5, 2.5 Hz), 7.41 (1H, d, J = 8.5 Hz), 6.08 (1H, d, J = 1.0 Hz), 5.56 (1H, d, J = 16 Hz), 5.49 (1H, d, J = 16 Hz), 3.40 (3H, s), 2.54 (3H, s). minor: $^1$H-NMR (CDCl$_3$) δ; 8.37 (1H, d, J = 2.5 Hz), 7.64 (1H, dd, J = 8.5, 2.5 Hz), 7.36 (1H, d, J = 8.5 Hz), 6.04 (1H, d, J = 1.0 Hz), 5.56 (1H, d, J = 16 Hz), 5.49 (1H, d, J = 16 Hz), 3.13 (3H, s), 2.47 (3H, s). |
| 76 | Solid | $^1$H-NMR (CDCl$_3$) δ: 8.37 (1H, d, J = 2.5 Hz), 7.65 (1H, dd, J = 8.5, 2.5 Hz), 7.37 (1H, d, J = 8.5 Hz), 6.07 (1H, d, 1.0 Hz), 5.55 (2H, s), 3.44 (3H, s), 2.49 (3H, s). |
| 77 | Solid | $^1$H-NMR (CDCl$_3$) δ: 8.38 (1H, d, J = 2.8 Hz), 7.64 (1H, dd, J = 8.3, 2.8 Hz), 7.41 (1H, td, J = 7.9, 1.6 Hz), 7.36 (1H, d, J = 8.3 Hz), 7.24-7.15 (3H, m), 5.94 (1H, s) 5.40 (2H, s), 2.41 (3H, s). |
| 78 | Solid | $^1$H-NMR (CDCl$_3$) δ: 8.46 (1H, d, J = 2.4 Hz), 7.68 (1H, dd, J = 8.3, 2.4 Hz), 7.36 (1H, d, J = 8.3 Hz) 5.22 (2H, s), 4.35 (3H, s), 3.07 (3H, s), 2.33 (3H, d, J = 0.6 Hz), 2.03 (3H, s). |

TABLE 6

| Compound No. | State | $^1$H-NMR Value δ (ppm) |
|---|---|---|
| 79 | Solid | $^1$H-NMR (CDCl$_3$) δ: 8.39 (1H, d, J = 2.8 Hz), 7.62 (1H, dd, J = 8.3, 2.8 Hz), 7.39 (1H, d, J = 8.3 Hz), 6.06 (1H, d, J = 0.6 Hz), 5.47 (2H, s), 2.51 (3H, d, J = 0.6 Hz). |
| 80 | Solid | $^1$H-NMR (DMSO-D6) δ: 8.51 (1H, d, J = 2.6 Hz), 8.45 (1H, dd, J = 2.8, 0.6 Hz), 7.90-7.87 (2H, m), 7.51 (1H, d, J = 8.3 Hz), 6.61 (1H, m), 6.13 (1H, s), 5.57 (2H, s), 2.38 (3H, s). |
| 81 | Solid | $^1$H-NMR (CDCl$_3$) δ: 8.32(1H, d, J = 2.4 Hz), 7.66-7.61 (2H, m), 7.52 (1H, dd, J = 8.3, 2.4 Hz), 7.41-7.37(3H, m), 7.29 (1H, d, J = 8.3 Hz), 5.88 (1H, s), 5.35 (2H, s), 2.41 (3H, s). |
| 82 | Solid | $^1$H-NMR (DMSO-D6) δ: 8.37 (1H, s), 7.70 (1H, d, J = 8.3 Hz), 7.49 (1H, d, J = 8.3 Hz), 5.71 (1H, s), 5.39 (2H, s), 2.27 (3H, s). |
| 83 | Solid (4:1 diastereo mixtures) | major: $^1$H-NMR (CDCl$_3$) δ: 8.39 (1H, d, J = 2.1 Hz), 7.91(1H, dd, J = 8.4, 2.1 Hz), 7.47-7.22(6H, m), 6.06(1H, s), 5.56(2H, s), 4.99(2H, s), 2.55 (3H, s). minor: $^1$H-NMR (CDCl$_3$) δ: 8.32 (1H, d, J = 2.1 Hz), 7.53(1H, dd, J = 2.1 Hz), 7.44-7.22 (6H, m), 6.02(1H, d, J = 0.6 Hz), 5.59-5.47 (2H, m), 4.55-4.46 (2H, m), 2.46 (3H, d, J = 0.6 Hz). |
| 84 | Solid | $^1$H-NMR (CDCl$_3$) δ: 8.38 (1H, d, J = 2.4 Hz), 7.63 (1H, dd, J = 8.3, 2.4 Hz), 7.45-7.35 (4H, m), 7.23-7.21 (2H, m), 5.52 (2H, s), 2.70 (3H, s), 2.24 (3H, s). |
| 85 | Solid | $^1$H-NMR (CDCl$_3$) δ: 7.74 (1H, d, J = 2.5 Hz), 7.58-7.62 (1H, m), 7.51-7.54 (2H, m), 7.41 (1H, dd, J = 8.5, 2.5 Hz), 7.25-7.27 (2H, m), 7.21 (1H, d, J = 8.5 Hz), 5.99 (1H, s), 5.30 (2H, s), 2.73 (3H, s). |
| 86 | Solid (4:1 diastereo mixtures) | major: $^1$H-NMR (CDCl$_3$) δ: 8.40 (1H, d, J = 2.4 Hz), 7.89 (1H, dd, J = 8.4, 2.4 Hz), 7.48-7.36 (4H, m), 7.25-7.22 (2H, m), 5.65-5.56 (2H, m), 3.38 (3H, s), 2.36 (3H, s). minor: $^1$H-NMR (CDCl$_3$) δ: 8.38 (1H, d, J = 2.4 Hz), 7.67 (1H, dd, J = 8.3, 2.4 Hz), 7.48-7.36 (4H, m), 7.25-7.22 (2H, m), 5.68-5.61(2H, m), 3.11 (3H, s), 2.31 (3H, s). |

TABLE 6-continued

| Compound No. | State | ¹H-NMR Value δ (ppm) |
|---|---|---|
| 87 | Solid | ¹H-NMR (DMSO-D6) δ: 8.50 (1H, d, J = 2.4 Hz), 7.91 (1H, dd, J = 8.3, 2.4 Hz), 7.55 (1H, d, J = 8.3 Hz), 7.49-7.46 (2H, m), 7.43-7.40 (1H, m), 7.30-7.29 (2H, m), 5.69 (2H, s), 3.46 (3H, s), 2.19 (3H, s). |
| 88 | Solid | ¹H-NMR (DMSO-D6) δ: 12.10 (1H, broad-s), 8.43 (1H, d, J = 2.4 Hz), 7.78 (1H, dd, J = 8.3, 2.4 Hz), 7.50 (1H, d, J = 8.3 Hz), 5.96 (1H, s), 5.42 (2H, s), 2.32 (3H, s). |
| 89 | Solid | ¹H-NMR (CDCl₃) δ: 8.37 (1H, d, J = 2.4 Hz), 7.61 (1H, dd, J = 8.4, 2.4 Hz), 7.35 (1H, d, J = 8.4 Hz), 5.93 (1H, d, J = 0.6 Hz), 5.54 (2H, s), 5.42 (2H, s), 3.59 (3H, s), 2.40 (3H, d, J = 0.6 Hz). |
| 90 | Solid | ¹H-NMR (CDCl₂) δ: 8.36 (1H, d, J = 2.6 Hz), 7.62 (1H, dd, J = 8.3, 2.6 Hz), 7.34 (1H, d, J = 8.3 Hz), 5.92 (1H, s), 5.40 (2H, s), 4.50 (2H, q, J = 7.2 Hz), 2.39 (3H, s), 1.46 (3H, t, J = 7.2 Hz). |
| 91 | Solid | ¹H-NMR (CDCl₃) δ: 8.39 (1H, d, J = 2.4 Hz), 7.66 (1h, dd, J = 8.3, 2.4 Hz), 7.37 (1H, d, J = 8.3 Hz), 6.01 (1H, s), 5.44 (2H, s), 3.54 (3H, s), 2.46 (3H, s). |
| 92 | Solid | ¹H-NMR (CDCl₃) δ: 8.39 (1H, d, J = 2.6 Hz), 7.63 (1H, dd, J = 8.4, 2.6 Hz), 7.35 (1H, d, J = 8.4 Hz), 5.95 (1H, s), 5.43 (2H, s), 2.43 (3H, s), 2.37 (3H, s). |

TABLE 7

| Compound No. | State | ¹H-NMR Value δ (ppm) |
|---|---|---|
| 93 | Solid | ¹H-NMR (CDCl₃) δ: 8.34 (1H, d, J = 2.4 Hz), 7.94 (2H, d, J = 8.3 Hz), 7.63 (1H, dd, J = 8.3, 2.4 Hz), 7.38-7.34 (3H, m), 5.95 (1H, s), 5.39 (2H, s), 2.47 (3H, s), 2.43 (3H, s). |
| 94 | Solid | ¹H-NMR (CDCl₃) δ : 8.38 (1H, d, J = 2.4 Hz), 7.63 (1H, dd, J = 8.3, 2.4 Hz), 7.35 (1H, d, J = 8.3 Hz), 5.93 (1H, s), 5.44 (2H, s), 3.12 (3H, s), 3.03 (3H, s), 2.41 (3H, s). |
| 95 | Solid | ¹H-NMR (CDCl₃) δ: 8.35 (1H, d, J = 2.4 Hz), 7.75 (1H, dd, J = 8.3, 2,4 Hz), 7.38 (1H, d, J = 8.3 Hz), 5.8 (1H, s), 5.33 (2H, s), 5.31-5.21 (2H, m), 4.88 (2H, d, J = 6.1 Hz), 2.36 (3H, s). |
| 96 | Solid | ¹H-NMR (DMSO-D6) δ: 8.45 (1H, d, J = 2.6 Hz), 7.88 (1H, dd, J = 8.3, 2.8 Hz), 7.54 (1H, d, J = 8.3 Hz), 6.10 (1H, s), 5.36 (2H, s), 5.08 (2H, s), 2.28 (3H, s). |
| 97 | Solid | ¹H-NMR (CDCl₃ + DMSO-D6) δ: 8.39 (1H, d, J = 2.4 Hz), 7.75 (1H, dd, J = 8.3, 2.4 Hz), 7.38 (1H, d, J = 8.3 Hz), 5.88 (1H, d, J = 0.9 Hz), 5.39 (2H, s), 4.98 (2H, d, J = 2.4 Hz), 2.39 (3H, d, J = 0.9 Hz), 2.36 (1H, t, J = 2.4 Hz). |
| 98 | Solid | ¹H-NMR (CDCl₃) δ: 8.36 (1H, d, J = 2.6 Hz), 7.75 (1H, dd, J = 8.4. 2.6 Hz), 7.36, (1H, d, J = 8.4 Hz), 5.84 (1H, s), 5.35 (2H, s), 4.96 (2H, d, J = 2.2 Hz), 2.37 (3H, s), 1.73 (3H, t, J = 2.2 Hz). |
| 99 | Solid | ¹H-NMR (CDCl₃) δ: 8.36 (1H, d, J = 2.4 Hz), 7.62 (1H, dd, J = 8.3, 2.4 Hz), 7.34 (1H, d, J = 8.3 Hz), 5.92 (1H, s), 5.41 (2H, s), 4.40 (2H, t, J = 7.0 Hz), 2.39 (3H, s), 1.89-1.82 (2H, m), 1.04 (3H, t, J = 7.0 Hz). |
| 100 | Solid | ¹H-NMR (CDCl₃) δ: 8.36 (1H, d, J = 2.4 Hz), 7.62 (1H, dd, J = 8.3, 2.8 Hz), 7.35 (1H, t, J = 8.3 Hz), 5.92 (1H, s), 5.40 (2H, s), 5.25-5.20 (1H, m), 2.39 (3H, s), 1.44 (6H, d, J = 6.1 Hz). |
| 101 | Solid | ¹H-NMR (CDCl₃) δ: 8.37 (1H, d, J = 2.8 Hz), 7.64 (1H, dd, J = 8.3, 2.4 Hz), 7.35 (1H, d, J = 8.3 Hz), 5.93 (1H, s), 5.41 (2H, s), 5.04 (2H, s), 2.41 (3H, s), 2.26 (3H, s). |
| 102 | Sold | ¹H-NMR (CDCl₃) δ: 8.39 (1H, d, J = 2.4 Hz), 7.62 (1H, dd, J = 8.3, 2.4 Hz), 7.35 (1H, d, J = 8.3 Hz), 5.95 (1H, s), 5.43 (2H, s), 2.68 (2H, q, J = 7.5 Hz), 2.43 (3H, s), 1.28 (3H, t, J = 7.5 Hz). |
| 103 | Solid | ¹H-NMR (CDCl₃) δ: 8.39 (1H, d, J = 2.4 Hz), 7.65 (1H, dd, J = 8.3, 2.4 Hz), 7.36 (1H, d, J = 8.3 Hz), 5.97 (1H, s), 5.43 (2H, s), 3.97 (3H, s), 2.44 (3H, s). |
| 104 | Solid | ¹H-NMR (CDCl₃) δ: 8.39 (1H, d, J = 2.4 Hz), 7.69 (1H, dd, J = 8.3, 2.4 Hz), 7.36 (1H, d, J = 8.3 Hz), 5.97 (1H, s), 5.44 (2H, s), 3.11 (6H, s), 2.45 (3H, s). |

TABLE 7-continued

| Compound No. | State | ¹H-NMR Value δ (ppm) |
|---|---|---|
| 105 | Solid | ¹H-NMR (CDCl₃) δ: 8.38 (1H, d, J = 2.4 Hz), 7.74 (1H, dd, J = 8.3, 2.4 Hz), 7.36 (1H, d, J = 6.3 Hz), 5.96 (1H, s), 5.63 (1H, q, J = 6.8 Hz), 5.41 (2H, s), 2.43 (3H, s), 1.84 (3H, d, J = 6.8 Hz). |
| 106 | Solid | ¹H-NMR (CDCl₃) δ: 8.35 (1H, d, J = 2.4 Hz), 7.68-7.53 (5H, m), 7.31 (1H, d, J = 2.4 Hz), 6.14 (1H, q, J = 6.5 Hz), 5.90 (1H, s), 5.42-5.33 (2H, m), 2.37 (3H, s), 2.03 (3H, d, J = 6.5 Hz). |
| 107 | Solid | ¹H-NMR (DMSO-D6) δ: 8.44 (1H, d, J = 2.4 Hz), 7.81 (1H, dd, J = 8.3, 2.4 Hz), 7.50 (1H, d, J = 6.3 Hz), 7.18 (1H, broad-s), 6.02 (1H, s), 5.44 (2H, s), 4.69 (2H, s), 2.35 (3H, s). |

TABLE 8

| Compound No. | State | ¹H-NMR Value δ (ppm) |
|---|---|---|
| 108 | Solid | ¹H-NMR (DMSO-D6) δ: 8.44 (1H, d, J = 2.6 Hz), 7.79 (1H, dd, J = 8.3, 2.6 Hz), 7.50 (1H, d, J = 8.3 Hz), 6.00 (1H, s), 5.43 (2H, s), 4.93 (1H, t, J = 4.9 Hz), 4.28 (1H, t, J = 4.9 Hz), 3.71 (1H, q, J = 4.9 Hz), 2.35 (3H, s). |
| 109 | Solid | ¹H-NMR (CDCl₃) δ: 8.33 (1H, d, J = 2.4 Hz), 7.54 (1H, dd, J = 8.3, 2.4 Hz), 7.32 (1H, d, J = 8.3 Hz), 6.19 (1H, s), 5.25 (2H, s), 3.95 (3H, s), 2.65 (3H, s), 2.24 (3H, s). |
| 110 | Amorphous | ¹H-NMR (CDCl₃) δ: 7.53 (1H, s), 6.17 (1H, d, J = 1.0 Hz), 5.29 (2H, s), 3.94 (3H, s), 2.68 (3H, s), 2.35 (3H, d, J = 1.0 Hz). |
| 111 | Solid | ¹H-NMR (CDCl₃) δ: 8.39 (1H, s), 7.67 (1H, d, J = 8.3 Hz), 7.37 (1H, d, J = 8.3 Hz), 5.99 (1H, s), 5.44 (2H, s), 3.70 (2H, q, J = 7.3 Hz), 2.46 (3H, s), 1.60 (3H, t, J = 7.3 Hz). |
| 112 | Solid | ¹H-NMR (CDCl₃) δ: 8.39 (1H, d, J = 2.4 Hz), 7.67 (1H, dd, J = 8.3, 2.4 Hz), 7.36 (1H, d, J = 8.3 Hz), 5.99 (1H, s), 5.44 (2H, s), 3.65-3.62 (2H, m), 2.46 (3H, s), 2.11-2.04 (2H, m), 1.15 (3H, t, J = 7.5 Hz). |
| 113 | Solid | ¹H-NMR (CDCl₃) δ: 8.36 (1H, d, J = 2.4 Hz), 7.61 (1H, dd, J = 8.4, 2.4 Hz), 7.34 (1H, d, J = 8.4 Hz), 5.92 (1H, s), 5.40 (2H, s), 4.44 (2H, t, J = 6.7 Hz), 2.39 (3H, s), 1.84-1.78 (2H, m), 1.52-1.47 (2H, m), 0.97 (3H, t, J = 6.7 Hz). |
| 114 | Solid | ¹H-NMR (CDCl₃) δ: 8.36 (1H, d, J = 2.7 Hz), 7.61 (1H, dd, J = 8.2, 2.7 Hz), 7.34 (1H, d, J = 8.2 Hz), 5.92 (1H, s), 5.41 (2H, s), 4.22 (2H, d, J = 6.7 Hz), 2.38 (3H, s), 2.17-2.12(1H, m), 1.07 (6H, d, J = 6.7 Hz). |
| 115 | Solid | ¹H-NMR (CDCl₃) δ: 8.36 (1H, d, J = 2.4 Hz), 7.61 (1H, dd, J = 8.3, 2.4 Hz), 7.34 (1H, d, J = 8.3 Hz), 5.92 (1H, d, J = 0.6 Hz), 5.40 (2H, s), 4.46 (2H, t, J = 6.7 Hz), 2.39 (3H, d, J = 0.6 Hz), 1.86-1.81 (1H, m), 1.72 (2H, q, J = 6.7 Hz), 0.96 (6H, d, J = 6.7 Hz). |
| 116 | Solid | ¹H-NMR (CDCl₃) δ: 8.36 (1H, d, J = 2.8 Hz), 7.61 (1H, dd, J = 8.3, 2.8 Hz), 7.34 (1H, d, J = 8.3 Hz), 5.92 (1H, s), 5.40 (2H, s), 4.43 (2H, t, J = 6.7 Hz), 2.39 (3H, s), 1.85-1.79 (2H, m), 1.47-1.45 (2H, m), 1.34-1.32 (4H, m), 0.89 (3H, t, J = 6.7 Hz). |
| 117 | Solid | ¹H-NMR (CDCl₃) δ: 8.37 (1H, d, J = 2.4 Hz), 7.64 (1H, dd, J = 8.3, 2.4 Hz), 7.35 (1H, d, J = 8.3 Hz), 5.93 (1H, s), 5.40 (2H, s), 5.02 (2H, s), 3.80 (3H, s), 2.40 (3H, s). |
| 118 | Solid | ¹H-NMR (CDCl₃) δ: 8.36 (1H, d, J = 2.4 Hz), 7.64 (1H, dd, J = 8.3, 2.4 Hz), 7.34 (1H, d, J = 8.3 Hz), 5.92 (1H, s), 5.39 (2H, s), 4.60-4.58 (2H, m), 3.79-3.77 (2H, m), 3.43 (3H, s), 2.39 (3H, s). |

TABLE 8-continued

| Compound No. | State | $^1$H-NMR Value δ (ppm) |
|---|---|---|
| 119 | Solid | $^1$H-NMR (CDCl$_3$) δ: 8.32 (1H, d, J = 2.4 Hz), 7.58 (1H, dd, J = 8.3, 2.4 Hz), 7.35 (1H, d, J = 8.3 Hz), 6.30 (1H, s), 5.33 (2H, s), 3.98 (3H, s), 3.38 (3H, s), 2.29 (3H, s). |
| 120 | Solid | $^1$H-NMR (CDCl$_3$) δ: 8.33 (1H, d, J = 2.6 Hz), 7.59 (1H, dd, J = 8.3, 2.6 Hz), 7.34 (1H, d, J = 8.3 Hz), 6.27 (1H, d, J = 0.9 Hz), 5.36 (2H, s), 3.97 (3H, s), 3.05 (3H, s), 2.29 (3H, d, J = 0.9 Hz). |
| 121 | Solid | $^1$H-NMR (CDCl$_3$) δ: 8.33 (1H, d, J = 2.4 Hz), 7.56 (1H, dd, J = 8.3, 2.4 Hz), 7.32 (1H, d, J = 8.3 Hz), 6.75 (1H, s), 6.26 (1H, s), 5.26 (2H, s), 2.65 (3H, s), 2.26 (3H, s). |

TABLE 9

| Compound No. | State | $^1$H-NMR Value δ (ppm) |
|---|---|---|
| 122 | Solid | $^1$H-NMR (CDCl$_3$) δ: 8.35 (1H, d, J = 2.6 Hz), 7.57 (1H, dd, J = 8.4, 2.6 Hz), 7.34-7.27 (5H, m), 7.00-6.97 (1H, m), 6.42 (1H, d, J = 0.9 Hz), 5.30 (2H, s), 2.68 (3H, s), 2.30 (3H, d, J = 0.9 Hz). |
| 123 | Solid | $^1$H-NMR (DMSO-D6) δ: 8.42 (1H, d, J = 2.4 Hz), 7.78 (1H, dd, J = 8.3, 2.4 Hz), 7.48 (1H, d, J = 8.3 Hz), 8.00 (1H, s), 5.42 (2H, s), 4.33 (2H, t, J = 7.2 Hz), 2.63 (2H, t, J = 7.2 Hz), 2.32 (3H, s), 2.07-2.02(2H, m). |
| 124 | Solid | $^1$H-NMR (CDCl$_3$) δ: 8.33 (1H, d, J = 2.4 Hz), 7.54 (1H, dd, J = 8.3, 2.4 Hz), 7.32 (1H, d, J = 8.3 Hz), 6.23 (1H, s), 5.25 (2H, s), 4.20 (2H, q, J = 7.0 Hz), 2.65 (3H, s), 2.24 (3H, s), 1.31 (3H, t, J = 7.0 Hz). |
| 125 | Solid | $^1$H-NMR (CDCl$_3$) δ: 8.33 (1H, d, J = 2.4 Hz), 7.53 (1H, dd, J = 8.3, 2.4 Hz), 7.31 (1H, d, J = 8.3 Hz), 6.21 (1H, d, J = 0.9 Hz), 5.25 (2H, s), 4.48-4.41 (1H, m), 2.64 (3H, s), 2.23 (3H, d, J = 0.9 Hz), 1.28 (6H, d, J = 6.1 Hz). |
| 126 | Solid | $^1$H-NMR (CDCl$_3$) δ: 8.33 (1H, d, J = 2.4 Hz), 7.54 (1H, dd, J = 8.3, 2.4 Hz), 7.32 (1H, d, J = 8.3 Hz), 6.24 (1H, d, J = 0.9 Hz), 6.09-6.01 (1H, m), 5.35 (1H, dq, J = 17.1, 1.5 Hz), 5.26 (2H, s), 5.25-5.22 (1H, m), 4.66 (2H, dt, J = 5.8, 1.2 Hz), 2.65 (3H, s), 2.24 (3H, d, J = 0.9 Hz). |
| 127 | Solid | $^1$H-NMR (CDCl$_3$) δ: 8.33 (1H, d, J = 2.4 Hz), 7.54 (1H, dd, J = 8.3, 2.4 Hz), 7.43-7.30 (6H, m), 6.24 (1H, s), 5.25 (2H, s), 5.18 (2H, s), 2.85 (3H, s), 2.22 (3H, s). |
| 128 | Solid | $^1$H-NMR (CDCl$_3$) δ: 8.41 (1H, d, J = 2.4 Hz), 7.63 (1H, dd, J = 8.3, 2.4 Hz), 7.37 (1H, d, J = 8.3 Hz), 6.58 (1H, s), 5.50 (2H, s), 2.70 (3H, s), 2.53 (3H, s). |
| 129 | Solid | $^1$H-NMR (CDCl$_3$) δ: 8.33 (1H, d, J = 2.4 Hz), 7.56 (1H, dd, J = 8.3, 2.4 Hz), 7.32 (1H, d, J = 8.3 Hz), 5.82 (1H, s), 5.29 (2H, s), 3.21 (3H, s), 2.68 (3H, s), 2.27 (3H, s). |
| 130 | Solid | $^1$H-NMR (CDCl$_3$) δ: 8 41 (1H, d, J = 2.4 Hz), 7.66 (1H, dd, J = 8.3, 2.4 Hz), 7.38 (1H, d, J = 8.3 Hz), 6.03 (1H, d, J = 0.9 Hz), 5.43 (2H, s), 2.49 (3H, d, J = 0.9 Hz). |
| 131 | Solid | $^1$H-NMR (DMSO-D6) δ: 10.01 (1H, s), 8.47 (1H, d, J = 2.4 Hz), 7.87 (1H, dd, J = 8.3, 2.4 Hz), 7.55 (1H, d, J = 8.3 Hz), 6.52 (1H, s), 5.67 (2H, s), 2.70 (3H, s), 2.55 (3H, s). |
| 132 | Solid | $^1$H-NMR (CDCl$_3$) δ: 8.34 (1H, d, J = 2.4 Hz), 7.57 (1H, dd, J = 8.4, 2.4 Hz), 7.33 (1H, d, J = 8.4 Hz), 5.75 (1H, s), 5.34 (2H, s), 3.96 (2H, q, J = 9.3 Hz), 2.67 (3H, s), 2.32 (3H, s). |
| 133 | Solid | $^1$H-NMR (CDCl$_3$) δ: 8.33 (1H, d, J = 2.4 Hz), 7.56 (1H, dd, J = 8,4. 2.4 Hz), 7.32 (1H, d, J = 8.4 Hz), 5.81 (1H, s), 5.28 (2H, s), 3.37-3.34 (2H, m), 2.66 (3H, s), 2.26 (3H, s), 1.75-1.72 (2H, m), 0.98 (3H, t, J = 7.3 Hz). |

TABLE 9-continued

| Compound No. | State | ¹H-NMR Value δ (ppm) |
|---|---|---|
| 134 | Solid | ¹H-NMR (CDCl₃) δ: 8.34 (1H, d, J = 2.4 Hz), 7.59 (1H, dd, J = 8.3, 2.4 Hz), 7.35-7.32 (3H, m), 7.10-7.07 (1H, m), 6.97-6.95 (2H, m), 5.67 (1H, d, J = 0.9 Hz), 5.32 (2H, s), 2.71 (3H, s), 2.18 (3H, d, J = 0.9 Hz). |
| 135 | Solid | ¹H-NMR (CDCl₃) δ: 8.35 (1H, d, J = 2.4 Hz), 7.61 (1H, dd, J = 8.3, 2.4 Hz), 7.59 (2H, d, J = 8.9 Hz), 7.35 (1H, d, J = 8.3 Hz), 7.05 (2H, d, J = 8.9 Hz), 5.60 (1H, s), 5.34 (2H, s), 2.72 (3H, s), 2.22 (3H, s). |

TABLE 10

| Compound No. | State | ¹H-NMR Value δ (ppm) |
|---|---|---|
| 136 | Solid | ¹H-NMR (CDCl₃) δ: 8.36 (1H, d, J = 2.4 Hz), 7.60 (1H, dd, J = 8.3, 2.4 Hz), 7.44 (1H, t, J = 7.8 Hz), 7.35 (1H, d, J = 8.3 Hz), 7.34 (1H, d, J = 7.8 Hz), 7.23 (1H, s), 7.14 (1H, d, J = 7.8 Hz), 5.60 (1H, d, J = 0.9 Hz), 5.34 (2H, s), 2.72 (3H, s), 2.22 (1H, d, J = 0.9 Hz), |
| 137 | Solid | ¹H-NMR (CDCl₃) δ: 8.42 (1H, d, J = 2.8 Hz), 7.69 (1H, dd, J = 8.3, 2.8 Hz), 7.37 (1H, d, J = 8.3 Hz), 5.99 (1H, s), 5.46 (2H, s), 2.49 (3H, s). |
| 138 | Solid | ¹H-NMR (CDCl₃) δ: 8.34 (1H, d, J = 2.4 Hz), 7.56 (1H, dd, J = 8.3, 2.4 Hz), 7.32 (1H, d, J = 8.3 Hz), 6.08 (1H, s), 5.29 (2H, s), 2.84-2.83 (1H, m), 2.64 (3H, s), 2.28 (3H, s), 0.82-0.81 (4H, m). |
| 139 | Viscous product | ¹H-NMR (CDCl₃) δ: 8,37 (1H, d, J = 2.4 Hz), 7.59 (1H, dd, J = 8.3, 2.4 Hz), 7.35 (1H, d, J = 8.3 Hz), 6.23 (1H, s), 5.38 (2H, s), 2.67 (3H, s), 2.42 (3H, s), 1.57 (2H, dd, J = 7.8, 5.0 Hz), 1.30 (2H, dd, J = 7.8, 5.0 Hz). |
| 140 | Visous product | ¹H-NMR (CDCl₃) δ: 8.34 (1H, d, J = 2.6 Hz), 7.56 (1H, dd, J = 8.3, 2.6 Hz), 7.32 (1H, d, J = 8.3 Hz), 5.80 (1H, s), 5.28 (2H, s), 3.73-3.68 (1H, m), 2.64 (3H, s), 2.25 (3H, s), 1.26 (6H, d, J = 6.4 Hz). |
| 141 | Solid | ¹H-NMR (CDCl₃) δ: 8.41 (1H, d, J = 2.8 Hz), 7.59 (1H, dd, J = 8.3, 2.6 Hz), 7.37 (1H, d, J = 8.3 Hz), 7.32 (1H, s), 5.56 (2H, s), 2.70 (3H, s), 2.56 (3H, s). |
| 142 | Solid | ¹H-NMR (CDCl₃) δ: 8.41(1H, d, J = 2.4 Hz), 7.67 (1H, d, J = 8.3, 2.4 Hz), 7.37 (1H, d, J = 8.3 Hz), 5.99 (1H, s), 5.47 (2H, s), 2.48 (3H, s). |
| 143 | Solid | ¹H-NMR (DMSO-D6) δ: 8.40 (1H, d, J = 1.5 Hz), 7.79 (1H, dd, J = 8.5 Hz, 1.5 Hz), 7.51 (1H, d, J = 8.5 Hz), 6.18 (1H, s), 5.59 (2H, s), 2.39 (3H, s). |
| 144 | Solid | ¹H-NMR (CDCl₃) δ: 8.35 (1H, d, J = 2.5 Hz), 7.63 (1H, d, J = 1.5 Hz), 7.59 (1H, dd, J = 8.5, 2.5 Hz), 7.31 (1H, d, J = 8.5 Hz), 7.17 (1H, d, J = 1.5 Hz), 5.74 (1H, d, J = 1.0 Hz), 5.52 (2H, s), 2.39 (3H, d, J = 1.0 Hz). |
| 145 | Solid | ¹H-NMR (CDCl₃) δ: 8.49 (1H, d, J = 8.5 Hz), 8.41 (1H, d, J = 2.5 Hz), 7.68 (1H, d, J = 8.5 Hz), 7.84 (1H, dd, J = 8.5, 2.5 Hz), 7.45 (1H, dt, J = 8.5, 1.0 Hz), 7.36 (1H, dt, J = 1.0 Hz, J = 8.5 Hz), 7.30 (1H, d, J = 8.5 Hz), 7.25 (1H, brs), 5.83 (1H, d, J = 1.0 Hz). |
| 146 | Solid | ¹H-NMR (CDCl₃) δ: 8.46 (1H, d, 4 J = 8.5 Hz), 7.75 (1H, d, J = 8.5 Hz), 7.63 (1H, s), 7.47 (1H, t, J = 8.5 Hz), 7.37 (1H, t, J = 8.5 Hz), 5.81 (1H, s), 5.61 (2H, s), 2.54 (3H, s). |
| 147 | Oily phase | ¹H-NMR (CDCl₃) δ: 8.38 (1H, d, J = 2.4 Hz), 7.94 (1H, d, J = 1.2 Hz), 7.85 (1H, dd, J = 8.3, 2.4 Hz), 7.34 (1H, d, J = 8.3 Hz), 5.80 (1H, s), 5.52 (2H, s), 2.43 (3H, s). |
| 148 | Oily phase | ¹H-NMR (CDCl₃) δ: 8.39 (1H, d, J = 2.4 Hz), 7.58 (1H, dd, J = 8.3, 2.4 Hz), 7.33 (1H, s), 7.32 (1H, d, J = 8.3 Hz), 5.94 (1H, s), 5.26 (2H, s), 2.35 (3H, s), 2.27 (3H, s). |

TABLE 10-continued

| Compound No. | State | $^1$H-NMR Value δ (ppm) |
|---|---|---|
| 149 | Visous product | $^1$H-NMR (CDCl$_3$) δ: 8.45 (1H, d, J = 2.4 Hz), 7.89 (1H, s), 7.85 (2H, d, J = 7.3 Hz), 7.70 (1H, dd, J = 8.3, 2.4 Hz), 7.41 (2H, t, J = 7.6 Hz), 7.34-7.31 (2H, m), 5.72 (1H, s), 5.55 (2H, s), 238 (3H, s). |
| 150 | Solid | $^1$H-NMR (DMSO-D6) δ: 8.41 (1H, d, J = 2.5 Hz), 7.91 (1H, d, J = 8.5 Hz), 7.86 (1H, dd, J = 8.5, 2.5 Hz), 7.41-7.50 (5H, m), 6.92 (1H, s), 5.86 (1H, s), 5.45 (2H, s), 2.38 (3H, s). |

TABLE 11

| Compound No. | State | $^1$H-NMR Value δ (ppm) |
|---|---|---|
| 151 | Solid | $^1$H-NMR (CDCl$_3$) δ: 8.39 (1H, d, J = 2.5 Hz), 7.87 (1H, d, J = 2.5 Hz), 7.50 (1H, dd, J = 8.5, 2.5 Hz), 7.41 (1H, d, J = 8.0 Hz), 7.37 (1H, d, J = 8.5 Hz), 5.98 (1H, d, J = 2.5 Hz), 5.94 (1H, d, J = 8.0 Hz), 5.13 (2H, s). |
| 152 | Solid | $^1$H-NMR (CDCl$_3$) δ: 8.96 (1H, d, J = 2.5 Hz), 8.57 (1H, d, J = 2.5 Hz), 7.93 (1H, d, J = 2.0 Hz), 7.90 (1H, dd, J = 8.5, 2.5 Hz), 7.52 (1H, d, J = 8.5 Hz), 6.47 (1H, d, J = 2.0 Hz), 5.49 (1H, s), 4.26 (2H, q, J = 7.3 Hz), 1.30 (3H, t, J = 7.3 Hz). |
| 153 | Solid | $^1$H-NMR (CDCl$_3$) δ: 8.29 (1H, d, J = 2.0 Hz), 7.83 (1H, d, J = 2.0 Hz), 7.32-7.36 (2H, m), 5.93 (1H, d, J = 2.0 Hz), 5.81 (1H, d, J = 2.0 Hz), 5.21 (2H, s), 2.37 (3H, d, J = 1.0 Hz). |
| 154 | Solid | $^1$H-NMR (CDCl$_3$) δ: 8.29 (1H, s), 7.345 (1H, s), 7.342 (1H, s), 5.81 (1H, s), 5.79 (1H, s), 5.12 (2H, s), 2.65 (3H, s), 2.34 (3H, s). |
| 155 | Solid | $^1$H-NMR (CDCl$_3$) δ: 8.30 (1H, brs), 7.34-7.35 (2H, m), 5.81 (1H, brs), 5.80 (1H, s), 5.16 (2H, s), 2.32 (3H, s), 1.35 (9H, s). |
| 156 | Solid | $^1$H-NMR (CDCl$_3$) δ: 8.29 (1H, d, J = 2.5 Hz), 7.26-7.34 (2H, m), 5.77 (1H, d, J = 1.0 Hz), 5.72 (1H, s), 5.15 (2H, s), 2.38 (3H, s), 2.35 (3H, s). |
| 157 | Solid | $^1$H-NMR (CDCl$_3$) δ: 8.30 (1H, dd, J = 1.0 Hz, J = 2.5 Hz), 7.34-7.39 (2H, m), 6.21 (1H, s), 5.95 (1H, d, J = 1.0 Hz), 5.23 (2H, s), 2.42 (3H, d, J = 1.0 Hz). |
| 158 | Solid | $^1$H-NMR (CDCl$_3$) δ: 8.28 (1H, brs), 7.25-7.35 (2H, m), 5.763 (1H, s), 5.756 (2H, s), 5.18 (2H, s), 2.74 (2H, q, J = 7.3 Hz), 2.34 (3H, s), 1.26 (3H, t, J = 7.3 Hz). |
| 159 | Solid | $^1$H-NMR (CDCl$_3$) δ: 8.29 (1H, d, J = 2.5 Hz), 7.33-7.36 (1H, m), 7.32 (1H, dd, J = 8.5, 2.5 Hz), 5.78 (1H, s), 5.60 (1H, s), 5.13 (2H, s), 2.33 (3H, s), 1.99-2.01 (1H, m), 0.89-1.01 (4H, m). |
| 160 | Solid | $^1$H-NMR (CDCl$_3$) δ: 8.26 (1H, d, J = 2.5 Hz), 7.36-7.39 (2H, m), 6.53 (1H, s), 5.95 (1H, s), 5.24 (2H, s), 3.01 (3H, s), 2.43 (3H, s). |
| 161 | Solid | $^1$H-NMR (CDCl$_3$) δ: 8.27 (1H, brs), 7.38 (2H, d, J = 1.5 Hz), 6.48 (1H, s), 5.98 (1H, s), 5.23 (2H, 3), 3.36 (3H, s), 2.44 (3H, s) |
| 162 | Solid | $^1$H-NMR (CDCl$_3$) δ: 7.51 (1H, s), 6.34 (1H, s), 5.91 (1H, s), 5.29 (2H, d, J = 1.5 Hz), 2.51 (3H, s). |
| 163 | Solid | $^1$H-NMR (CDCl$_3$) δ: 8.26 (1H, d, J = 2.5 Hz), 7.35 (1H, d, J = 8.5 Hz), 7.28 (1H, dd, J = 8.5, 2.5 Hz), 5.76 (1H, d, J = 1.0 Hz.), 5.29 (2H, s), 2.25 (2H, q, J = 7.3 Hz), 2.35 (3H, s), 2.28 (3H, d, J = 1.0 Hz), 1.09 (3H, t, J = 7.3 Hz). |
| 164 | Solid | $^1$H-NMR (CDCl$_3$) δ: 8.92 (1H, d, J = 2.0 Hz), 8.34 (1H, d, J = 2.0 Hz), 8.26 (1H, d, J = 8.0, 2.0 Hz), 7.33-7.38 (2H, m), 7.23 (1H, d, J = 8.0 Hz), 6.26 (1H, s), 5.91 (1H, s), 5.26 (2H, s), 2.60 (3H, s), 2.39 (3H, s). |
| 165 | Solid | $^1$H-NMR (DMSO-D6) δ: 8.56 (1H, d, J = 2.5 Hz), 8.41 (1H, d, J = 2.5 Hz), 7.80 (1H, dd, J = 8.5, 2.5 Hz), 7.55 (1H, dd, J = 8.5, 2.5 Hz), 7.31 (1H, d, J = 8.5 Hz), 7.22 (1H, d, J = 8.5 Hz), 6.23 (1H, d, J = 1.0 Hz), 5.53 (2H, s), 5.28 (2H, s), 2.53 (3H, d, J = 1.0 Hz). |
| 166 | Solid | $^1$H-NMR (CDCl$_3$) δ: 8.29 (1H, d, J = 2.5 Hz), 7.36 (1H, dd, J = 8.5, 2.5 Hz), 7.33 (1H, d, J = 8.5 Hz), 5.81 (1H, s), 5.36 (1H, s), 5.08 (2H, s), 4.05 (3H, s), 2.32 (3H, s). |

TABLE 12

| Compound No. | State | ¹H-NMR Value δ (ppm) |
|---|---|---|
| 167 | Solid | ¹H-NMR (CDCl₃) δ: 8.23 (1H, brs), 7.93-7.94 (1H, m), 7.46-7.47 (1H, m), 7.34-7.37 (2H, m), 6.90 (1H, dd, J = 1.0 Hz, J = 2.0 Hz), 6.00 (1H, s), 5.85 (1H, s), 5.20 (2H, s), 2.36 (3H, s). |
| 168 | Solid | ¹H-NMR (CDCl₃) δ: 8.21 (1H, d, J = 2.5 Hz), 7.45 (1H, dd, J = 8.5, 2.5 Hz), 7.40 (1H, d, J = 8.5 Hz), 8.02 (1H, d, J = 1.0 Hz), 5.50 (2H, s), 2.71 (3H, s), 2.41 (3H, d, J = 1.0 Hz). |
| 169 | Solid | ¹H-NMR (CDCl₃) δ: 8.26 (1H, d, J = 2.5 Hz), 7.31-7.37 (2H, m), 5.84 (1H, s), 5.67 (2H, brs), 2.39 (3H, s), 2.33 (3H, s). |
| 170 | Solid | ¹H-NMR (CDCl₃) δ: 8.25 (1H, d, J = 2.5 Hz), 7.36 (1H, d, J = 8.5 Hz), 7.28 (1H, dd, J = 8.5. 2.5 Hz), 5.78 (1H, s), 5.32 (2H, s), 2.79-2.84 (2H, m), 255-2.56 (2H, m), 1.71-1.84 (4H, m). |
| 171 | Solid | ¹H-NMR (CDCl₃) δ: 8.25 (1H, d, J = 2.5 Hz), 7.38 (1H, d, J = 8.5 Hz), 7.29 (1H, dd, J = 8.5, 2.5 Hz), 5.81 (1H, s), 5.22 (2H, s), 4.09 (2H, s), 3.80 (2H, s), 2.32 (3H, s). |
| 172 | Solid | ¹H-NMR (CDCl₃) δ: 8.23 (1H, d, J = 2.5 Hz), 7.38 (1H, d, J = 8.5 Hz), 7.32 (1H, dd, J = 8.5, 2.5 Hz), 5.81 (1H, s), 5.23 (1H, d, J = 17.5 Hz), 5.18 (1H, d, J = 17.5 Hz), 4.32 (1H, d, J = 15.0 Hz), 3.99 (1H, d, J = 1.50 Hz), 3.98 (1H, d, J = 15.0 Hz), 3.76 (1H, d, J = 1.0 Hz). |
| 173 | Solid | ¹H-NMR (CDCl₃) δ: 8.25 (1H, d, J = 2.5 Hz), 7.43 (1H, d, J = 8.5 Hz), 7.30 (1H, dd, J = 8.5, 2.5 Hz), 5.95 (1H, s), 5.20 (2H, s), 4.39 (2H, s), 4.11 (2H, s), 2.38 (3H, s). |
| 174 | Solid | ¹H-NMR (CDCl₃) δ: 8.38 (1H, d, J = 2.5 Hz), 8.03-8.05 (2H, m), 7.63 (1H, dd, J = 8.5, 2.5 Hz), 7.26-7.55 (4H, m), 7.10 (1H, t, J = 7.5 Hz), 5.48 (1H, s), 4.49 (2H, d, J = 6.0 Hz), 2.62 (3H, s). |
| 175 | Solid | ¹H-NMR (CDCl₃) δ: 8.34 (1H, d, J = 2.4 Hz), 7.42 (1H, dd, J = 8.3, 2.4 Hz), 7.35 (1H, d, J = 8.3 Hz), 5.81 (1H, s), 5.70 (1H, q, J = 6.9 Hz), 5.33 (1H, s), 2.60 (3H, s), 2.48 (3H, s), 1.97 (3H, d, J = 6.9 Hz). |
| 176 | Solid | ¹H-NMR (CDCl₃) δ: 8.26 (1H, d, J = 2.5 Hz), 7.44 (1H, dd, J = 8.5, 2.5 Hz), 7.40 (1H, d, J = 8.5 Hz), 8.67 (1H, s), 5.99 (1H, s), 5.30 (1H, d, J = 17.5 Hz), 5.25 (1H, d, J = 17.5 Hz), 3.30 (3H, s), 2.45 (3H, s). |
| 177 | Solid | ¹H-NMR (CDCl₃) δ: 7.47 (1H, s), 5.91 (1H, s), 5.75 (1H, d, J = 1.0 Hz), 5.18 (2H, d, J = 1.0 Hz), 2.67 (3H, s), 2.42 (3H, d, J = 1.0 Hz). |
| 178 | Solid | ¹H-NMR (CDCl₃) δ: 8.42 (1H, d, J = 2.5 Hz), 7.70 (1H, dd, J = 8.5, 2.5 Hz), 7.37 (1H, d, J = 8.5 Hz), 5.97 (1H, d, J = 1.0 Hz), 5.54 (2H, s), 2.52 (3H, d, J = 1.0 Hz). |
| 179 | Solid | ¹H-NMR (CDCl₃) δ: 7.69 (1H, s), 5.95 (1H, s), 5.60 (2H, d, J = 1.0 Hz), 2.62 (3H, d, J = 1.0 Hz). |
| 180 | Solid | ¹H-NMR (CDCl₃) δ: 8.34 (1H, d, J = 2.4 Hz), 8.02 (1H, s), 7.58 (1H, dd, J = 8.3, 2.4 Hz), 7.33 (1H, d, J = 8.3 Hz), 5.53 (2H, s), 2.69 (2H, t, J = 6.3 Hz), 2.64 (2H, t, J = 6.3 Hz), 1.87-1.85 (2H, m), 1.75-1.73 (2H, m). |
| 181 | Solid | ¹H-NMR (CDCl₃) δ: 8.37 (1H, d, J = 2.4 Hz), 7.55 (1H, dd, J = 8.3, 2.4 Hz), 7.34 (1H, d, J = 8.3 Hz), 6.61 (1H, s), 5.41 (2H, s), 2.68 (3H, s), 2.37 (6H, s). |
| 182 | Solid | ¹H-NMR (CDCl₃) δ: 8.34 (1H, s), 7.56 (1H, d, J = 8.3 Hz), 7.34 (1H, d, J = 8.3 Hz), 6.20 (1H, s), 5.33 (2H, s), 2.67 (3H, s), 2.34 (3H, s), 2.25 (3H, s). |

TABLE 13

| Compound No. | State | ¹H-NMR Value δ (ppm) |
|---|---|---|
| 183 | Solid | ¹H-NMR (CDCl₃) δ: 8.37 (1H, d, J = 2.4 Hz), 7.56 (1H, dd, J = 8.3, 2.4 Hz), 7.34 (1H, d, J = 8.3 Hz), 6.92 (1H, s), 5.44 (2H, s), 3.82 (3H, s), 2.70 (3H, s), 2.41 (3H, s). |
| 184 | Solid | ¹H-NMR (CDCl₃) δ: 8.40 (1H, d, J = 2.4 Hz), 7.56 (1H, dd, J = 8.3, 2.4 Hz), 7.35 (1H, d, J = 8.3 Hz), 6.93 (1H, s), 5.49 (2H, s), 3.22 (3H, s), 2.68 (3H, s), 2.49 (3H, s). |

TABLE 13-continued

| Compound No. | State | ¹H-NMR Value δ (ppm) |
|---|---|---|
| 185 | Solid | ¹H-NMR (CDCl₃) δ: 8.36 (1H, d, J = 2.4 Hz), 7.58 (1H, dd, J = 8.3, 2.4 Hz), 7.35 (1H, d, J = 8.3 Hz), 6.00 (1H, d, J = 0.9 Hz), 5.28 (2H, s), 2.95 (3H, s), 2.69 (3H, s), 2.27 (3H, d, J = 0.9 Hz). |
| 186 | Solid | ¹H-NMR (CDCl₃) δ: 11.22 (1H, brs), 8.35 (1H, d, J = 2.4 Hz), 7.57 (1H, dd, J = 8.3, 2.4 Hz), 7.33 (1H, d, J = 8.3 Hz), 5.76 (1H, s), 5.16 (2H, s), 3.80 (3H, s), 2.61 (3H, s), 2.15 (3H, s). |

TABLE 14

| Compound No. | State | ¹H-NMR Value δ (ppm) |
|---|---|---|
| 187 | Solid | 1H-NMR (CDCl3) δ: 8.37 (1H, d, J = 2.4 Hz), 7.64 (1H, dd, J = 8.3, 2.4 Hz), 7.37 (1H, d, J = 8.3 Hz), 6.06 (1H, s), 5.55 (2H, s), 3.57 (2H, q, J = 7.5 Hz), 2.49 (3H, s), 1.48 (3H, t, J = 7.5 Hz). |
| 188 | Solid | 1H-NMR (CDCl3) δ: 8.37 (1H, d, J = 2.4 Hz), 7.63 (1H, dd, J = 8.3, 2.4 Hz), 7.36 (1H, d, J = 8.3 Hz), 6.03 (1H, d, J = 0.6 Hz), 5.60 (1H, d, J = 16.5 Hz), 5.54 (1H, d, J = 16.5 Hz), 3.34-3.30 (2H, m), 2.48 (3H, d, J = 0.6 Hz), 1.37 (3H, t, J = 7.5 Hz). |
| 189 | Solid | 1H-NMR (CDCl3) δ: 8.37 (1H, d, J = 2.4 Hz), 7.61 (1H, dd, J = 8.4, 2.4 Hz), 7.38 (1H, d, J = 8.4 Hz), 6.07 (1H, s), 5.58 (1H, d, J = 16.5 Hz), 5.53 (1H, d, J = 16.5 Hz), 4.26-4.22 (1H, m), 4.04-4.00 (1H, m), 2.49 (3H, s). |
| 190 | Solid | 1H-NMR (CDCl3) δ: 8.38 (1H, d, J = 2.0 Hz), 7.62 (1H, dd, J = 8.3, 2.4 Hz), 7.38 (1H, d, J = 8.3 Hz), 6.10 (1H, s), 5.54 (2H, s), 4.41 (2H, q, J = 8.8 Hz), 2.51 (3H, s). |

TABLE 15

| Compound No. | State | ¹H-NMR Value δ (ppm) |
|---|---|---|
| 191 | Amorphous | 1H-NMR (CDCl3) δ: 8.40 (1H, d, J = 2.4 Hz), 7.64 (1H, dd, J = 8.3, 2.4 Hz), 7.32 (1H, d, J = 8.3 Hz), 6.06 (1H, s), 5.52 (2H, s), 4.37 (2H, s), 3.42 (3H, s), 2.68 (3H, s). |
| 192 | Solid | 1H-NMR (CDCl3) δ: 8.40 (1H, d, J = 2.6 Hz), 7.69 (1H, dd, J = 8.2, 2.6 Hz), 7.35 (1H, d, J = 8.2 Hz), 6.23 (1H, s), 5.63 (2H, s), 4.42 (2H, s), 3.47 (3H, s), 3.43 (3H, s). |
| 193 | Amorphous | 1H-NMR (CDCl3) δ: 8.41 (1H, d, J = 2.4 Hz), 7.69 (1H, dd, J = 8.3, 2.4 Hz), 7.34 (1H, d, J = 8.3 Hz), 6.20 (1H, s), 5.66 (1H, d, J = 16.2 Hz), 5.62 (1H, d, J = 16.2 Hz), 4.44 (1H, d, J = 13.5 Hz), 4.40 (1H, d, J = 13.5 Hz), 3.46 (3H, s), 3.12 (3H, s). |
| 194 | Amorphous | 1H-NMR (CDCl3) δ: 8.38 (1H, d, J = 2.6 Hz), 7.59 (1H, dd, J = 8.3, 2.6 Hz), 7.35 (1H, d, J = 8.3 Hz), 6.14 (1H, s), 5.63 (2H, s), 4.38 (2H, s), 2.69 (3H, s). |
| 195 | Solid | 1H-NMR (CDCl3) δ: 8.49 (1H, d, J = 2.5 Hz), 8.11 (1H, s), 7.75 (1H, dd, J = 8.5 Hz, J = 2.5 Hz), 7.51 (1H, d, J = 8.5 Hz), 7.37 (1H, d, J = 8.5 Hz), 6.10 (1H, d, J = 8.0 Hz), 5.34 (3H, s). |
| 196 | Solid | 1H-NMR (CDCl3) δ: 8.13 (1H, s), 7.68 (1H, s), 7.53 (1H, d, J = 8.5 Hz), 6.11 (1H, d, J = 8.5 Hz), 5.46 (2H, d, J = 1.0 Hz). |
| 197 | Solid | 1H-NMR (CDCl3) δ: 8.61 (1H, s), 8.58 (1H, d, J = 2.5 Hz), 8.10 (1H, s), 7.84 (1H, dd, J = 8.5 Hz, J = 2.5 Hz), 7.38 (1H, d, J = 8.5 Hz), 5.45 (2H, s), 4.37 (2H, q, J = 7.3 Hz), 1.37 (3H, t, J = 7.0 Hz). |
| 198 | Oily phase | 1H-NMR (CDCl3) δ: 8.12 (1H, s), 7.46 (1H, d, J = 8.0 Hz), 6.07 (1H, d, J = 8.0 Hz), 4.20 (1H, dd, J = 14.0 Hz, J = 8.0 Hz), 4.12 (1H, dd, J = 14.0 Hz, J = 8.0 Hz), 4.00 (1H, dt, J = 8.0 Hz, J = 5.0 Hz), 3.81-3.75 (2H, m), 3.65 (1H, dd, J = 8.0 Hz, J = 5.0 Hz), 3.03-2.93 (1H, m), 2.18-2.06 (1H, m), 1.73-1.64 (1H, m). |
| 199 | Solid | 1H-NMR (DMSO-D6) δ: 8.50 (1H, d, J = 2.1 Hz), 7.93 (1H, d, J = 7.0 Hz), 7.49 (1H, d, J = 8.6 Hz), 8.07 (1H, s), 5.72 (1H, s), 2.76-2.20 (8H, m), 0.86 (3H, t, J = 7.2 Hz). |
| 200 | Solid | 1H-NMR (DMSO-D6) δ: 8.52 (1H, d, J = 2.4 Hz), 7.93 (1H, dd, J = 8.3, 2.4 Hz), 7.57 (1H, d, J = 8.6 Hz), 5.74 (2H, s), 3.50 (3H, s), 2.52 (3H, s). |

TABLE 15-continued

| Compound No. | State | $^1$H-NMR Value δ (ppm) |
|---|---|---|
| 201 | Solid | 1H-NMR (CDCl3) δ: 8.52 (1H, d, J = 2.5 Hz), 7.78 (1H, dd, J = 8.5 Hz, J = 2.5 Hz), 7.59 (1H, d, J = 8.0 Hz), 7.40 (1H, d, J = 8.5 Hz), 6.19 (1H, d, J = 8.0 Hz), 5.38 (2H, s). |
| 202 | Solid | 1H-NMR (CDCl3) δ: 8.57 (1H, d, J = 2.5 Hz), 8.57 (1H, s), 7.81 (1H, dd, J = 8.5 Hz, J = 2.5 Hz), 7.24 (1H, d, J = 8.5 Hz), 5.42 (2H, s), 4.42 (2h, q, J = 7.3 Hz), 1.39 (t, J = 7.3 Hz). |

TABLE 16

| Compound No. | State | $^1$H-NMR Value δ (ppm) |
|---|---|---|
| 203 | Solid | 1H-NMR (CDCl3) δ: 8.50 (1H, d, J = 2.5 Hz), 7.79 (1H, dd, J = 8.5 Hz, J = 2.5 Hz), 7.56 (1H, d, J = 8.0 Hz), 7.39 (1H, d, J = 8.5 Hz), 6.18 (1H, d, J = 8.0 Hz), 5.44 (1H, d, J = 15.0 Hz), 5.41 (1H, d, J = 15.0 Hz), 3.14 (3H, s). |
| 204 | Solid | 1H-NMR (CDCl3) δ: 8.50 (1H, d, J = 2.5 Hz), 7.80 (1H, dd, J = 8.5 Hz, J = 2.5 Hz), 7.58 (1H, d, J = 8.0 Hz), 7.41 (1H, d, J = 8.5 Hz), 6.21 (1H, d, J = 8.0 Hz), 5.40 (2H, s), 3.46 (3H, s). |
| 205 | Solid | 1H-NMR (CDCl3) δ: 8.57 (1H, d, J = 2.5 Hz), 8.55 (1H, s), 7.84 (1H, dd, J = 8.5 Hz, J = 2.5 Hz), 7.41 (1H, d, J = 8.5 Hz), 5.49 (1H, d, J = 15.0 Hz), 5.45 (1H, d, J = 15.0 Hz), 4.42 (2H, q, J = 7.3 Hz), 3.20 (3H, s), 1.40 (3H, t, J = 7.3 Hz). |
| 206 | Solid | 1H-NMR (CDCl3) δ: 8.71 (1H, s), 8.57 (1H, d, J = 2.5 Hz), 7.78 (1H, dd, J = 8.5 Hz, J = 2.5 Hz), 7.39 (1H, d, J = 8.5 Hz), 5.75 (2H, brs), 5.36 (2H, s), 2.71 (3H, s). |
| 207 | Solid | 1H-NMR (DMSO-D6) δ: 8.51 (1H, d, J = 2.4 Hz), 8.42 (1H, s), 7.90 (1H, dd, J = 8.3, 2.4 Hz), 7.53 (1H, d, J = 8.3 Hz), 5.68 (2H, s), 2.49 (3H, s). |
| 208 | Solid | 1H-NMR (CDCl3) δ: 8.55 (1H, d, J = 2.4 Hz), 7.78 (1H, dd, J = 8.4, 2.4 Hz), 7.35 (1H, d, J = 8.4 Hz), 6.22 (1H, s), 5.57 (2H, s), 2.70 (3H, s). |
| 209 | Amorphous | 1H-NMR (CDCl3) δ: 8.48 (1H, d, J = 2.4 Hz), 7.78 (1H, dd, J = 8.3, 2.4 Hz), 7.32 (1H, d, J = 8.3 Hz), 5.39 (1H, s), 5.33 (2H, s), 4.01 (3H, s), 2.69 (3H, s). |
| 210 | Solid | 1H-NMR (DMSO-D6) δ: 8.51 (1H, d, J = 2.1 Hz), 7.91 (1H, dd, J = 8.3, 2.4 Hz), 7.56 (1H, d, J = 8.3 Hz), 7.30 (1H, t, J = 52.4 Hz), 5.72 (2H, s), 2.50 (3H, s). |
| 211 | Solid | 1H-NMR (DMSO-D6) δ: 8.51 (1H, d, J = 2.4 Hz), 7.90 (1H, dd, J = 8.6, 2.4 Hz), 7.53 (1H, d, J = 8.3 Hz), 5.65 (2H, s), 2.78-2.74 (2H, m), 2.45 (3H, s), 1.28-1.24 (3H, m). |
| 212 | Solid | 1H-NMR (CDCl3) δ: 8.40 (1H, d, J = 2.4 Hz), 8.10 (1H, s), 7.65 (1H, dd, J = 8.3, 2.4 Hz), 7.44-7.38 (4H, m), 7.26-7.25 (2H, m), 5.59 (2H, s), 2.30 (3H, s). |
| 213 | Amorphous | 1H-NMR (CDCl3) δ: 9.73 (1H, s), 8.55 (1H, d, J = 2.4 Hz), 7.84 (1H, dd, J = 8.3, 2.4 Hz), 7.35 (1H, d, J = 8.3 Hz), 5.44 (2H, s), 3.11 (3H, s), 2.83 (3H, s). |
| 214 | Solid | 1H-NMR (CDCl3) δ: 8.17 (1H, d, J = 2.1 Hz), 7.45 (1H, d, J = 2.1 Hz), 5.82 (1H, s), 5.77 (1H, s), 5.11 (2H, s), 2.65 (3H, s), 2.35 (3H, s). |

TABLE 17

| Compound No. | State | $^1$H-NMR Value δ (ppm) |
|---|---|---|
| 215 | Solid | 1H-NMR (CDCl3) δ: 8.41 (1H, d, J = 2.5 Hz), 7.53 (1H, dd, J = 8.5 Hz, J = 2.5 Hz), 7.47 (1H, d, J = 8.5 Hz), 7.41 (1H, d, J = 8.5 Hz), 6.27 (1H, s), 6.06 (1H, d, J = 8.5 Hz), 5.05 (2H, s). |

TABLE 17-continued

| Compound No. | State | ¹H-NMR Value δ (ppm) |
|---|---|---|
| 216 | Solid | 1H-NMR (CDCl3) δ: 7.83 (1H, s), 7.45 (1H, d, J = 8.0 Hz), 6.39 (1H, s), 6.05 (1H, d, J = 8.0 Hz), 5.25 (2H, s). |
| 217 | Solid | 1H-NMR (CDCl3) δ: 7.43 (1H, d, J = 2.5 Hz), 6.39 (1H, s), 6.00 (1H, d, J = 7.5 Hz), 4.02 (1H, dt, 6.0 Hz, J = 8.0 Hz), 3.94 (2H, dd, J = 8.0 Hz, J = 6.0 Hz), 3.80 (1H, dt, J = 6.0 Hz, J = 8.0 Hz), 3.74 (1H, dd, J = 8.0 Hz, J = 6.0 Hz), 3.64 (1H, dd, J = 8.0 Hz, J = 4.0 Hz), 2.96-2.86 (1H, m), 2.18-2.06 (1H, m), 1.71-1.64 (1H, m). |
| 218 | Solid | 1H-NMR (CDCl3) δ: 8.37 (1H, d, J = 2.5 Hz), 7.49 (1H, dd, J = 8.5 Hz), J = 2.5 Hz), 7.37 (1H, d, J = 8.5 Hz), 7.30 (1H, d, J = 7.5 Hz), 5.92 (1H, d, J = 7.5 Hz), 5.83 (1H, s), 5.04 (2H, s), 2.66 (3H, s). |
| 219 | Solid | 1H-NMR (CDCl3) δ: 7.58 (1H, s), 7.27 (1H, d, J = 7.5 Hz), 5.96 (1H, s), 5.92 (1H, d, J = 7.5 Hz), 5.13 (2H, s), 2.68 (3H, s). |
| 220 | Solid | 1H-NMR (CDCl3) δ: 8.41 (1H, brs), 8.32 (1H, brs), 7.53 (1H, brd, J = 8.5 Hz), 7.39 (1H, d, J = 8.5 Hz), 5.84 (1H, s), 5.13 (2H, s), 4.37 (2H, q, J = 7.3 Hz), 2.63 (3H, s), 1.38 (3H, t, J = 7.3 Hz). |
| 221 | Solid | 1H-NMR (CDCl3) δ: 8.28 (1H, s), 7.64 (1H, s), 6.02 (1H, s), 5.23 (2H, s), 4.37 (2H, q, J = 7.3 Hz), 2.65 (3H, s), 1.38 (3H, t, J = 7.3 Hz). |
| 222 | Solid | 1H-NMR (CDCl3) δ: 8.48 (1H, s), 8.45 (1H, d, J = 2.5 Hz), 7.57 (1H, dd, J = 8.5 Hz, J = 2.5 Hz), 7.43 (1H, d, J = 8.5 Hz), 6.32 (1H, s), 5.24 (2H, s), 4.40 (2H, q, J = 7.0 Hz), 1.30 (3H, t, J = 7.0 Hz). |
| 223 | Amorphous | 1H-NMR (CDCl3) δ: 8.38 (1H, d, J = 2.4 Hz), 7.25 (1H, dd, J = 8.0, 2.4 Hz), 7.15 (1H, d, J = 8.0 Hz), 5.81 (1H, s), 5.78 (1H, d, J = 0.6 Hz), 5.10 (2H, s), 2.64 (3H, s), 2.56 (3H, s), 2.34 (3H, d, J = 0.6 Hz). |
| 224 | Solid | 1H-NMR (CDCl3) δ: 8.62 (1H, d, J = 1.5 Hz), 7.70 (1H, d, J = 8.3 Hz), 7.55 (1H, dd, J = 8.3, 1.5 Hz), 5.78 (1H, s), 5.75 (1H, s), 5.23 (2H, s), 2.63 (3H, s), 2.34 (3H, s). |
| 225 | Solid | 1H-NMR (CDCl3) δ: 8.38 (1H, d, J = 2.5 Hz), 7.49 (1H, dd, J = 8.5 Hz, J = 2.5 Hz), 7.37 (1H, d, J = 8.5 Hz), 7.33 (1H, d, J = 7.5 Hz), 5.91 (1H, d, J = 7.5 Hz), 5.80 (1H, s), 5.08 (2H, s), 2.77 (2H, q, J = 7.0 Hz), 1.28 (3H, t, J = 7.0 Hz). |

TABLE 18

| Compound No. | State | ¹H-NMR Value δ (ppm) |
|---|---|---|
| 226 | Solid | 1H-NMR (CDCl3) δ: 7.59 (1H, s), 7.31 (1H, d, J = 7.5 Hz), 5.93 (1H, s), 5.90 (1H, d, J = 7.5 Hz), 5.15 (2H, s), 2.81 (2H, q, J = 7.0 Hz), 1.32 (3H, t, J = 7.0 Hz). |
| 227 | Solid | 1H-NMR (CDCl3) δ: 8.42 (1H, d, J = 2.5 Hz), 8.35 (1H, s), 7.53 (1H, dd, J = 8.5 Hz, J = 2.5 Hz), 7.40 (1H, d, J = 8.5 Hz), 5.88 (1H, s), 5.16 (2H, s), 4.39 (2H, q, J = 7.3 Hz), 2.76 (2H, q, J = 7.3 Hz), 1.39 (3H, t, J = 7.3 Hz), 1.28 (3H, t, J = 7.0 Hz). |
| 228 | Solid | 1H-NMR (CDCl3) δ: 8.27 (1H, d, J = 2.5 Hz), 7.34 (1H, d, J = 8.5 Hz), 7.31 (1H, dd, J = 8.5 Hz), J = 2.5 Hz), 5.85 (1H, s), 5.76 (1H, s), 5.13 (2H, s), 2.64 (3H, s), 2.60 (2H, q, J = 7.3 Hz), 1.30 (3H, t, J = 7.3 Hz). |
| 229 | Solid | 1H-NMR (CDCl3) δ: 7.46 (1H, s), 5.91 (1H, s), 5.82 (1H, brs), 5.19 (2H, d, J = 1.0 Hz), 2.69 (2H, q, J = 7.3 Hz), 2.68 (3H, s), 1.34 (3H, t, J = 7.3 Hz). |
| 230 | Amorphous | 1H-NMR (CDCl3) δ: 8.35 (1H, d, J = 2.8 Hz), 7.42 (1H, dd, J = 8.3, 2.8 Hz), 7.34 (1H, d, J = 8.3 Hz), 5.82 (1H, s), 5.45 (1H, dd, J = 10.4, 4.6 Hz), 5.35 (1H, br s), 2.61 (3H, s), 2.49 (5H, br s), 0.97 (3H, t, J = 6.9 Hz), |
| 231 | Solid | 1H-NMR (CDCl3) δ: 8.39 (1H, d, J = 2.5 Hz), 7.56 (1H, dd, J = 8.0 Hz, J = 2.5 Hz), 7.45 (1H, d, J = 8.0 Hz), 7.40 (1H, d, J = 8.5 Hz), 6.60 (1H, s), 6.05 (1H, d, J = 8.0 Hz), 5.15 (2H, s), 3.02 (3H, s). |

TABLE 18-continued

| Compound No. | State | ¹H-NMR Value δ (ppm) |
|---|---|---|
| 232 | Solid | 1H-NMR (CDCl3) δ: 8.39 (1H, d, J = 2.5 Hz), 7.55 (1H, dd, J = 8.5 Hz, J = 2.5 Hz), 7.50 (1H, d, J = 8.0 Hz), 7.41 (1H, d, J = 8.5 Hz), 6.55 (2H, s), 6.08 (1H, d, J = 8.0 Hz), 5.16 (2H, s), 3.36 (3H, s). |
| 233 | Solid | 1H-NMR (DMSO-D6) δ: 8.45 (1H, d, J = 2.4 Hz), 8.05 (1H, d, J = 1.8 Hz), 7.77 (1H, dd, J = 8.3, 2.4 Hz), 7.51 (1H, d, J = 8.3 Hz), 6.58 (1H, d, J =1.8 Hz), 5.57 (2H, s), 2.48 (3H, s). |
| 234 | Solid | 1H-NMR (DMSO-D6) δ: 8.45 (1H, d, J = 2.4 Hz), 7.82 (1H, dd, J = 8.3, 2.4 Hz), 7.54 (1H, d, J = 8.3 Hz), 7.24 (1H, s), 5.64 (2H, s), 3.42 (3H, s), 2.49 (3H, s). |
| 235 | Solid | 1H-NMR (CDCl3) δ: 8.31 (1H, d, J = 2.1 Hz), 7.88 (1H, d, J = 1.8 Hz), 7.41-7.38 (5H, m), 7.28 (2H, d, J = 7.0 Hz), 5.97 (1H, d, J = 1.8 Hz), 5.28 (2H, s), 2.23 (3H, s). |
| 236 | Amorphous | 1H-NMR (CDCl3) δ: 8.27 (1H, s), 7.33 (2H, d, J = 1.5 Hz), 5.73 (1H, s), 5.14 (2H, s), 2.63 (3H, s), 2.31 (3H, s), 2.17 (3H, s). |
| 237 | Amorphous | 1H-NMR (CDCl3) δ: 8.29 (1H, s), 7.35-7.34 (2H, m), 5.79 (1H, s), 5.13 (2H, s), 2.65 (3H, s), 2.41 (3H, d, J = 3.7 Hz). |

TABLE 19

| Compound No. | State | ¹H-NMR Value δ (ppm) |
|---|---|---|
| 238 | Solid | 1H-NMR (CDCl3) δ: 8.41 (1H, d, J = 2.4 Hz), 7.67 (1H, dd, J = 8.3, 2.4 Hz), 7.45 (1H, d, J = 8.6 Hz), 7.39 (1H, d, J = 8.0 Hz), 6.14 (1H, d, J = 8.0 Hz), 5.44 (2H, s), 2.75 (3H, s). |
| 239 | Solid | 1H-NMR (CDCl3) δ: 8.30 (1H, s), 7.35 (1H, d, J = 8.3 Hz), 7.32 (1H, dd, J = 8.3, 2.1 Hz), 6.78 (1H, s), 5.92 (1H, s), 5.17 (2H, s), 2.67 (3H, s), 2.32 (3H, s). |
| 240 | Solid | 1H-NMR (CDCl3) δ: 8.25 (1H, d, J = 1.8 Hz), 7.35 (1H, dd, J = 8.3, 1.8 Hz), 7.31 (1H, d, J = 8.3 Hz), 6.12 (1H, s), 5.62 (1H, s), 4.97 (2H, s), 3.97 (3H, s), 2.56 (3H, s), 2.21 (3H, s). |
| 241 | Solid | 1H-NMR (CDCl3) δ: 8.29 (1H, s), 7.37 (2H, d, J = 1.2 Hz), 6.77 (1H, t, J = 54.2 Hz), 6.18 (1H, s), 5.87 (1H, s), 5.23 (2H, s), 2.40 (3H, s). |
| 242 | Solid | 1H-NMR (CDCl3) δ: 8.27 (1H, d, J = 1.2 Hz), 7.38 (1H, d, J = 8.3, 2.4 Hz), 7.36 (1H, d, J = 8.3 Hz), 6.16 (1H, s), 5.86 (1H, s), 5.23 (2H, s), 2.40 (3H, s), 2.09 (3H, t, J = 18.7 Hz). |
| 243 | Solid | 1H-NMR (CDCl3) δ: 8.28 (1H, s), 7.35 (2H, d, J = 1.5 Hz), 5.79 (1H, s), 5.77 (1H, s), 5.12 (2H, s), 3.22 (2H, q, J = 7.4 Hz), 2.34 (3H, s), 1.38 (3H, t, J = 7.4 Hz). |
| 244 | Solid | 1H-NMR (CDCl3) δ: 8.26 (1H, d, J = 2.3 Hz), 7.39 (1H, dd, J = 8.4, 2.3 Hz), 7.36 (1H, d, J = 8.4 Hz), 6.53 (1H, s), 5.93 (1H, s), 5.24 (2H, s), 3.25-3.10 (2H, m), 2.42 (3H, s), 1.30 (3H, t, J = 7.5 Hz). |
| 245 | Solid | 1H-NMR (CDCl3) δ: 8.25 (1H, d, J = 2.4 Hz), 7.40 (1H, dd, J = 8.3, 2.4 Hz), 7.37 (1H, d, J = 8.3 Hz), 6.48 (1H, s), 5.95 (1H, s), 5.25 (2H, s), 3.47 (2H, q, J = 7.5 Hz), 2.44 (3H, s), 1.36 (3H, t, J = 7.5 Hz). |
| 246 | Solid | 1H-NMR (CDCl3) δ: 8.27 (1H, d, J = 2.1 Hz), 7.53 (1H, d, J = 8.3 Hz), 7.28-7.28 (1H, m), 6.20 (1H, s), 5.88 (1H, s), 5.23 (2H, s), 2.42 (3H, s). |
| 247 | Solid | 1H-NMR (CDCl3) δ: 8.27 (1H, d, J = 2.4 Hz), 7.50 (1H, d, J = 8.3 Hz), 7.24 (1H, dd, J = 8.3, 2.4 Hz), 5.80 (1H, s), 5.77 (1H, s), 5.09 (2H, s), 3.23 (2H, q, J = 7.4 Hz), 2.34 (3H, s), 1.38 (3H, t, J = 7.4 Hz). |
| 248 | Solid | 1H-NMR (CDCl3) δ: 7.78 (1H, s), 7.54 (1H, s), 6.14 (1H, s), 5.98 (1H, s), 5.27 (2H, s), 2.41 (3H, s). |
| 249 | Amorphous | 1H-NMR (CDCl3) δ: 7.79 (1H, s), 7.50 (1H, s), 5.83 (1H, s), 5.70 (1H, s), 5.16 (2H, s), 3.22 (2H, q, J = 7.3 Hz), 2.34 (3H, s), 1.38 (3H, t, J = 7.3 Hz). |

TABLE 20

| Compound No. | State | ¹H-NMR Value δ (ppm) |
|---|---|---|
| 250 | Solid | 1H-NMR (CDCl3) δ: 8.24 (1H, d, J = 2.4 Hz), 7.52 (1H, d, J = 8.3 Hz), 7.28-7.28 (1H, m), 6.52 (1H, s), 5.94 (1H, s), 5.21 (2H, s), 3.28-3.06 (2H, m), 2.42 (3H, s), 1.30 (3H, t, J = 7.3 Hz). |
| 251 | Solid | 1H-NMR (CDCl3) δ: 7.72 (1H, s), 7.53 (1H, s), 6.44 (1H, s), 5.99 (1H, s), 5.27 (2H, s), 3.25-3.10 (2H, m), 2.41 (3H, s), 1.29 (3H, t, J = 7.3 Hz). |
| 252 | Solid | 1H-NMR (CDCl3) δ: 8.11 (1H, d, J = 1.8 Hz), 7.19 (1H, dd, J = 7.8, 1.8 Hz), 5.81 (1H, s), 5.76 (1H, s), 5.14 (2H, s), 3.23 (2H, q, J = 7.4 Hz), 2.35 (3H, s), 1.39 (3H, t, J = 7.4 Hz). |
| 253 | Solid | 1H-NMR (CDCl3) δ: 8.12 (1H, d, J = 2.1 Hz), 7.20 (1H, dd, J = 8.0, 2.1 Hz), 6.20 (1H, s), 5.96 (1H, d, J = 0.6 Hz), 5.25 (2H, s), 2.43 (3H, d, J = 0.6 Hz). |
| 254 | Solid | 1H-NMR (CDCl3) δ: 8.09 (1H, d, J = 2.0 Hz), 7.24 (1H, dd, J = 8.1, 2.0 Hz), 6.53 (1H, s), 5.94 (1H, s), 5.29 (2H, s), 3.26-3.22 (1H, m), 3.12-3.07 (1H, m), 2.43 (3H, s), 1.30 (3H, t, J = 7.3 Hz). |
| 255 | Solid | 1H-NMR (CDCl3) δ: 8.28 (1H, s), 7.35 (2H, d, J = 1.2 Hz), 5.79 (1H, s), 5.79 (1H, s), 5.12 (2H, s), 3.97-3.92 (1H, m), 2.34 (3H, s), 1.39 (6H, d, J = 6.7 Hz). |
| 256 | Solid | 1H-NMR (CDCl3) δ: 8.25 (1H, s), 7.37 (2H, s), 6.51 (1H, s), 5.93 (1H, s), 5.23 (2H, s), 3.28-3.26 (1H, m), 2.41 (3H, s), 1.39 (3H, d, J = 6.8 Hz), 1.19 (3H, d, J = 6.8 Hz). |
| 257 | Amorphous | 1H-NMR (CDCl3) δ: 8.24 (1H, d, J = 2.4 Hz), 7.40 (1H, dd, J = 8.3, 2.4 Hz), 7.37 (1H, dd, J = 8.3, 0.6 Hz), 6.47 (1H, s), 5.93 (1H, s), 5.26 (2H, s), 3.70-3.65 (1H, m), 2.43 (3H, s), 1.36 (6H, d, J = 7.0 Hz). |
| 258 | Solid | 1H-NMR (CDCl3) δ: 8.26 (1H, s), 7.33 (2H, d, J = 1.5 Hz), 5.72 (1H, s), 5.11 (2H, s), 2.67 (2H, t, J = 6.2 Hz), 2.62 (3H, s), 2.55 (2H, t, J = 6.2 Hz), 1.86-1.71 (4H, m). |
| 259 | Solid | 1H-NMR (CDCl3) δ: 8.29 (1H, dd, J = 2.8, 0.6 Hz), 7.39 (1H, dd, J = 8.3, 2.4 Hz), 7.34 (1H, d, J = 8.3 Hz), 5.75 (1H, s), 5.06 (2H, s), 2.95-2.93 (4H, m), 2.63 (3H, s), 2.21-2.18 (2H, m). |
| 260 | Amorphous | 1H-NMR (CDCl3) δ: 8.24 (1H, d, J = 2.4 Hz), 7.53 (1H, d, J = 8.3 Hz), 7.28 (1H, dd, J = 8.3, 2.4 Hz) 6.48 (1H, s), 5.95 (1H, d, J = 0.6 Hz), 5.22 (2H, s), 3.47 (2H, d, J = 7.4 Hz), 2.43 (3H, s), 1.37 (3H, t, J = 7.4 Hz). |
| 261 | Solid | 1H-NMR (CDCl3) δ: 8.09 (1H, d, J = 2.1 Hz), 7.21 (1H, dd, J = 8.0, 2.1 Hz), 6.48 (1H, s), 5.99 (1H, d, J = 0.6 Hz), 5.25 (2H, s), 3.50 (2H, q, J = 7.4 Hz), 2.45 (3H, s), 1.38 (3H, t, J = 7.4 Hz). |

TABLE 21

| Compound No | State | ¹H-NMR Value δ (ppm) |
|---|---|---|
| 262 | Solid | 1H-NMR (CDCl3) δ: 7.75 (1 H, s), 7.54 (1 H, s), 6.42 (1 H, s), 6.03 (1 H, d, J = 0.6 Hz), 5.27 (2 H, s), 3.50 (2 H, q, J = 7.4 Hz), 2.43 (3 H, d, J = 0.6 Hz), 1.38 (3 H, t, J = 7.4 Hz). |
| 263 | Solid | 1H-NMR (CDCl3) δ: 8.29 (1 H, s), 7.34 (2 H, d, J = 1.5 Hz), 5.80 (1 H, d, J = 0.6 Hz), 5.78 (1 H, s), 5.11 (2 H, s), 3.20 (2 H, t, J = 7.2 Hz), 2.34 (3 H, d, J = 0.6 Hz), 1.76-1.73 (2 H, m), 1.03 (3 H, t, J = 7.3 Hz). |
| 264 | Solid | 1H-NMR (CDCl3) δ: 8.29 (1 H, d, J = 2.4 Hz), 7.44 (1 H, dd, J = 8.3, 2.4 Hz), 7.36 (1 H, d, J = 8.3 Hz), 6.52 (1 H, s), 5.16 (2 H, s), 3.01 (4 H, t, J = 7.6 Hz), 3.00 (3 H, s), 2.28-2.22 (2 H, m). |
| 265 | Solid | 1H-NMR (CDCl3) δ: 8.28 (1 H, d, J = 2.8 Hz), 7.43 (1 H, dd, J = 8.3, 2.8 Hz), 7.37 (1 H, d, J = 8.3 Hz), 6.45 (1 H, s), 5.17 (2 H, s), 3.34 (3 H, s), 3.03-3.01 (4 H, m), 2.29-2.23 (2 H, m). |
| 266 | Solid | 1H-NMR (CDCl3) δ: 8.26 (1 H, d, J = 2.2 Hz), 7.38-7.37 (2 H, m), 6.52 (1 H, s), 5.94 (1 H, d, J = 0.6 Hz), 5.23 (2 H, s), 3.20-3.05 (2 H, m), 2.42 (3 H, d, J = 0.6 Hz), 1.96-1.73 (2 H, m), 1.08 (3 H, t, J = 7.3 Hz). |
| 267 | Solid | 1H-NMR (CDCl3) δ: 8.26-8.26 (1 H, m), 7.38 (2 H, d, J = 1.8 Hz), 6.48 (1 H, s), 5.97 (1 H, d, J = 0.6 Hz), 5.23 (2 H, s), 3.47-3.43 (2 H, m), 2.44 (3 H, d, J = 0.6 Hz), 1.86-1.85 (2 H, m), 1.06 (3 H, t, J = 7.3 Hz). |
| 268 | Solid | 1H-NMR (DMSO-D6) δ: 8.49 (1 H, d, J = 2.4 Hz), 7.87 (1 H, dd, d = 8.4, 2.6 Hz), 7.54 (1 H, d, J = 8.3 Hz), 5.73 (2 H, s), 2.57 (3 H, s). |
| 269 | Solid | 1H-NMR (DMSO-d6) δ: 8.45 (1 H, dd, J = 2.8, 0.6 Hz), 7.84 (1 H, dd, J = 8.3, 2.8 Hz). 7.62 (1 H, t, J = 71.6 Hz), 7.51 (1 H, dd, J = 8.3, 0.6 Hz), 6.12 (1 H, d, J = 0.6 Hz), 5.47 (2 H, s), 2.35 (3 H, d, J = 0.6 Hz). |
| 270 | Solid | 1H-NMR (CDCl3) δ: 8.39 (1 H, d, J = 2.6 Hz), 7.59 (1 H, dd, J = 8.4, 2.6 Hz), 7.33 (1 H, d, J = 8.4 Hz), 6.19 (1 H, d, J = 1.8 Hz), 5.68-5.48 (3 H, m), 2.68 (3 H, s), 1.75 (5 H, dd, J = 23.9, 6.4 Hz). |

TABLE 21-continued

| Compound No | State | ¹H-NMR Value δ (ppm) |
|---|---|---|
| 271 | Solid | 1H-NMR (DMSO-d6) δ: 8.44 (1 H, d, J = 2.6 Hz), 7.83 (1 H, dd, J = 8.4, 2.6 Hz), 7.50 (1 H, c, J = 8.4 Hz), 6.40(1 H, s), 5.96 (1 H, m) 5.63-5.54 (2 H, m), 3.425(3 H, s), 1.58 (3 H, dd, J = 24.8, 6.4 Hz). |
| 272 | Solid | 1H-NMR (CDCl3) δ: 8.45 (1 H, d, J = 2.6 Hz), 7.66 (1 H, dd, J = 8.4, 2.6 Hz), 7.34 (1 H, d, J = 8.4 Hz), 6.58 (1 H, t, J = 52.3), 6.31 (1 H, s), 5.54 (2 H, s), 2.68 (3 H, s). |
| 273 | Solid | 1H-NMR (CDCl3) δ: 8.43 (1 H, d, J = 2.8 Hz), 7.73 (1 H, dd, J = 8.3, 2.8 Hz), 7.35 (1 H, d, J = 8.3 Hz), 6.68 (1 H, t, J = 52.3), 6.48 (1 H, s), 5.65 (2 H, s), 3.39 (3 H, s). |

TABLE 22

| Compound No | State | ¹H-NMR Value δ (ppm) |
|---|---|---|
| 274 | Solid | 1H-NMR (CDCl3) δ: 8.58 (1 H, d, J = 2.1 Hz), 8.54 (2 H, d, J = 2.1 Hz), 5.78 (1 H, s), 5.77 (1 H, s), 5.22 (2 H, s), 2.61 (3 H, s), 2.45 (3 H, s). |
| 275 | Solid | 1H-NMR (DMSO-d6) δ: 8.84 (1 H, d, J = 1.5 Hz), 8.61 (1 H, d, J = 2.4 Hz), 8.56 (1 H, dd, J = 2.4, 1.5 Hz), 6.06 (1 H, s), 5.64(2 H, s), 2.56 (3 H, s), 2.41 (3 H, s). |
| 276 | Solid | 1H-NMR (CDCl3) δ: 5.84(1 H, s), 4.41 (1 H, dd, J = 14.5, 2.6 Hz), 4.32 (1 H, m), 4.02 (1 H, m), 3.88 (1 H, m), 3.73(1 H, m), 2.68 (3 H, s), 2.50 (3 H, s), 2.17 (1 H, m), 1.98-1.92 (2 H, m), 1.62 (1 H, m). |
| 277 | Solid | 1H-NMR (CDCl3) δ: 8.80 (1 H, s), 7.96 (1 H, s), 5.88 (1 H, s), 5.61 (2 H, s), 2.71 (3 H, s), 2.52 (3 H, s). |
| 278 | Solid | 1H-NMR (CDCl3) δ: 8.77 (1 H, s), 7.78 (1 H, s), 5.88 (1 H, s), 5.67 (1 H, s), 5.27 (2 H, s), 2.61 (3 H, s), 2.40 (3 H, s). |
| 279 | Solid | 1H-NMR (CDCl3) δ: 9.16 (1 H, s), 8.52 (2 H, s), 7.78 (1 H, d, J = 2.0 Hz), 5.87 (1 H, d, J = 2.0 Hz), 5.78 (1 H, s), 5.16 (2 H, s), 2.34 (3 H, s). |
| 280 | Solid | 1H-NMR (CDCl3) δ: 9.23 (1H, s), 8.77 (2 H, s), 5.93 (1 H, s), 5.45 (2 H, s), 2.69(3 H, s), 2.46 (3 H, s). |
| 281 | Solid | 1H-NMR (CDCl3) δ: 9.24 (1 H, s), 8.58 (2 H, s), 5.81 (1 H, s), 5.79 (1 H, s), 5.16 (2 H, s), 2.65 (3 H, s), 2.38 (3 H, s). |
| 282 | Solid | 1H-NMR (CDCl3) δ: 7.77 (1 H, d, J = 8.6 Hz), 7.57 (1 H, d, J = 8.6 Hz), 5.92 (1 H, d, J = 0.9 Hz), 5.65 (2 H, s), 2.69(3 H, s), 2.62 (3 H, d, J = 0.9 Hz). |
| 283 | Solid | 1H-NMR (CDCl3) δ: 7.55 (1 H, d, J = 8.9 Hz), 7.25 (1 H, d, J = 8.9 Hz), 5.82(1 H, s), 5.81 (1 H, s), 5.40 (2 H, s), 2.64(3 H, s), 2.42 (3 H, s). |
| 284 | Solid | 1H-NMR (CDCl3) δ: 8.57 (1 H, d, J = 2.0 Hz), 8.45 (1 H, d, J = 2.0 Hz), 7.57 (1 H, t, J = 2.0 Hz), 5.93 (1 H, s), 5.45 (2 H, s), 2.70 (3 H, s), 2.40 (3 H, s). |
| 285 | Solid | 1H-NMR (CDCl3) δ: 8.57 (1 H, d, J = 2.1 Hz), 8.36 (1 H, d, J = 2.1 Hz), 7.35 (1 H, t, J = 2.1 Hz), 5.78 (1 H, s), 5.77 (1 H, s), 5.14 (2 H, s), 2.64 (3 H, s), 2.35 (3 H, s). |

TABLE 23

| Compound No | State | ¹H-NMR Value δ (ppm) |
|---|---|---|
| 286 | Solid | 1H-NMR (CDCl3) δ: 8.64 (1 H, s), 7.96 (1 H, s), 6.42 (2 H, s), 5.91 (1 H, s), 2.81 (3 H, s), 2.68 (3 H, s). |
| 287 | Solid | 1H-NMR (DMSO-d6) δ: 9.00 (1 H, s), 8.09 (1 H, s), 6.69 (1 H, s), 6.43 (2 H, s), 5.82 (1 H, s), 2.66 (3 H, s), 2.55 (3 H, s). |
| 288 | Solid | 1H-NMR (DMSO-d6) δ: 8.69 (1 H, d, J = 1.5 Hz), 7.93 (1 H, d, J = 8.3 Hz), 7.85 (1 H, dd, J = 8.3, 1.5 Hz), 5.95 (1 H, s), 5.50 (2 H, s), 2.49 (3 H, s), 2.24 (3 H, s). |
| 289 | Solid | 1H-NMR (CDCl3) δ: 8.61 (1 H, d, J = 1.5 Hz), 7.72 (1 H, d, J = 8.3 Hz), 7.51 (1 H, dd, J = 8.3, 1.5 Hz), 5.81 (1 H, s), 5.73 (1 H, s ), 5.22 (2 H, s), 2.64(3 H, s), 2.33 (3 H, s). |
| 290 | Solid | 1H-NMR (CDCl3) δ: 7.91 (1 H, d, J = 2.2 Hz), 7.54 (1 H, d, J = 2.2 Hz), 6.39 (2 H, s), 6.29 (1 H, t, J = 2.2 Hz), 5.87 (1 H, d, J = 1.0 Hz), 2.81 (3 H, d, J = 1.0 Hz), 2.24 (3 H, s). |
| 291 | Solid | 1H-NMR (CDCl3) δ: 8.02 (1 H, d, J = 2.4 Hz), 6.56 (1 H, d, J = 2.4 Hz), 6.41 (2 H, s), 5.91 (1 H, s), 2.79 (3 H, s), 2.70 (3 H, s). |
| 292 | Solid | 1H-NMR (CDCl3) δ: 8.10 (1 H, d, J = 2.9 Hz), 7.51 (1 H, dt, J = 8.4, 2.9 Hz), 6.96 (1 H, dd, J = 8.4, 2.9 Hz), 5.79 (1 H, s), 5.77 (1 H, d, J = 0.6 Hz), 5.13 (2 H, s), 2.64 (3 H, s), 2.35 (3 H, d, J = 0.6 Hz). |
| 293 | Solid | 1H-NMR (CDCl3) δ: 8.35 (1 H, dd, J = 2.4, 1.0 Hz), 7.50 (1 H, dd, J = 8.3, 1.0 Hz), 7.47 (1 H, dd, J = 8.3, 2.4 Hz), 5.91 (1 H, s), 5.41 (2 H, s), 2.69 (3 H, s), 2.40 (3 H, s). |
| 294 | Solid | 1H-NMR (CDCl3) δ: 7.93 (1 H, s), 7.59 (1 H, s), 6.28 (2 H, s), 5.94 (1 H, s), 2.70 (3 H, s), 2.58 (3 H, s). |
| 295 | Solid | 1H-NMR (CDCl3) δ: 7.64 (1 H, s), 5.87 (1 H, s), 5.51 (2 H, s), 2.71 (3 H, s), 2.67 (3 H, s), 2.51 (3 H, s). |
| 296 | Solid | 1H-NMR (CDCl3) δ: 7.90 (1 H, s), 7.47 (1 H, s), 5.97 (1 H, s), 5.51 (2 H, s), 2.67 (3 H, s), 2.35 (3 H, s). |
| 297 | Solid | 1H-NMR (CDCl3) δ: 7.49 (1 H, s), 7.46 (1 H, s), 5.85 (1 H, s), 5.25 (2 H, s), 3.87 (3 H, s), 2.67 (3 H, s), 2.35 (3 H, s). |
| 298 | Solid | 1H-NMR (CDCl3) δ: 8.68(2 H, s), 5.93 (1 H, s), 5.41 (2 H, s), 2.68(3 H, s), 2.47 (3 H, s). |
| 299 | Solid | 1H-NMR (CDCl3) δ: 8.46(2 H, s), 5.81 (1 H, s), 5.77 (1 H, s), 5.14 (2 H, s), 2.64 (3 H, 2.37 (3 H, s). |

TABLE 24

| Compound No | State | ¹H-NMR Value δ (ppm) |
|---|---|---|
| 300 | Solid | 1H-NMR (CDCl3) δ: 8.26 (1 H, d, J = 2.8 Hz), 7.49 (1 H, d, J = 8.3 Hz), 7.23 (1 H, dd, J = 8.3, 2.8 Hz), 5.78 (1 H, d, J = 0.6 Hz), 5.77 (1 H, s), 5.10 (2 H, s), 2.64 (3 H, s), 2.34 (3 H, d, J = 0.6 Hz). |
| 301 | Solid | 1H-NMR (CDCl3) δ: 7.79 (1 H, s), 7.50 (1 H, s), 5.85 (1 H, s), 5.71 (1 H, s), 5 16 (2 H, d, J = 0.6 Hz), 2.65 (3 H, s), 2.34 (3 H, d, J = 0.6 Hz). |
| 302 | Solid | 1H-NMR (CDCl3) δ: 8.43 (1 H, d, J = 1.8 Hz), 8.36 (1 H, d, J = 1.8 Hz), 7.31 (1 H, s), 5.91 (1 H, d, J = 0.6 Hz), 5.44 (2 H, s), 2.70 (3 H, s), 2.37 (3 H, d, J = 0.6 Hz), 2.32 (3 H, s). |
| 303 | Solid | 1H-NMR (CDCl3) δ: 8.29 (1 H, d, J = 2.8 Hz), 8.14 (1 H, d, J = 1.8 Hz), 7.09 (1 H, dd, J = 2.8, 1.8 Hz), 5.91 (1 H, d, J = 0.9 Hz), 5.44 (2 H, s), 2.83 (3 H, s), 2.70 (3 H, s), 2.30 (3 H, d, J = 0.9 Hz). |
| 304 | Solid | 1H-NMR (CDCl3) δ: 9.22 (1 H, dd, J = 5.4, 1.5 Hz), 9.18 (1 H, m), 7.27 (1 H, m), 5.97 (1 H, s), 5.47 (2 H, s), 2.68 (3 H, s), 2.37 (3 H, s). |

TABLE 24-continued

| Compound No. | State | ¹H-NMR Value δ (ppm) |
|---|---|---|
| 305 | Solid | 1H-NMR (CDCl3) δ: 8.19 (1 H, d, J = 2.1 Hz), 7.02 (1 H, d, J = 2.1 Hz), 5.80 (1 H, s), 5.76 (1 H, s), 5.07 (2 H, s), 2.64 (3 H, s), 2.49 (3 H, s), 2.34 (3 H, s), 2.24 (3 H, s). |
| 306 | Solid | 1H-NMR (CDCl3) δ: 8.21 (1 H, d, J = 2.0 Hz), 7.47 (1 H, dd, J = 8.3, 2.0 Hz), 5.92 (1 H, s), 5.45 (2 H, s), 2.69 (3 H, s), 2.42 (3 H, s), |
| 307 | Solid | 1H-NMR (CDCl3) δ: 8.10 (1 H, d, J = 2.1 Hz), 7.20 (1 H, dd, J = 8.3, 2.1 Hz) 5.79 (1 H, S), 5.77 (1 H, s), 5.15 (2 H, s), 2.62 (3 H, s), 2.35 (3 H, s). |
| 308 | Solid | 1H-NMR (CDCl3) δ: 8.11 (1 H, d, J = 1.8 Hz), 7.18 (1 H, d, J = 1.8 Hz), 5.79 (1 H, d, J = 0.6 Hz), 5.78 (1 H, s), 5.09 (2 H, s), 2.65 (3 H, s), 2.35 (3 H, s), 2.34 (3 H, d, J = 0.6 Hz). |
| 309 | Solid | 1H-NMR (CDCl3) δ: 8.20 (1 H, d, J = 2.4 Hz), 7.61 (1 H, d, J = 2.4 Hz), 5.82 (1 H, d, J = 1.0 Hz), 5.77 (1 H, s), 5.10 (2 H, s), 2.66 (3 H, s), 2.35 (3 H, d, J = 1.0 Hz). |
| 310 | Solid | 1H-NMR (CDCl3) δ: 8.31 (1 H, d, J = 2.4 Hz), 7.86 (1 H, d, J = 2.4 Hz), 5.93 (1 H, d, J = 0.9 Hz), 5.41 (2 H, s), 2.69 (3 H, s), 2.42 (3 H, d, J = 0.9 Hz). |
| 311 | Solid | 1H-NMR (CDCl3) δ: 8.10 (1 H, d, J = 2.1 Hz), 7.13 (1 H, dd, J = 7.6, 2.1 Hz), 5.77 (1 H, s), 5.76 (1 H, s), 5.13 (2 H, s), 2.63 (3 H, s), 2.35 (3 H, s). |

TABLE 25

| Compound No. | State | ¹H-NMR Value δ (ppm) |
|---|---|---|
| 312 | Solid | 1H-NMR (CDCl3) δ: 8.21 (1 H, d, J = 2.0 Hz), 7.40 (1 H, dd, J = 7.8, 2.0 Hz), 5.92 (1 H, d, J = 0.6 Hz), 5.43 (2 H, s), 2.69 (3 H, s), 2.41 (3 H, d, J = 0.6 Hz). |
| 313 | Solid | 1H-NMR (CDCl3) δ: 8.25 (1 H, d, J = 2.1 Hz), 7.72 (1 H, d, J = 8.3 Hz), 7.01 (1 H, dd, J = 8.3, 2.1 Hz), 5.78 (1 H, s), 5.75 (1 H, d, J = 0.6 Hz), 5.08 (2 H, s), 2.62 (3 H, s), 2.33 (3 H, d, J = 0.6 Hz). |
| 314 | Solid | 1H-NMR (CDCl3) δ: 8.35 (1 H, d, J = 2.4 Hz), 7.73 (1 H, d, J = 8.3 Hz), 7.24 (1 H, dd, J = 8.3, 2.4 Hz), 5.91 (1 H, d, J = 0.6 Hz), 5.39 (2 H, s), 2.69 (3 H, s), 2.39 (3 H, d, J = 0.6 Hz). |
| 315 | Solid | 1H-NMR (CDCl3) δ: 7.80 (1 H, d, J = 2.1 Hz), 6.84 (1 H, d, J = 2.1 Hz), 5.80 (1 H, s), 5.77 (1 H, d, J = 0.6 Hz), 5.12 (2 H, s), 3.84 (3 H, s), 2.64 (3 H, s), 2.35 (3 H, d, J = 0.6 Hz). |
| 316 | Solid | 1H-NMR (CDCl3) δ: 7.91 (1 H, d, J = 2.1 Hz), 7.29 (1 H, d, J = 2.1 Hz), 5.91 (1 H, s), 5.42 (2 H, s), 3.87 (3 H, s), 2.69 (3 H, s), 2.44 (3 H, s). |
| 317 | Solid | 1H-NMR (CDCl3) δ: 8.34 (1 H, d, J = 2.4 Hz), 6.67 (1 H, dd, J = 8.5, 2.4 Hz), 5.82 (1 H, s), 5.66 (1 H, s), 5.04 (2 H, s), 2.64 (3 H, s), 2.61 (3 H, s), 2.30 (3 H, s). |
| 318 | Solid | 1H-NMR (CDCl3) δ: 8.53 (1 H, d, J = 2.4 Hz), 8.02 (1 H, d, J = 2.4 Hz), 5.94 (1 H, d, J = 0.9 Hz), 5.47 (2 H, s), 2.69 (3 H, s), 2.44 (3 H, 3, J = 0.6 Hz). |
| 319 | Solid | 1H-NMR (CDCl3) δ: 8.37 (1 H, d, J = 2.4 Hz), 7.73 (1 H, d, J = 2.4 Hz), 5.83 (1 H, J = 0.9 Hz), 5.75 (1 H, s), 5.18 (2 H, s), 2.65 (3 H, s), 2.36 (3 H, d, J = 0.9 Hz). |
| 320 | Solid | 1H-NMR (CDCl3) δ: 8.29 (1 H, s), 7.37 (1 H, dd, J = 8.2, 2.0 Hz), 7.34 (1 H, d, J = 8.2 Hz), 5.80 (1 H, s), 5.35 (1 H, s), 5.08 (2 H, s), 4.44 (2 H, q, J = 7.0 Hz), 2.32 (3 H, s), 1.39 (3 H, t, J = 7.0 Hz). |

TABLE 25-continued

| Compound No. | State | ¹H-NMR Value δ (ppm) |
|---|---|---|
| 321 | Solid | 1H-NMR (CDCl3) δ: 8.12 (1 H, d, J = 2.0 Hz), 7.21 (1 H, dd, J = 8.0, 2.0 Hz), 5.80 (1 H, s), 5.34 (1 H, s), 5.10 (2 H, s), 4.44 (2 H, q, J = 7.1 Hz), 2.33 (3 H, s), 1.39 (3 H, t, J = 7.1 Hz). |
| 322 | Solid | 1H-NMR (CDCl3) δ: 8.29 (1 H, dd, J = 2.7, 0.7 Hz), 7.37 (1 H, dd. J = 8.3, 2.7 Hz). 7.34 (1 H, dd, J = 8.3, 0.7 Hz), 5.79 (1 H, s), 5.31 (1 H, s), 5.31-5.24 (1 H, m), 5.07 (2 H, s), 2.32 (3 H, s), 1.36 (6 H, d, J = 6.1 Hz). |
| 323 | Solid | 1H-NMR (CDCl3) δ: 8.30 (1 H, dd, J = 2.4, 0.9 Hz), 7.37 (1 H, dd, J = 8.4, 0.9 Hz), 7.35 (1 H, dd, J = 8.4, 2.4 Hz), 5.90 (1 H, s), 5.86 (1 H, s), 5.14 (2 H, s), 2.38 (3 H, s). |

TABLE 26

| Compound No. | State | ¹H-NMR Value δ (ppm) |
|---|---|---|
| 324 | Solid | 1H-NMR (CDCl3) δ: 8.12 (1 H, d, J = 2.1 Hz), 7.19 (1 H, dd, J = 8.0, 2.1 Hz), 5.89 (1 H, s), 5.88 (1 H, s), 5.16 (2 H, s), 2.38 (3 H, s). |
| 325 | Solid | 1H-NMR (CDCl3) δ: 8.30-8.27 (1 H, m), 7.37-7.36 (2 H, m), 5.85 (1 H, s, 5.49 (1 H, s), 5.11 (2 H, s), 4.79 (2 H, q, J = 8.5 Hz), 2.35 (3 H, s). |
| 326 | Solid | 1H-NMR (CDCl3) δ: 8.29 (1 H, dd, J = 2.4, 0.7 Hz), 7.37 (1 H, dd, J = 8.4, 2.4 Hz), 7.34 (1 H, dd, J = 8.4, 0.7 Hz), 5.80 (1 H, s), 5.35 (1 H, s), 5.08 (2 H, s), 4.34 (2 H, t, J = 6.6 Hz), 2.32 (3 H, s), 1.82-1.73 (2 H, m), 1.00 (3 H, t, J = 7.3 Hz). |
| 327 | Solid | 1H-NMR (CDCl3) δ: 8.29 (1 H, br s), 7.37 (1 H, br s), 7.36 (1 H, br s), 7.31 (1 H, t, J = 72.5 Hz), 5.88 (1 H, s), 5.57 (1 H, s), 5.13 (2 H, s), 2.37 (3 H, s). |
| 328 | Solid | 1H-NMR (CDCl3) δ: 8.29 (1 H, dd, J = 2.1, 0.7 Hz), 7.38 (1 H, d, J = 2.1 Hz), 7.38 (1 H, d, J = 0.7 Hz), 5.90-5.90 (2 H, m), 5.17 (2 H, s), 3.42 (3 H, s), 2.38 (3 H, d, J = 0.6 Hz). |
| 329 | Solid | 1H-NMR (CDCl3) δ: 8.29 (1 H. dd, J = 2.4, 0.9 Hz), 7.37 (1 H, dd, J = 8.3, 0.9 Hz), 7.35 (1 H, dd, J = 8.3, 2.4 Hz), 5.97 (1 H, s), 5.82 (1 H, s), 5.15 (2 H, s), 2.38 (3 H, s). |
| 330 | Solid | 1H-NMR (CDCl3) δ: 8.30 (1 H, dd, J = 2.4, 0.7 Hz), 7.38 (1 H, dd, J = 8.4, 0.7 Hz), 7.35 (1 H, dd, J = 8.6, 2.4 Hz), 5.91 (1 H, s), 5.73 (1 H, s), 5.16 (2 H, s), 2.37 (3 H, s). |
| 331 | Solid | 1H-NMR (CDCl3) δ: 8.28 (1 H, dd, J = 2.4, 1.0 Hz), 7.37 (1 H, dd, J = 8.3, 2.4 Hz), 7.34 (1 H, dd, J = 8.3, 1.0 Hz), 5.81 (1 H, s) 5.39 (1 H, s) 5.09 (2 H, s), 4.62 (2 H, t, J = 6.3 Hz), 2.64-2.59 (2 H, m), 2.33 (3 H, s). |
| 332 | Solid | 1H-NMR (CDCl3) δ: 8.02 (1 H, d, J = 9.2 Hz), 7.19 (1 H, d, J = 9.2 Hz), 5.80 (1 H, d, J = 0.6 Hz), 5.76 (1 H, s) 5.14 (2 H, s), 2.64 (3 H, s), 2.39 (3 H, d, J = 0.6 Hz). |
| 333 | Solid | 1H-NMR (CDCl3) δ: 8.40 (1 H, d, J = 9.5 Hz), 7.16 (1 H, d, J = 9.5 Hz), 5.92 (1 H, d, J = 0.6 Hz), 5.43 (2 H, s), 2.67 (3 H, s), 2.45 (3 H, d, J = 0.6 Hz). |
| 334 | Solid | 1H-NMR (CDCl3) δ: 8.30 (1 H, s), 8.23 (2 H, d, J = 8.9 Hz), 7.40-7.37 (4 H, m), 5.88 (1 H, s), 5.64 (1 H, s), 5.17 (2 H, s), 2.39 (3 H, s). |
| 335 | Solid | 1H-NMR (CDCl3) δ: 8.29 (1 H, s), 7.34 (2 H, d, J = 1.5 Hz), 5.80 (1 H, s), 5.77 (1 H, s), 5.11 (2 H, s), 3.22 (2 H, t, J = 7.3 Hz), 2.34 (3 H, s), 1.74-1.68 (2 H, m), 1.42-1.39 (2 H, m), 1.36-1.26 (2 H, m), 0.89 (3 H, t, J = 7.3 Hz). |

TABLE 27

| Compound No. | State | ¹H-NMR Value δ (ppm) |
|---|---|---|
| 336 | Solid | 1H-NMR (CDCl3) δ: 8.26 (1 H, d, J = 2.4 Hz), 7.39 (1 H, dd, J = 8.3, 2.4 Hz), 7.36 (1 H, d, J = 8.3 Hz), 6.53 (1 H, s), 5.93 (1 H, s) 5.24 (2 H, s), 3.20-3.17 (1 H, m), 3.10-3.04 (1 H, m), 2.42 (3 H, s), 1.90-1.85 (1 H, m), 1.73-1.64 (1 H, m), 1.49-1.30 (4 H, m), 0.89 (3 H, t, J = 7.3 Hz). |
| 337 | Solid | 1H-NMR (CDCl3) δ: 8.25 (1 H, d, J = 2.4 Hz), 7.39 (1 H, dd, J = 8.3, 2.4 Hz), 7.37 (1 H, d, J = 8.3 Hz), 6.46 (1 H, s), 5.95 (1 H, s), 5.25 (2 H, s), 3.44-3.42 (2 H, m), 2.44 (3 H, s), 1.83-1.77 (2 H, m), 1.43-1.29 (4 H, m), 0.88 (3 H, t, J = 7.2 Hz). |
| 338 | Solid | 1H-NMR (CDCl3) δ: 8.29 (1 H, s), 7.34 (2 H, d. J = 1.5 Hz). 5.80 (1 H, s), 5.77 (1 H, s), 5.11 (2 H, s), 3.22 (2 H, t, J = 7.3 Hz), 2.34 (3 H, s), 1.72-1.66 (2 H, m), 1.47-1.44 (2 H, m), 0.92 (3 H, t, J = 7.3 Hz). |
| 339 | Solid | 1H-NMR (CDCl3) δ: 8.29 (1 H, s), 7.35 (2 H, d, J = 1.5 Hz), 5.80 (1 H, s), 5.79 (1 H, s), 5.12 (2 H, s), 3.83-3.78 (1 H, m), 2.34 (3 H, s), 1.74-1.61 (2 H, m), 1.38 (3 H, d, J = 6.7 Hz), 1.00 (3 H, t, J = 7.3 Hz). |
| 340 | Solid | 1H-NMR (CDCl3) δ: 8.26 (1 H, d, J = 1.2 Hz), 7.40-7.35 (2 H, m), 6.52 (1 H, s), 5.94 (1 H, s), 5.23 (2 H, s), 3.21-3.18 (1 H, m), 3.11-3.05 (1 H, m), 2.42 (3 H, s), 1.91-1.79 (1 H, m), 1.71-1.60 (1 H, m), 1.51-1.45 (2 H, m), 0.94 (3 H, t, J = 7.3 Hz). |
| 341 | Solid | 1H-NMR (CDCl3) δ: 8.26 (1 H, s), 7.38 (2 H, s), 6.47 (1 H, s), 5.96 (1 H, s), 5.24 (2 H, s), 3.45 (2 H, t, J = 8.1 Hz), 2.44 (3 H, s), 1.81-1.77 (2 H, m), 1.47-1.44 (2 H, m), 0.92 (3 H, t, J = 7.3 Hz). |
| 342 | Solid | 1H-NMR (CDCl3) δ: 8.25 (1H, s), 7.38-7.36 (2 H, m), 6.52 (1 H, s), 5.93 (1 H, s), 5.23 (2 H, s), 3.10-3.03 (1 H, m), 2.41 (3 H, s), 2.05-2.00 (1 H, m), 1.67-1.61 (1 H, m), 1.29 (1 H, d, J = 7.0 Hz), 1.13 (2 H, t, J = 7.6 Hz), 1.12 (2 H, d, J = 7.0 Hz), 0.99 (1 H, t, J = 7.6 Hz). |
| 343 | Solid | 1H-NMR (CDCl3) δ: 8.25 (1 H, s), 7.38 (2 H, d, J = 1.2 Hz), 6.49 (1 H, s), 5.95 (1 H, s), 5.24 (2 H, s), 3.53-3.51 (1 H, m), 2.43 (3 H, s), 2.09-2.01 (1 H, m), 1.62-1.61 (1 H, m), 1.34 (3 H, d, J = 7.0 Hz), 1.02 (3 H, t, J = 7.5 Hz). |

Comparative Example 1

Synthesis of 4-((6-bromopyridin-3-yl)methyl)-2-(methylthio)-[1,2,4]triazolo[1,5-a]pyrimidin-7(4H)-one (Compound E2.8 According to Patent Document 5, Reference Example 3 of the Present Specification)

To a suspension of 2-(methylthio)-[1,2,4]triazolo[1,5-a]pyrimidin-7-ol (0.18 g, 1.0 mmol) in N,N-dimethyl formamide (DMF, 2 mL) contained in a 100 mL branched flask, potassium carbonate (0.17 g, 1.2 mmol) and 2-bromo-5-(bromomethyl)pyridine (0.25 g, 1.0 mmol) were added and stirred fir 30 minutes after heating to 70° C. After cooling to room temperature, water (30 ml) and ethyl acetate (30 ml) were added. Accordingly, a solid was precipitated, and the obtained solid was collected by filtration to obtain the target product (0.19 g) as a white solid with yield of 55%.

¹H-NMR(CDCl₃)δppm: 8.46(1H,d,J=2.4 Hz), 7.63(1H, dd,J=8.3, 2.4 Hz), 7.53(1H,d,J=8.3 Hz), 7.40(1H,d,J=8.0 Hz), 6.06(1H,d,J=8.0 Hz), 5.26(2H,s), 2.70(3H,s).

Comparative Example 2

Synthesis of 4-((6-chloropyridin-3-yl)methyl)-7-methyl-2-(methylthio)-[1,2,4]triazolo[1,5-a]pyrimidin-5(4H)-one (Reference Example 4 of the Present Specification)

To a suspension of N-((6-chloropyridin-3-yl)methyl)-5-methylthio-1,2,4-triazole-3-amine (0.20 g, 0.78 mmol) in DMF (5 ml) contained in a 50 mL branched flask, ethyl acetoacetate (0.15 g, 12.2 mmol) was added and stirred for at 150° C. 3 hours. After cooling to room temperature, water (20 ml) was added, and the resulting product was collected by filtration to obtain the target product (0.08 g) as a white solid with yield of 32%.

¹H-NMR(CDCl₃)δppm: 8.69(1H,d,J=2.6 Hz), 7.90(1H, dd,J=8.3, 2.6 Hz), 7.28(1H,d,J=8.3 Hz), 5.96(1H,s), 5.30 (2H,s), 2.63(3H,s), 2.51(3H,s).

Next, examples of the formulation containing the compound of the invention as an effective component are described but the invention is not limited to them. Meanwhile, in the formulation example, the term "parts" indicate "parts by weight."

Formulation Example 1

20 parts of the compound represented by the formula (1) according to the invention, 10 parts of polyoxyethylene styrylphenyl ether, and 70 parts of xylene were homogeneously mixed to obtain an emulsion.

Formulation Example 2

10 parts of the compound represented by the formula (1) according to the invention, 2 parts of sodium laurylsulfuric acid, 2 parts of dialkylsulfosuccinate, 1 part of sodium β-naphthalene sulfonic acid formalin condensate, and 85 parts of diatomaceous earth were homogeneously mixed to obtain a wettable powder.

Formulation Example 3

0.3 part of the compound represented by the formula (1) according to the invention and 0.3 part of white carbon were mixed homogeneously, and 99.2 parts of clay and 0.2 part of DRILESS A (manufactured by Sankyo Agro Co., Ltd.) were added thereto, followed by pulverizing and mixing homogeneously, thereby obtaining a dustable powder.

Formulation Example 4

3 parts of the compound represented by the formula (1) according to the invention, 1.5 parts of a polyoxyethylene/polyoxypropylene condensate, 3 parts of carboxymethyl cellulose, 64.8 parts of clay, and 27.7 parts of talc were pulverized and mixed homogeneously, and water was added thereto, followed by kneading, granulating, and drying, thereby obtaining granules.

Formulation Example 5

10 parts of the compound represented by the formula (1) according to the invention, 3 parts of sodium β-naphthalene sulfonic acid formalin condensate, 1 part of tristyrylphenol, 5 parts of propylene glycol, 0.5 part of a silicon-based defoaming agent, and 33.5 parts of water were sufficiently stirred and mixed, and then 0.3 part of xanthan gum and 46.7 parts of water were mixed therewith, followed by stirring and mixing again, thereby obtaining a flowable formulation.

Formulation Example 6

20 parts of the compound represented by the formula (1) according to the invention, 6 parts of a naphthalene sulfonic acid formaldehyde condensate metal salt, 1 part of dialkyl-sulfosuccinate metal salt, and 73 parts of calcium carbonate were pulverized and mixed homogeneously, and water was added thereto, followed by kneading, granulating, and drying, thereby obtaining water dispersible granules.

When the formulations obtained above are used, they are diluted with water (1 to 10000 times) or directly applied without any dilution.

Next, usefulness of the compound of the invention as a pest control agent is described specifically in view of Test Examples shown below. However, the invention is not limited to them.

Test Example 1

Insecticidal Test Against *Laodelphax striatellus*

12.5 ml of 2% aqueous acetone solution prepared to have the test compound at 100 ppm was added to a conical flask, and root parts of a young rice plant were immersed therein. Furthermore, 2.5 ml of acetone solution prepared to have the test compound at 1000 ppm was sprayed onto leaf parts of a young rice plant followed by air drying. After applying a transparent plastic container on the flask, ten *Laodelphax striatellus* (3-stage or 4-stage) were released inside the container, which was then covered with a sponge stopper. After keeping them in an incubator at 25° C., the numbers of living insects and dead insects were determined after 6 days. There was no series.

As a result of the test, the compounds of the following Compound Nos. 1, 2, 3, 4, 5, 6, 9, 10, 12, 14, 19, 20, 22, 23, 24, 25, 26, 27, 29, 30, 32, 33, 35, 36, 38, 40, 42, 45, 46, 47, 50, 52, 56, 57, 58, 59, 60, 62, 64, 65, 66, 68, 69, 71, 72, 73, 74, 75, 76, 77, 81, 82, 88, 89, 90, 91, 92, 93, 94, 95, 96, 97, 98, 99, 100, 101, 102, 103, 104, 105, 106, 108, 109, 111, 112, 113, 114, 117, 118, 119, 120, 121, 123, 124, 125, 126, 128, 129, 130, 131, 132, 133, 134, 137, 138, 139, 140, 142, 144, 151, 153, 154, 155, 156, 157, 158, 159, 160, 161, 162, 166, 175, 176, 177, 178, 179, 181, 182, 183, 185, 186, 187, 188, 189, 190, 193, 194, 195, 196, 200, 201, 203, 204, 211, 214, 215, 216, 218, 219, 223, 224, 225, 228, 229, 230, 231, 232, 236, 237, 239, 240, 241, 242, 243, 244, 245, 246, 247, 248, 249, 250, 251, 252, 253, 254, 255, 256, 257, 260, 261, 262, 263, 265, 266, 267, 269, 272, 273, 274, 277, 278, 281, 282, 284, 285, 286, 287, 292, 293, 294, 295, 296, 297, 298, 299, 300, 301, 303, 305, 306, 307, 308, 309, 310, 311, 312, 313, 314, 317, 318, 319, 320, 321, 322, 323, 324, 325, 326, 327, 328, 329, 330, 331, 332, 333, 334, 335, 336, 337, 338, 339, 340, 341, 342, and 343 exhibited the insect death ratio of 70% or higher.

Test Example 2

Insecticidal Test Against *Myzus persicae*

15 to 20 ml of 2% aqueous acetone solution prepared to have the test compound at 100 ppm was added to a tubular bottle, and root parts of a young white radish plant having 1-stage *Myzus persicae* larvae were immersed therein. Furthermore, 2.5 ml of 20% aqueous acetone solution prepared to have the test compound at 1000 ppm was sprayed onto leaf parts followed by air drying. After keeping them in an incubator at 25° C., the numbers of living insects and dead insects were determined after 5 days. There was no series.

As a result of the test, the compounds of the following Compound Nos. 3, 4, 5, 6, 12, 18, 19, 25, 26, 27, 28, 29, 30, 32, 33, 35, 40, 41, 44, 45, 46, 47, 48, 50, 52, 53, 56, 57, 58, 59, 60, 62, 69, 71, 76, 77, 90, 91, 94, 95, 97, 99, 100, 108, 109, 113, 114, 115, 117, 118, 120, 121, 124, 140, 142, 144, 147, 151, 152, 153, 154, 155, 156, 157, 159, 160, 161, 162, 166, 175, 176, 177, 178, 179, 182, 183, 185, 187, 188, 189, 190, 195, 196, 197, 201, 202, 203, 208, 214, 215, 218, 219, 222, 223, 224, 225, 228, 229, 230, 231, 232, 234, 236, 237, 238, 239, 240, 241, 242, 243, 244, 245, 246, 247, 248, 249, 250, 251, 252, 253, 254, 255, 256, 257, 260, 261, 263, 266, 267, 268, 269, 279, 281, 282, 284, 285, 292, 293, 294, 295, 296, 298, 299, 300, 301, 303, 305, 306, 307, 308, 309, 310, 311, 312, 315, 316, 317, 318, 319, 320, 321, 322, 323, 324, 325, 326, 327, 328, 329, 330, 331, 332, 333, 334, 335, 336, 337, 338, 339, 340, 341, 342, and 343 exhibited the insect death ratio of 70% or higher.

Test Example 3

Insecticidal Test Against *Nilaparvata lugens*

2.5 ml of acetone solution prepared to have the test compound at the pre-determined concentration described in the following Table 28 was sprayed to young rice plant followed by air drying. Then, it was added to a glass bottle (diameter of 3 cm and height of 13 cm) added with water. Ten sensitive *Nilaparvata lugens* (3-stage) were released therein, and then the bottle was covered with a cap. After keeping them in an incubator at 25° C., the numbers of living insects and dead insects were determined after 6 days (two series). Meanwhile, as a comparative compound, imidacloprid was used.

The results are shown in the following Table 28.

As it is clearly shown in the results of Table 28, the compound of the invention exhibited high dead insect ratio against *Nilaparvata lugens*.

TABLE 28

| Test Compound | Concentration (ppm) | Sensitive insect death ratio (%) | Resistant insect death ratio (%) |
|---|---|---|---|
| Compound No. 5 | 10 | 100 | 95 |
|  | 100 | 100 | 100 |
| Compound No 154 | 10 | 100 | 100 |
|  | 100 | 100 | 100 |
| Imidacloprid (Comparative compound) | 10 | 100 | 21.7 |
|  | 100 | 100 | 50.4 |

Test Example 4

Insecticidal Test Against *Plutella xylostella*

A piece of a cabbage leaf was immersed for 30 seconds in a chemical solution in which the test compound had been added at a predetermined concentration, and air dried, and then put into a 7 cm polyethylene cup having a filter paper laid on the bottom thereof, and five 3-stage larvae of *Plutella xylostella* were released. They were left to stand in an incubator at 25° C., and the numbers of living insects and dead insects were examined after 6 days. There was no series.

As a result of the test, the compounds of Compound Nos. 16, 22, 23, 24, 25, 28, 29, 106, 189, 236, 237, 241, and 243 exhibited the insect death ratio of 70% or higher at concentration of 1000 ppm.

Test Example 5

Insecticidal Test Against *Callosobruchus chinensis*

1 ml of acetone solution in which a test compound had been diluted at a predetermined concentration was added dropwise to a petri dish having a diameter of 9 cm, and air dried, and then ten adults of *Callosobruchus chinensis* were released and the petri dish was covered. They were left to stand in an incubator at 25° C., and the numbers of living insects and dead insects were examined after 1 day. There was no series.

As a result of the test, the compounds of Compound Nos. 10, 26, 45, 46, 59, 76, 80, 121, 190, 244, 248, 252, 253, 299, 306, and 307 exhibited the insect death ratio of 70% or higher at concentration of 1000 ppm.

Test Example 6

Insecticidal Test Against *Spodopteta litura*

A piece of a cabbage leaf was immersed for 30 seconds in a chemical solution in which a test compound had been added at a predetermined concentration, and air dried, and then put into a 7 cm polyethylene cup having a filter paper laid on the bottom thereof, and five 2-stage larvae of *Spodopteta litura* were released. They were left to stand in an incubator at 25° C., and the numbers of living insects and dead insects were examined after 6 days. There was no series.

As a result of the test, the compounds of Compound Nos. 191, 236, 237, 241, and 242 exhibited the insect death ratio of 70% or higher at concentration of 1000 ppm.

Test Example 7

Insecticidal Test Against *Ctenocephalides felis*

To a round filter paper (diameter of 4.0 cm) hold by tweezers, 0.2 ml, of acetone solution was added dropwise such that the chemical amount of the compound is 50 µg/cm². After the dropwise addition, the filter paper was dried for 24 hours at room temperature and used for the test.

Three vials (each with 200 mL volume) were used for each compound, and the filter paper was inserted to a vial cap without any gap such that *Ctenocephalides felis* is in contact with the surface of the filter paper which has been treated with the test material.

Emerged adult *Ctenocephalides felis* was collected by suction using an insect suction tube and added to the 200 mL vial (about 20 insects per vial), which was quickly sealed with the vial cap inserted with the filter paper previously treated with the test compound. At that time, it was determined whether or not dead *Ctenocephalides felis* are added to the vial per se, and if there are dead *Ctenocephalides felis*, the number of them was subtracted from the total number.

The vial was stood upside down (i.e., vial cap is placed downward) such that *Ctenocephalides felis* are constantly in contact with the filter paper. 24, 48, and 72 hours after the exposure, state of the *Ctenocephalides felis* was examined, i.e., survival or death (including dying condition), and the insect death ratio was calculated (three series).

Meanwhile, the insect death ratio was calculated according to the following equation.

Insect death ratio (%)=(Number of dead insects including dying condition)/Number of tested insects×100

As a result, the compounds of Compound Nos. 10 and 45 exhibited the insect death ratio of 50% or higher according to the examination after 72 hours.

Test Example 8

Insecticidal Test Against *Haemaphyxalis longicornis*

To an angular filter paper (3×5 cm) hold by tweezers, 0.239 mL of acetone solution was added dropwise such that the chemical amount of the compound is 50 µg/cm². After the dropwise addition, the filter paper was dried for 24 hours at room temperature and used for the test.

Three pieces of the angular filter paper were used for each compound. The long side of the filter paper treated with the test material was folded such that the chemical treated surface becomes an inner side, and by fixing both sides with a clip, the filter paper was prepared to have an envelope shape. About twenty young *Haemaphyxalis longicornis* were added through the opening, and then the opening was sealed by fixing with a clip.

24, 48, and 72 hours after the exposure, state of the *Haemaphyxalis longicornis* was examined, i.e., survival or death (including dying condition), and the insect death ratio was calculated (three series).

Meanwhile, the insect death ratio was calculated according to the following equation.

Insect death ratio (%)=(Number of dead insects including dying condition)/Number of tested insects×100

As a result, the compound of the invention exhibited the insecticidal effect according to the examination after 72 hours.

Test Example 9

Insecticidal Test Against *Laodelphax striatellus*

A chemical solution diluted to have a pre-determined concentration was sprayed to young rice plant (breed: Koshihikari) followed by air drying. Then, it was added to a glass test tube (diameter of 3 cm and height of 10 cm) added with water together with ten 3-stage larvae of *Laodelphax striatellus*. The tube was then covered. The number of living insects was determined after 6 days and the dead insect ratio was calculated. There were two series, i.e., 10 insects per group. The results are shown in the following Table 29. Meanwhile, in Table 29, when combination of two types of test chemicals are used (i.e., A and B), the combination of the two types was described as A+B, and in the concentration column (ppm), it was described as concentration of A+concentration of B.

TABLE 29

| Test agent | Concentration for treatment (ppm) | Insect death ratio (%) |
|---|---|---|
| Compound No. 5 + Ethofenprox | 3 + 30 | 100 |
| Compound No. 5 + Dinotefuran | 3 + 1 | 100 |
| Compound No. 5 + Pymetrozine | 3 + 10 | 100 |

TABLE 29-continued

| Test agent | Concentration for treatment (ppm) | Insect death ratio (%) |
|---|---|---|
| Compound No. 5 + Buprofezin | 3 + 1 | 100 |
| Compound No. 5 + Fipronil | 3 + 1 | 100 |
| Compound No. 5 + Ethiprole | 3 + 3 | 100 |
| Compound No. 5 + Imidacloprid | 3 + 0.1 | 100 |
| Compound No. 5 + Acephate | 3 + 3 | 100 |
| Compound No. 5 + Hydroxyisoxazole | 3 + 600 | 50 |
| Compound No. 154 + Ethofenprox | 3 + 30 | 100 |
| Compound No. 154 + Dinotefuran | 3 + 1 | 100 |
| Compound No. 154 + Pymetrozine | 3 + 10 | 100 |
| Compound No. 154 + Buprofezin | 3 + 1 | 100 |
| Compound No. 154 + Fipronil | 3 + 1 | 100 |
| Compound No. 154 + Ethiprole | 3 + 3 | 100 |
| Compound No. 154 + Imidacloprid | 3 + 0.1 | 100 |
| Compound No. 154 + Acephate | 3 + 3 | 100 |
| Compound No. 154 + Hydroxyisoxazole | 3 + 600 | 60 |
| Compound No. 5 | 3 | 20 |
| Compound No. 154 | 3 | 40 |
| Ethofenprox | 30 | 40 |
| Dinotefuran | 1 | 45 |
| Pymetrozine | 10 | 30 |
| Buprofezin | 1 | 70 |
| Fipronil | 1 | 70 |
| Ethiprole | 3 | 20 |
| Imidacloprid | 0.1 | 30 |
| Acephate | 3 | 20 |
| Hydroxyisoxazole | 600 | 0 |
| Not treated | — | 0 |

Test Example 10

Insecticidal Test Against *Chilo suppressalis*

A stem part was cut from a rice plant (breed: Koshihikari) cultivated in water and it was immersed in a chemical solution which has been diluted to have a pre-determined concentration. After air drying, it was put into a 9 cm polyethylene cup having a water-wetted filter paper laid on the bottom thereof, and 3-stage larvae of *Chilo suppressalis* were released and covered. They were left to stand in an incubator at 25° C., and the numbers of living insects and dead insects were examined after 6 days. There were two series, i.e., 5 insects per group. The results are shown in the following Table 30. Meanwhile, in Table 30, when combination of two types of test chemicals are used (i.e., A and B), the combination of the two types was described as A+B, and in the concentration column (ppm), it was described as concentration of A+concentration of B.

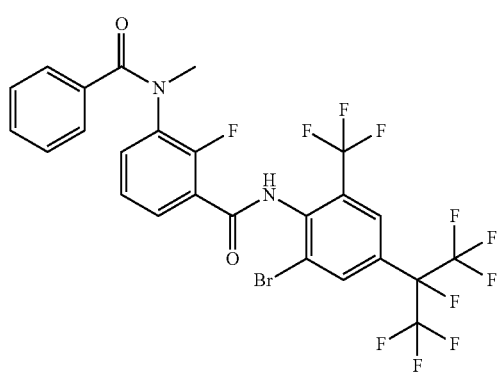
(DD-1)

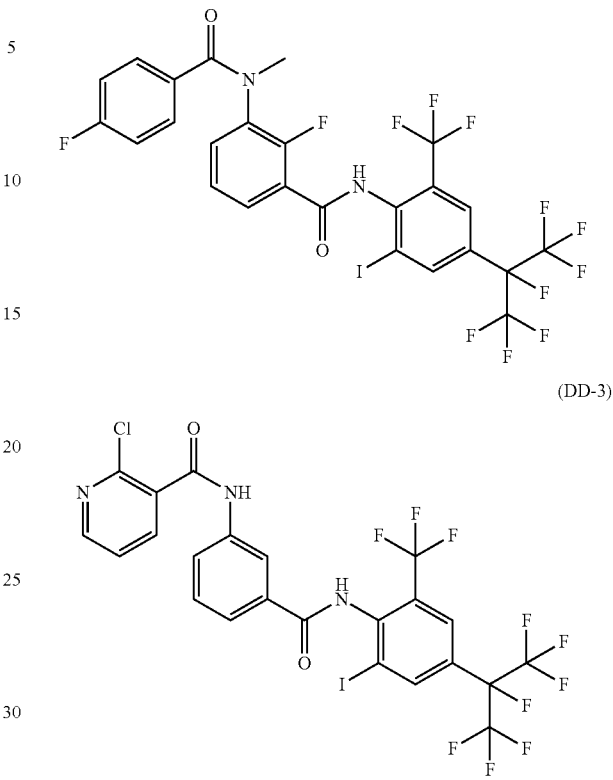
(DD-2)

(DD-3)

TABLE 30

| Test agent | Concentration for treatment (ppm) | Insect death ratio (%) |
|---|---|---|
| Compound No. 5 + DD-1 | 100 + 0.1 | 100 |
| Compound No. 5 + DD-2 | 100 + 0.1 | 100 |
| Compound No. 5 + DD-3 | 100 + 0.1 | 100 |
| Compound No. 5 + Chlorantraniliprole | 100 + 1 | 100 |
| Compound No. 5 + Flubendiamide | 100 + 1 | 100 |
| Compound No. 5 + Spinosad | 100 + 1 | 100 |
| Compound No. 5 + Ethofenprox | 100 + 100 | 100 |
| Compound No. 5 + Cartap | 100 + 300 | 100 |
| Compound No. 5 + Spinetoram | 100 + 1 | 100 |
| Compound No. 5 + Cyantraniliprole | 100 + 1 | 100 |
| Compound No. 154 + DD-1 | 100 + 0.1 | 100 |
| Compound No. 154 + DD-2 | 100 + 0.1 | 100 |
| Compound No. 154 + DD-3 | 100 + 0.1 | 100 |
| Compound No. 154 + Chlorantraniliprole | 100 + 1 | 100 |
| Compound No. 154 + Flubendiamide | 100 + 1 | 100 |
| Compound No. 154 + Spinosad | 100 + 1 | 100 |
| Compound No. 5 + Ethofenprox | 100 + 100 | 100 |
| Compound No. 5 + Cartap | 100 + 300 | 100 |
| Compound No. 5 + Spinetoram | 100 + 1 | 100 |
| Compound No. 5 + Cyantraniliprole | 100 + 1 | 100 |
| Compound No. 5 | 100 | 0 |
| Compound No. 154 | 100 | 0 |
| DD-1 | 0.1 | 90 |
| DD-2 | 0.1 | 100 |
| DD-3 | 0.1 | 100 |
| Chlorantraniliprole | 1 | 80 |
| Flubendiamide | 1 | 80 |
| Spinosad | 1 | 70 |
| Ethofenprox | 100 | 100 |
| Cartap | 300 | 90 |
| Spinetoram | 1 | 100 |
| Cyantraniliprole | 1 | 80 |
| Not treated | — | 0 |

Test Example 11

Control Test Against *Pyricularia oryzae*

To two pots with rice plant (breed: Koshihikari; 4-leaf stage), a chemical solution which has been diluted to have a pre-determined concentration was sprayed. One day after the spray, it was placed in an artificial weather chamber (setting condition: 25° C., 12 hours of light and dark cycle), and sprayed with a suspension of rice blast spore. The inside of the weather chamber was kept at high humidity condition, and the number of rice blast spots was examined 7 days later. Then, the control value was calculated according to the following calculation formula (two series). The results are shown in the following Table 31. Meanwhile, in Table 31, when combination of two types of test chemicals (i.e., A and B) or three types of test chemicals (i.e., A, B, and C) are used, the combination of the two types was described as A+B and the combination of the three types was described as A+B+C. In the concentration column (ppm), it was described as concentration of A+concentration of B, or concentration of A+concentration of B+concentration of C.

Control value=(1−Number of disease spots in treatment group/Number of disease spots in non-treatment group)×100

(EE-1)

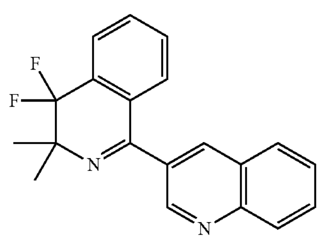

(EE-2)

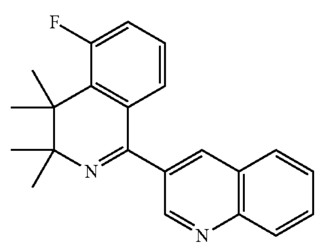

(EE-3)

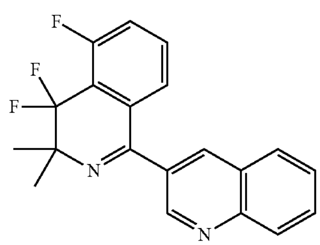

TABLE 31

| Test agent | Concentration (ppm) | Rice blast control value |
|---|---|---|
| Compound No. 5 + Tolprocarb | 100 + 50 | 98 |
| Compound No. 5 + EE-1 | 100 + 50 | 97 |
| Compound No. 5 + EE-2 | 100 + 50 | 96 |
| Compound No. 5 + EE-3 | 100 + 50 | 96 |

TABLE 31-continued

| Test agent | Concentration (ppm) | Rice blast control value |
|---|---|---|
| Compound No. 5 + Probenazole | 100 + 12 | 95 |
| Compound No. 5 + Diclocymet | 100 + 1.5 | 95 |
| Compound No. 5 + Orysastrobin | 100 + 3.5 | 96 |
| Compound No. 5 + Tricyclazole | 100 + 2 | 97 |
| Compound No. 5 + Isoprothiolane | 100 + 6 | 96 |
| Compound No. 5 + Isotianil | 100 + 1 | 98 |
| Compound No. 5 + Tebufloquin | 100 + 100 | 99 |
| Compound No. 5 + Kasugamycin + Fthalide | 100 + 12 + 150 | 98 |
| Compound No. 5 + Ferimzone + Fthalide | 100 + 150 + 150 | 98 |
| Compound No. 5 + Tricyclazole | 100 + 200 | 99 |
| Compound No. 154 + Tolprocarb | 100 + 50 | 99 |
| Compound No. 154 + EE-1 | 100 + 50 | 97 |
| Compound No. 154 + EE-2 | 100 + 50 | 98 |
| Compound No. 154 + EE-3 | 100 + 50 | 96 |
| Compound No. 154 + Probenazole | 100 + 12 | 96 |
| Compound No. 154 + Diclocymet | 100 + 1.5 | 95 |
| Compound No. 154 + Orysastrobin | 100 + 3.5 | 98 |
| Compound No. 154 + Tricyclazole | 100 + 2 | 95 |
| Compound No. 154 + Isoprothiolane | 100 + 6 | 95 |
| Compound No. 154 + Isotianil | 100 + 1 | 97 |
| Compound No. 154 + Tebufloquin | 100 + 100 | 98 |
| Compound No. 154 + Kasugamycin + Fthalide | 100 + 12 + 150 | 99 |
| Compound No. 154 + Ferimzone + Fthalide | 100 + 150 + 150 | 99 |
| Compound No. 154 + Tricyclazole | 100 + 200 | 98 |
| Compound No. 5 | 100 | 0 |
| Compound No. 154 | 100 | 0 |
| Tolprocarb | 50 | 97 |
| EE-1 | 50 | 97 |
| EE-2 | 50 | 95 |
| EE-3 | 50 | 97 |
| Probenazole | 12 | 96 |
| Diclocymet | 1.5 | 95 |
| Orysastrobin | 3.5 | 95 |
| Tricyclazole | 2 | 98 |
| Isoprothiolane | 6 | 97 |
| Isotianil | 1 | 97 |
| Tebufloquin | 100 | 98 |
| Kasugamycin + Fthalide | 12 + 150 | 98 |
| Ferimzone + Fthalide | 150 + 150 | 97 |
| Tricyclazole | 200 | 97 |
| Not treated | — | 0 |

Test Example 12

Insecticidal Test Against *Myzus persicae*

A chemical solution which has been diluted to have a pre-determined concentration was sprayed on a leaf part of young white radish plant having 1-stage larvae *Myzus persicae* present thereon. After air drying, they were left to stand in an incubator at 25° C. and the numbers of living insects and dead insects were examined after 5 days (2 series). The results are shown in the following Table 32. Meanwhile, in Table 32, when combination of two types of test chemicals are used (i.e., A and B), the combination of the two types was described as A+B, and in the concentration column (ppm), it was described as concentration of A+concentration of B.

TABLE 32

| Test agent | Concentration for treatment (ppm) | Insect death ratio (%) |
|---|---|---|
| Compound No. 5 + Lepimectin | 100 + 10 | 100 |
| Compound No. 5 + Milbemectin | 100 + 10 | 100 |
| Compound No. 5 + Penthiopyrad | 100 + 100 | 73 |
| Compound No. 5 + Imidacloprid | 100 + 1 | 94 |
| Compound No. 5 + Thiamethoxam | 100 + 1 | 98 |

TABLE 32-continued

| Test agent | Concentration for treatment (ppm) | Insect death ratio (%) |
|---|---|---|
| Compound No. 5 + Dinotefuran | 100 + 10 | 93 |
| Compound No. 5 + Flonicamid | 100 + 1 | 83 |
| Compound No. 5 + Pymetrozine | 100 + 1 | 98 |
| Compound No. 5 + Pyrifluquinazon | 100 + 1 | 100 |
| Compound No. 154 + Lepimectin | 100 + 10 | 100 |
| Compound No. 154 + Milbemectin | 100 + 10 | 100 |
| Compound No. 154 + Penthiopyrad | 100 + 100 | 75 |
| Compound No. 154 + Imidacloprid | 100 + 1 | 100 |
| Compound No. 154 + Thiamethoxam | 100 + 1 | 94 |
| Compound No. 154 + Dinotefuran | 100 + 10 | 95 |
| Compound No. 154 + Flonicamid | 100 + 1 | 94 |
| Compound No. 154 + Pymetrozine | 100 + 1 | 98 |
| Compound No. 154 + Pyrifluquinazon | 100 + 1 | 100 |
| Compound No. 5 | 100 | 73 |
| Compound No. 154 | 10 | 70 |
| Lepimectin | 10 | 88 |
| Milbemectin | 10 | 86 |
| Penthiopyrad | 100 | 13 |
| Imidacloprid | 1 | 100 |
| Thiamethoxam | 1 | 94 |
| Dinotefuran | 10 | 75 |
| Flonicamid | 1 | 79 |
| Pymetrozine | 1 | 89 |
| Pyrifluquinazon | 1 | 100 |
| Not treated | — | 0 |

Test Example 13

Insecticidal Test Against *Nilaparvata lugens* Using Paddy Field Rice Cultivating Box A rice plant (breed: Koshihikari) cultivated in cultivating box was treated with granules with a pre-determined chemical amount, and it was transplanted in two pots, i.e., four plants per 1/5000a pot. Twenty-two days after the treatment, 10 female adults of *Nilaparvata lugens* were released and the young plants were covered with a mesh. Then, the insect death ratio was determined after 5 days. In addition, the number of the next generation larvae was determined after 22 days. There were two series. The results are shown in the following Table 33. Meanwhile, in Table 33, when combination of two types of test chemicals (i.e., A and B), the combination of the two types was described as A+B, and in the chemical amount column (g a.i./box), it was described as chemical amount of A+chemical amount of B.

TABLE 33

| Test agent | Chemical amount (g a.i./box) | Adult insect death ratio (%) | Number of larvaes (number of insects) |
|---|---|---|---|
| Compound No. 154 | 2 | 90 | 0 |
| Compound No. 154 + simeconazole | 2 + 2.25 | 90 | 0 |
| Simeconazole | 2.25 | 20 | 69 |
| Not treated | — | 20 | 72 |

Test Example 14

Insecticidal Test Against *Laodelphax striatellus*

A young rice plant (breed: Koshihikari) was sprayed with a chemical solution which has been diluted to a pre-determined concentration followed by air drying. Then, it was added to a glass test tube (diameter of 3 cm and height of 10 cm) added with water, together with ten *Laodelphax striatellus* larvae (3-stage), and then the tube was covered with a cap. The number of dead insects was determined after 6 days and the insect death ratio was calculated. There were two series, i.e., 10 insects per group. The results are shown in the following Table 34.

Meanwhile, as a comparative compound, Reference Example 3 disclosed in the pamphlet of International Publication No. 2013/144088 and Reference Example 4 with C=O position different from the present compound were used.

From the results, it was found the invention has a higher effect than Reference Example 3 and Reference Example 4 with different C=O position.

Reference Example 3

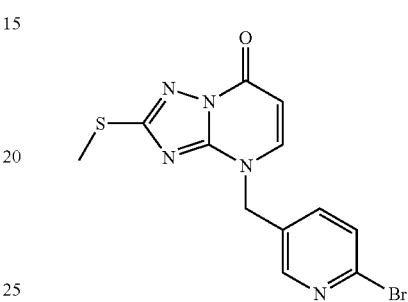

Reference Example 4

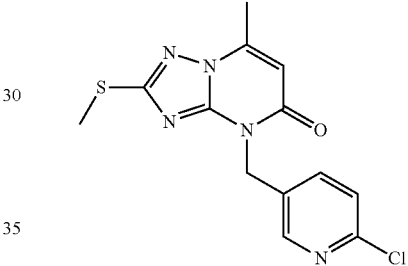

TABLE 34

| Test compound | Concentration (ppm) | Insect death ratio (%) |
|---|---|---|
| Compound No. 5 | 10 | 100 |
| Compound No. 154 | 10 | 100 |
| Reference Example 3 | 100 | 21 |
| Reference Example 4 | 1000 | 40 |
| Not treated | | 0 |

INDUSTRIAL APPLICABILITY

According to the invention, it is possible to provide a novel fused ring pyrimidine compound. The fused ring pyrimidine compound exhibits an effect of controlling various pests, for example, *Laodelphax striatellus*, *Myzus persicae*, and *Plutella xylostella*. Furthermore, as it also exhibits an effect of controlling *Nilaparvata lugens*, the pest control agent containing the compound as an effective component has high industrial usefulness.

Spectrum of the pest for which the fused ring pyrimidine compound of the invention exhibits a control effect is not limited to the above.

The disclosure of Japanese Patent Application No. 2013-017758 which was filed on Jan. 31, 2013 is herein incorporated by reference in its entirety.

All documents, patent applications, and technical standards which have been described in the specification are herein incorporated by reference to the extent that incorporation of the individual document, patent application, and technical standard by reference is the same as specific or separate description of them.

The invention claimed is:
1. A fused ring pyrimidine compound represented by the following formula (I), or a salt thereof:

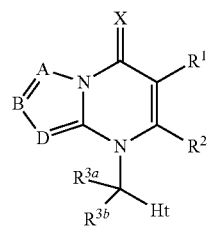

wherein, in formula (I), A represents a nitrogen atom or C—$R^4$;
B represents a nitrogen atom or C—$R^5$;
D represents C—$R^6$ and $R^6$ is a hydrogen atom;
X represents an oxygen atom, a sulfur atom, or N—$R^7$;
each of $R^1$ and $R^4$ independently represents a hydrogen atom, a halogen atom, a hydroxy group, a nitro group, a cyano group, an amino group, an alkyl group having 1 to 6 carbon atoms, a haloalkyl group having 1 to 6 carbon atoms, an alkenyl group having 2 to 6 carbon atoms, an alkynyl group having 2 to 6 carbon atoms, an alkoxy group having 1 to 6 carbon atoms, a haloalkoxy group having 1 to 6 carbon atoms, an alkoxyalkyl group having 2 to 6 carbon atoms, an alkoxycarbonyl group having 2 to 6 carbon atoms, an aminocarbonyl group having 1 to 6 carbon atoms, an alkylamino group having 1 to 6 carbon atoms, a benzyl group that may be substituted, a heterocyclylmethyl group that may be substituted, a phenyl group that may be substituted, or a heterocyclyl group that may be substituted;
$R^2$ represents a halogen atom, a hydroxy group, a nitro group, a cyano group, an amino group, an alkyl group having 1 to 6 carbon atoms, a haloalkyl group having 1 to 6 carbon atoms, an alkenyl group having 2 to 6 carbon atoms, an alkynyl group having 2 to 6 carbon atoms, an alkoxy group having 1 to 6 carbon atoms, a haloalkoxy group having 1 to 6 carbon atoms, an alkoxyalkyl group having 2 to 6 carbon atoms, an alkoxycarbonyl group having 2 to 6 carbon atoms, an aminocarbonyl group having 1 to 6 carbon atoms, an alkylamino group having 1 to 6 carbon atoms, a benzyl group that may be substituted, a heterocyclylmethyl group that may be substituted, a phenyl group that may be substituted, or a heterocyclyl group that may be substituted;
each of $R^{3a}$ and $R^{3b}$ independently represents a hydrogen atom, a halogen atom, a nitro group, a cyano group, an alkyl group having 1 to 6 carbon atoms, a haloalkyl group having 1 to 6 carbon atoms, an alkoxy group having 1 to 6 carbon atoms, an alkylthio group having 1 to 6 carbon atoms, an alkylsulfinyl group having 1 to 6 carbon atoms, or an alkylsulfonyl group having 1 to 6 carbon atoms;
$R^5$ represents a hydrogen atom, a cyano group, a hydroxy group, a thiol group, a halogen atom, an alkyl group having 1 to 6 carbon atoms, a haloalkyl group having 1 to 6 carbon atoms, an alkenyl group with 2 to 6 carbon atoms, an alkynyl group having 2 to 6 carbon atoms, an alkoxyalkyl group having 2 to 6 carbon atoms, a benzyl group that may be substituted, a phenyl group that may be substituted, a heterocyclyl group that may be substituted, an alkoxy group that has 1 to 6 carbon atoms and that may be substituted, an alkenyloxy group having 2 to 6 carbon atoms, an alkynyloxy group having 2 to 6 carbon atoms, a haloalkoxy group having 1 to 6 carbon atoms, an alkoxyalkoxy group having 2 to 6 carbon atoms, an alkylcarbonyloxy group having 2 to 6 carbon atoms, an alkylcarbamate group having 2 to 6 carbon atoms, an alkylcarbonate group having 2 to 6 carbon atoms, a benzyloxy group that may be substituted, a phenoxy group that may be substituted, a heterocyclyloxy group that may be substituted, an alkylthio group having 1 to 6 carbon atoms, a haloalkylthio group having 1 to 6 carbon atoms, an alkylsulfinyl group having 1 to 6 carbon atoms, an alkylsulfonyl group having 1 to 6 carbon atoms, a haloalkylsulfinyl group having 1 to 6 carbon atoms, a haloalkylsulfonyl group with 1 to 6 carbon atoms, an alkylsulfonyloxy group having 1 to 6 carbon atoms, a haloalkylsulfonyloxy group having 1 to 6 carbon atoms, an alkylaminosulfonyloxy group having 1 to 6 carbon atoms, a benzylthio group that may be substituted, a phenylthio group that may be substituted, a phenylsulfinyl group that may be substituted, a phenylsulfonyl group that may be substituted, a phenylsulfonyloxy group that may be substituted, a heterocyclylthio group that may be substituted, a heterocyclylsulfinyl group that may be substituted, a heterocyclylsulfonyl group that may be substituted, a substituted iminosulfinyl group, a substituted iminosulfoxy group, an alkylcarbonyl group having 2 to 6 carbon atoms, an alkoxycarbonyl group having 2 to 6 carbon atoms, an alkylaminocarbonyl group having 2 to 6 carbon atoms, an alkylamino group that has 1 to 6 carbon atoms and that may be substituted, or an alkylcarbonylamino group having 2 to 6 carbon atoms;
when A represents C—$R^4$ and B represents C—$R^5$, $R^4$ and $R^5$ may bind to each other to form, together with the carbon atom to which each of $R^4$ and $R^5$ is bonded, a saturated or unsaturated ring;
$R^7$ represents a hydrogen atom, a cyano group, a hydroxy group, an alkyl group having 1 to 6 carbon atoms, a haloalkyl group having 1 to 6 carbon atoms, a phenyl group that may be substituted, an alkoxy group having 1 to 6 carbon atoms, an alkenyloxy group having 2 to 6 carbon atoms, an alkylcarbonyloxy group having 2 to 6 carbon atoms, a benzyloxy group that may be substituted, a phenoxy group that may be substituted, an alkylsulfonyl group having 1 to 6 carbon atoms, an alkylcarbonyl group having 2 to 6 carbon atoms, a haloalkylcarbonyl group having 2 to 6 carbon atoms, an alkoxycarbonyl group having 2 to 6 carbon atoms, or an amino group that may be substituted; and
Ht represents a 5-membered or 6-membered aromatic or non-aromatic heterocycle, selected from the group consisting of a pyridyl group that may be substituted, a pyrimidyl group that may be substituted, a pyrazyl group that may be substituted, a pyridazyl group that may be substituted, a pyrazolyl group that may be substituted, an imidazolyl group that may be substituted, a triazolyl group that may be substituted, a thiazolyl group that may be substituted, a thiophenyl group that may be substituted, a furyl group that may be substituted, a thiadiazolyl group that may be substituted and a tetrahydrofuryl group that may be substituted.

2. The fused ring pyrimidine compound or a salt thereof according to claim 1, wherein, in formula (I):
$R^1$ represents a hydrogen atom, a halogen atom, a hydroxy group, a nitro group, an alkyl group having 1 to 6 carbon atoms, a haloalkyl group having 1 to 6 carbon atoms, an alkoxy group having 1 to 6 carbon atoms, an alkoxyalkyl group having 2 to 6 carbon atoms, an alkoxycarbonyl group having 2 to 6 carbon atoms, an aminocarbonyl group having 1 to 6 carbon atoms, a benzyl group that may be substituted, a heterocyclylmethyl group that may be substituted, or a phenyl group that may be substituted;
$R^2$ represents a halogen atom, a hydroxy group, a nitro group, an alkyl group having 1 to 6 carbon atoms, a haloalkyl group having 1 to 6 carbon atoms, an alkoxy group having 1 to 6 carbon atoms, an alkoxyalkyl group having 2 to 6 carbon atoms, an alkoxycarbonyl group having 2 to 6 carbon atoms, an aminocarbonyl group having 1 to 6 carbon atoms, a benzyl group that may be substituted, a heterocyclylmethyl group that may be substituted, or a phenyl group that may be substituted;
$R^4$ represents a hydrogen atom, a cyano group, or an alkyl group having 1 to 6 carbon atoms;
$R^5$ represents a hydrogen atom, a cyano group, a hydroxy group, a thiol group, a halogen atom, an alkyl group having 1 to 6 carbon atoms, a haloalkyl group having 1 to 6 carbon atoms, an alkoxyalkyl group having 2 to 6 carbon atoms, a benzyl group that may be substituted, a phenyl group that may be substituted, a heterocyclyl group that may be substituted, an alkoxy group that has 1 to 6 carbon atoms and that may be substituted, an alkenyloxy group having 2 to 6 carbon atoms, an alkynyloxy group having 2 to 6 carbon atoms, a haloalkoxy group having 1 to 6 carbon atoms, an alkoxyalkoxy group having 2 to 6 carbon atoms, an alkylcarbonyloxy group having 2 to 6 carbon atoms, an alkylcarbamate group having 2 to 6 carbon atoms, an alkylcarbonate group having 2 to 6 carbon atoms, a benzyloxy group that may be substituted, a phenoxy group that may be substituted, a heterocyclyloxy group that may be substituted, an alkylthio group having 1 to 6 carbon atoms, a haloalkylthio group having 1 to 6 carbon atoms, an alkylsulfinyl group having 1 to 6 carbon atoms, an alkylsulfonyl group having 1 to 6 carbon atoms, a haloalkylsulfinyl group having 1 to 6 carbon atoms, a haloalkylsulfonyl group having 1 to 6 carbon atoms, an alkylsulfonyloxy group having 1 to 6 carbon atoms, a haloalkylsulfonyloxy group having 1 to 6 carbon atoms, an alkylaminosulfonyloxy group having 1 to 6 carbon atoms, a benzylthio group that may be substituted, a phenylthio group that may be substituted, a phenylsulfinyl group that may be substituted, a phenylsulfonyl group that may be substituted, a phenylsulfonyloxy group that may be substituted, a heterocyclylthio group that may be substituted, a heterocyclylsulfinyl group that may be substituted, a heterocyclylsulfonyl group that may be substituted, a substituted iminosulfinyl group, a substituted iminosulfoxy group, an alkylcarbonyl group having 2 to 6 carbon atoms, an alkyloxycarbonyl group having 2 to 6 carbon atoms, an alkylaminocarbonyl group having 2 to 6 carbon atoms, an alkylamino group that has 1 to 6 carbon atoms and that may be substituted, or an alkylcarbonylamino group having 2 to 6 carbon atoms; and
Ht represents a pyridyl group that may be substituted, a pyrimidyl group that may be substituted, a pyrazyl group that may be substituted, a pyridazyl group that may be substituted, a pyrazolyl group that may be substituted, an imidazolyl group that may be substituted, a triazolyl group that may be substituted, a thiazolyl group that may be substituted, or a tetrahydrofuryl group that may be substituted.

3. The fused ring pyrimidine compound or a salt thereof according to claim 2, wherein, in formula (I):
$R^1$ represents a hydrogen atom, a halogen atom, a nitro group, an alkyl group having 1 to 6 carbon atoms, an aminocarbonyl group having 1 to 6 carbon atoms, a benzyl group that may be substituted, a heterocyclylmethyl group that may be substituted, or a phenyl group that may be substituted;
$R^2$ represents a halogen atom, a hydroxy group, an alkyl group having 1 to 6 carbon atoms, a haloalkyl group having 1 to 6 carbon atoms, an alkoxy group having 1 to 6 carbon atoms, an alkoxyalkyl group having 2 to 6 carbon atoms, or a phenyl group that may be substituted;
each of $R^{3a}$ and $R^{3b}$ independently represents a hydrogen atom, or an alkyl group having 1 to 6 carbon atoms; and
$R^5$ represents a hydrogen atom, a cyano group, a hydroxy group, a thiol group, a halogen atom, an alkyl group having 1 to 6 carbon atoms, a haloalkyl group having 1 to 6 carbon atoms, an alkoxyalkyl group having 2 to 6 carbon atoms, a benzyl group that may be substituted, a phenyl group that may be substituted, a heterocyclyl group that may be substituted, an alkoxy group that has 1 to 6 carbon atoms and that may be substituted, an alkenyloxy group having 2 to 6 carbon atoms, an alkynyloxy group having 2 to 6 carbon atoms, a haloalkoxy group having 1 to 6 carbon atoms, an alkoxyalkoxy group having 2 to 6 carbon atoms, an alkylcarbonyloxy group having 2 to 6 carbon atoms, an alkylcarbamate group having 2 to 6 carbon atoms, an alkylcarbonate group having 2 to 6 carbon atoms, a benzyloxy group that may be substituted, a phenoxy group that may be substituted, a heterocyclyloxy group that may be substituted, an alkylthio group having 1 to 6 carbon atoms, a haloalkylthio group having 1 to 6 carbon atoms, an alkylsulfinyl group having 1 to 6 carbon atoms, an alkylsulfonyl group having 1 to 6 carbon atoms, a haloalkylsulfinyl group having 1 to 6 carbon atoms, a haloalkylsulfonyl group having 1 to 6 carbon atoms, an alkylsulfonyloxy group having 1 to 6 carbon atoms, a haloalkylsulfonyloxy group having 1 to 6 carbon atoms, an alkylaminosulfonyloxy group having 1 to 6 carbon atoms, a benzylthio group that may be substituted, a phenylthio group that may be substituted, a phenylsulfonyloxy group that may be substituted, a heterocyclylthio group that may be substituted, a substituted iminosulfinyl group, a substituted iminosulfoxy group, an alkylcarbonyl group having 2 to 6 carbon atoms, an alkoxycarbonyl group having 2 to 6 carbon atoms, an alkylaminocarbonyl group having 2 to 6 carbon atoms, an alkylamino group that has 1 to 6 carbon atoms and that may be substituted, or an alkylcarbonylamino group having 2 to 6 carbon atoms.

4. The fused ring pyrimidine compound or a salt thereof according to claim 1, wherein, in formula (I), B is C—$R^5$, and $R^5$ is a hydrogen atom, a halogen atom, an alkyl group having 1 to 3 carbon atoms, a haloalkyl group having 1 to 3 carbon atoms, an alkoxyalkyl group having 2 or 3 carbon atoms, an alkoxy group that has 1 to 3 carbon atoms and that may be substituted, an alkenyloxy group having 2 or 3 carbon atoms, an alkynyloxy group having 2 to 4 carbon atoms, a haloalkoxy group having 1 to 3 carbon atoms, an alkoxyalkoxy group having 2 or 3 carbon atoms, an alkylcarbonyloxy group having 2 or 3 carbon atoms, a phenoxy group that may be substituted, a heterocyclyloxy group that may be substituted, an alkylthio group having 1 to 3 carbon atoms, a haloalkylthio group having 1 to 3 carbon atoms, an alkylsulfinyl group having 1 to 3 carbon atoms, an alkylsulfonyl group having 1 to 3 carbon atoms, a haloalkylsulfinyl group having 1 to 3 carbon atoms, a haloalkylsulfonyl group having 1 to 3 carbon atoms, an alkylsulfonyloxy group having 1 to 3 carbon atoms, a haloalkylsulfonyloxy group having 1 to 3 carbon atoms, a phenylthio group that may be substituted, a phenylsulfonyloxy group that may be substituted, a substituted iminosulfinyl group, a substituted iminosulfoxy group, or an alkylamino group having 1 to 3 carbon atoms.

5. The fused ring pyrimidine compound or a salt thereof according to claim 4, wherein, in formula (I), $R^5$ is a hydrogen atom, a halogen atom, an alkyl group having 1 to 3 carbon atoms, a haloalkyl group having 1 to 3 carbon atoms, an alkoxy group having 1 to 3 carbon atoms, a haloalkoxy group having 1 to 3 carbon atoms, a phenoxy group that may be substituted, an alkylthio group having 1 to 3 carbon atoms, a haloalkylthio group having 1 to 3 carbon atoms, an alkylsulfinyl group having 1 to 3 carbon atoms, an alkylsulfonyl group having 1 to 3 carbon atoms, a haloalkylsulfinyl group having 1 to 3 carbon atoms, a haloalkylsulfonyl group having 1 to 3 carbon atoms, an alkylsulfonyloxy group having 1 to 3 carbon atoms, a substituted iminosulfinyl group, or a substituted iminosulfoxy group.

6. The fused ring pyrimidine compound or a salt thereof according to claim 1, wherein, in formula (I), B is a nitrogen atom.

7. The fused ring pyrimidine compound or a salt thereof according to claim 1, wherein, in formula (I), A is a nitrogen atom.

8. The fused ring pyrimidine compound or a salt thereof according to claim 1, wherein, in formula (I), A is C—$R^4$ and $R^4$ is a hydrogen atom.

9. The fused ring pyrimidine compound or a salt thereof according to claim 1, wherein, in formula (I), A is a nitrogen atom, and B is C—$R^5$.

10. The fused ring pyrimidine compound or a salt thereof according to claim 1, wherein, in formula (I), X is an oxygen atom.

11. The fused ring pyrimidine compound or a salt thereof according to claim 1, wherein, in formula (I), X is N—$R^7$, is a hydrogen atom, a cyano group, a hydroxy group, an alkyl group having 1 to 3 carbon atoms, a haloalkyl group having 1 to 3 carbon atoms, a phenyl group that may be substituted, an alkoxy group having 1 to 3 carbon atoms, an alkylcarbonyloxy group having 2 or 3 carbon atoms, an alkylsulfonyl group having 1 to 3 carbon atoms, an alkylcarbonyl group having 2 or 3 carbon atoms, a haloalkylcarbonyl group having 2 or 3 carbon atoms, an alkoxycarbonyl group having 2 or 3 carbon atoms, or an alkylamino group that has 1 to 3 carbon atoms and that may be substituted.

12. The fused ring pyrimidine compound or a salt thereof according to claim 11, wherein, in formula (I), $R^7$ is a hydroxy group, an alkyl group having 1 to 3 carbon atoms, a haloalkyl group having 1 to 3 carbon atoms, a phenyl group that may be substituted, an alkoxy group having 1 to 3 carbon atoms, an alkylcarbonyloxy group having 2 or 3 carbon atoms, an alkylsulfonyl group having 1 to 3 carbon atoms, an alkylcarbonyl group having 2 or 3 carbon atoms, a haloalkylcarbonyl group having 2 or 3 carbon atoms, an alkoxycarbonyl group having 2 or 3 carbon atoms, or an alkylamino group that has 1 to 3 carbon atoms and that may be substituted.

13. The fused ring pyrimidine compound or a salt thereof according to claim 1, wherein, in formula (I), $R^2$ is a hydroxy group, an alkyl group having 1 to 6 carbon atoms, or a haloalkyl group having 1 to 6 carbon atoms.

14. The fused ring pyrimidine compound or a salt thereof according to claim 13, wherein, in formula (I), $R^2$ is a methyl group or an ethyl group.

15. The fused ring pyrimidine compound or a salt thereof according to claim 1, wherein, in formula (I), $R^1$ is a hydrogen atom, a halogen atom, or an alkyl group having 1 to 6 carbon atoms.

16. The fused ring pyrimidine compound or a salt thereof according to claim 15, wherein, in formula (I), $R^1$ is a hydrogen atom, a methyl group, an ethyl group, or a fluorine atom.

17. The fused ring pyrimidine compound or a salt thereof according to claim 1, wherein, in formula (I), Ht is a pyridyl group that may be substituted, a pyrimidyl group that may be substituted, or a thiazolyl group that may be substituted.

18. The fused ring pyrimidine compound or a salt thereof according to claim 17, wherein, in formula (I), Ht is a 3-pyridyl group that may be substituted or a 3-thiazolyl group that may be substituted.

19. The fused ring pyrimidine compound or a salt thereof according to claim 18, wherein, in formula (I), Ht is a 6-chloro-3-pyridyl group.

20. The fused ring pyrimidine compound or a salt thereof according to claim 1, wherein, in formula (I), at least one of $R^{3a}$ or $R^{3b}$ is a hydrogen atom.

21. The fused ring pyrimidine compound or a salt thereof according to claim 20, wherein, in formula (I), one of $R^{3a}$ and $R^{3b}$ is a hydrogen atom and the other is a hydrogen atom, a methyl group, or an ethyl group.

22. A pest control agent comprising, as an effective component, the fused ring pyrimidine compound or a salt thereof according to claim 1.

23. A method of controlling a pest comprising:
treating crops or soil with a medicament that comprises an effective amount of the fused ring pyrimidine compound or a salt thereof according to claim 1, or applying the medicament to a subject of control.

* * * * *